US010010601B2

(12) United States Patent
Gallei et al.

(10) Patent No.: US 10,010,601 B2
(45) Date of Patent: Jul. 3, 2018

(54) PRRS VIRUS VARIANT, EUROPEAN PRRS VIRUS CDNA CLONE, AND USES THEREOF

(71) Applicant: Boehringer Ingelheim Vetmedica GmbH, Ingelheim am Rhein (DE)

(72) Inventors: Andreas Gallei, Hannover (DE); Christoph Keller, Burgdorf (DE); Erik Schacht, Hannover (DE); Marieke Herrel, Hannover (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

(21) Appl. No.: 15/105,760

(22) PCT Filed: Dec. 19, 2014

(86) PCT No.: PCT/EP2014/078929
§ 371 (c)(1),
(2) Date: Jun. 17, 2016

(87) PCT Pub. No.: WO2015/092058
PCT Pub. Date: Jun. 25, 2015

(65) Prior Publication Data
US 2016/0317642 A1 Nov. 3, 2016

(30) Foreign Application Priority Data

Dec. 20, 2013 (EP) ..................................... 13199177
Jul. 3, 2014 (EP) ..................................... 14175691

(51) Int. Cl.
| | | |
|---|---|---|
| A61K 39/12 | (2006.01) | |
| C07K 14/005 | (2006.01) | |
| C12Q 1/02 | (2006.01) | |
| C12N 7/00 | (2006.01) | |
| C12N 15/86 | (2006.01) | |
| A61K 39/00 | (2006.01) | |

(52) U.S. Cl.
CPC ............ *A61K 39/12* (2013.01); *C07K 14/005* (2013.01); *C12N 7/00* (2013.01); *C12N 15/86* (2013.01); *C12Q 1/02* (2013.01); *A61K 2039/5254* (2013.01); *A61K 2039/552* (2013.01); *C12N 2770/10021* (2013.01); *C12N 2770/10034* (2013.01); *C12N 2770/10043* (2013.01); *G01N 2333/08* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,959,457 A | 5/1976 | Speaker et al. |
| 4,015,100 A | 3/1977 | Gnanamuthu et al. |
| 4,205,060 A | 5/1980 | Monsimer et al. |
| 5,597,721 A | 1/1997 | Brun et al. |
| 5,620,691 A | 4/1997 | Wensvoort et al. |
| 5,695,766 A | 12/1997 | Paul et al. |
| 5,698,203 A | 12/1997 | Visser et al. |
| 5,858,729 A | 1/1999 | Van Woensel et al. |
| 5,866,401 A | 2/1999 | Hesse |
| 5,888,513 A | 3/1999 | Plana Duran et al. |
| 5,925,359 A | 7/1999 | Van Woensel et al. |
| 6,001,370 A | 12/1999 | Burch et al. |
| 6,110,467 A | 8/2000 | Paul et al. |
| 6,197,310 B1 | 3/2001 | Wensvoort et al. |
| 6,268,199 B1 | 7/2001 | Meulenberg et al. |
| 6,455,245 B1 | 9/2002 | Wensvoort et al. |
| 6,495,138 B1 | 12/2002 | van Nieuwstadt et al. |
| 6,806,086 B2 | 10/2004 | Wensvoort et al. |
| 7,312,030 B2 | 12/2007 | van Rijn et al. |
| 7,335,473 B2 | 2/2008 | Wensvoort et al. |
| 7,368,117 B2 | 5/2008 | Fetzer et al. |
| 7,897,343 B2 | 3/2011 | Wensvoort et al. |
| 8,765,142 B2 * | 7/2014 | Burgard ................ A61K 39/12 424/221.1 |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |

(Continued)

FOREIGN PATENT DOCUMENTS

| | | |
|---|---|---|
| CA | 2103460 A1 | 12/1992 |
| EP | 587780 A1 | 3/1994 |

(Continued)

OTHER PUBLICATIONS

Sun et al. (Biomedical Research International. 2014; 2014: 430508. doi: 10.1155/2014/430508).*

(Continued)

*Primary Examiner* — Shanon A. Foley
(74) *Attorney, Agent, or Firm* — Judy Jarecki-Black; Richard Seeger

(57) ABSTRACT

The present invention belongs to the field of animal health and provides means to study Porcine Reproductive and Respiratory Syndrome (PRRS), a viral disease affecting swine, and for the development of vaccines, therapeutics and diagnostics for the prophylaxis, treatment and diagnosis of PRRS. In a first consideration, the invention relates to a new PRRS virus variant, and, in a second consideration, to a nucleic acid sequence which comprises the genome of an infectious genotype I (EU) PRRS virus clone. Based on this, new PRRS vaccine candidates with improved properties are provided.

11 Claims, 7 Drawing Sheets

(56) References Cited

U.S. PATENT DOCUMENTS

Figure 1:
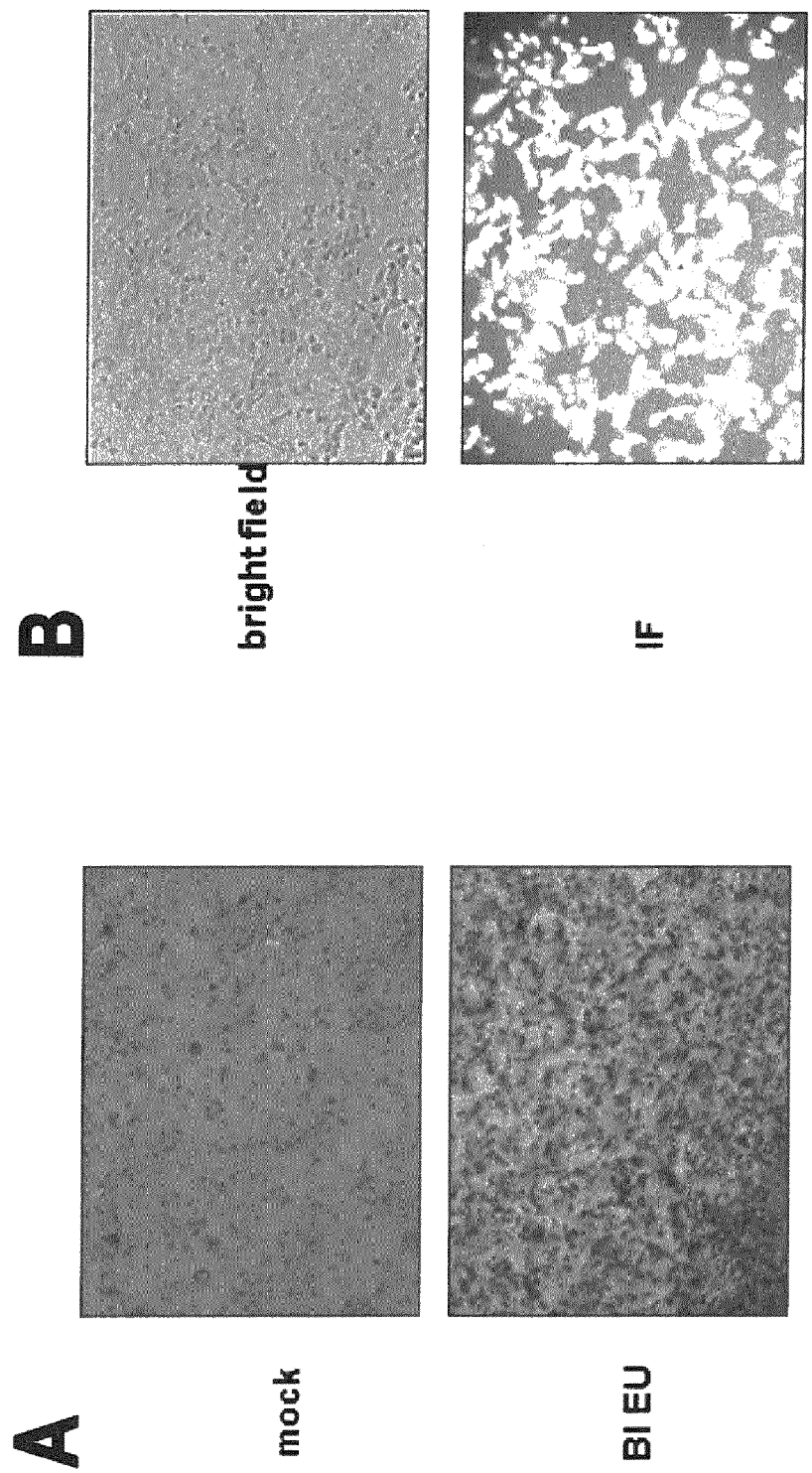

| | | | |
|---|---|---|---|
| 2004/0132014 A1 | 7/2004 | Wensvoort et al. | |
| 2004/0197872 A1 | 10/2004 | Meulenberg et al. | |
| 2004/0224327 A1 | 11/2004 | Meulenberg et al. | |
| 2006/0205033 A1 | 9/2006 | Meulenberg et al. | |
| 2006/0240041 A1 | 10/2006 | Meulenberg et al. | |
| 2010/0136047 A1* | 6/2010 | Fang | C07K 14/005 424/199.1 |
| 2011/0104201 A1 | 5/2011 | Mengeling et al. | |
| 2012/0213741 A1 | 8/2012 | Berry et al. | |
| 2012/0213810 A1* | 8/2012 | Burgard | A61K 39/12 424/186.1 |
| 2016/0317642 A1* | 11/2016 | Gallei | C12N 7/00 |
| 2017/0065709 A1 | 3/2017 | Burgard et al. | |

FOREIGN PATENT DOCUMENTS

| | | |
|---|---|---|
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| GB | 2282811 A | 4/1995 |
| GB | 2289279 A | 11/1995 |
| WO | 199221375 A1 | 12/1992 |
| WO | 199307898 A1 | 4/1993 |
| WO | 199314196 A1 | 7/1993 |
| WO | 199531550 A1 | 11/1995 |
| WO | 1996036356 A1 | 11/1996 |
| WO | 1998018933 A1 | 5/1998 |
| WO | 199850426 A1 | 11/1998 |
| WO | 2000053787 A1 | 9/2000 |
| WO | 200159077 A1 | 8/2001 |
| WO | 200190363 A1 | 11/2001 |
| WO | 2002095040 A1 | 11/2002 |
| WO | 2006002193 A2 | 1/2006 |
| WO | 2006034319 A2 | 3/2006 |
| WO | 2006074986 A2 | 7/2006 |
| WO | 2008121958 A1 | 10/2008 |
| WO | 2010025109 A1 | 3/2010 |
| WO | 20110128415 A1 | 10/2011 |
| WO | 2012110489 A2 | 8/2012 |
| WO | 2014150822 A2 | 9/2014 |
| WO | 2015092058 A1 | 6/2015 |

OTHER PUBLICATIONS

Sequence alignment of nt 1-10000 of Seq ID No. 48 with Geneseq database access No. AZZ01652 by Burgard et al in USPgPub 2012213810 on Dec. 2012.*

Sequence alignment of nt 10001-14843 of Seq ID No. 48 with Geneseq database access No. AZZ01652 by Burgard et al in USPgPub 2012213810 on Dec. 2012.*

"Dutch Team Isolates Mystery Pig Disease Agent", Animal Pharm, vol. 230, Abstract No. 00278268, Jun. 21, 1991, p. 21.

Albina et al., "Immune responses in pigs infected with porcine reproductive and respiratory syndrome virus (PRRSV)". Veterinary Immunology and Immunopathology, vol. 61, 1998, pp. 49-66.

Allende et al., "Mutations in the genome of porcine reproductive and respiratory syndrome virus responsible for the attenuated phenotype". Archives of Virology, vol. 145, No. 6, Jun. 2000, pp. 1149-1161.

Allende et al., "North American and European porcine reproductive and respiratory syndrome viruses differ in non-structural protein coding regions". Journal of General Virology, vol. 80, 1999, pp. 307-315.

Allende et al., "Porcine Reproductive and Respiratory Syndrome Virus: Description of Persistence in Individual Pigs upon Experimental Infection†". Journal of Virology, vol. 74, No. 22, Nov. 2000, pp. 10834-10837.

Andreyev et al., "Genetic variation and phylogenetic relationships of 22 porcine reproductive and respiratory syndrome virus (PRRSV) field strains based on sequence analysis of open-reading frame 5". Archives of Virology, vol. 142, 1997, pp. 993-1001.

Barfoed et al., "DNA vaccination of pigs with open reading frame 1-7 of PRRS virus". Vaccine, vol. 22, 2004, pp. 3628-3641.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.

Bramel-Verheije et al., "Expression of a Foreign Epitope by Porcine Reproductive and Respiratory Syndrome Virus". Virology, vol. 278, 2000, pp. 380-389.

Brinton-Darnell, M. "Lactate Dehydrogenase-Elevating, Equine Arteritis and Lelystad Viruses". Encyclopedia of Virology, vol. 2, 1999, pp. 763-771.

Brockmeier et al., "Genomic sequence and virulence comparison of four Type 2 porcine reproductive and respiratory syndrome virus strains". Virus Research, vol. 169, No. 1, 2012, pp. 212-221.

Christianson et al., "Porcine reproductive and respiratory syndrome: A review"., Journal of Swine Health and Production, vol. 2, No. 2, Mar. and Apr. 1994, pp. 10-28.

Conzelmann et al., "Molecular Characterization of Porcine Reproductive and Respiratory Syndrome Virus, a Member of the Arterivirus Group". Virology, vol. 193, 1993, pp. 329-339.

Darwich et al., "Genetic and immunobiological diversities of porcine reproductive and respiratory syndrome genotype I strains". Veterinary Microbiology, vol. 150, 2011, pp. 49-62.

Database EMBL Accession No. EU759247, "Porcine respiratory and reproductive syndrome virus isolate PRRSV2000000079 envelope glycoprotein gene, complete cds". Aug. 10, 2008, 1 page.

Database WPIL Week 8702, Derwent Publications Ltd., London, GB; AN 87-009295 [2] & EP, A,208672 (Regional Wallonne-Chiron Corp, Wallonne Regional) Jan. 14, 1987, 1 page.

Database WPIL Week 8741, Derwent Publications Ltd., London, GB; AN 87-286929 [41] & EP, A,62, 198626 (Za Bieseibutsu Kagaku Ken) Sep. 2, 1987, 1 page.

Database WPIL Week 8821, Derwent Publications Ltd., London, GB; AN 88-147502 [21] & WO,A,8 803 410 (Inst Pasteur) May 19, 1988, 1 page.

Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.

Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.

Dea et al., "Swine reproductive and respiratory syndrome in Quebec: Isolation of an enveloped virus serologically-elated to Lelystad virus". Canadian Veterinary Journal, vol. 33, No. 12, Dec. 1992, pp. 801-808.

Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.

Den Boon et al., "Processing and Evolution of the N-Terminal Region of the Arterivirus Replicase ORF1a Protein: dentification of Two Papainlike Cysteine Proteases". Journal of Virology, vol. 69, No. 7, Jul. 1995, pp. 4500-4505.

Drew et al., "Production, characterization and reactivity of monoclonal antibodies to porcine reproductive and respiratory syndrome virus". Journal of General Virology, vol. 76, 1995, pp. 1361-1369.

Drew, T., "Porcine Reproductive and Respiratory Syndrome Virus: A Review". Apr. 1996, 3 pages.

Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.

Duran et al. "Recombinant Baculovirus Vaccines Against Porcine Reproductive and Respiratory Syndrome (PRRS)". Abstracts PRRS, Aug. 9-10, 1995, Copenhagen, Denmark, 2 pages.

Genbank Accession No. ACY56808, Version ACY56808.1 GI:262358373, Nov. 8, 2009, pp. 1-2.

(56) References Cited

OTHER PUBLICATIONS

Goyal, S., "Porcine Reproductive and Respiratory Syndrome", Journal of Veterinary Diagnostic Investigation, vol. 5, No. 4, 1993, pp. 656-664.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
International Search Report and Written Opinion for PCT/EP2014/078929 dated Apr. 24, 2015.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Kvisgaard et al., "Genetic and antigenic characterization of complete genomes of Type 1 Porcine Reproductive and Respiratory Syndrome viruses (PRRSV) isolated in Denmark over a period of 10 years". Virus Research, vol. 178, 2013, pp. 197-205.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.
Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.
McCullough et al., "9. Experimental Transmission of Mystery Swine Disease", The New Pig Disease Porcine Respiration and Reproductive Syndrome, a report on the seminar/workshop held in Brussels on Apr. 29-30, 1991, pp. 46-52.
Meng et al., "Molecular cloning and nucleotide sequencing of the 3'-terminal genomic RNA of the porcine reproductive and respiratory syndrome virus". Journal of General Virology, vol. 75, 1994, pp. 1795-1801.
Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.
Meng, X.J., "Heterogeneity of porcine reproductive and respiratory syndrome virus: implications for current vaccine efficacy and future vaccine development". Veterinary Microbiology, vol. 74, 2000, pp. 309-329.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.
Mengeling et al., "Comparative safety and efficacy of attenuated single-strain and multi-strain vaccines for porcine reproductive and respiratory syndrome". Veterinary Microbiology, vol. 93, 2003, pp. 25-38.
Mengeling et al., "Comparison among strains of porcine reproductive and respiratory syndrome virus for their ability to cause reproductive failure". American Journal of Veterinary Research, vol. 57, No. 6, Jun. 1996, pp. 834-839.
Mengeling et al., "Strain specificity of the immune response of pigs following vaccination with various strains of porcine reproductive and respiratory syndrome virus". Veterinary Microbiology, vol. 93, 2003, pp. 13-24.
Meredith, MJ, "Porcine Reproductive and Respiratory Syndrome (PRRS)", Pig Disease Information Center, 1st North American Edition, University of Cambridge, Aug. 1994, pp. 1-57.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.
Xiao et al., "The Level of Virus-Specific T-Cell and Macrophage Recruitment in Porcine Reproductive and Respiratory Syndrome Virus Infection in Pigs Is Independent of Virus Load". Journal of Virology, vol. 78, No. 11, Jun. 2004, pp. 5923-5933.
Xue et al., "The Crystal Structure of Porcine Reproductive and Respiratory Syndrome Virus Nonstructural Protein Nsp1b Reveals a Novel Metal-Dependent NucleaseN". Journal of Virology, vol. 84, No. 13, Jul. 2010, pp. 6461-6471.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains'[Virus Research 74 (2001) 99-110]". Virus Research, vol. 79, 2001, p. 187.
Zhou et al., "The 30-Amino-Acid Deletion in the Nsp2 of highly Pathogenic Porcine Reproductive and Respiratory Syndrome Virus Emerging in China is Not Related to Its Virulence". Journal of Virology, vol. 83, No. 10, May 2009, pp. 5156-5167.
Zimmerman et al., "General overview of PRRSV: A perspective from the United States". Veterinary Microbiology, vol. 55, Nos. 1-4, Apr. 1997, pp. 187-196.
Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

(56) References Cited

OTHER PUBLICATIONS

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Murtaugh et al., "Comparison of the structural protein coding sequences of the VR-2332 and Lelystad virus strains of the PRRS virus". Archives of Virology, vol. 140, No. 8, 1995, pp. 1451-1460.

Murtaugh et al., "Genetic Variation in the PRRS Virus". Coronaviruses and Ateriviruses, Plenum Press, New York, 1998, pp. 787-794.

Nam et al. "Complete genomic characterization of a European type 1 porcine reproductive and respiratory syndrome virus isolate in Korea". Archives of Virology, vol. 154, No. 4, 2009, pp. 629-638.

NCBI: Accession No. AF159149. "Porcine reproductive and respiratory syndrome virus isolate MLV RespPRRS/Repro, complete genome." Aug. 28, 2000.

NCBI: Accession No. AF176348. "Porcine reproductive and respiratory syndrome virus isolate PA8 complete genome." Sep. 3, 2002.

NCBI: Accession No. AF184212. "Porcine reproductive and respiratory syndrome virus strain SP, complete genome." Sep. 28, 2000.

NCBI: Accession No. AF325691. "Porcine reproductive and respiratory syndrome virus isolate NVSL 977985 IA 1-4-2, complete genome." Feb. 11, 2001.

NCBI: Accession No. AF331831. "Porcine reproductive and respiratory syndrome virus BJ-4, complete genome." Jan. 15, 2001.

NCBI: Accession No. B4ZWR2. "Porcine reproductive and respiratory syndrome virus (PRRSV)." May 2008, 1 page.

NCBI: Accession No. M96262.2. "Lelystad virus, complete genome." Nov. 8, 2000.

NCBI: Accession No. NC_001961. "Porcine reproductive and respiratory syndrome virus, complete genome." Jan. 12, 2004.

NCBI: Accession No. NC_002533. "Lelystad virus, complete genome." Nov. 11, 2000.

NCBI: Accession No. U87392 AF030244 000153. "Porcine reproductive and respiratory syndrome virus strain VR-2332, complete genome." Nov. 17, 2000.

Nelsen et al., "Porcine Reproductive and Respiratory Syndrome Virus Comparison: Divergent Evolution on Two Continents". Journal of Virology, vol. 73, No. 1, Jan. 1999, pp. 270-280.

Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.

Nodelijk et al., "A quantitative assessment of the effectiveness of PRRSV vaccination in pigs under experimental conditions". Vaccine, vol. 19, 2000, pp. 3636-3644.

Oleksiewicz et al., "Epitope Mapping Porcine Reproductive and Respiratory Syndrome Virus by Phage Display: the hsp2 Fragment of the Replicase Polyprotein Contains a Cluster of B-Cell Epitopes". Journal of Virology, vol. 75, No. 7, Apr. 2001, pp. 3277-3290.

Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 31, 2001, pp. 109-125.

Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.

Pesch et al., "New insights into the genetic diversity of European porcine reproductive and respiratory syndrome virus (PRRSV)". Veterinary Microbiology, vol. 107, 2005, pp. 31-48.

Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.

Porcine Reproductive and Respiratory Syndrome: A Report on the Seminar Held in Brussels on Nov. 4-5, 1991 and Organized by the European Commission, pp. 1-74.

Prieto et al., "Similarity of European porcine reproductive and respiratory syndrome virus strains to vaccine strain is lot necessarily predictive of the degree of protective immunity conferred". The Veterinary Journal, vol. 175, No. 3, Mar. 2008, pp. 356-363.

Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.

Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.

Shin et al "Assessment of Porcine Reproductive and Respiratory Syndrome Virus RNA Load in Sera and Tissues during Acute Infection". Journal of Veterinary Science, vol. 3, No. 2, 2002, pp. 75-85.

Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.

Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.

Sun et al., "Crystal Structure of Porcine Reproductive and Respiratory Syndrome Virus Leader Protease Nsp1aÑ". Journal of Virology, vol. 83, No. 21, Nov. 2009, pp. 10931-10940.

Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.

Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.

Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.

Verheije et al., "Safety and protective efficacy of porcine reproductive and respiratory syndrome recombinant virus vaccines in young pigs". Vaccine, vol. 21, 2003, pp. 2556-2563.

(56) References Cited

OTHER PUBLICATIONS

Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.

\* cited by examiner

Figure 3

Figure 4

| | 1 | 10 | 20 | 30 | 40 | 50 | 60 | |
|---|---|---|---|---|---|---|---|---|
| nsp1b-delALEV_BIEU | (1) | SSIYRWEKFVIFMDSSSDGRSRMMWTPESDDST------LPPELEHQVKVLVRSFPAHHLVDLADWELTES |
| nsp1b-delEV_BIEU | (1) | SSIYRWEKFVIFMDSSSDGRSRMMWTPESDDSTA----ELPPELEHQVKVLVRSFPAHHLVDLADWELTES |
| nsp1b-delLEVL_BIEU | (1) | SSIYRWEKFVIFMDSSSDGRSRMMWTPESDDST----APPELEHQVKVLVRSFPAHHLVDLADWELTES |
| nsp1b-delLE_BIEU | (1) | SSIYRWEKFVIFMDSSSDGRSRMMWTPESDDSTA----VLPPELEHQVKVLVRSFPAHHLVDLADWELTES |
| nsp1b-delIDD_BIEU | (1) | SSIYRWEKFVIFMDSSSDGRSRMMWTPE---SSTALEVLPPELEHQVKVLVRSFPAHHLVDLADWELTES |
| nsp1b-SDDS_BIEU | (1) | SSIYRWEKFVIFMDSSSDGRSRMMWTP-----ETALEVLPPELEHQVKVLVRSFPAHHLVD

```
                           SEQUENCE LISTING

<160> NUMBER OF SEQ ID NOS: 99

<210> SEQ ID NO 1
<211> LENGTH: 22
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(19)
<223> OTHER INFORMATION: Any naturally occurring amino acid

<400> SEQUENCE: 1

Phe Xaa Val Leu Xaa Xaa Xaa Xaa Xaa Xaa Xaa Xaa Xaa Xaa Xaa Xaa
1               5                   10                  15

Xaa Xaa Xaa Gln Cys Arg
            20

<210> SEQ ID NO 2
<211> LENGTH: 21
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(18)
<223> OTHER INFORMATION: Any naturally occurring amino acid

<400> SEQUENCE: 2

Phe Xaa Val Leu Xaa Xaa Xaa Xaa Xaa Xaa Xaa Xaa Xaa Xaa Xaa Xaa
1               5                   10                  15

Xaa Xaa Gln Cys Arg
            20

<210> SEQ ID NO 3
<211> LENGTH: 20
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(17)
<223> OTHER INFORMATION: Any naturally occurring amino acid

<400> SEQUENCE: 3

Phe Xaa Val Leu Xaa Xaa Xaa Xaa Xaa Xaa Xaa Xaa Xaa Xaa Xaa Xaa
1               5                   10                  15

Xaa Gln Cys Arg
            20

<210> SEQ ID NO 4
<211> LENGTH: 19
<212> TYPE: PRT
<213> ORGANISM: Porcine reproductive and respiratory syndrome virus
<220> FEATURE:
<221> NAME/KEY: MOD_RES
<222> LOCATION: (2)..(2)
```

-continued

<223> OTHER INFORMATION: Any naturally occurring amino acid
<220> FEATURE:
<221> NAME/KEY: MOD_RES
<222> LOCATION: (5)..(16)
<223> OTHER INFORMATION: Any naturally occurring amino acid

<400> SEQUENCE: 4

Phe Xaa Val Leu Xaa Xaa Xaa Xaa Xaa Xaa Xaa Xaa Xaa Xaa Xaa
1               5                   10                  15

Gln Cys Arg

<210> SEQ ID NO 5
<211> LENGTH: 18
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(15)
<223> OTHER INFORMATION: Any naturally occurring amino acid

<400> SEQUENCE: 5

Phe Xaa Val Leu Xaa Xaa Xaa Xaa Xaa Xaa Xaa Xaa Xaa Xaa Gln
1               5                   10                  15

Cys Arg

<210> SEQ ID NO 6
<211> LENGTH: 17
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(14)
<223> OTHER INFORMATION: Any naturally occurring amino acid

<400> SEQUENCE: 6

Phe Xaa Val Leu Xaa Xaa Xaa Xaa Xaa Xaa Xaa Xaa Xaa Gln Cys
1               5                   10                  15

Arg

<210> SEQ ID NO 7
<211> LENGTH: 16
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(13)
<223> OTHER INFORMATION: Any naturally occurring amino acid

<400> SEQUENCE: 7

Phe Xaa Val Leu Xaa Xaa Xaa Xaa Xaa Xaa Xaa Xaa Xaa Gln Cys Arg
1               5                   10                  15

<210> SEQ ID NO 8
<211> LENGTH: 15
<212> TYPE: PRT
<213> ORGANISM: Porcine reproductive and respiratory syndrome virus

```
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(12)
<223> OTHER INFORMATION: Any naturally occurring amino acid

<400> SEQUENCE: 8

Phe Xaa Val Leu Xaa Xaa Xaa Xaa Xaa Xaa Xaa Xaa Gln Cys Arg
1               5                   10                  15

<210> SEQ ID NO 9
<211> LENGTH: 14
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(11)
<223> OTHER INFORMATION: Any naturally occurring amino acid

<400> SEQUENCE: 9

Phe Xaa Val Leu Xaa Xaa Xaa Xaa Xaa Xaa Xaa Gln Cys Arg
1               5                   10

<210> SEQ ID NO 10
<211> LENGTH: 13
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(10)
<223> OTHER INFORMATION: Any naturally occurring amino acid

<400> SEQUENCE: 10

Phe Xaa Val Leu Xaa Xaa Xaa Xaa Xaa Xaa Gln Cys Arg
1               5                   10

<210> SEQ ID NO 11
<211> LENGTH: 12
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(9)
<223> OTHER INFORMATION: Any naturally occurring amino acid

<400> SEQUENCE: 11

Phe Xaa Val Leu Xaa Xaa Xaa Xaa Xaa Gln Cys Arg
1               5                   10

<210> SEQ ID NO 12
<211> LENGTH: 11
<212> TYPE: PRT
<213> ORGANISM: Porcine reproductive and respiratory syndrome virus
<220> FEATURE:
<221> NAME/KEY: MOD_RES
<222> LOCATION: (2)..(2)
```

```
<223> OTHER INFORMATION: Any naturally occurring amino acid
<220> FEATURE:
<221> NAME/KEY: MOD_RES
<222> LOCATION: (5)..(8)
<223> OTHER INFORMATION: Any naturally occurring amino acid

<400> SEQUENCE: 12

Phe Xaa Val Leu Xaa Xaa Xaa Xaa Gln Cys Arg
1               5                   10

<210> SEQ ID NO 13
<211> LENGTH: 24
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(19)
<223> OTHER INFORMATION: Any naturally occurring amino acid
<220> FEATURE:
<221> NAME/KEY: MOD_RES
<222> LOCATION: (23)..(23)
<223> OTHER INFORMATION: Any naturally occurring amino acid

<400> SEQUENCE: 13

Phe Xaa Val Leu Xaa Xaa Ile Xaa Xaa Xaa Xaa Xaa Xaa Xaa Xaa Xaa
1               5                   10                  15

Xaa Xaa Xaa Gln Cys Arg Xaa Ala
            20

<210> SEQ ID NO 14
<211> LENGTH: 23
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(18)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid

<400> SEQUENCE: 14

Phe Xaa Val Leu Xaa Xaa Ile Xaa Xaa Xaa Xaa Xaa Xaa Xaa Xaa Xaa
1               5                   10                  15

Xaa Xaa Gln Cys Arg Xaa Ala
            20

<210> SEQ ID NO 15
<211> LENGTH: 22
<212> TYPE: PRT
<213> ORGANISM: Porcine reproductive and respiratory syndrome virus
<220> FEATURE:
<221> NAME/KEY: MOD_RES
<222> LOCATION: (2)..(2)
```

-continued

```
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(17)
<223> OTHER INFORMATION: Any naturally occurring amino acid
<220> FEATURE:
<221> NAME/KEY: MOD_RES
<222> LOCATION: (21)..(21)
<223> OTHER INFORMATION: Any naturally occurring amino acid

<400> SEQUENCE: 15

Phe Xaa Val Leu Xaa Xaa Ile Xaa Xaa Xaa Xaa Xaa Xaa Xaa Xaa
1               5                   10                  15

Xaa Gln Cys Arg Xaa Ala
            20

<210> SEQ ID NO 16
<211> LENGTH: 21
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(16)
<223> OTHER INFORMATION: Any naturally occurring amino acid
<220> FEATURE:
<221> NAME/KEY: MOD_RES
<222> LOCATION: (20)..(20)
<223> OTHER INFORMATION: Any naturally occurring amino acid

<400> SEQUENCE: 16

Phe Xaa Val Leu Xaa Xaa Ile Xaa Xaa Xaa Xaa Xaa Xaa Xaa Xaa
1               5                   10                  15

Gln Cys Arg Xaa Ala
            20

<210> SEQ ID NO 17
<211> LENGTH: 20
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(15)
<223> OTHER INFORMATION: Any naturally occurring amino acid
<220> FEATURE:
<221> NAME/KEY: MOD_RES
<222> LOCATION: (19)..(19)
<223> OTHER INFORMATION: Any naturally occurring amino acid

<400> SEQUENCE: 17

Phe Xaa Val Leu Xaa Xaa Ile Xaa Xaa Xaa Xaa Xaa Xaa Xaa Gln
1               5                   10                  15
```

```
Cys Arg Xaa Ala
        20

<210> SEQ ID NO 18
<211> LENGTH: 19
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(14)
<223> OTHER INFORMATION: Any naturally occurring amino acid
<220> FEATURE:
<221> NAME/KEY: MOD_RES
<222> LOCATION: (18)..(18)
<223> OTHER INFORMATION: Any naturally occurring amino acid

<400> SEQUENCE: 18

Phe Xaa Val Leu Xaa Xaa Ile Xaa Xaa Xaa Xaa Xaa Xaa Xaa Gln Cys
1               5                   10                  15

Arg Xaa Ala

<210> SEQ ID NO 19
<211> LENGTH: 18
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(13)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid

<400> SEQUENCE: 19

Phe Xaa Val Leu Xaa Xaa Ile Xaa Xaa Xaa Xaa Xaa Xaa Gln Cys Arg
1               5                   10                  15

Xaa Ala

<210> SEQ ID NO 20
<211> LENGTH: 17
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(12)
<223> OTHER INFORMATION: Any naturally occurring amino acid
<220> FEATURE:
```

```
<221> NAME/KEY: MOD_RES
<222> LOCATION: (16)..(16)
<223> OTHER INFORMATION: Any naturally occurring amino acid

<400> SEQUENCE: 20

Phe Xaa Val Leu Xaa Xaa Ile Xaa Xaa Xaa Xaa Xaa Gln Cys Arg Xaa
1               5                   10                  15

Ala

<210> SEQ ID NO 21
<211> LENGTH: 16
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(11)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 21

Phe Xaa Val Leu Xaa Xaa Ile Xaa Xaa Xaa Xaa Gln Cys Arg Xaa Ala
1               5                   10                  15

<210> SEQ ID NO 22
<211> LENGTH: 15
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(10)
<223> OTHER INFORMATION: Any naturally occurring amino acid
<220> FEATURE:
<221> NAME/KEY: MOD_RES
<222> LOCATION: (14)..(14)
<223> OTHER INFORMATION: Any naturally occurring amino acid

<400> SEQUENCE: 22

Phe Xaa Val Leu Xaa Xaa Ile Xaa Xaa Xaa Gln Cys Arg Xaa Ala
1               5                   10                  15

<210> SEQ ID NO 23
<211> LENGTH: 14
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
```

```
<221> NAME/KEY: MOD_RES
<222> LOCATION: (8)..(9)
<223> OTHER INFORMATION: Any naturally occurring amino acid
<220> FEATURE:
<221> NAME/KEY: MOD_RES
<222> LOCATION: (13)..(13)
<223> OTHER INFORMATION: Any naturally occurring amino acid

<400> SEQUENCE: 23

Phe Xaa Val Leu Xaa Xaa Ile Xaa Xaa Gln Cys Arg Xaa Ala
1               5                   10

<210> SEQ ID NO 24
<211> LENGTH: 13
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(8)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid

<400> SEQUENCE: 24

Phe Xaa Val Leu Xaa Xaa Ile Xaa Gln Cys Arg Xaa Ala
1               5                   10

<210> SEQ ID NO 25
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid

<400> SEQUENCE: 25

Phe Xaa Val Leu
1

<210> SEQ ID NO 26
<211> LENGTH: 7
<212> TYPE: PRT
<213> ORGANISM: Porcine reproductive and respiratory syndrome virus
<220> FEATURE:
<221> NAME/KEY: MOD_RES
<222> LOCATION: (4)..(5)
<223> OTHER INFORMATION: Any naturally occurring amino acid

<400> SEQUENCE: 26

Tyr Ile Thr Xaa Xaa Ala Asn
1               5

<210> SEQ ID NO 27
<211> LENGTH: 6
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
```

```
<220> FEATURE:
<221> NAME/KEY: MOD_RES
<222> LOCATION: (5)..(5)
<223> OTHER INFORMATION: Any naturally occurring amino acid

<400> SEQUENCE: 27

Phe Xaa Val Leu Xaa Asp
1               5

<210> SEQ ID NO 28
<211> LENGTH: 8
<212> TYPE: PRT
<213> ORGANISM: Porcine reproductive and respiratory syndrome virus
<220> FEATURE:
<221> NAME/KEY: MOD_RES
<222> LOCATION: (5)..(5)
<223> OTHER INFORMATION: Any naturally occurring amino acid

<400> SEQUENCE: 28

Val Tyr Ile Thr Xaa Thr Ala Asn
1               5

<210> SEQ ID NO 29
<211> LENGTH: 5
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid

<400> SEQUENCE: 29

Phe Xaa Val Leu Gln
1               5

<210> SEQ ID NO 30
<211> LENGTH: 8
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 30

Gln Tyr Ile Thr Ile Xaa Ala Asn
1               5

<210> SEQ ID NO 31
<211> LENGTH: 22
<212> TYPE: PRT
<213> ORGANISM: Porcine reproductive and respiratory syndrome virus

<400> SEQUENCE: 31

Phe Met Val Leu Gln Lys Ile Glu Cys Leu Gln Ala Pro Gly Thr Arg
1               5                   10                  15

Ser Gln Cys Arg Glu Ala
            20

<210> SEQ ID NO 32
<211> LENGTH: 23
<212> TYPE: PRT
<213> ORGANISM: Porcine reproductive and respiratory syndrome virus

<400> SEQUENCE: 32

Gln Lys Ile Glu Cys Leu Gln Ala Pro Gly Thr Arg Ser Gln Cys Arg
1               5                   10                  15
```

Glu Ala Ile Gly Thr Pro Gln
            20

<210> SEQ ID NO 33
<211> LENGTH: 21
<212> TYPE: PRT
<213> ORGANISM: Porcine reproductive and respiratory syndrome virus

<400> SEQUENCE: 33

Asp Ile Ser Cys Leu Arg His Gly Arg Lys Ser Arg Gln Cys Arg Thr
1               5                   10                  15

Ala Ile Gly Thr Pro
            20

<210> SEQ ID NO 34
<211> LENGTH: 9
<212> TYPE: PRT
<213> ORGANISM: Porcine reproductive and respiratory syndrome virus

<400> SEQUENCE: 34

Glu Cys Leu Gln Ala Pro Gly Thr Arg
1               5

<210> SEQ ID NO 35
<211> LENGTH: 10
<212> TYPE: PRT
<213> ORGANISM: Porcine reproductive and respiratory syndrome virus

<400> SEQUENCE: 35

Ser Cys Leu Arg His Gly His Lys Ser Arg
1               5                   10

<210> SEQ ID NO 36
<211> LENGTH: 172
<212> TYPE: PRT
<213> ORGANISM: Porcine reproductive and respiratory syndrome virus

<400> SEQUENCE: 36

Met Ala Ala Ala Ile Leu Phe Phe Leu Val Gly Ala Gln His Leu Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Gly Phe Met Val Leu Gln
            35                  40                  45

Lys Ile Glu Cys Leu Gln Ala Pro Gly Thr Arg Ser Gln Cys Arg Glu
50                  55                  60

Ala Ile Gly Thr Pro Gln Tyr Ile Thr Ile Gln Ala Asn Val Thr Asp
65                  70                  75                  80

Glu Ser Tyr Leu Tyr Asn Ala Asp Leu Leu Met Leu Ser Ala Cys Leu
            85                  90                  95

Phe Tyr Ala Ser Glu Met Ser Glu Lys Gly Phe Asn Val Ile Phe Gly
            100                 105                 110

Asn Val Ser Gly Val Val Ser Ala Cys Val Asn Phe Thr Asp Tyr Val
            115                 120                 125

Ala His Val Thr Gln His Thr Gln Gln His His Leu Val Ile Asp His
            130                 135                 140

Val Arg Leu Leu His Phe Leu Ser Pro Pro Val Met Arg Trp Ala Thr
145                 150                 155                 160

Thr Ile Ala Cys Leu Phe Ala Ile Leu Leu Ala Ile

<210> SEQ ID NO 37
<211> LENGTH: 519
<212> TYPE: DNA
<213> ORGANISM: Porcine reproductive and respiratory syndrome virus

<400> SEQUENCE: 37

| | | | | | |
|---|---|---|---|---|---|
| atggctgcgg | ccattctttt | cttcctggtt | ggtgctcaac | atctcatggt | ttctgaggcg | 60 |
| ttcgcctgca | agccctgctt | ctcgacgcat | ttatcagata | ttaagaccaa | cacgaccgcg | 120 |
| gctgccggtt | tcatggtcct | tcagaaaatt | gaatgcctcc | aagcccctgg | acacggtcg | 180 |
| caatgtcgtg | aagccatcgg | taccccccag | tacatcacga | tacaggccaa | cgtgaccgac | 240 |
| gaatcatact | tgtataacgc | ggacttgctg | atgctctctg | cgtgcctctt | ctacgcctca | 300 |
| gaaatgagcg | agaaaggctt | caacgtcatc | tttgggaatg | tttctggcgt | tgtttccgct | 360 |
| tgtgtcaatt | tcacagatta | cgtagcccac | gtgactcaac | acacccagca | gcatcacctg | 420 |
| gtaatcgacc | acgttaggct | actacatttc | ctgtcaccac | tgtaatgag | gtgggccaca | 480 |
| accatcgctt | gtttgttcgc | cattcttttg | gcgatatga | | | 519 |

<210> SEQ ID NO 38
<211> LENGTH: 14854
<212> TYPE: DNA
<213> ORGANISM: Porcine reproductive and respiratory syndrome virus

<400> SEQUENCE: 38

| | | | | | |
|---|---|---|---|---|---|
| acctcttggc | ccctgttcta | gcccaacagg | tatccttctc | tctcggggcg | agtgcgccgc | 60 |
| ctgctgctct | cttgcagcgg | gaaggacctc | ccgagtattt | ccggagagca | cctgctttac | 120 |
| gggatctcca | ccctttaacc | atgtctggga | ctctctcccg | tgcatgtgc | accccggctg | 180 |
| ctcgggtatt | ttggaacgcc | ggtcaagtct | tctgcacacg | tgtctcagt | gcgcggtctc | 240 |
| ttctccctcc | tgagcttcag | gacactgacc | ttgctgcaat | tggtttgttt | tacaagccta | 300 |
| aggacaagat | caaatggaaa | gttcccattg | gcattcctca | ggtggaatgt | actccatccg | 360 |
| ggtgctgttg | gctctccgct | attttcccct | tagcgcgcat | gacctccggt | aatcacaact | 420 |
| tccttcaacg | gcttgtgaag | gttgctgacg | ttttgtaccg | tgacggttac | ttggcacccc | 480 |
| aacaccttcg | tgaactccaa | gtctacgaac | gcggctgcag | ctggtacccg | atcacggggc | 540 |
| ctgtgcccgg | aatgggtttg | tatgcaaact | ccatgcacgt | gtctgatcag | ccgtttcctg | 600 |
| gtgccactca | tgtgttaacc | aactcaccct | tgcctcaaca | ggcttgtcgg | caaccattct | 660 |
| gtccatttga | ggaggctcat | tccgacgtgt | acaggtggaa | gaaatttgtg | attttcgtgg | 720 |
| attctcctct | taacggtcga | ctcgtatga | tgtggacacc | ggggtccgat | gactcggctg | 780 |
| ccttagaagt | gcttccgcct | gaactagaac | gtcgagtcga | atcctcatt | cgaagttttc | 840 |
| ctgctcatca | ctctgttgat | ctcaccgaat | gggaactcac | tgaatcacct | gagcacggtt | 900 |
| tttccttcag | cacgttccat | tctagtggtc | acctcgccca | aaaccccgac | atgtttgatg | 960 |
| gcaagtgttg | gctatcttgc | tttttgagcc | tgccgccga | agtgtggcgc | catgaagaac | 1020 |
| agctggccaa | cactctcggt | taccaaacca | gtggggtgt | gcacgtaag | tacctccagc | 1080 |
| gcaggcttca | aattaacggc | gtccgtgctg | tggttgaccc | taatggtccc | attcacgttg | 1140 |
| aagcgctatc | ttgctcccag | tcttggatca | gacatctgac | tctggaagat | gatgtaactc | 1200 |
| cggggttcgt | tcgcctaatg | tctctccgta | ttgtgccgaa | cacagaaccc | accatcctcc | 1260 |
| aggttttccg | gtttgggca | cacaagtggt | atggtgctgc | cggcaagcga | gctcgcacta | 1320 |

```
agcgtgcagc aaagaaaggg aaggactcga ctatcactcc cgagactgcc caaccaacct      1380
ccgcttgcga aatcatcacc tattccccac cggcggacgg atcttgtggc tggcatgttc      1440
ttgccgccat agtgaaccga atgataagtg gtgacttcac gtcccccta actcagtaca       1500 ataggccaga ggatgattgg gcttctgatt atgatcttgc tcaagcgatt caatgcctgc      1560
aactgcctgc taccctggtt cggggtcgcg cctgtcctaa cgccaagtac cttataaaac      1620
ttaacggggt tcactgggag gtagaggtga ggcctggaat ggctcctcgc tcccttcccc      1680
gcgaatgcgt ggttggcgtc tgctctgaag gctgtgtcgc gccgccttat ccagaaaacg      1740
ggctaccaaa acgcgcactc gaggccttgg cgtctgctta caggctacct tccgactgcg      1800
ttagctgtgg tattgctgac tttctcgcta accctcccct tccggaattc tggaccctcg      1860
acaaaatgtt gacctccccg tcaccagaac ggtccggctt ctctagtttg tataaattac      1920
ttttggaggt tgttccgcag aaatgtggtg cctcggaggg ggcttttatt tgtgctgttg      1980
aaaggatgtt gaaggattgt ccgagctcca aacaggccat ggcccttttg gcaaaaatta      2040
gaatcccatc ctcaagggcc ccgtctgttt ccttggatga gtgttttcct acggatgtcc      2100
cagccgactt tgaatcagcg tctcaggaaa ggccccaaac ttccggtgtc gctgttgccc      2160
agtgtctacc ggatgcaaaa gagctcgagg aaacagcccc gggaaaagtt caagagaatg      2220
gtcacaaggc catccatcct gcgcctcttg ctggttgtcc taacgacgag caagtacagg      2280
tgattgccag cgagcaactg aggcccggcg actgtgtttc gacagtcagg ggtgctcgcg      2340
atgatgctcc agtctcagcc ggcctgacta acctggcagg cgggaacccc ccttttccaa      2400
accccacgga aggaaatagg ccccatgact gggaagacgg acctttggat ctatcccgac      2460
cgaaaccagt tgccgagatg acccttgtaa gagagcaagt accctacaac ccaggtccta      2520
acactgatgt ctcccccgtc gccgctccgg gctttatccc gacggggctc gtatttcgtc      2580
atgttgagca ttgtggctcg gagtccggtg agagcgactc ccctctaaac ttgtctaatg      2640
tgcaaatttc ggaccagccc ctaaaccttt ccctgaccgc atggccggtg aaggccaccg      2700
cctctgaccc cggttgggtt catggtcgac gtgagcctgt ctttgcgaag cctcgaaatg      2760
ccttctctga cggtgactca gttgttcagt tcggggagct ttctgaatcc agctccgtcg      2820
tcgagtttga ccgagcaaaa aatgttacaa cggttgacgc ccctgtcgac ttgacgactc      2880
cgaataaggc cctctctgtg gtcgatcctt tcgagttcgc tgagcccaag cgcccacgtt      2940
tctccgcgca agccctgatt gaccgaggag gtccacttgc tgatgtccac gcaaaaataa      3000
agaatcgggt atacgaacag tgcctccagg cttgcgagcc cggtagtcgc gcaaccccag      3060
ccactagaga ctggctcgac aaaatgtggg agagggtgga catgaaaact tggcgctgca      3120
cctcacagtt tcaagctggt cgcattctcg cgtccctcaa gttcctccct gacatgattc      3180
aggacacacc gcctcctgct cccaggaaga gccgggctgg tgacagcacc ggcctaaaac      3240
aactggtggc acagtgggat aggaaattga gtgcggcccc cctccgaaaa ctggttgggt      3300
cagtgcctga ccagactgtc ctcccgtccg cggacaccca gcaagaagac gctgaccctc      3360
ctgatgggcc gccccacgcg ccggacattc ctagtcgagt aggtacagtc aggaattgga      3420
aaggttgcat gctttccggc acccgttttg cggggtccat gagtcagcgc ttcatgacat      3480 gggttttga ggttctctcc catctcccag cttttgcgct cacactttc tcgccgcggg        3540 gctctatggc tccaggtgat tggctgtttg caggtgttgt tttacttgct ctcctgctct      3600
gtcgctctta cccaatttc gggtgccttc ccttattggg tgtctttct ggttctgtgc        3660
```

```
ggcgcgttcg tctgggtgtt tttggttctt ggatggcttt tgctgtattt ctattctcga    3720
ctccatccaa cccagtcggt tcttcttgtg accacgattc gccggagtgt cacgctgagc    3780
ttttggctct tgagcagcgc caactttggg aacctgtgcg cggccttgtg gtgggcccct    3840
caggtctctt atgcgtcgtt cttggcaagc tactcggtgg gtcacgttat ctctggcata    3900
ttctcttacg tttatgcatg cttgcagatt tggcccttc tcttgtttat gtggtgtccc     3960
aagggcgttg tcacaagtgt tggggaaagt gtataaggac agctcctgcg gaggtggctc    4020
tcaatgtatt tcctttctcg cgcgccaccc gttcctctat tgtatcctta tgtgatcgat    4080
tccaggcgcc aaaagggggtt gatcccgtac atttggcaac gggttggcgc gggtgctggt   4140
gcggcgatag ccccatccat caaccacacc agaaacccat agcttacgcc aacttggatg    4200
aaaagaaaat atctgcccag acggtggtcg ctgttccata cgatcccagc caggccatca    4260
aatgcctgaa agtcctacag gctggaggag ctattgtaga ccagccaaca cctgaggttg    4320
ttcgtgtttc cgaaatcccc ttctcagccc catttttcc gaaagttccg gtcaatccaa      4380
actgtagggt tgtggtagat tcggacacct tgtggccgc ggttcgctgc ggttactcaa      4440
caacacaact ggtcctgggc cggggcaact tcgccaagtt gaatcaaaca cctcttggga    4500
actctgtctc caccaaaacg actggtgtg cctcttacac ccttgctgtg gcgcaagtgt      4560
ccgtgtggac tctcatccat ttcatcctcg gtctttggtt cacatcgcct caagtgtgcg    4620
gccgaggtac cgctgatcca tggtgttcaa atcctttttc atatcccacc tatggccctg    4680
gagttgtctg ctcctctcga ctttgcgtgt ctgccgatgg agtcaccctg ccattgttct    4740
cagccgtggc acaactctcc ggtagggagg tgggaatttt cattctggtg ctcgtctcct    4800
tgatcgcttt ggcccaccat atggctctta aagcagatat gttggtgatc tttttggctt    4860
tctgcgccta cgcctggcct atgagttctt ggttaatttg tttctttccc atgcttttga    4920
agtgggttac ccttcacct cttaccatgc tttgggtaca ctcttcctta gtgttttgtc      4980
tgccagcagc tggcatcctt tcactaggga caactggcct tctctgggca gtcggccgct    5040
tcacccaggt agccggaatt attacacctt atgacattca ccgatacact tctgggccgc    5100
gtggtgctgc cgctgtagcc acagcccag aaggcactta catggccgcc gtccgtagag      5160
ctgccttaac tgggcgaact tgatcttca ccccgtctgc agttgggtcc cttctcgagg      5220
gtgccttcag gactcataaa ccctgcctca cacgtgaa tgtcgtgggt tcttcttttg       5280
gttctggagg agtcttttacc attgatggga aaaaactgtt gttactgcga cacatgtgtt    5340
gaacggcgac acagccaggg tcaccggtga ctcctataac cgcatgctca ccttcaggac    5400
caacggtgat tacgcctggt cccatgctga tgactggcaa ggcgttgccc cagtggtcaa    5460
gatcgcgaaa gggtatcgcg tcgtgcctta ttggcaaaca tcaactggtg tcgaacccgg    5520
tgttgttggt gaaggattcg ccttctgttt tactaactgt ggtgactcgg ggtcacccgt    5580
catttcagaa tctggtgatc tcattggaat ccacaccggt tcgaacaaac ttggttctgg    5640
tcttgtgaca accccgaag gggagacctg cactattaaa gaaaccaagc tctctgacct     5700
ttccagacac ttcgcgggcc caagcgttcc ccttgggac ataaaattaa gcccggccat     5760
catccctgat gtgacgtcca tcccaagtga cttggcatcg ctcctggctt ccgtccctgt    5820
agtggaaggc ggtctttcga ccgttcaact cttgtgtgtc ttttccttc tctggcgtat     5880
gatgggcat gcttggacac ccattgttgc cgtgggtttc tttttgctga atgaaattct      5940
tccagcagtc ttggtccgag ccgtgttctc ttttgcgctc tttgcgtttg catggctcac    6000
cccctggtct gcgcaggtgt tgatgatcag actcctcacg gcctccctca accgcaacaa    6060
```

```
gctttctctg gcgttctacg cactcggggg tgtcgtcggt ttggccgctg agatcgggac   6120
tttcgctggt aggttgtctg aattgtctca agccatttca acatactgct ttttacctag   6180
ggtccttgct atgaccagct gtgtcgccat catcatcatt ggtggactcc atgctcttgg   6240
tgtaatcctg tggttgttca atatcggtg tctccacaac acgctagttg gtgatgggag   6300
tttttcaagc gccttcttcc tgcggtactt tgcagagggt aatctcagaa aaggtgtttc   6360
acagtcctgt ggcatgagta atgaatcctt gacggctgct ttggcttgta agttgtcaca   6420
ggctgacctt gactttctgt ccggcctaac gaatttcaag tgttttgtgt ctgcttcaaa   6480
tatgaagaat gctgctggcc aatatattga agcagcgtac gccaaggcct tgcgccacga   6540
gttggcttcc ttagttcagg tcgacaaaat gaagggggtt ttgtccaagc tagaagcttt   6600
tgctgagacg gccacccccat cccttgatac aggtgacgta gttgttctgc ttggacaaca   6660
tcctcatgga tctattcttg acattaacgt agggactgaa aggaaaactg tgtctgtgca   6720
ggagactcgg agtttgggtg ctccaaatt cagtgtctgc accgttgtgt ccaacacacc   6780
tgtagacgcc ctgaccagca tcccacttca gacaccaact ccgcttttcg agaatggccc   6840
gcgtcatcgc ggtgaggaag acgatcttaa agtcgagagg atgaagaagc actgcatatc   6900
cctcggcttt cataacatta atggcaaagt ttactgcaaa atttgggaca gtctaccgg   6960 tgacaccttc tacacggatg actcccgata cacccaagac tgtgcctttc aggacaggtc   7020
agccgactat agagacaggg attatgaagg tgtgcagacc gccccccagc acggatttga   7080
cccaaagtcc gagacccctg tcggcactgt tgtgatcggc ggcattacgt ataacaggta   7140
tctggttaaa ggtaaagagg tcttgatccc caagcctgac aactgccttg aagccgccaa   7200
gctatcccct gaacaagctc tcgctggtat gggccagact tgtgacctca cggctgctga   7260
agtggaaaag ctaaagcgca ttattagcca actccaaggc ttgaccaccg agcaggcttt   7320
aaactgctag ccgccagtgg cttgacccgc tgtggccgcg gcggcttagt tgtgactgaa   7380
acggcggtga aaattgtgaa ataccacagc agaaccttca ccctaggccc tttagacctg   7440
aaagtcacct ctgaagtgga ggtgaagaaa tcaacagagc agggccacgc cgttgtagca   7500
aacctatgct ccggtgttgt gttgatgaga cctcaccctc cgtcccttgt tgatgttctt   7560
ctaaagcctg gacttgacac gacacctggc atccaaccgg ggcatggggc tggaaacatg   7620
ggtgtgaacg gttccatttg ggattttgaa actgccccca caaaggcgga actcgagtta   7680
tccaaacaaa taatccaagc gtgtgagatt aggcgcgggg atgccccgaa cctccaactc   7740
ccttataagc tctatcctgt tagggggat cctgagcggc atgaaggtcg ccttatcaat   7800
accaggttcg gggacttacc ttataagact cctcaagaca ccaagtccgc agtccacgcg   7860
gcttgttgcc tacaccccaa tggagccccg gtatttgacg gtaaatccat gctgggcacc   7920
actcttcagc atggttttga gctttatgtc cccactgtgc cctatagtgt tatggagtac   7980
cttgactcac gccctgacac tcctttatg tgtactaagc atggcacttc cagtgctgct   8040
gcagaggacc tccaaaagta tgacctatcc acccaaggat ttgtcttgcc tggtgtcttg   8100
cgcttagtgc gcaggttcat cttcagccat attggtaaag cgccaccatt gttcctccca   8160
tcaacttacc ccgctaagaa ctccatggca gggattaatg gtcagaggtt ccgacaaag   8220 gatattcaga gcatacctga aatcgatgaa atgtgtgccc gcgctgtcaa ggaaaattgg   8280
caaactgtta caccttgcac cctcaagaaa cagtattgtt ctaagcccaa aaccaggacc   8340
atcctgggca ctaacaactt tattgccttg gcccacagat cagcgcttag tggtgtcacc   8400
```

```
caggcgttca tgaaaaaggc ttggaattcc ccaattgcct tggggaagaa taaattcaag    8460
gagctgcatt gcaccgttgc cggcaggtgt cttgaggctg acttggcctc ctgcgaccgc    8520
agtacccccg ccattgtgag atggtttgtt gccaacctcc tgtatgaact tgcaggatgt    8580
gaagagtacc tgcccagcta cgtgcttaat tgctgccatg acctcgtggc aacacaaaat    8640
ggtgccttca caaacgcggt tggcctgtcg tctggggacc ctgtcaccag tgtgtccaac    8700
accgtatatt cactgataat ttacgcccag cacatggtgt tgtcagccct aaaaatgggt    8760
catgagattg gtcttaagtt tcttgaggag caactcaagt tcgaagacct ccttgaaatt    8820
cagcctatgt tggtgtattc tgatgatctt gttttgtatg ctgaaaggcc ctccttcccc    8880
aattaccatt ggtgggtcga gcaccttgac ttgatgctgg gtttcaagac agacccaaag    8940
aagaccgtta taactgacaa gcccagcttt ctcggttgca gaattgaggc ggggcgacag    9000
ctagccccca atcgtgaccg cattctggct gctctcgcat atcacatgaa agcgcaggac    9060
gcatcagagt actatgcgtc tgctgccgca attctgatgg actcgtgtgc ttgcattgac    9120
tatgatcctg agtggtatga agacctcatc tgtggcatcg ctcagtgcgc ccgccaggat    9180
ggttatcgct tcccaggacc ggcatttttc atgtccatgt gggagagact gagaagccat    9240
aatgagggga agaaattccg ccattgcggc atctgtgacg ccaaagctga tcacgcgtct    9300
gcctgtgggc ttgacttgtg cttgtttcac tcgcactttc atcaacactg ccctgttatc    9360
ttgagttgcg gccaccatgc cggttccaaa gaatgttcgc agtgtcagtc acctgttggg    9420
tctggcaaga cccctcttga tgccgtgctg aagcaaatcc catacaaacc tcctcgtaca    9480
gcaatcatga gggtaagcga caaagtgaca gccctggatc cagggaggta ccagtctcgt    9540
cggggcctcg ttgcagtcaa aaggggtatc gcaggtaatg aagttgatct ccctgatggg    9600
gactatcagg tagtgcctct tttgccgacc tgcaaagaca ttaatatggt gaaggtggct    9660
tgtaatgttc tactcagcaa attcatagtg gggccaccag gttccgggaa gacaacctgg    9720
ctgctgagtc aagtccagga tgatgatgtt atttacacac ccactcatca gaccatgttt    9780
gatatagtca gtgctctcaa agtttgcagg tattccatcc caggggcctc aggactccct    9840
ttcccaccac ctgccaggtc cgggccatgg gtcaagctca ttgccagcgg acacgtccca    9900
ggccgagtgt catacctcga tgaggctgga tattgtaatc atctggacat cctcagactg    9960
cttttccaaa cacctcttgt gtgtttgggt gaccttcagc aacttcaccc tgttggcttt   10020
gattcctact gttatgtgtt cgatcagatg cctcagaagc agctgaccac tatttataga   10080
tttggtccta acatctgtgc agccatccag ccttgttaca gggaaaaact tgaatctaag   10140
gctaggaaca ccagggtggg tttcaccacc cggcctgtgg ccttcggtca ggtgttgaca   10200
ccataccaca agaccgtac tggctctgcg ataaccatag attcatccca aggggccact   10260
tttgatattg tgacattgca tctaccatcg ccgaagtcct taaacaaatc ccgagcactt   10320
gtagccatta ctcgagcaag acatgggttg ttcatttatg accctcataa ccagctccag   10380 gaattttta atttaacccc tgagagcact gattgcaacc ttgtgttttg ccacggggat   10440
gagctggtag ttttggacgc cggtaatgca gtcacaactg tggcgaaggc cctagaaact   10500
ggtccgtcgc ggttccgtgt gtcggacccg agatgcaagt ccctcttagc tgcctgttca   10560
gccagtctgg aagggagctg catgccacta ccgcaagtgg cacataacct gggatttac   10620 ttttcccctg acagcccagc atttgcacct ctgccaaaag agctggcgcc acactggcca   10680
gtggtcactc atcagaataa tcgggcgtgg cctgatcgac ttgtcgccag catgcgcccg   10740
ctcgacaacc gttacagcaa gccaatggtc ggtgcagggt atgtggtcgg gccgtccacc   10800
```

```
tttctcggta cacccggcgt ggtgtcatac tatcttacac tatacattaa gggtgagccc   10860
caggccttac ctgaaacact cgtttccacg ggacgcatag ctacagattg tcgggagtac   10920
ctcgacacag ctgaggaaga ggcagcaaaa gaactccccc acgcattcat gggtgatgtc   10980
aaaggcacca caattggtgg ttgtcatcac attcatcaa aatacctacc caggtccta    11040 cccaaggact ccattgccgt agttggggta agttcacctg gcaaggccgc caaagcctta   11100
tgcactctca ctgatgtgta cctcccagaa ctccggccgt atttgcaacc tgagacagcg   11160
tcgaaatgct ggaaactcaa actggacttc agggacgtcc ggctaatggt ctggaaaggg   11220
gccaccgcct acttccagtt ggaagggctc acttggtctg cactgcctga ctatgccagg   11280
tttattcagc tgcccaagaa cgccattgtg tacatcgatc cgtgcatagg accggcgaca   11340
gccaaccgta aagttgtgcg aaccacagat tggcgagctg acctggcagt gacaccgtac   11400
gactacggtg ctcaacacat tttgacaacc gcctggttcg aggacctcgg gccgcagtgg   11460
aaaattttgg ggttgcagcc cttcaggcga acatttggcc ttgaaaatac tgaagattgg   11520
gcaattcttg cacgccgtat gaatgacggt aaggactaca ctgattacaa ctggagttgc   11580
gttcgagaac gcccacacgc tatctatggg cgtgctcgtg accatacata ccactttgcc   11640
cttggcacag aattacaagt ggagctaggt aaacccagat tgtcgcctga gcaagtcccg   11700
tgaattcgga gggatgcaat ggggtcactg tggagcaaaa tcagccagtt gttcgtggac   11760
gctttcactg aattccttgt tagtgtggtt gacattgtca ttttccttgc catattgttt   11820
gggttcacag tcgcaggatg gttactggtc tttcttctca gggtggtttg ctccgcgttt   11880
ctccgttcgc gctctgccat tcactctccc gaactatcga agtcctatg agggcttgtt   11940 acccaactgt agaccggatg ttccacaatt tgcgtttaag cacccattgg gcatgttttg   12000
gcacatgaag gtctcccact tgattgatga gatggtctct cgtcgcgtct accaaaccat   12060
ggagcattcg ggccaagcgg cctggaaaca ggtggtcgct gaggccactc tcacgaagtt   12120
gtccaggctc gacattgtca ctcacttcca acacctagcc gcagtggagg cggattcttg   12180
ccactttctt agctcgcgac tcgtgatgct aaaaaatctt gctgtaggca atgtaagtct   12240
acaatacaac accacgttgg atcgcgttga gctcattttc cccacgccag gcacgaggcc   12300
caagttgacc gattttaggc aatggctcat cagtgtgcac gcttccattt tctcctctgt   12360
ggcttcatct gttaccttgt ttgtagtgct ttggcttcga attccagctc tacgctatgt   12420
ttttggtttc cattggccca cggcaacaca tcatttgaac taactgtgaa ttacaccata   12480
tgtaagccct gccttaccag tcaagcggcc aaacaacggc tcgaacccgg tcatagcatg   12540
tggtgcagga tagggcacac cagctgcgag gagagtgacc atgatgagtt gtcaatgacc   12600
atcccgcctg ggtatgataa ccttaagctc gagggctact acgcttggct agccttcttg   12660
tccttttcct acgcggcaca gttccatccg gagctattcg gaatagggaa tgtatcgcgt   12720 gttttgtgg acaagcaacg tcaggccatc tgtgcggagc acgacggatc caattcaacc   12780
gtgtccacta agtacaacat ctccgcatcg tatgcggcgt actatcatca ccagatagac   12840
gggggtaatt ggtttcacct agaatggctg cggccattct tttcttcctg gttggtgctc   12900
aacatctcat ggtttctgag gcgttcgcct gcaagccctg cttctcgacg catttatcag   12960
atattaagac caacacgacc gcggctgccg gtttcatggt ccttcagaaa attgaatgcc   13020
tccaagcccc tgggacacgg tcgcaatgtc gtgaagccat cggtaccccc cagtacatca   13080
cgatacaggc caacgtgacc gacgaatcat acttgtataa cgcggacttg ctgatgctct   13140
```

-continued

```
ctgcgtgcct cttctacgcc tcagaaatga gcgagaaagg cttcaacgtc atctttggga    13200
atgtttctgg cgttgtttcc gcttgtgtca atttcacaga ttacgtagcc cacgtgactc    13260
aacacaccca gcagcatcac ctggtaatcg accacgttag gctactacat ttcctgtcac    13320
cacctgtaat gaggtgggcc acaaccatcg cttgtttgtt cgccattctt ttggcgatat    13380
gagatgttct cacaaattgg ggcgcttctt gattccgcac tcttgctttt ggtggctttt    13440
ttgctgtgta ccggcttgtc ctggtccttt gccgatggca acggcaacag ctcgacatac    13500
caatacatat ataacttgac gatatgcgag cttaatggga ccacctggct gtctagccat    13560
tttgattggg cagtcgagac ttttgtgctc tacccggtcg cgactcacat tctctcactg    13620
ggttttctca caacaagcca tttctttgac gcgctcggtc tcagtgctgt gtccgtcaca    13680
ggattttatg accagcggta cgtgctcagc agtgtctacg cgtctgtgc cctcgcagcg    13740 ctcgtgtgtt ttgccatccg tgctgctaaa aattgtatgg cttgtcgcta cgcccgcacc    13800
cggttcacca acttcatcgt ggacgaccgg gggaggattc atcggtggaa atccccaata    13860
gtggtggaga aattgggcaa agctgaggtc ggcagcgacc ttgtcaccat taaacatgtc    13920
gtcctcgaag gggttaaagc tcaacccttg acgaggactt cggctgagca atgggaggcc    13980
tagatggttt ttgttatgac cctactgctg tacaaaagct tgtgttggcc ttcagcatca    14040
cgtatacacc tataatgata tatgccctta aggtgtcacg cggtcgactc ctagggctgt    14100
tgcacatcct gatatttctg aactgttcct tcactttcgg atacatgacg tatgtgcatt    14160
ttcagtccgc caaccgtgtt gtactcactt tgggggccgt tgttgccctc ctgtggggta    14220
tttacagctt cacagagtca tggaagttca tcacttccag atgcagattg tgttgccttg    14280
gccggcgata cattctggcc cctgcccacc acgtagaaag tgctgcaggt ctccatccta    14340
tcccagcgtc tggcaaccga gcatacgctg tgaggaagcc cggactaaca tcagtgaacg    14400
gcactctggt accaggactt cggagcctcg tgttgggcgg caaacgagct gttaaacgag    14460
gagtggttaa cctcgtcaaa tatggccggt aaaaaccaag gccagaagaa aagaaaagt    14520 acagctccaa tggggaatgg ccagccagtc aatcaactgt gccagttgct gggtgcaatg    14580
ataaggaccc agcgccagca acctagggga ggacaggcca aaaagaaaag gcctgagaag    14640
ccgcattttc ccctagctgc tgaagatgac atacggcacc acctcaccca gactgaacga    14700
tccctctgtt tgcaatcgat ccagacggct tttaatcaag cgcaggagc tgcgtcgctt    14760 tcgtccagcg ggaaagtcag ttttcaggtt gagttcatgc tgccggttgc tcatacagtg    14820
cgcctgattc gcgtgacttc cacatccgcc aatc                                14854
```

<210> SEQ ID NO 39
<211> LENGTH: 17
<212> TYPE: PRT
<213> ORGANISM: Porcine reproductive and respiratory syndrome virus

<400> SEQUENCE: 39

Ser Ser His Leu Gln Leu Ile Tyr Asn Leu Thr Ile Cys Glu Leu Asn
1               5                   10                  15

Gly

<210> SEQ ID NO 40
<211> LENGTH: 17
<212> TYPE: PRT
<213> ORGANISM: Porcine reproductive and respiratory syndrome virus

<400> SEQUENCE: 40

Gln Ser His Arg Ala Ser Thr Ala Gln Gly Thr Thr Pro Leu Arg Arg
1               5                   10                  15

Ser

<210> SEQ ID NO 41
<211> LENGTH: 15111
<212> TYPE: DNA
<213> ORGANISM: Porcine reproductive and respiratory syndrome virus

<400> SEQUENCE: 41

| | | |
|---|---|---|
| atgatgtgta gggtattccc cctacataca cgacacttct agtgtttgtg taccttggag | 60 |
| gcgtgggtac agccccgccc cacccctcgg cccctgttct agcccaacag gtatccttct | 120 |
| ctctcggggc gagtgcgccg cctgctgctc ccttgcagcg ggaaggacct cccgagtatt | 180 |
| tccggagagc acctgcttta cgggatctcc acccttaac catgtctggg acgttctccc | 240 |
| ggtgcatgtg cacccggct gcccgggtat tttggaacgc cggccaagtc ttttgcacac | 300 |
| ggtgtctcag tgcgcggtct cttctctctc cagagcttca ggacactgac ctcggtgcag | 360 |
| ttggcttgtt ttacaagcct agggacaagc ttcactggaa agtccctatc ggcatccctc | 420 |
| aggtggaatg tactccatcc gggtgctgtt ggctctcagc tgttttccct ttggcgcgta | 480 |
| tgacctccgg caatcacaac ttcctccaac gacttgtgaa ggttgctgat gttttgtacc | 540 |
| gtgacggttg cttggcacct cgacaccttc gtgaactcca gtttacgag cgcggctgca | 600 |
| actggtaccc gatcacgggg cccgtgcccg gatggttt gtttgcgaac tccatgcacg | 660 |
| tatccgacca gccgttccct ggtgccaccc atgtgttgac taactcgcct ttgcctcaac | 720 |
| aggcttgtcg gcagccgttc tgtccatttg aggaggctca ttctagcgtg tacaggtgga | 780 |
| agaaatttgt ggttttcacg gactcctccc tcaacggtcg atctcgcatg atgtggacgc | 840 |
| cggaatccga tgattcagcc gccctggagg tactaccgcc tgagttagaa cgtcaggtcg | 900 |
| aaatcctcat tcggagtttt cctgctcatc accctgtcga cctggccgac tgggagctca | 960 |
| ctgagtcccc tgagaacggt ttttccttca acacgtctca ttcttgcggt caccttgtcc | 1020 |
| agaaccccga cgtgtttgat ggcaagtgct ggctctcctg cttttttggc cagtcggtcg | 1080 |
| aagtgcgctg ccatgaggaa catctagctg acgccttcgg ttaccaaacc aagtggggcg | 1140 |
| tgcatggtaa gtacctccag cgcaggcttc aagttcgcgg cattcgtgct gtagtcgatc | 1200 |
| ctgatggtcc cattcacgtt gaagcgctgt cttgccccca gtcttggatc aggcacctga | 1260 |
| ctctggatga tgatgtcacc ccaggattcg ttcgcctgac atcccttcgc attgtgccga | 1320 |
| acacagagcc taccacttcc cggatctttc ggtttggagc gcataagtgg tatggcgctg | 1380 |
| ccggcaaacg ggctcgtgct aagcgtgccg ctaaaagtga aaggattcg gctcccaccc | 1440 |
| ccaaggttgc cctgccggtc cccacctgtg aattaccac ctactctcca ccgacagacg | 1500 |
| ggtcttgtgg ttggcatgtc cttgccgcca taatgaaccg gatgataaat ggtgacttca | 1560 |
| cgtcccctct gactcagtac aacagaccag aggatgattg gcttctgat tatgatcttg | 1620 |
| ttcaggcgat tcaatgtcta cgactgcctg ctaccgtggt tcggaatcgc gcctgtccta | 1680 |
| acgccaagta cctataaaa cttaacggag ttcactggga ggtagaggtg aggtctggaa | 1740 |
| tggctcctcg ctccctttct cgtgaatgtg tggttggcgt ttgctctgaa ggctgtgtcg | 1800 |
| caccgccta ccagcagac gggctaccta acgtgcact cgaggccttg cgtctgctt | 1860 |
| acagactacc ctccgattgt gttagctctg gtattgctga cttcttgct aatccacctc | 1920 |
| ctcaggaatt ctggaccctc gacaaaatgt tgacctcccc gtcaccagag cggtccggct | 1980 |

```
tctctagttt gtataaatta ctattagagg ttgttccgca aaaatgcggt gccacggaag    2040
gggctttcat ctatgctgtt gagaggatgt tgaaggattg tccgagctcc aaacaggcca    2100
tggcccttct ggcaaaaatt aaagttccat cctcaaaggc cccgtctgtg tccctggacg    2160
agtgtttccc tacgatgttt ttagccgact tcgagccagc atctcaggaa aggccccaaa    2220
gttccggcgc tgctgttgtc ctgtgttcac cggatgcaaa agagttcgag gaagcagccc    2280
cggaagaagt tcaagagagt ggccacaagg ccgtccactc tgcactcctt gccgagggtc    2340
ctaacaatga gcaggtacag tggttgccg gtgagcaact gaagctcggc ggttgtggtt    2400
tggcagtcgg gaatgctcat gaaggtgctc tggtctcagc tggtctaatt aacctggtag    2460
gcgggaattt gtccccctca gaccccatga aagaaaacat gctcaatagc cgggaagacg    2520
aaccactgga tttgtcccaa ccagcaccag cttccacaac gacccttgtg agagagcaaa    2580
cacccgacaa cccaggttct gatgccggtg ccctccccgt caccgttcga aatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaacccca gccaccaggg agtggctcga caaaatgtgg gatagggtgg    3180
acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360
cccccccaaa accggttggg ccagtgcttg accagatcgt ccctccgcct acggatatcc    3420
agcaagaaga tgtcacccccс tccgatgggc caccccatgc gccggatttt cctagtcgag    3480
tgagcacggg cgggagttgg aaaggcctta tgctttccgg cacccgtctc gcggggtcta    3540
tcagccagcg ccttatgaca tgggttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt acccgatact cggatgcctt cccttattgg    3720
gtgtctttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggccctttt    4020
ctcttgttta tgtggtgtcc caggggcgtt gtcacaagtg ttggggaaag tgtataagga    4080
cagctcctgc ggaggtggct cttaatgtat tcctttctc gcgcgccacc cgtgtctctc    4140
ttgtatcctt gtgtgatcga ttccaaacgc caaaggggt tgatcctgtg cacttggcaa    4200
cgggttggcg cgggtgctgg cgtggtgaga gccccatcca tcaaccacac caaaagccca    4260
tagcttatgc caatttggat gaaaagaaaa tgtctgccca acggtggtt gctgtcccat    4320
acgatcccag tcaggctatc aaatgcctga agttctgca ggcgggaggg gccatcgtgg    4380
```

```
accagcctac acctgaggtc gttcgtgtgt ccgagatccc cttctcagcc ccattttttcc    4440 caaaagttcc agtcaaccca gattgcaggg ttgtggtaga ttcggacact tttgtggctg    4500
cggttcgctg cggttactcg acagcacaac tggttctggg ccggggcaac tttgccaagt    4560
taaatcagac cccccccagg aactctatct ccaccaaaac gactggtggg gcctcttaca    4620
cccttgctgt ggctcaagtg tctgcgtgga ctcttgttca tttcatcctc ggtctttggt    4680
tcacatcacc tcaagtgtgt ggccgaggaa ccgctgaccc atggtgttca aatccttttt    4740
catatcctac ctatggcccc ggagttgtgt gctcctctcg actttgtgtg tctgccgacg    4800
gggtcaccct gccattgttc tcagccgtgg cacaactctc cggtagagag gtggggattt    4860
ttattttggt gctcgtctcc ttgactgctt tggcccaccg catggctctt aaggcagaca    4920
tgttagtggt cttttcggct ttttgtgctt acgcctggcc catgagctcc tggttaatct    4980
gcttctttcc tatactcttg aagtgggtta cccttcaccc tcttactatg ctttgggtgc    5040
actcattctt ggtgttttgt ctgccagcag ccggcatcct ctcactaggg ataactggcc    5100
ttctttgggc aattggccgc tttacccagg ttgccggaat tattacacct tatgacatcc    5160
accagtacac ctctgggcca cgtggtgcag ctgctgtggc cacagcccca gaaggcactt    5220
atatggccgc cgtccggaga gctgctttaa ctgggcgaac tttaatcttc accccgtctg    5280
cagttggatc ccttctcgaa ggtgctttca ggactcataa accctgcctt aacaccgtga    5340
atgttgtagg ctcttccctt ggttccggag gggttttcac cattgatggc agaagaactg    5400
tcgtcactgc tgcccatgtg ttgaacggcg acacagctag agtcaccggc gactcctaca    5460
accgcatgca cacttttcaag accaatggtg attatgcctg gtcccatgct gatgactggc    5520
agggcgttgc ccctgtggtc aaggttgcga aggggtaccg cggtcgtgcc tactggcaaa    5580
catcaactgg tgtcgaaccc ggtatcattg gggaagggtt cgccttctgt tttactaact    5640
gcggcgattc ggggtcaccc gtcatctcag aatctggtga tcttattgga atccacaccg    5700
gttcaaacaa acttggttct ggtcttgtga caaccccctga aggggagacc tgcaccatca    5760
aagaaaccaa gctctctgac cttttccagac atttttgcagg cccaagcgtt cctcttgggg    5820
acattaaatt gagtccggcc atcatccctg atgtaacatc cattccgagt gacttggcat    5880
cgctcctagc ctccgtccct gtagtggaag gcggcctctc gaccgttcaa cttttgtgtg    5940 tcttttttcct tctctggcgc atgatgggcc atgcctggac acccattgtt gccgtgggct    6000 tcttttttgct gaatgaaatt cttccagcag ttttggtccg agccgtgttt tcttttgcac    6060
tctttgtgct tgcatgggcc acccctggt ctgcacaggt gttgatgatt agactcctca    6120
cggcatctct caaccgcaac aagctttctc tggcgttcta cgcactcggg ggtgtcgtcg    6180
gtttggcagc tgaaatcggg acttttgctg gcagattgtc tgaattgtct caagctcttt    6240
cgacatactg cttcttacct agggtccttg ctatgaccag ttgtgttccc accatcatca    6300
ttggtggact ccatacccctc ggtgtgattc tgtggttatt caaataccgg tgcctccaca    6360
acatgctggt tggtgatggg agttttttcaa gcgccttctt cctacggtat tttgcagagg    6420
gtaatctcag aaaaggtgtt tcacagtcct gtggcatgaa taacgagtcc ctaacggctg    6480
ctttagcttg caagttgtca caggctgacc ttgatttttt gtccagctta acgaacttca    6540
agtgctttgt atctgcttca aacatgaaaa atgctgccgg ccagtacatt gaagcagcgt    6600
atgccaaggc cctgcgccaa gagttggcct ctctagttca gattgacaaa atgaaaggag    6660
ttttgtccaa gctcgaggcc tttgctgaaa cagccacccc gtcccttgac ataggtgacg    6720
```

```
tgattgttct gcttgggcaa catcctcacg gatccatcct cgatattaat gtggggactg    6780
aaaggaaaac tgtgtccgtg caagagaccc ggagcctagg cggctccaaa ttcagtgttt    6840
gtactgtcgt gtccaacaca cccgtggacg ccttgaccgg catcccactc cagacaccaa    6900
cccctctttt tgagaatggt ccgcgtcatc gcagcgagga agacgatctt aaagtcgaga    6960
ggatgaagaa acactgtgta tccctcggct tccacaacat caatggcaaa gtttactgca    7020
aaatttggga caagtctacc ggtgacacct tttacacgga tgattcccgg tacacccaag    7080
accatgcttt tcaggacagg tcagccgact acagagacag ggactatgag ggtgtgcaaa    7140 ccaccccccca cagggatttt gatccaaagt ctgaaacccc tgttggcact gttgtgatcg    7200
gcggtattac gtataacagg tatctgatca aggtaagga ggttctggtc cccaagcctg    7260
acaactgcct tgaagctgcc aagctgtccc ttgagcaagc tctcgctggg atgggccaaa    7320
cttgcgacct tacagctgcc gaggtggaaa agctaaagcg catcattagt caactccaag    7380
gtttgaccac tgaacaggct ttaaactgtt agccgccagc ggcttgaccc gctgtggccg    7440
cggcggccta gttgtgactg aaacggcggt aaaaattata aataccaca gcagaacttt    7500 caccttaggc cctttagacc taaaagtcac ttccgaggtg gaggtaaaga aatcaactga    7560
gcagggccac gctgttgtgg caaacttatg ttccggtgtc atcttgatga acctcaccc    7620 accgtccctt gtcgacgttc ttctgaaacc cggacttgac acaatacccg gcattcaacc    7680
agggcatggg gccgggaata tgggcgtgga cggttctatt tgggattttg aaaccgcacc    7740
cacaaaggca gaactcgagt tatccaagca ataatccaa gcatgtgaag ttaggcgcgg    7800
ggacgccccg aacctccaac tcccttacaa gctctatcct gttagggggg atcctgagcg    7860
gcataaaggc cgccttatca ataccaggtt tggagattta ccttacaaaa ctcctcaaga    7920
caccaagtcc gcaatccacg cggcttgttg cctgcacccc aacggggccc ccgtgtctga    7980
tggtaaatcc acactaggta ccactcttca acatggtttc gagctttatg tccctactgt    8040
gccctatagt gtcatggagt accttgattc acgccctgac ccccttttta tgtgtactaa    8100
acatggcact tccaaggctg ctgcagagga cctccaaaaa tacgacctat ccacccaagg    8160
atttgtcctg cctggggtcc tacgcctagt acgcagattc atctttggcc atattggtaa    8220
ggcgccgcca ttgttcctcc catcaaccta tcccgccaag aactctatgg cagggatcaa    8280
tggccagagt ttcccaacaa aggacgttca gagcatacct gaaattgatg aaatgtgtgc    8340
ccgcgctgtc aaggagaatt ggcaaactgt gacaccttgc accctcaaga aacagtactg    8400
ttccaagccc aaaaccagga ccatcctggg caccaacaac tttattgcct tggctcacag    8460
atcggcgctc agtggtgtca cccaggcatt catgaagaag gcttggaagt ccccaattgc    8520
cttggggaaa aacaaattca aggagctgca ttgcactgtc gccggcaggt gtcttgaggc    8580
cgacttggcc tcctgtgacc gcagcacccc cgccattgta agatggtttg ttgccaacct    8640
cctgtatgaa cttgcaggat gtgaagagta cttgcctagc tatgtgctta attgctgcca    8700
tgacctcgtg gcaacacagg atggtgcctt cacaaaacgc ggtggcctgt cgtccgggga    8760
ccccgtcacc agtgtgtcca acaccgtata ttcactggta atttatgccc agcacatggt    8820
attgtcggcc ttgaaaatgg gtcatgaaat tggtcttaag ttcctcgagg aacagctcaa    8880
gttcgaggac ctccttgaaa ttcagcctat gttggtatac tctgatgatc ttgtcttgta    8940
cgctgaaaga cccacatttc ccaattacca ctggtgggtc gagcaccttg acctgatgct    9000
gggtttcaga acgaccccaa agaaaaccgt cataactgat aaacccagct tcctcggctg    9060
cagaattgag gcagggcgac agctagtccc caatcgcgac cgcatcctgg ctgctcttgc    9120
```

```
atatcacatg aaggcgcaga acgcctcaga gtattatgcg tctgctgccg caatcctgat   9180
ggattcatgt gcttgcattg accatgaccc tgagtggtat gaggacctca tctgcggtat   9240
tgcccggtgc gcccgccagg atggttatag cttcccaggt ccggcatttt tcatgtccat   9300
gtgggagaag ctgagaagtc ataatgaagg aagaaattc cgccactgcg gcatctgcga    9360
cgccaaagcc gactatgcgt ccgcctgtgg gcttgatttg tgtttgttcc attcgcactt   9420
tcatcaacac tgccctgtca ctctgagctg cggtcaccat gccggttcaa aggaatgttc   9480
gcagtgtcag tcacctgttg gggctggcag atcccctctt gatgccgtgc taaaacaaat   9540
tccatacaaa cctcctcgta ctgtcatcat gaaggtgggg aataaaacaa cggccctcga   9600
tccggggagg taccagtccc gtcgaggtct cgttgcagtc aagagggta ttgcaggcaa    9660 tgaagttgat ctttctgatg gggactacca agtggtgcct cttttgccga cttgcaaaga   9720
cataaacatg gtgaaggtgg cttgcaatgt actactcagc aagttcatag tagggccacc   9780
aggttccgga aagaccacct ggctactgag tcaagtccag gacgatgatg tcatttacac   9840
acccacccat cagactatgt ttgatatagt cagtgctctc aaagtttgca ggtattccat   9900
tccaggagcc tcaggactcc ctttcccacc acctgccagg tccggccgt gggttaggct    9960 tattgccagc gggcacgtcc ctggccgagt atcatacctc gatgaggctg gatattgtaa  10020
tcatctggac attcttagac tgcttttccaa acaccccctt gtgtgtttgg gtgaccttca  10080
gcaacttcac cctgtcggct tgattcccta ctgttatgtg ttcgatcaga tgcctcagaa  10140
gcagctgacc actatttaca gatttggccc taacatctgc gcagccatcc agccttgtta  10200
cagggagaaa cttgaatcta aggctaggaa cactagggtg gttttttacca cccggcctgt  10260 ggcctttggt caggtgctga caccatacca taaagatcgc atcggctctg cgataaccat  10320
agattcatcc caggggggcca cctttgatat tgtgacattg catctaccat cgccaaagtc  10380
cctaaataaa tcccgagcac ttgtagccat cactcgggca agacacgggt tgttcattta  10440
tgaccctcat aaccagctcc aggagttttt caacttaacc cctgagcgca ctgattgtaa  10500
ccttgtgttc agccgtgggg atgagctggt agttctgaat gcggataatg cagtcacaac  10560
tgtagcgaag gcccttgaga caggtccatc tcgatttcga gtatcagacc cgaggtgcaa  10620
gtctctctta gccgcttgtt cggccagtct ggaagggagc tgtatgccac taccgcaagt  10680
ggcacataac ctgggtttt actttttcccc ggacagtcca acatttgcac ctctgccaaa  10740
agagttggcg ccacattggc cagtggttac ccaccagaat aatcgggcgt ggcctgatcg  10800
acttgtcgct agtatgcgcc caattgatgc ccgctacagc aagccaatgg tcggtgcagg  10860
gtatgtggtc gggccgtcca ccttttcttgg tactcctggt gtggtgtcat actatctcac  10920
actatacatc aggggtgagc cccaggcctt gccagaaaca ctcgtttcaa cagggcgtat  10980
agccacagat tgtcgggagt atctcgacgc ggctgaggaa gaggcagcaa aagaactccc  11040
ccacgcattc attggcgatg tcaaaggtac cacggttggg gggtgtcatc acattacatc  11100
aaaataccta cctaggtccc tgcctaagga ctctgttgcc gtagttggag taagttcgcc  11160
cggcagggct gctaaagccg tgtgcactct caccgatgtg tacctccccg aactccggcc  11220
atatctgcaa cctgagacgg catcaaaatg ctggaaactc aaattagact tcaggacgt   11280 ccgactaatg gtctggaaag gagccaccgc ctatttccag ttggaagggc ttacatggtc  11340
ggcgctgccc gactatgcca ggtttattca gctgccaag gatgccgttg tatacattga   11400
tccgtgtata ggaccggcaa cagccaaccg taaggtcgtg cgaaccacag actggcgggc  11460
```

```
cgacctggca gtgacaccgt atgattacgg tgcccagaac attttgacaa cagcctggtt    11520
cgaggacctc gggccgcagt ggaagatttt ggggttgcag ccctttaggc gagcatttgg    11580 cttttgaaaac actgaggatt gggcaatcct tgcacgccgt atgaatgacg gcaaggacta  11640
cactgactat aactggaact gtgttcgaga acgcccacac gccatctacg ggcgtgctcg    11700
tgaccatacg tatcattttg ccctggcac agaattgcag gtagagctag gtaaaccccg    11760
gctgccgcct gggcaagtgc cgtgaattcg gggtgatgca atggggtcac tgtggagtaa    11820
aatcagccag ctgttcgtgg acgccttcac tgagttcctt gttagtgtgg ttgatattgc    11880
cattttcctt gccatactgt ttgggttcac cgtcgcagga tggttactgg tctttcttct    11940
cagagtggtt tgctccgcgc ttctccgttc gcgctctgcc attcactctc ccgaactatc    12000
gaaggtccta tgaaggcttg ttgcccaact gcagaccgga tgtcccacaa tttgcagtca    12060
agcacccatt gggtatgttt tggcacatgc gagtttccca cttgattgat gagatggtct    12120
ctcgtcgcat ttaccagacc atggaacatt caggtcaagc ggcctggaag caggtggttg    12180
gtgaggccac tctcacgaag ctgtcagggc tcgatatagt tactcatttc aacacctgg    12240 ccgcagtgga ggcggattct tgccgctttc tcagctcacg actcgtgatg ctaaaaaatc    12300
ttgccgttgg caatgtgagc ctacagtaca acaccacgtt ggaccgcgtt gagctcatct    12360
tccccacgcc aggtacgagg cccaagttga ccgatttcag acaatggctc atcagtgtgc    12420
acgcttccat tttttcctct gtggcttcat ctgttacctt gttcatagtg ctttggcttc    12480
gaattccagc tctacgctat gttttttggtt tccattggcc cacggcaaca catcattcga    12540
gctgaccatc aactacacca tatgcatgcc ctgttctacc agtcaagcgg ctcgccaaag    12600
gctcgagccc ggtcgtaaca tgtggtgcaa ataggggcat gacaggtgtg aggagcgtga    12660
ccatgatgag ttgttaatgt ccatcccgtc cgggtacgac aacctcaaac ttgagggtta    12720
ttatgcttgg ctggcttttt tgtcctttc ctacgcggcc caattccatc cggagttgtt    12780 cgggatagggg aatgtgtcgc gcgtcttcgt ggacaagcga caccagttca tttgtgccga    12840
gcatgatgga cacaattcaa ccgtatctac cggacacaac atctccgcat tatatgcggc    12900
atattaccac caccaaatag acgggggcaa ttggttccat ttggaatggc tgcggccact    12960 ctttttcttcc tggctggtgc tcaacatatc atggtttctg aggcgttcgc ctgtaagccc    13020
tgtttctcga cgcatctatc agatattgag accaacacga ccgcggctgc cggtttcatg    13080
gtccttcagg acatcaattg tttccgacct cacggggtct cagcagcgca agagaaaatt    13140
tccttcggaa agtcgtccca atgtcgtgaa gccgtcggta ctccccagta catcacgata    13200
acggctaacg tgaccgacga atcatacttg tacaacgcgg acctgctgat gctttctgcg    13260
tgccttttct acgcctcaga aatgagcgag aaaggcttca aagtcatctt tgggaatgtc    13320
tctggcgttg tttctgcttg tgtcaatttc acagattatg tggcccatgt gacccaacat    13380
acccagcagc atcatctggt aattgatcac attcggttgc tgcatttcct gacaccatct    13440
gcaatgaggt gggctacaac cattgcttgt tgttcgcca ttctcttggc aatatgagat    13500
gttctcacaa attggggcgt ttcttgactc cgcactcttg cttctggtgg ctttttttgc    13560
tgtgtaccgg cttgtcctgg tcctttgccg atggcaacgg cgacagctcg acataccaat    13620
acatatataa cttgacgata tgcgagctga atgggaccga ctggttgtcc agccattttg    13680
gttgggcagt cgagaccttt gtgctttacc cggttgccac tcatatcctc tcactgggtt    13740
ttctcacaac aagccatttt tttgacgcgc tcggtctcgg cgctgtatcc actgcaggat    13800
ttgttggcgg gcggtacgta ctctgcagcg tctacggcgc ttgtgctttc gcagcgttcg    13860
```

```
tatgttttgt catccgtgct gctaaaaatt gcatggcctg ccgctatgcc cgtacccggt    13920
ttaccaactt cattgtggac gaccggggga gagttcatcg atggaagtct ccaatagtgg    13980
tagaaaaatt gggcaaagcc gaagtcgatg gcaacctcgt caccatcaaa catgtcgtcc    14040
tcgaaggggt taaagctcaa cccttgacga ggacttcggc tgagcaatgg gaggcctaga    14100 cgattttttgc aacgatccta tcgccgcaca aaagctcgtg ctagccttta gcatcacata    14160
cacacctata atgatatacg cccttaaggt gtcacgcggc cgactcctgg ggctgttgca    14220
catcctaata tttctgaact gttccttta c attcggatac atgacatatg tgcatttttca    14280 atccaccaac cgtgtcgcac ttaccctggg ggctgttgtc gcccttctgt ggggtgttta    14340
cagcttcaca gagtcatgga agtttatcac ttccagatgc agattgtgtt gccttggccg    14400
gcgatacatt ctggccctg cccatcacgt agaaagtgct gcaggtctcc attcaatctc    14460
agcgtctggt aaccgagcat acgctgtgag aaagcccgga ctaacatcag tgaacggcac    14520
tctagtacca ggacttcgga gcctcgtgct gggcggcaaa cgagctgtta acgaggagt    14580 ggttaacctc gtcaagtatg gccggtaaaa accagagcca gaagaaaaag aaaagtacag    14640
ctccgatggg gaatggccag ccagtcaatc aactgtgcca gttgctgggt gcaatgataa    14700
agtcccagcg ccagcaacct aggggaggac aggccaaaaa gaaaaagcct gagaagccac    14760
attttcccct ggctgctgaa gatgacatcc ggcaccacct cacccagact gaacgctccc    14820
tctgcttgca atcgatccag acggctttca atcaaggcgc aggaactgcg tcgctttcat    14880
ccagcgggaa ggtcagtttt caggttgagt ttatgctgcc ggttgctcat acagtgcgcc    14940
tgattcgcgt gacttctaca tccgccagtc agggtgcaag ttaatttgac agtcaggtga    15000
atggccgcga ttggcgtgtg gcctctgagt cacctattca attagggcga tcacatgggg    15060
gtcatactta atcaggcagg aaccatgtga ccgaaattaa aaaaaaaaa a                 15111
```

<210> SEQ ID NO 42
<211> LENGTH: 15182
<212> TYPE: DNA
<213> ORGANISM: Porcine reproductive and respiratory syndrome virus

<400> SEQUENCE: 42

```
tttctccacc cctttaacca tgtctgggat acttgatcgg tgcacgtgta cccccaatgc      60
cagggtgttt atggcggagg ccaagtctac tgcacacga tgcctcagtg cacggtctct     120
ccttcccctg aacctccaag tttctgagct cggggtgcta ggcctattct acaggcccga    180
agagccactc cggtggacgt tgccacgtgc attccccact gttgagtgct ccccgccgg     240 ggcctgctgg ctctctgcaa tctttccaat cgcacgaatg accagtggaa acctgaactt    300
ccaacaaaga atgatacggg tcgcagctga gctttacaga gccggccagc tcaccccctgc   360 agtcttgaag gctctacaag tttatgaacg gggttgccgc tggtacccca ttgttggacc    420
tgccccctga gtgccgtttt acgccaattc cctacatgtg agtgataaac ctttcccggg    480
agcaactcac gtgttgacca acctgccgct cccgcagaga cccaagcctg aagactttg     540 cccctttgag tgtgctatgg ctactgtcta tgacattggt catgacgccg tcatgtatgt    600
ggccgaaagg aaaatctcct gggcccctcg tggcggggat gaagtgaaat tgaagctgt     660 ccccggggag ttgaggttga ttgcgaaccg gctccgcacc tccttcccgc cccaccacac    720
agtggacatg tctaagttcg ccttcacagc cctgggtgt ggtgtttcta tgcgggttga    780
acgccaacac ggctgccttc ccgctgacac tgtccctgaa ggcaactgct ggtggagctt    840
```

```
gtttgactcg cttccactgg aagttcagaa caaagaaatt cgccatgcta accaatttgg    900
ctaccagacc aagcatggtg tctctggcaa gtacctacag cggaggctgc aagttaatgg    960
tctccgagca gtaactgacc taaacggacc tatcgtcgta cagtacttct ccgttaagga   1020
gagttggatc cgccatttga aactggcggg agaacccagc tactctgggt ttgaggacct   1080
cctcagaata agggttgagc ctaacacgtc gccattggct gacaaggaag aaaaaatttt   1140
ccggtttggc agtcacaagt ggtacggcgc tggaaagaga gcaagaaaag cacgctcttg   1200
tgcgactgcc acagtcgctg ccgcgctttt gtccgttcgt gaaacccggc aggccaagga   1260
gcacgaggtt gccggcgcca acaaggctga gcacctcaaa cactactccc cgcctgccga   1320
agggaattgt ggttggcatt gcatttccgc catcgccaac cggatggtga attccaaatt   1380
tgaaaccacc cttcccgaaa gagtgagacc tccagatgac tgggctactg acgaggatct   1440
tgtgaatgcc atccaaatcc tcagactccc tgcggcctta gacaggaacg gtgcttgtac   1500
tagcgccaag tacgtactta agctggaagg tgagcattgg actgtcactg tggcccctgg   1560
gatgtcccct tctttgctcc ctcttgaatg tgttcagggc gttgtgggc acaagggcgg    1620 tcttggttcc ccagatgcag tcgaggtctc cggatttgac cctgcctgcc ttgaccggct   1680
ggctgaggtg atgcacctgc ctagcagtgc tatcccagcc gctctggccg aaatgtctgg   1740
cgattccgat cgttcggctt ctccggtcac caccgtgtgg actgtttcgc agttctttgc   1800
ccgtcacagc ggagggaatc accctgatca agtgcgctta gggaaaatta tcagcctttg   1860
tcaggtgatt gaggactgct gctgttccca gaacaaaacc aaccgggtca ccccggagga   1920
ggtcgcagca agattgacc tgtacctccg tggtgcaaca atcttgaag aatgcttggc     1980 caggcttgag aaagcgcgcc cgccacgcgt aatcgacacc ttctttgatt gggatgttgt   2040
gctccctggg gttgaggcgg caacccagac gatcaagctg ccccaggtca accagtgtcg   2100
tgctctggtc cctgttgtga ctcaaaagtc cttggacgac aactcggtcc cctgaccgc    2160 cttttcactg gctaactact actaccgtgc gcaaggtgac gaagttcgtc accgtgaaag   2220
actaaccgcc gtgctctcca gttggaaaaa ggttgttcga aagaatatg gctcatgcc    2280 aaccgagcct ggtccacggc ccacactgcc acgcgggctc gacgaactca agaccagat   2340 ggaggaggac ttgctgaagc tggctaacgc ccagacgact tcggacatga tggcctgggc   2400
agtcgagcag gttgacctaa aaacttgggt caagaactac ccgcggtgga caccaccacc   2460
ccctccgcca aaagttcagc ctcgaaaaac gaagcctgtc aagagcttgc cggagagaaa   2520
gcctgtcccc gccccgcgca ggaaggttgg gtccgattgt ggcagccggg tttcattagg   2580
cggcgatgtc tctaacagtt gggaagattt ggctgttagt agcccctttg atctcccgac   2640
cccacctgag ccggcaacac cttcaagtga gctggtgatt gtgtcctcac cgcaatgcat   2700
cttcaggccg gcgacaccct tgagtgagcc ggctccaatt cccgcacctc gcggaactgt   2760
gtctcgaccg gtgacaccct tgagtgagcc gatccctgtg cccgcaccgc ggcgtaagtt   2820
tcagcaggtg aaaagattga gttcggcggc ggcaatccca ccgtaccaga acgagcccct   2880
ggatttgtct gcttcctcac agactgaaca tgaggcctct cccccagcac cgccgcagag   2940
cgggggcgtt ccgggagtag aggggcatga agctgaggaa accctgagtg aaatctcgga   3000
catgtcgggt aacattaaac ctgcgtccgt gtcatcaagc agctccttgt ccagcgtgag   3060
aatcacacgc ccaaaatact cagctcaagc catcatcgac tcgggcgggc cctgcagtgg   3120
gcatctccaa gaggtaaagg aaacatgcct tagtgtcatg cgcgaggcat gtgatgcgac   3180
taagcttgat gaccctgcta cgcaggaatg gctttctcgc atgtgggatc gggtggacat   3240
```

```
gctgacttgg cgcaacacgt ctgtttacca ggcgatttgc acctagatg gcaggttaaa    3300 gttcctccca aaatgatac tcgagacacc gccgccctat ccgtgtgagt ttgtgatgat    3360
gcctcacacg cctgcacctt ccgtaggtgc ggagagcgac cttaccattg gctcagttgc    3420
tactgaagat gttccacgca tcctcgagaa aatagaaaat gtcggcgaga tggccaacca    3480
gggacccttg gccttctccg aggataaacc ggtagatgac caacttgtca acgaccccg    3540 gatatcgtcg cggaggcctg acgagagcac atcagctccg tccgcaggca caggtggcgc    3600
cggctctttt accgatttgc cgccttcaga tggcgcggat acggacgggg ggggccgtt    3660 tcggacggca aaaagaaaag ctgaaaggct ctttgaccaa ctgagccgtc aggttttga    3720 cctcgtctcc catctccctg ttttcttctc acgccttttc taccctggcg gtggttattc    3780
tccgggtgat gggttttg cagcttttac tctattgtgc ctcttttat gttacagtta    3840 cccagccttt ggtattgctc ccctcttggg tgtgttttct gggtcttctc ggcgcgttcg    3900
aatgggggtt tttggctgct ggttggcttt tgctgttggt ctgttcaagc ctgtgtccga    3960
cccagtcggc gctgcttgtg agtttgactc gccagagtgt agaaacatcc ttcattcttt    4020
tgagcttctc aaaccttggg accctgttcg cagccttgtt gtgggccccg tcggtctcgg    4080
tcttgccatt cttggcaggt tactgggcgg ggcacgctgc atctggcact ttttgcttag    4140
gcttggcatt gttgcagact gtatcttggc tggagcttac gtgctttctc aaggtaggtg    4200
taaaaagtgc tggggatctt gtataagaac tgctcctaat gaggtcgctt ttaacgtgtt    4260
tcctttcaca cgtgcgacca ggtcgtcact tatcgacctg tgcgatcggt tttgtgcgcc    4320
aaaaggaatg gaccccattt ttctcgccac tgggtggcgc gggtgctggg ccggccgaag    4380
ccccattgag caaccctctg aaaaacccat cgcgtttgcc caattggatg aaaagaagat    4440
tacggctagg actgtggtcg cccagcctta tgaccccaac caagccgtaa agtgcttgcg    4500
ggtattgcag gcgggtgggg cgatggtggc taaggcggtc ccaaaagtgg ttaaggtttc    4560
cgctgttcca ttccgagctc ccttctttcc cactggagtg aaagttgacc ctgattgcag    4620
ggtcgtggtt gaccctgaca ctttcactgc agctctccgg tctggctact ccaccacaaa    4680
cctcgtcctt ggtgtagggg actttgccca gctaaatgga ttaaaaatca ggcaaatttc    4740
caagccttca gggggaggcc cacatctcat ggctgccctg catgttgcct gctcgatggc    4800
tctgcacatg cttgctggga tttatgtgac tgcggtgggt tcttgcggca ccggcaccaa    4860
cgacccgtgg tgcgctaacc cgtttgccgt ccctggctac ggacctggct ctctctgtac    4920
gtccagattg tgcatttccc aacacggcct taccctgccc ttgtcagcac ttgtggcggg    4980
attcggtatt caagaaattg ccttggtcgt tttgattttt gtttccatcg gaggcatggc    5040
tcataggttg agctgtaagg ctgacatgct gtgtgttttg cttgcaattg ccagctatgt    5100
ttgggtacct cttacctggt tgctttgtgt gtttccttgc tggttgcgct gttttctttt    5160 gcacccctc accatcctat ggttggtgtt tttcttgatt tctgtgaata tgccttcagg    5220
aatcttggcc atggtgttgt tggtttctct ttggcttctt ggtcgttata ctaatgttgc    5280
tggccttgtc accccctacg acattcatca ttacaccagt ggcccccgcg tgttgccgc    5340 cttggctacc gcaccagatg ggacctactt ggccgctgtc cgccgcgctg cgttgactgg    5400
ccgcaccatg ctgtttaccc cgtcccagct tgggtctctt cttgagggtg ccttcagaac    5460
tcgaaagccc tcactgaaca ccgtcaatgt gatcgggtcc tccatgggct ctggcggggt    5520
gtttaccatc gacgggaaag tcaagtgcgt aactgccgca catgtcctta cgggcaattc    5580
```

```
agctcgggtt tccggggtcg gcttcaatca aatgcttgac tttgacgtaa agggagattt      5640
cgctatcgct gattgcccga attggcaagg ggctgccccc aagacccaat tctgcacgga      5700
tggatggact ggccgtgcct attggctaac atcctctggc gtcgaacccg gcgtcattgg      5760
aaaaggattc gccttctgct tcaccgcatg tggcgattcc gggtcccag tgatcaccga       5820 ggccggtgag cttgtcggcg ttcacacggg atcgaataaa caagggggg gcattgttac       5880 gcgcccctca ggcagttttt gtaatgtggc acccatcaag ctaagcgaat taagtgaatt      5940
ctttgctggg cctaaggtcc cgctcggtga tgtgaaggtc ggcagccaca taattaaaga      6000
cataagcgag gtgccttcag atctttgtgc cttgcttgct gccaaacctg aactggaagg      6060
aggcctctcc accgtccaac ttctttgtgt gttttttctc ctgtggagaa tgatgggaca      6120 tgcctgacg cccttggttg ctgtgagttt ctttattttg aatgaggttc tccctgccgt       6180
cctggtccgg agtgttttct cctttggaat gtttgtgcta tcctggctca cgccatggtc     6240
tgcgcaagtt ctgatgatca ggcttctgac agcagctctt aacaggaaca gatggtcact     6300 tgccttttc agcctcggtg cagtgaccgg ttttgtcgca gatcttgcgg ccactcaggg      6360
gcatccgttg caggcagtga tgaatttgag cacctatgca ttcctgcctc ggatgatggt     6420
tgtgacctca ccagtcccag tgatcacgtg tggtgtcgtg cacctacttg ccatcatttt     6480
gtacttgttt aagtaccgtg gcctgcacca tatccttgtt ggcgatggag tgttctctgc     6540 ggcttcttc ttgagatact ttgccgaggg aaagttgagg gaaggggtgt cgcaatcctg      6600
cggaatgaat catgagtctc tgactggtgc cctcgctatg agactcaatg acgaggactt     6660
ggatttcctt atgaaatgga ctgattttaa gtgctttgtt tctgcgtcca acatgaggaa     6720
tgcagcgggt caatttatcg aggctgccta tgctaaagca cttagagtag aactggccca     6780
gttggtacag gttgataaag ttcgaggtac tttggccaaa cttgaagctt ttgctgatac     6840
cgtggctcct caactctcgc ccggtgacat tgttgtcgct ctcggccaca cgcctgttgg     6900
cagtatcttc gacctaaagg ttggtagcac caagcatacc ctccaagcca ttgagaccag     6960
agtccttgct gggtccaaaa tgaccgtggc gcgcgtcgtc gacccgaccc ccacgccccc     7020
acccgcaccc gtgcccatcc ccctcccacc gaaagttctg gagaatggcc caacgcttg     7080 gggggatgag gaccgtttga ataagaagaa gaggcgcagg atggaagccc tcggcatcta     7140
tgttatgggc gggaaaaagt accagaaatt ttgggacaag aattccggtg atgtgttta     7200 tgaggaggtc cataataaca cagatgagtg ggagtgtctc agagttggcg accctgccga     7260 ctttgacccct gagaagggaa ctctgtgtgg acatgtcacc attgaaaata aggcttacca     7320
tgtttacacc tccccatctg gtaagaagtt cttggtcccc gtcaacccag agaatggaag     7380
agttcaatgg gaagctgcaa agcttttccgt ggagcaggcc ctaggtatga tgaatgtcga    7440
cggcgaactg actgccaaag aactggagaa actgaaaaga ataattgaca aactccaggg    7500
cctgactaag gagcagtgtt taaactgcta gccgccagcg acttgacccg ctgtggtcgc    7560
ggcggcttgg ttgttactga aacagcggta aaaatagtca aatttcacaa ccggaccttc    7620
accctgggac ctgtgaattt aaaagtggcc agtgaggttg agctaaaaga cgcggttgag    7680
cacaaccaac acccgttgc gagaccgatc gatggtggag ttgtgctctt gcgttccgcg     7740
gttccttcgc ttatagacgt cttgatctcc ggtgctgatg catctcccaa gttacttgcc    7800
catcacgggc cggaaacac tgggatcgat ggcacgctct gggattttga gtccgaagcc     7860
actaaagagg aagtcgcact cagtgcgcaa ataatacagg cttgtgacat taggcgcggc    7920
gacgctcctg aaattggtct cccttacaag ctgtacctg ttagggtaa ccctgagcgg      7980
```

```
gtgaaaggag ttctgcagaa tacaaggttt ggagacatac cttacaaaac ccccagtgac   8040
actggaagcc cagtgcacgc ggctgcctgc cttacgccca cgccactcc ggtgactgat    8100 gggcgctccg tcttggccac gaccatgccc cccgggtttg agttatatgt accgaccata   8160
ccagcgtctg tccttgatta ccttgactct aggcctgact gccctaaaca gctgacagag   8220
cacggctgcg aagatgccgc actgaaagac ctctctaaat atgacttgtc cacccaaggc   8280
tttgttttac ctggagttct tcgccttgtg cggaaatacc tgtttgccca tgtaggtaag   8340
tgcccacccg ttcatcggcc ttctacttac cctgctaaga attctatggc tggaataaat   8400
gggaacaggt tcccaaccaa ggacattcag agcgtccctg aaatcgacgt tctgtgcgca   8460
caggctgtgc gagaaaactg gcaaactgtc accccttgta ctcttaagaa acagtattgc   8520
gggaagaaga agactaggac catactcggc accaataact tcatcgcact agcccaccga   8580
gcagtgttga gtggtgttac ccagggcttc atgaaaaagg cgtttaactc gcccatcgcc   8640
ctcggaaaga acaagtttaa ggagctacag actccggtcc tgggcaggtg ccttgaagct   8700
gatctcgcat cctgcgatcg atccacgcct gcaattgtcc gctggtttgc cgccaacctt   8760
ctttatgaac ttgcctgtgc tgaagagcat ctaccgtcgt acgtgctgaa ctgctgccac   8820
gacttactgg tcacgcagtc cggcgcagtg actaagagag gtggcctgtc gtctggcgac   8880
ccgatcacct ctgtgtctaa caccatttat agtttggtga tctatgcaca gcatatggtg   8940
cttagttact tcaaaagtgg tcaccccat ggccttctgt tcttacaaga ccagctaaag    9000
tttgaggaca tgctcaaggt tcaacccctg atcgtctatt cggacgacct cgtgctgtat   9060
gccgagtctc ccaccatgcc aaactatcac tggtgggttg aacatctgaa tttgatgctg   9120
gggtttcaga cggacccaaa gaagacagca ataacagact cgccatcatt tctaggctgt   9180
agaataataa atgggcgcca gctagtcccc aaccgtgaca ggatcctcgc ggccctcgcc   9240
tatcacatga aggcgagtaa tgtttctgaa tactatgcct cagcggctgc aatactcatg   9300
gacagctgtg cttgtttgga gtatgatcct gaatggtttg aagaacttgt agttggaata   9360
gcgcagtgcg cccgcaagga cggctacagt tttcccggca cgccgttctt catgtccatg   9420
tgggaaaaac tcaggtccaa ttatgagggg aagaagtcga gagtgtgcgg gtactgcggg   9480
gccccggccc cgtacgctac tgcctgtggc ctcgacgtct gcatttacca cacccacttc   9540
caccagcatt gtccagtcac aatctggtgt ggccatccag cgggtctgg ttcttgtagt     9600 gagtgcaaat cccctgtagg gaaaggcaca agcccttag acgaggtgct ggaacaagtc     9660
ccgtataagc ccccacggac cgttatcatg catgtggagc agggtctcac ccccttgat    9720 ccaggtagat accaaactcg ccgcggacta gtctctgtca ggcgtggaat taggggaaat   9780
gaagttgaac taccagacgg tgattatgct agcaccgcct tgctccctac ctgcaaagag   9840
atcaacatgg tcgctgtcgc ttccaatgta ctgcgcagca ggttcatcat cggcccaccc   9900
ggtgctggga aaacatactg gctccttcaa caggtccagg atggtgatgt tatttacaca   9960
ccaactcacc agaccatgct tgacatgatt agggctttgg ggacgtgccg gttcaacgtc  10020
ccggcaggca caacgctgca attccccgtc ccctcccgca ccggtccgtg ggttcgcatc  10080
ctagccggcg gttggtgtcc tggcaagaat tccttcctag atgaagcagc gtattgcaat  10140
caccttgatg tttgaggct tcttagtaaa actaccctca cctgtctagg agacttcaag  10200
caactccacc cagtgggttt tgattctcat tgctatgttt ttgacatcat gcctcaaact  10260
caactgaaga ccatctggag gtttggacag aatatctgtg atgccgttca gccagattac  10320
```

```
agggacaaac tcatgtccat ggtcaacaca acccgtgtga cctacgtgga aaaacctgtc   10380
aggtatgggc aggtcctcac cccctaccac agggaccgag aggacgacgc catcactatt   10440
gactccagtc aaggcgccac attcgatgtg gttacattgc atttgcccac taaagattca   10500
ctcaacaggc aaagagccct tgttgccatc accagggcaa gacacgctat ctttgtgtat   10560
gacccacaca ggcagctgca gggcttgttt gatcttcctg caaaaggcac acccgtcaac   10620
ctcgcagtgc accgcgacgg gcagctgatc gtgctggata gaaataacaa agaatgcacg   10680
gtcgctcagg ctctaggcaa cggggataaa tttagggcca cagataagcg tgttgtagat   10740
tctctccgcg ccatttgtgc tgatctagaa gggtcgagct ctccgctccc caaggtcgca   10800
cacaacttgg gattttattt ctcacctgat ttaacacagt ttgctaaact cccagtagaa   10860
cttgcacctc actgggccgt ggtgacaacc cagaacaatg aaaagtggcc agatcggctg   10920
gttgccagcc ttcgccctat ccataaatac agccgcgcgt gcatcggtgc cggctatatg   10980
gtgggcccct cggtgtttct aggcactcct ggggtcgtgt catactatct cacaaaattt   11040
gttaagggcg aggctcaatt gcttccggag acggttttca gcaccggccg aattgaggta   11100
gactgccggg aatatcttga tgatcgggag cgagaagttg ctgcgtccct cccacacgct   11160
ttcattggcg acgtcaaagg cactaccgtt ggaggatgtc atcatgtcac ctccagatac   11220
ctcccacgcg tccttcccaa ggaatcagtt gcggtagtcg gggtttcaag ccccggaaaa   11280
gccgcgaaag cattgtgcac actgacagat gtgtacctcc cagatcttga cgcctatctc   11340 caccccggaga cccagtccaa gtgctggaaa atgatgttgg acttcaaaga agttcgacta   11400
atggtctgga aagacaaaac agcctatttc caacttgaag gtcgctattt cacctggtat   11460
cagcttgcca gctatgcctc gtacatccgt gttcctgtca actctacggt gtacttggac   11520
ccctgcatgg gcccgccct  ttgcaacagg agagtcgtcg ggtccaccca ctgggggggct   11580 gacctcgcgg tcacccctta tgattacggc gctaaaatta tcctgtctag cgcgtaccat   11640
ggtgaaatgc ccccggata caaaattctg gcgtgcgcgg agttctcgtt ggatgaccca   11700
gttaagtaca acatacctg ggggtttgaa tcggatacag cgtatctgta tgagttcacc   11760
ggaaacggtg aggactggga ggattacaat gatgcgtttc gtgcgcgcca ggaagggaaa   11820
atttataagg ccactgccac cagcttgaag ttttattttc cccgggccc  tgtcattgaa   11880 ccaactttag gcctgaattg aaatgaaatg gggtccatgc aaagcctttt ttacaaaatt   11940
ggccaacttt ttgtggatgc tttcacggag ttcttggtgt ccattgttga tatcactata   12000
tttttggcca ttttgtttgg cttcaccatc gccggttggc tggtggtctt ttgcatcaga   12060 ttggttgct ccgcgatact ccgtacgcgc tctgccattc actctgagca attacagaag   12120
atcttatgag gcctttcttt cccagtgcca agtggacatt cccacctggg gaactaaaca   12180
tcctttgggg atgctttggc accataaggt gtcaaccctg attgatgaaa tggtgtcgcg   12240
tcgaatgtac cgcatcatgg aaaaagcagg gcaggctgcc tggaaacagg tggtgagcga   12300
ggctacgctg tctcgcatta gtagtttgga tgtggtggct cattttcagc atctagccgc   12360
cattgaagcc gagacctgta aatatttggc ctcccggctg cccatgctac acaacctgcg   12420
catgacaggt tcaaatgtaa ccatagtgta ataatagcact ttgaatcagg tgtttgctat   12480
ttttccaacc cctggttccc ggccaaagct taatgatttt cagcaatggt taatagctgt   12540
acattcctcc atattttcct ctgttgcaac ttcttgtact cttttgttg tgctgtggtt   12600 gcgggttcca atactacgta ctgctttggg tttccgctgg ttaggggcaa ttttttcttc   12660
gaactcacag tgaattacac ggtgtgtcca ccttgcctca cccggcaagc agccgcagag   12720
```

```
atctacgaac ccggtaggtc tctttggtgc aggatagggt atgaccgatg tgaggaggat   12780
gatcatgacg agctagggtt tatggtaccg cctggcctct ccagcgaagg ccacttgact   12840
agtgtttacg cctggttggc gttcttgtcc ttcagctaca cggcccagtt ccatcccgag   12900
atattcggga tagggaatgt gagtcgagtt tatgttgaca tcaaacatca actcatctgc   12960
gccgaacatg acgggcagaa caccaccttg cctcgtcatg acaacatttc agccgtgttt   13020
cagacctatt accaacatca agtcgacggc ggcaattggt ttcacctaga atggcttcgt   13080
cccttctttt cctcgtggtt ggttttaaat gtctcttggt ttctcaggcg ttcgcctgca   13140
aaccatgttt cagttcgagt cttgcagata ttaagaccaa caccaccgca gcggcaagct   13200
ttgctgtcct ccaagacatc agttgcctta ggcatcgcga ctcggcctct gaggcgattc   13260
gcaaaatccc tcagtgccgt acggcgatag ggacacccgt gtatgttacc atcacagcca   13320
atgtgacaga tgagaattat ttacattctt ctgatctcct catgctttct tcttgccttt   13380
tctatgcttc tgagatgagt gaaaagggat ttaaggtggg atttggcaat gtgtcaggca   13440
tcgtggctgt gtgtgtcaat tttaccagct acgtccaaca tgtcaaggag tttacccaac   13500
gctccctggt ggtcgaccat gtgcggttgc tccatttcat gacacctgag accatgaggt   13560
gggcaactgt tttagcctgt cttttttgcca ttctgttggc aatttgaatg tttaagtatg   13620
ttggagaaat gcttgaccgc gggctgttac tcgcaattgc tttctttgtg gtgtatcgtg   13680
ccgttctgtt ttgctgtgct cgtcaacgcc agcaacgaca gcagctccca tctacagctg   13740
atttacaact tgacgctatg tgagctgaat ggcacagatt ggctagctaa caaatttgat   13800
tgggcagtgg agagttttgt catctttccc gttttgactc acattgtctc ctatggtgcc   13860
ctcactacta gccatttcct tgacacagtc gctttagtca ctgtgtctac cgccgggttt   13920
gttcacgggc ggtatgtcct aagtagcatc tacgcggtct gtgccctggc tgcgttgact   13980
tgcttcgtca ttaggtttgc aaagaattgc atgtcctggc gctacgcgtg taccagatat   14040
accaactttc ttctggacac taagggcaga ctctatcgtt ggcggtcgcc tgtcatcata   14100
gagaaagggg gcaaagttga ggtcgaaggt catctgatcg acctcaaaag agttgtgctt   14160
gatggttccg tggcaacccc tataaccaga gtttcagcgg aacaatgggg tcgtccttag   14220
atgacttctg tcatgatagc acggctccac aaaaggtgct tttggcgttt tctattacct   14280
acacgccagt gatgatatat gccctaaagg tgagtcgcgg ccgactgcta gggcttctgc   14340 acctttgat cttcctgaat tgtgctttca ccttcgggta catgactttc gcgcactttc   14400
agagtacaaa taaggtcgcg ctcactatgg gagcagtagt tgcactcctt tggggggtgt   14460
actcagccat agaaacctgg aaattcatca cctccagatg ccgtttgtgc ttgctaggcc   14520
gcaagtacat tctggcccct gcccaccacg ttgaaagtgc cgcaggcttt catccgattg   14580
cggcaaatga taaccacgca tttgtcgtcc ggcgtcccgg ctccactacg gtcaacggca   14640
cattggtgcc cggttaaaaa agcctcgtgt tgggtggcag aaaagctgtt aaacaggag   14700 tggtaaacct tgtcaaatat gccaaataac aacggcaagc agcagaatag aaagaagggg   14760
gatggccagc cagtcaatca gctgtgccag atgctgggta agatcatcgc tcagcaaaac   14820
cagtccagag gcaagggacc gggaaagaaa aataagaaga aaacccggaa gagcccccat   14880
tttcctctag cgactgaaga tgatgtcaga catcacttta cccctagtga gcggcaattg   14940
tgtctgtcgt caatccagac cgcctttaat caaggcgctg ggacttgcac cctgtcagat   15000
tcagggagga taagttacac tgtggagttt agtttgccta cgcatcatac tgtgcgcctg   15060
```

```
attcgcgtca cagcatcacc ctcagcatga tgggctggca ttcttgaggc atctcagtgt    15120
ttgaattgga agaatgtgtg gtgaatggca ctgattgaca ttgtgcctct aagcactata    15180
tt                                                                  15182
```

<210> SEQ ID NO 43
<211> LENGTH: 183
<212> TYPE: PRT
<213> ORGANISM: Porcine reproductive and respiratory syndrome virus

<400> SEQUENCE: 43

```
Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Asn Cys Phe Arg Pro His Gly Val Ser Ala Ala Gln Glu Lys
    50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180
```

<210> SEQ ID NO 44
<211> LENGTH: 178
<212> TYPE: PRT
<213> ORGANISM: Porcine reproductive and respiratory syndrome virus

<400> SEQUENCE: 44

```
Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Leu Ala
            20                  25                  30

Asp Ile Lys Thr Asn Thr Thr Ala Ala Ala Ser Phe Ala Val Leu Gln
        35                  40                  45

Asp Ile Ser Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Val Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110
```

```
Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 45
<211> LENGTH: 14622
<212> TYPE: DNA
<213> ORGANISM: Porcine reproductive and respiratory syndrome virus

<400> SEQUENCE: 45
```

| | | | | |
|---|---|---|---|---|
| atgtctggga tgttctcccg gtgcatgtgc accccggctg cccgggtatt ttggaacgcc | 60 |
| ggccaagtct attgcacacg tgtctcagt gcacggtctc ttctctctcc agaacttcag | 120 |
| gacacggacc tcggtgcagt tggcttgttt cacaagccta agacaagct ccattggaaa | 180 |
| gttcccattg gtatccccca ggtggaatgt tctccatctg gtgttgctg gctgtcaacc | 240 |
| atttttcctt tagcgcgcat gacctccggc aatcacaact tccttcaacg actcgtgaag | 300 |
| gttgctgatg tattgtaccg tgacggttgc ttaaccccta gacacctccg tgaactccaa | 360 |
| gtttacgagc gtggttgcaa ttggtatccg attacggggc ctgtgcctgg atggctgtg | 420 |
| tacgcgaact ccatgcacgt gtccgaccaa ccgttcctg tgccactca tgtgttaaca | 480 |
| aattccctt tgcctcaacg ggcttgtcgg cagccgttct gtccgttcga gaggcccat | 540 |
| tctagcatat acaggtggga aaaatttgta atttttatgg attcctcctc cgacggtcga | 600 |
| tctcgcatga tgtggactcc ggaatccgat gactccacgg ctttggaagt tctgccgccc | 660 |
| gagctagaac accaggtcaa ggtccttgtt cggagctttc ccgcccatca ccttgtcgac | 720 |
| cttgccgatt gggagctcac tgagtcccct gataacggtt tttccttcag cacgtcacat | 780 |
| ccttgcggct accttgttcg ggacccggct gtatccgaag caagtgttg ctttcctgc | 840 |
| tttttgagcc agtcagccga agtgctcagt cgcgaggcgc atctggctac cgcctatggt | 900 |
| taccaaacca gtgggggtgt gcctggcaag tacatccagc gcagacttca gttcacggt | 960 |
| ctccgtgctg tggtcgaccc tgatggtccc attcacgttg aagcattgtc ttgccccag | 1020 |
| tcttggatca ggcacttgac cctgaatgat gatgtcaccc cgggattcgt tcgcctaatg | 1080 |
| tctcttcgca ttgtgccgaa cacagagcct accacacacc ggatctttcg ttttggagtg | 1140 |
| cacaagtggt atggtgccgc cggcaaacgg gccgtggca agcgtgccgc caaaagtgag | 1200 |
| aaagactcgg cttccaccct caaggttgcc cgaccgactt ccaccagtgg aatcgtcacc | 1260 |
| tactccccac ctgcggacgg tcttgtggt tggcatgccc ttgccgccat actgaaccgg | 1320 |
| atgattaata tgacttcac gtcccctctg cctcggtaca caggccgga ggacgattgg | 1380 |
| gcttctgatg gtgaccttgc tcaggccatt caatgtttgc aactacctgc cgccatagct | 1440 |
| cggaaccgcg cctgccctaa cgccaaatac ctcataaaac tcaacggagt tcattgggag | 1500 |
| gtagaggtga ggcctggaat ggctcctcgc tccctctctc gtgagtgcgt tgttggcgtc | 1560 |
| tgctctgaag gctgtgtcgc gtcgccttac ccggaggacg ggttgcctaa cgtgcactt | 1620 |
| gaggccctgg cgtctgctta tagactgcct tcagactgtg tttgtgatgg tattattgac | 1680 |
| ttccttgcca atccacctcc ccaggagttc tggactcttg acaaaatgtt gacttccccg | 1740 |

```
tcaccggagc agtccggctt ctctagtctg tataaattgt tgttagagat cttgccgcag  1800
aaatgcggat ccacagaagg ggaattcatc tatactgttg agaggatgtt gaaggattgt  1860
ccgagctcca aacaggccat ggccctcctt gcaaaaatta aggtcccatc ctcaaaggcc  1920
ccatccgtga ctctgaacga gtgcttcccc acgatgttc cagtcaactc tgagttaata  1980
tcttgggaag agcccaaaga ccctggcgct gctgttgtcc tatgtccatc ggatgcaaaa  2040
gaatctaagg aaacagcccc tgaagaagct caagcgagaa accgtaaggt ccttcaccct  2100
gtggtcctta ccgaggaact tagcgagcaa caggtgcagg tggttgaggg tgatcaggat  2160
atgccactgg atttgacttg gccaacctta accgctacgg cgaccctgt tagagggccg  2220 gtaccggaca atttgagctc tggcattggt gcccagcccg ctaccgttca agaactcatt  2280
ctggcgaggc ctgcacccg tcttgttgag cgctgtggca cggagtcgaa cggcagcagt  2340
tcatttctgg atttgcctga cgtgcagacc tcggaccagc ctttagacct gtccctggcc  2400
gcgtggcctg taagggctac cgcgtctgac cccggttgga tccacggtag gcgtgagcct  2460
gtctttgtga agcctcgagg tgttttctct gatggcgagt cggcccttca gttcggagag  2520 cttccgaag ccagttctgt cgtcgatgac cggacaaaag aagctccggt ggttgacgcc  2580
cccatcgatt tgacaacttc gaacgagacg ctctctgggt ctgacccctt tgaattcgcc  2640
aaattcaggc gcccgcgttt ctccgcgcaa gctttaatcg accgaggtgg tccgcttgcc  2700
gatgttcatg caaagataaa gagtcgggta tatgaacaat gccttcaagc ttgtgaacct  2760
ggtagtcgtg cgaccccagc caccaagaag tggctcgaca aaatgtggga cagggtggac  2820
atgaaaactt ggcgctgcac ctcgcagttc caagctggtc acattcttga gtccctcaaa  2880
ttcctccctg acatgattca agacacaccg cctcctgttc caggaagaa ccgagctggt  2940 gacagtgccg gcctgaagca actggtggcg cagtgggata ggaaatcgag tgtgacaccc  3000
cccacaaaac cggttggacc ggtgcttgac caggccgtcc ctctgcctat ggacatccag  3060
caaggagatg ccatctccgc tgacaagcca ccccattcgc aaaacccttc tagtcaagta  3120
gatgtgggtg gaggttggaa aagttttatg ctctccggca cccgtttcgc ggggtccgtt  3180
agtcagcgcc ttacgacatg ggttttgag ttctctcccc atctcccagc ttttatgctc  3240
acacttttct cgccacgggg ctctatggct ccaggtgatt ggctgtttgc aggtgctgtt  3300
ctacttgctc tcctgctctg ccgttcttac ccaatactcg gatgccttcc cttattgggt  3360
gtcttttctg gttctgtgcg gtgtgttcgt ttgggtgttt ttggttcttg gatggctttt  3420
gctgtatttt tattctcgac tccacccgac ccagtcggtt cttcttgtga ccacgattcg  3480
ccggagtgtc atgctgagct tttggctctt gagcagcgcc aactttggga acctgtgcgc  3540
agccttgtgg tcgggccatc gggcctctta tgcgtcattc ttggcaagtt actcggtggg  3600
tcacgttgtc tctggtttgt tctcctacgt atatgcatgc tcgcagattt ggcaatttct  3660
cttatttatg tggtgtccca agggcgttgt cacaagtgtt ggggaaagtg tataaggacg  3720
gctcctgcag aagtggccct taatgtgttt cctttttcgc gcgccacccg ctcatctctt  3780
gtgtccttgt gtgatcggtt ccaagcgcca aaaggagttg accccgtgca cttggcgaca  3840
ggctggcgcg ggtgctggtg tggtgagagc cctattcatc aatcacacca aaaccgata  3900 gcttatgcca acttggatga aaagaagata tccgcccaga cggtgattgc tgtcccgtat  3960
gatcctagtc aggccattaa atgcctgaaa gttttgcagg caggagggc tattgtggac  4020 cagcctacgc ccgaggtcgt ccgtgtgtct gagattccct tctcggcccc atttttccg  4080
```

```
aaggtcccag tcaacccaga ctgcagggtt gtggtagatt cggacacttt tgtggctgcg    4140
gtccgctgcg gttattcgac agcacaactg gtccttggtc ggggcaactt tgccaagcta    4200
aatcagaccc ccctcaggaa ctctgtcccc accaaaacaa ctggtggggc ctcatacacc    4260
cttgccgtgg cccaggtatc tgtgtggact cttgttcatt tcatcctcgg cctttggtta    4320
acgtcacctc aagtgtgtgg tcgagggacc tctgacccgt ggtgttcgaa cccttttttcg   4380 tatcctactt atggcccccgg agttgtgtgt tcctctcgac tctgcgtgtc tgccgacgga   4440
gttaccctgc cattgttctc agccgttgcc catctttccg gtagagaggt ggggattttt    4500
attttggtgc ttgcctcctt gggcgcttta gcccaccgct tggctcttaa ggcagacatg    4560
tcaatggtct ttttggcgtt ttgtgcttac gcctggccca tgagctcctg gttaatttgc    4620
ttctttccta tgctcttgag gtgggtaacc cttcatcctc tcactatgct ttgggtgcac    4680 tcattttttgg tgttttgcct accagctgcc ggcgttctct cgctgggaat aaccggtctt   4740
ctttgggcag ttggccgttt cacccaggtt gccggaatta tcacacctta tgacatccac    4800
cagtatacct ccggaccacg tggtgcagct gctgtagcaa cggctccaga aggtacttac    4860
atggcggccg ttcggagagc cgcttttgact ggacggactt tgatcttcac accatctgca   4920
gtcggatccc ttcttgaagg tgcttttcaga actcaaaagc cctgccttaa caccgtgaat   4980
gtcgtaggct cttcccttgg ttctggagga gttttcacca ttgatggcag aagagtcatc    5040
gtcactgcca cccatgtgtt gaatggtaac acagccaggg tcactggtga ttcctacaac    5100
cgcatgcaca cgttcaatac taatggtgat tatgcctggt cccatgctga tgactggcaa    5160
ggcgttgccc ctatggttaa gatcgctaag gggtatcgcg tcgtgcccta ctggcaaacg    5220
tcaaccggag tcgaacctgg catcatgggg gaaggattcg ccttctgttt cactaactgt    5280
ggcgactcag ggtcacctgt catttcagaa gctggtgacc ttattggagt ccataccggt    5340
tcaaacaaac tcggttctgg tcttgtgaca accccctgaag gggagacctg ctccatcaag   5400
gaaactaggc tctctgacct ttctagacat tttgcaggtc caagcgtccc tcttggggac    5460
attaagttga gcccagccat catccctgat gtgacaacta ttccgagtga cttggcatcg    5520
ctccttgctt ctgtccccgt gatggaaggt ggcctctcaa ctgtccagct tttgtgcgtc    5580 ttttttccttc tctggcgcat gatgggccat gcctggacac ccattgttgc cgtaggcttc    5640 ttttttgctga atgaaattct cccagcagtc ttggtccgag ctgtgttctc ttttgcactc   5700
tttgtacttg catgggccac cccctggtcg gcacaagtgt tgatgattag actcctcacg    5760
gcggctctca accgcaacag gttgtccctg gcgttctacg cattcggagg tgtcgttggc    5820
ctggccacag aaatcgggac ttttgctggt ggatggcctg aactgtccca gccctctcg    5880 acatactgct tcctgcccag gttccttgct gtgactagtt atgtccccac catcatcatc    5940
ggtgggctcc atgccctcgg cgtaattttg tggttattca ataccgatg cctccacaac    6000 atgctggttg gtgatgggag tttctcaagc gctttcttcc tacggtattt tgctgagggt    6060
aatcttagga aaggcgtgtc gcagtcctgt ggcatgaata acgaatccct gacagctgct    6120
ttggcttgca agttgtcgca agctgacctt gattttttgt ccagtttaac gaacttcaag    6180
tgctttgtgt ccgcttcaaa catgaaaaat gcagctggcc aatacatcga ggcggcgtat    6240
gctagagctc tgcgtcagga gctggcctcc ttggttcagg ttgacaagat gaaaggagta    6300
ttggccaagc tcgaggcttt cgctgagacg gccactccgt cacttgacac aggggacgtg    6360
attgttctgc ttgggcaaca ccccatgga tccatcctcg acattaatgt ggggggtgaa    6420
aggaaaactg tgtctgtgca agaaacacga tgcctgggtg gttccaaatt cagtgtctgc    6480
```

```
actgtcgtgt ccaacacgcc cgtggatacc ttgaccggta tcccacttca gacgccaacc   6540
ccactttttg aaaatggccc gcgccatcgc agcgaggacg acgacctcaa agttgagaga   6600
atgaaaaaac actgtgtatc cctcggcttc cacaaaatca atggtaaagt ttactgcaaa   6660
atttgggaca agtctaacgg cgacaccttt tacacggatg attcccgata cactcaagac   6720
catgcttttc aggacaggtc aaccgactat agagacaggg attatgaagg tgtacagacc   6780
gccccccaac agggattcga tccaaagtcc gaagccctg ttggcactgt tgtaatcggt     6840
ggcattacgt ataacaggca tctggtcaaa ggtaaggagg tcctagttcc caaacctgac   6900
aactgccttg aagctgccag actgtccctt gagcaagctc ttgctgggat gggccaaact   6960
tgtgacctta cagctaccga agtggagaaa ctaaagcgca tcattagtca actccaaggt   7020
ctgaccactg aacaggcttt aaactgctag ccgccagcgg cttgaccgc tgtggccgcg    7080 gcggcctagt tgtaactgaa acggcggtaa aaatcgtaaa ataccacagc agaactttca   7140
ccttaggctc tttagaccta aaagtcacct ccgaggtgga ggtgaagaaa tcaactgagc   7200
aggggcacgc tgtcgtggcg aacttatgtt ccggtgtcgt cttgatgagg cctcacccac   7260
cgtcccttgt tgacgttctc ctcaaacccg gacttgacac aacacccggc attcaaccag   7320
ggcatggggc cgggaatatg ggcgtgaacg ttctatttg ggatttttgaa actgcaccca    7380 caaaggtaga actagagttg tccaagcaaa taatccaagc atgtgaagtc aggcgcgggg   7440
acgcccctaa cctccaactc cctacaagc tttatcctgt caggggggac cccgagcggc    7500
gtaaaggtcg ccttgtcaac actaggtttg gagatttacc ttacaaaact ccccaagaca   7560
ccaagtccgc aattcatgcg gcttgttgcc tgcatcccaa tggggtcctc gtgtctgatg   7620
gcaaatccac gctgggtacc actcttcaac atggtttcga gctttatgtc cccactgtac   7680
cttatagtgt catggaatac cttgattcac gccctgacac ccctttatg tgtactaaac    7740 atggcacttc caaggctgct gcagaggacc tccaaaaata tgacctatcc actcaagggt   7800
ttgtcttgcc tgggggtccta cgcctagtgc gcaggttcat ctttagccat gttggtaagg   7860
cgccaccact gttccttcca tcaacctacc ctgccaagaa ctccatggca ggggtcaatg   7920
gccagaggtt cccaacaaag gatgtccaga gcatacctga aattgatgaa atgtgcgccc   7980
gtgccgtcaa ggaaaattgg cagactgtga caccttgcac cctcaaaaaa cagtactgtt   8040
ccaaacctaa aactagaacc atcctaggta ccaacaactt catagccttg gctcacaggt   8100
cagcactcag tggtgtcacc caggcgttca tgaagaaggc ctggaagtcc ccaattgcct   8160
tggggaaaaa caagtttaag gaattgcatt gcactgtcgc cggcagatgc cttgaggctg   8220
acctggcttc ctgcgatcgc agcacccccg ccattgtgag gtggtttgtt gccaacctcc   8280
tgtatgaact tgcaggatgt gaagagtact tgcctagcta cgtgctcaac tgttgccatg   8340
accttgtggc aacgcaggat ggcgctttca caaaacgcgg tggcctgtcg tccggggacc   8400
ccgtcaccag tgtgtccaac accgtctact cactgataat ttacgcccag cacatggtgc   8460
tttcggcctt gaagatgggt catgaaattg gtctcaagtt ccttgaggaa cagctcaaat   8520
ttgaggacct tcttgaaatc cagcccatgt tagtgtattc tgatgacctc gtcttgtatg   8580
cggaaagacc cacttttccc aactaccatt ggtgggtcga gcatcttgac ctgatgttgg   8640 gcttttaaaac ggacccaaag aaaactgtca taactgataa acccagtttt ctcggctgca   8700
gaattgaagc aggacggcag ttagtcccca atcgcgaccg tattctggct gctcttgcat   8760
atcatatgaa ggcgcagaac gcctcagagt attatgcgtc cgctgccgca attctgatgg   8820
```

```
attcgtgtgc ttgcattgac catgaccccg agtggtatga ggatcttatc tgcggcatcg    8880
cccggtgtgc tcgccaggac ggttaccgtt ttccaggccc ggcatttttc atgtccatgt    8940
gggagaagct gaaaagtcat aatgaaggga agaaatgccg tcactgcggc atctgcgacg    9000
ccaaagccga ctatgcgtcc gcctgtggac ttgatttgtg tttgttccat tcacactttc    9060
atcaacactg cccagtcact ctgagctgtg ccaccatgc cggttcaaag gaatgttcgc     9120
agtgtcagtc acctgtcggg gctggcaaat ccccccttga cgctgtgctg aaacaaatcc    9180
cgtacaaacc tcctcgtacc attatcatga aggtggacaa caaaacaacg acccttgacc    9240
cgggaagata tcagtcccgt cgaggtcttg ttgcagtcaa aagaggtatt gcaggtaatg    9300
aggttgatct ttctgatgga gactaccaag tggtgcctct tttgccgact tgcaaagaca    9360
taaacatggt gaaggtggct tgcaacgtac tactcagcaa gtttatagta gggccgccag    9420
gttccggaaa aaccacctgg ctactgaacc aagtccagga cgatgatgtc atttacacac    9480
ctactcatca gacaatgttt gacatagtca gtgctcttaa agtttgcagg tattccatcc    9540
caggagcctc aggactccct tttccaccac ctgccaggtc cgggccgtgg gttaggctca    9600
tcgccagcgg acatgtccct ggccgagtgt catatctcga tgaggcagga tattgcaatc    9660
atctagacat tctaaggctg ctttccaaaa caccccttgt gtgtttgggt gaccttcagc    9720
aacttcaccc ggtcggcttt gattcctatt gttatgtgtt cgatcagatg cctcagaagc    9780
agctgaccac catttataga tttggcccta acatctgtgc agccatccag ccttgttaca    9840
gggagaaact tgaatccaag gccaggaaca ccagagtggt tttcaccacc ggcctgtgg    9900
cctttggtca ggtcctgaca ccgtaccaca agatcgtac cggctctgca ataactatag     9960
attcatccca gggggcgacc ttcgacattg tgacattgca tctaccatcg ccaaagtccc   10020
taaacaaatc ccgagcactt gtagccatca ctcgggcaag acatgggttg ttcatttatg   10080
accctcatga ccaactccag gagttttttca acttaacccc cgagcgcact gattgtaacc   10140
ttgcgttcag ccgtggggat gagctggttg ttttgaatgt ggataatgcg gtcacaactg   10200
tagcgaaggc cctagagaca ggttcacccc gatttcgagt atcggacccg aggtgcaagt   10260
ctctcttagc cgcttgttcg gccagtctag aagggagctg catgccacta ccacaagtag   10320
cacataacct ggggttttac ttttcccccgg acagcccagc ttttgcaccc ctgccaaaag   10380
agctggcgcc acattggcca gtggtcaccc accagaataa tcgagcgtgg cctgatcgac   10440
ttgtcgctag tatgcgccca attgatgccc gctacagcaa gccaatggtc ggtgcagggt   10500
atgtggtcgg gccatccatt tttcttggca ctcctggtgt ggtgtcatac tatctcacat   10560
tatacatcgg gggcgagcct caggccctgc cagaaacact cgtttcaaca ggacgtatag   10620
ccacagattg tcgggaatat ctcgacgcgg ctgaggaaga ggcagcgaga gaacttcccc   10680
acgcatttat tggcgatgtc aaaggcacta cgatcggggg gtgtcaccac attacatcga   10740
aataccttacc taggtccctg cctaaagact ctgttgctgt ggttggggtg agttcgcccg   10800
gtagggctgc taaagccgtg tgcactctca ccgatgtgta cctccccgaa ctccgaccat   10860
atttgcaacc ggagacggca tcaaaatgct ggaaacttaa actggatttc agggatgttc   10920
gactgatggt ctgaaaggc gccacagcct atttccagtt ggaagggctg acatggtcag   10980
cgctgcccga ttatgctagg ttcattcagc tacccaagga tgccgttgtg tacatcgatc   11040
cgtgtatagg gccggcaaca gccaatcgca aggttgtgcg aaccacagac tggcgggccg   11100
acctggcagt gacaccgtat gattacgtgt ctcaggtcat tttgacaaca gcctggttcg   11160
aggaccttgg gccgcagtgg aagatttggg ggttgcagcc tttcagacga acatttggct   11220
```

```
ttgagaacac tgaagattgg gcaattctcg cacgccgtat gaatgacggc aaagattaca  11280
ctgactataa ttggcattgt gtacgagaac gcccacacgc aatttacggg cgcgcccgtg  11340
accatacgta tcattttgcc cttggcactg aactgcaagt agagctgggc agaccccggc  11400
tgcctcctga gcaagtgccg tgaacgcgga gtgatgcaat gggtttactg tggagtaaaa  11460
tcagtcagtt gttcgtggat gccttcactg agttccttgt tagtgtggtt gacattgtca  11520
tctttctcgc catattgttt gggttcactg ttgcaggctg ttattggtc ttccttctca  11580 gagtggtttg ctccgcgttt ctccgttcgc gctctgccat tcactcttcc gaactatcga  11640
aggtcctatg agggcttgct acccaactgc agaccggatg tcccacaatt cgcagttaag  11700
cacccgttgg gtatactttg gcatatgcga gtctcccacc taattgacga aatggtctct  11760
cgccgcattt accggaccat ggaacattcg ggtcaagcgg cctggaagca ggttgttagt  11820
gaagccactc tcacaaaact gtcaaggctt gacgtagtca ctcatttcca cacctggcc   11880 gcagtggagg ctgattcttg ccgcttcctt agctcacgac tcgcgatgct gaaaaacctt  11940
gccgttggca atgtgagcct ggagtacaac actactttgg accgcgttga gctcatcttt  12000
cccacaccag gtacgaggcc caagttgacc gattttaggc aatggcttat cagcgtgcac  12060
gcttccatct tctcctctgt ggcttcgtct gttaccttgt tcacagtgct ttggcttcga  12120
attccagctc tacgctatgt ttttggtttc cattggccca cggcaacaca tcattcgaac  12180
taactatcaa ttacactata tgtaagccat gccctaccag tcaagctgcc caacaaagac  12240
tcgagcctgg ccgtaacgtg tggtgcaaaa tagggcacga caggtgtgag gaacgtgacc  12300
atgatgagtt gtcaatgtcc attccgtccg ggtacgacaa cctcaaactt gagggttatt  12360
atgcttggct ggcttttttg tccttttcct acgcggccca attccatccg gagctgttcg  12420
gaataggaaa cgtgtcgcgc gtctttgtgg ataagcgaca ccagttcatt tgcgccgagc  12480
atgatgagga aaattcaacc atatctgcca gacacaacat ctccgcgtcg tatgcggtgt  12540
attaccatca tcaaatagac gggggcaatt ggtttcattt ggaatggctg cgaccattct  12600
tttcctcctg gctggtgctc aacatctcat ggtttctgag gcgttcgcct gcaagccctg  12660
cttctcgacg catctatcag atattaagac caacacgacc gcggctgccg gtttcatggt  12720
ccttcagaac atcaattgtt tccaatctca cagggcctca acagcgcaag gtaccactcc  12780
cctcaggagg tcgtcccaat gtcgtgaagc cgtcggcatt ccccagtaca tcacgataac  12840
ggctaatgtg accgatgaat cgtatttgta caacgcggac ttgctgatgc tttccgcgtg  12900
ccttttctac gcctcggaaa tgagcgagaa aggcttcaaa gtcatctttg gaatatttc   12960 tggcgttgtt ccgcttgtg ttaatttcac agattatgtg gcccatgtga cccaacacac   13020
tcagcagcac catttggtaa ttgatcacat tcggttacta cacttcttga caccgtctac  13080
gatgaggtgg gctacaacca ttgcttgttt gcttgccatt cttttggcgg tatgaaatgt  13140
tcttgcaagt tgggcatttt cttgactcct cactcttgct tctggtggct ttttttgctg  13200
tgtaccggct tgtcttggtc ctttgtcgat ggcaacgacg acagctcgac atcccaatac  13260
atatataatt tgacgatatg cgagctgaat gggaccgaat ggttgtccgg tcattttgat  13320
tgggcagtcg aaacctttgt gctttaccca gttgccactc atatcatttc actgggtttt  13380
ctcacaacaa gccatttcct tgatgcgctc ggtctcggcg ctgtgtccgc cacaggattc  13440 attgcgagc ggtatgtact tagcagcatg tacggcgttt gcgccttcgc ggcgttcgta  13500
tgttttgtca tccgtgctgc taaaaattgc atggcttgcc gctatgcccg cacccggttt  13560
```

```
accaacttca tcgtggacga ccggggaaga atccatcgat ggaagtcttc aatagtggtg    13620
gagaaattgg gcaaagctga agtcggtggt gaccttgtca acattaagca tgttgtcctc    13680 gaagggtta aagctcaacc tttgacgagg acttcggctg agcaatggga agcctagacg    13740
acttttgcaa cgatcccacc gccgcacaaa aactcgtgct ggcctttagc atcacatata    13800
cacccataat gatatacgcc cttaaggtgt cacgcggccg actcctgggg ctgttgcaca    13860
tcttgatatt tctgaattgt tcctttactt ttgggtacat gacatatgtg cattttcaat    13920
ccaccaaccg tgtcgcattc actctggggg ctgtagtcgc ccttttgtgg ggtgtttaca    13980
gcctcacaga gtcatggaag ttcatcactt ccagatgcag attgtgttgc ctaggccggc    14040
gatacattct ggcccctgcc catcacgtag aaagtgctgc aggcctccat tcaatcccag    14100
cgtctggtaa ccgagcatac gctgtgagaa agcccggact aacatcagtg aacggcactc    14160
tagtacctgg gcttcggagc ctcgtgctgg gcggcaaacg agctgttaaa cgaggagtgg    14220
ttaacctcgt caagtatggc cggtaagaac cagagccaga agaaaagaag aaatgcagct    14280
ccgatgggga aaggccagcc agtcaatcaa ctgtgccagt tgctgggtac aatgataaag    14340
tcccagcgcc agcaatctag gggaggacag gccaaaaaga gaagcctga gaagccacat    14400 tttcccctag ctgctgaaga tgacattcgg caccatctca cccaggccga acgttccctc    14460
tgcttgcaat cgatccagac ggcttcaat caaggcgcag gaactgcgtc gctttcatcc    14520
agcgggaagg tcagttttca ggttgagttc atgctgccgg ttgctcatac agtgcgcctg    14580
attcgcgtga cttctacatc cgccagtcag ggtgcaaatt aa                      14622
```

<210> SEQ ID NO 46
<211> LENGTH: 221
<212> TYPE: DNA
<213> ORGANISM: Porcine reproductive and respiratory syndrome virus

<400> SEQUENCE: 46

```
atgatgtgta gggtattccc cctacataca cgacactctt agtgtttgtg taccttggag    60
gcgtgggtac agccctgccc cacccttggg tccctgttct agcccgacag gtacccttct   120
ctctcggggc gagcgcgccg cctgctgctc ccttgcggcg ggaaggacct cccgagtatt   180
tccggagagc acctgcttta cgggatctcc gcccttttaac c                      221
```

<210> SEQ ID NO 47
<211> LENGTH: 114
<212> TYPE: DNA
<213> ORGANISM: Porcine reproductive and respiratory syndrome virus

<400> SEQUENCE: 47

```
tttgacagtc aggtgaatgg ccgcgattga cgtgtggcct ctaagtcacc tattcaatta    60
gggcgatcac atgggggtca aacttaatta ggcaggaacc atgtgaccga aatt         114
```

<210> SEQ ID NO 48
<211> LENGTH: 14984
<212> TYPE: DNA
<213> ORGANISM: Porcine reproductive and respiratory syndrome virus

<400> SEQUENCE: 48

```
atgatgtgta gggtattccc cctacataca cgacactctt agtgtttgtg taccttggag    60
gcgtgggtac agccctgccc cacccttggg tccctgttct agcccgacag gtacccttct   120
ctctcggggc gagcgcgccg cctgctgctc ccttgcggcg ggaaggacct cccgagtatt   180
tccggagagc acctgcttta cgggatctcc gcccttttaac catgtctggg atgttctccc   240
```

```
ggtgcatgtg caccccggct gcccgggtat tttggaacgc cggccaagtc tattgcacac      300
ggtgtctcag tgcacggtct cttctctctc cagaacttca ggacacggac ctcggtgcag      360
ttggcttgtt tcacaagcct aaagacaagc tccattggaa agttcccatt ggtatccccc      420
aggtggaatg ttctccatct gggtgttgct ggctgtcaac cattttttcct ttagcgcgca     480 tgacctccgg caatcacaac ttccttcaac gactcgtgaa ggttgctgat gtattgtacc      540
gtgacggttg cttaacccct agacacctcc gtgaactcca agtttacgag cgtggttgca      600
attggtatcc gattacgggg cctgtgcctg ggatggctgt gtacgcgaac tccatgcacg      660
tgtccgacca accgttccct ggtgccactc atgtgttaac aaattcccct ttgcctcaac      720
gggcttgtcg gcagccgttc tgtccgttcg aagaggccca ttctagcata tacaggtggg      780
aaaaatttgt aattttatg gattcctcct ccgacggtcg atctcgcatg atgtggactc       840
cggaatccga tgactccacg gctttggaag ttctgccgcc cgagctagaa caccaggtca      900
aggtccttgt tcggagcttt cccgcccatc accttgtcga ccttgccgat gggagctca      960 ctgagtcccc tgataacggt ttttccttca gcacgtcaca tccttgcggc taccttgttc     1020
gggacccggc tgtatccgaa ggcaagtgtt ggctttcctg cttttttgagc cagtcagccg    1080 aagtgctcag tcgcgaggcg catctggcta ccgcctatgg ttaccaaacc aagtggggtg    1140
tgcctggcaa gtacatccag cgcagacttc aagttcacgg tctccgtgct gtggtcgacc    1200
ctgatggtcc cattcacgtt gaagcattgt cttgccccca gtcttggatc aggcacttga    1260
ccctgaatga tgatgtcacc ccgggattcg ttcgcctaat gtctcttcgc attgtgccga    1320
acacagagcc taccacacac cggatctttc gttttggagt gcacaagtgg tatggtgccg    1380
ccggcaaacg ggcccgtggc aagcgtgccg ccaaaagtga aaagactcg gcttccaccc    1440 tcaaggttgc ccgaccgact tccaccagtg gaatcgtcac ctactcccca cctgcggacg    1500
ggtcttgtgg ttggcatgcc cttgccgcca tactgaaccg gatgattaat aatgacttca    1560
cgtcccctct gcctcggtac aacaggccgg aggacgattg ggcttctgat ggtgaccttg    1620
ctcaggccat tcaatgtttg caactacctg ccgccatagc tcggaaccgc gcctgccta    1680 acgccaaata cctcataaaa ctcaacggag ttcattggga ggtagaggtg aggcctggaa    1740
tggctcctcg ctccctctct cgtgagtgcg ttgttggcgt ctgctctgaa ggctgtgtcg    1800
cgtcgcctta cccggaggac gggttgccta aacgtgcact tgaggcctg gcgtctgctt    1860 atagactgcc ttcagactgt gtttgtgatg gtattattga cttccttgcc aatccacctc    1920
cccaggagtt ctggactctt gacaaaatgt tgacttcccc gtcaccggag cagtccggct    1980
tctctagtct gtataaattg ttgttagaga tcttgccgca gaaatgcgga tccacagaag    2040
gggaattcat ctatactgtt gagaggatgt tgaaggattg tccgagctcc aaacaggcca    2100
tggccctcct tgcaaaaatt aaggtcccat cctcaaaggc cccatccgtg actctgaacg    2160
agtgcttccc cacggatgtt ccagtcaact ctgagttaat atcttgggaa gagcccaaag    2220
accctggcgc tgctgttgtc ctatgtccat cggatgcaaa agaatctaag gaaacagccc    2280
ctgaagaagc tcaagcgaga aaccgtaagg tccttcaccc tgtggtcctt accgaggaac    2340
ttagcgagca acaggtgcag gtggttgagg gtgatcagga tatgccactg gatttgactt    2400
ggccaacctt aaccgctacg gcgacccctg ttagagggcc ggtaccggac aatttgagct    2460
ctggcattgg tgcccagccc gctaccgttc aagaactcat tctggcgagg cctgcaccc     2520 gtcttgttga gcgctgtggc acggagtcga acggcagcag ttcatttctg gatttgcctg    2580
```

```
acgtgcagac ctcggaccag cctttagacc tgtccctggc cgcgtggcct gtaagggcta    2640
ccgcgtctga ccccggttgg atccacggta ggcgtgagcc tgtctttgtg aagcctcgag    2700
gtgttttctc tgatggcgag tcggcccttc agttcggaga gctttccgaa gccagttctg    2760
tcgtcgatga ccggacaaaa gaagctccgg tggttgacgc ccccatcgat ttgacaactt    2820
cgaacgagac gctctctggg tctgacccct ttgaattcgc caaattcagg cgcccgcgtt    2880
tctccgcgca agctttaatc gaccgaggtg gtccgcttgc cgatgttcat gcaaagataa    2940
agagtcgggt atatgaacaa tgccttcaag cttgtgaacc tggtagtcgt gcgacccag     3000 ccaccaagaa gtggctcgac aaaatgtggg acagggtgga catgaaaact tggcgctgca    3060
cctcgcagtt ccaagctggt cacattcttg agtccctcaa attcctccct gacatgattc    3120
aagacacacc gcctcctgtt cccaggaaga accgagctgg tgacagtgcc ggcctgaagc    3180
aactggtggc gcagtgggat aggaaatcga gtgtgacacc ccccacaaaa ccggttggac    3240
cggtgcttga ccaggccgtc cctctgccta tggacatcca gcaaggagat gccatctccg    3300
ctgacaagcc accccattcg caaaacccct ctagtcaagt agatgtgggt ggaggttgga    3360
aaagttttat gctctccggc acccgtttcg cggggtccgt tagtcagcgc cttacgacat    3420 gggttttga ggttctctcc catctcccag cttttatgct cacacttttc tcgccacggg     3480
gctctatggc tccaggtgat tggctgtttg caggtgctgt tctacttgct ctcctgctct    3540
gccgttctta cccaatactc ggatgccttc ccttattggg tgtcttttct ggttctgtgc    3600
ggtgtgttcg tttgggtgtt tttggttctt ggatggcttt tgctgtattt ttattctcga    3660
ctccacccga cccagtcggt tcttcttgtg accacgattc gccggagtgt catgctgagc    3720
ttttggctct tgagcagcgc caactttggg aacctgtgcg cagccttgtg gtcgggccat    3780
cgggcctctt atgcgtcatt cttggcaagt tactcggtgg gtcacgttgt ctctggtttg    3840
ttctcctacg tatatgcatg ctcgcagatt tggcaatttc tcttatttat gtggtgtccc    3900
aagggcgttg tcacaagtgt tggggaaagt gtataaggac ggctcctgca gaagtggccc    3960
ttaatgtgtt tccttttcg cgcgccaccc gctcatctct tgtgtccttg tgtgatcggt      4020
tccaagcgcc aaaaggagtt gacccgtgc acttggcgac aggctggcgc gggtgctggt     4080
gtggtgagag ccctattcat caatcacacc aaaaaccgat agcttatgcc aacttggatg    4140
aaaagaagat atccgcccag acggtgattg ctgtcccgta tgatcctagt caggccatta    4200
aatgcctgaa agttttgcag gcaggagggg ctattgtgga ccagcctacg cccgaggtcg    4260
tccgtgtgtc tgagattccc ttctcggccc catttttttcc gaaggtccca gtcaacccag   4320
actgcagggt tgtggtagat tcggacactt ttgtggctgc ggtccgctgc ggttattcga    4380
cagcacaact ggtccttggt cggggcaact ttgccaagct aaatcagacc cccctcagga    4440
actctgtccc caccaaaaca actggtgggg cctcatacac ccttgccgtg gcccaggtat    4500
ctgtgtggac tcttgttcat ttcatcctcg gcctttggtt aacgtcacct caagtgtgtg    4560
gtcgagggac ctctgacccg tggtgttcga acccttttc gtatcctact tatgccccg     4620 gagttgtgtg ttcctctcga ctctgcgtgt ctgccgacgg agttaccctg ccattgttct    4680
cagccgttgc ccatctttcc ggtagagagg tggggatttt tatttggtg cttgcctcct    4740 tgggcgcttt agcccaccgc ttggctctta aggcagacat gtcaatggtc tttttggcgt    4800
tttgtgctta cgcctggccc atgagctcct ggttaatttg cttctttcct atgctcttga   4860
ggtgggtaac ccttcatcct ctcactatgc tttgggtgca ctcattttg gtgttttgcc    4920 taccagctgc cggcgttctc tcgctgggaa taaccggtct tctttgggca gttggccgtt   4980
```

```
tcacccaggt tgccggaatt atcacacctt atgacatcca ccagtatacc tccggaccac    5040
gtggtgcagc tgctgtagca acggctccag aaggtactta catggcggcc gttcggagag    5100
ccgctttgac tggacggact ttgatcttca ccatctgc agtcggatcc cttcttgaag     5160
gtgctttcag aactcaaaag ccctgcctta acaccgtgaa tgtcgtaggc tcttcccttg    5220
gttctggagg agttttcacc attgatggca gaagagtcat cgtcactgcc acccatgtgt    5280
tgaatggtaa cacagccagg gtcactggtg attcctacaa ccgcatgcac acgttcaata    5340
ctaatggtga ttatgcctgg tcccatgctg atgactggca aggcgttgcc cctatggtta    5400
agatcgctaa ggggtatcgc ggtcgtgcct actggcaaac gtcaaccgga gtcgaacctg    5460
gcatcatggg ggaaggattc gccttctgtt tcactaactg tggcgactca gggtcacctg    5520
tcatttcaga agctggtgac cttattggag tccataccgg ttcaaacaaa ctcggttctg    5580
gtcttgtgac aaccctgaa ggggagacct gctccatcaa ggaaactagg ctctctgacc    5640
tttctagaca ttttgcaggt ccaagcgtcc ctcttgggga cattaagttg agcccagcca    5700
tcatccctga tgtgacaact attccgagtg acttggcatc gctccttgct tctgtccccg    5760
tgatggaagg tggcctctca actgtccagc ttttgtgcgt cttttccctt ctctggcgca    5820
tgatgggcca tgcctggaca cccattgttg ccgtaggctt cttttgctg aatgaaattc     5880 tcccagcagt cttggtccga gctgtgttct cttttgcact ctttgtactt gcatgggcca    5940 cccctggtc ggcacaagtg ttgatgatta gactcctcac ggcggctctc aaccgcaaca     6000
ggttgtccct ggcgttctac gcattcggag gtgtcgttgg cctggccaca gaaatcggga    6060
cttttgctgg tggatggcct gaactgtccc aagccctctc gacatactgc ttcctgccca    6120
ggttccttgc tgtgactagt tatgtcccca ccatcatcat cggtgggctc catgccctcg    6180
gcgtaatttt gtggttattc aaataccgat gcctccacaa catgctggtt ggtgatggga    6240
gtttctcaag cgctttcttc ctacggtatt tgctgaggg taatcttagg aaaggcgtgt     6300
cgcagtcctg tggcatgaat aacgaatccc tgacagctgc tttggcttgc aagttgtcgc    6360
aagctgacct tgatttttg tccagtttaa cgaacttcaa gtgctttgtg tccgcttcaa     6420
acatgaaaaa tgcagctggc caatacatcg aggcggcgta tgctagagct ctgcgtcagg    6480
agctggcctc cttggttcag gttgacaaga tgaaaggagt attggccaag ctcgaggctt    6540
tcgctgagac ggccactccg tcacttgaca caggggacgt gattgttctg cttgggcaac    6600
acccccatgg atccatcctc gacattaatg tgggggtga aaggaaaact gtgtctgtgc     6660
aagaaacacg atgcctgggt ggttccaaat tcagtgtctg cactgtcgtg tccaacacgc    6720
ccgtggatac cttgaccggt atcccacttc agacgccaac cccactttt gaaaatggcc     6780 cgcgccatcg cagcgaggac gacgacctca agttgagaa atgaaaaaa cactgtgtat      6840 ccctcggctt ccacaaaatc aatggtaaag tttactgcaa aatttgggac aagtctaacg    6900
gcgacacctt ttacacggat gattcccgat acactcaaga ccatgctttt caggacaggt    6960
caaccgacta tagagacagg gattatgaag gtgtacagac cgccccccaa cagggattcg    7020
atccaaagtc cgaagcccct gttggcactg ttgtaatcgg tggcattacg tataacaggc    7080
atctggtcaa aggtaaggag gtcctagttc ccaaacctga caactgcctt gaagctgcca    7140
gactgtccct tgagcaagct cttgctggga tgggccaaac ttgtgacctt acagctaccg    7200
aagtggagaa actaaagcgc atcattagtc aactccaagg tctgaccact gaacaggctt    7260
taaactgcta gccgccagcg gcttgacccg ctgtggccgc ggcggcctag ttgtaactga    7320
```

-continued

```
aacggcggta aaaatcgtaa aataccacag cagaactttc accttaggct ctttagacct    7380
aaaagtcacc tccgaggtgg aggtgaagaa atcaactgag caggggcacg ctgtcgtggc    7440
gaacttatgt tccggtgtcg tcttgatgag gcctcaccca ccgtcccttg ttgacgttct    7500
cctcaaaccc ggacttgaca caacacccgg cattcaacca gggcatgggg ccgggaatat    7560
gggcgtgaac ggttctattt gggattttga aactgcaccc acaaaggtag aactagagtt    7620
gtccaagcaa ataatccaag catgtgaagt caggcgcggg gacgcccta acctccaact    7680 cccctacaag ctttatcctg tcagggggga ccccgagcgg cgtaaaggtc gccttgtcaa    7740
cactaggttt ggagatttac cttacaaaac tccccaagac accaagtccg caattcatgc    7800
ggcttgttgc ctgcatccca atggggtcct cgtgtctgat ggcaaatcca cgctgggtac    7860
cactcttcaa catggtttcg agctttatgt ccccactgta ccttatagtg tcatggaata    7920
ccttgattca cgccctgaca cccctttat gtgtactaaa catggcactt ccaaggctgc    7980
tgcagaggac ctccaaaaat atgacctatc cactcaaggg tttgtcttgc ctggggtcct    8040
acgcctagtg cgcaggttca tctttagcca tgttggtaag gcgccaccac tgttccttcc    8100
atcaacctac cctgccaaga actccatggc aggggtcaat ggccagaggt tcccaacaaa    8160
ggatgtccag agcatacctg aaattgatga atgtgcgcc cgtgccgtca aggaaaattg    8220
gcagactgtg acaccttgca ccctcaaaaa acagtactgt tccaaaccta aaactagaac    8280
catcctaggt accaacaact tcatagcctt ggctcacagg tcagcactca gtggtgtcac    8340
ccaggcgttc atgaagaagg cctggaagtc cccaattgcc ttggggaaaa acaagtttaa    8400
ggaattgcat tgcactgtcg ccggcagatg ccttgaggct gacctggctt cctgcgatcg    8460
cagcaccccc gccattgtga ggtggtttgt tgccaacctc ctgtatgaac ttgcaggatg    8520
tgaagagtac ttgcctagct acgtgctcaa ctgttgccat gaccttgtgg caacgcagga    8580
tggcgctttc acaaaacgcg gtggcctgtc gtccggggac cccgtcacca gtgtgtccaa    8640
caccgtctac tcactgataa tttacgccca gcacatggtg ctttcggcct tgaagatggg    8700
tcatgaaatt ggtctcaagt tccttgagga acagctcaaa tttgaggacc ttcttgaaat    8760
ccagcccatg ttagtgtatt ctgatgacct cgtcttgtat gcggaaagac ccacttttcc    8820
caactaccat tggtgggtcg agcatcttga cctgatgttg ggctttaaaa cggacccaaa    8880
gaaaactgtc ataactgata aacccagttt tctcggctgc agaattgaag caggacggca    8940
gttagtcccc aatcgcgacc gtattctggc tgctcttgca tatcatatga aggcgcagaa    9000
cgcctcagag tattatgcgt ccgctgccgc aattctgatg gattcgtgtg cttgcattga    9060
ccatgacccc gagtggtatg aggatcttat ctgcggcatc gcccggtgtg ctcgccagga    9120
cggttaccgt tttccaggcc cggcattttt catgtccatg tgggagaagc tgaaaagtca    9180
taatgaaggg aagaaatgcc gtcactgcgg catctgcgac gccaaagccg actatgcgtc    9240
cgcctgtgga cttgatttgt gtttgttcca ttcacacttt catcaacact gcccagtcac    9300
tctgagctgt ggccaccatg ccggttcaaa ggaatgttcg cagtgtcagt cacctgtcgg    9360
ggctggcaaa tccccccttg acgctgtgct gaaacaaatc ccgtacaaac tcctcgtac    9420 cattatcatg aaggtggaca caaaacaac gaccccttgac ccgggaagat atcagtcccg    9480
tcgaggtctt gttgcagtca aaagaggtat tgcaggtaat gaggttgatc tttctgatgg    9540
agactaccaa gtggtgcctc ttttgccgac ttgcaaagac ataaacatgg tgaaggtggc    9600
ttgcaacgta ctactcagca gtttatagt agggccgcca ggttccggaa aaaccacctg    9660
gctactgaac caagtccagg acgatgatgt catttacaca cctactcatc agacaatgtt    9720
```

-continued

```
tgacatagtc agtgctctta aagtttgcag gtattccatc ccaggagcct caggactccc    9780
ttttccacca cctgccaggt ccgggccgtg ggttaggctc atcgccagcg acatgtccc     9840 tggccgagtg tcatatctcg atgaggcagg atattgcaat catctagaca ttctaaggct   9900
gctttccaaa acaccccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc aggggcgac   10200 cttcgacatt gtgacattgc atctaccatc gccaaagtcc ctaaacaaat cccgagcact  10260
tgtagccatc actcgggcaa gacatgggtt gttcatttat gaccctcatg accaactcca  10320 ggagttttc aacttaaccc ccgagcgcac tgattgtaac cttgcgttca gccgtgggga   10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta aagggagct gcatgccact accacaagta gcataaacc tggggttta    10560 cttttcccg acagcccag cttttgcacc cctgccaaaa gagctggcgc cacattggcc    10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg ggggcgagcc  10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaataccta ctaggtccct   10980 gcctaaagac tctgttgctg tggttgggt gagttcgccc ggtagggctg ctaaagccgt   11040
gtgcactctc accgatgtgt acctccccga actccgacca tatttgcaac cggagacggc  11100
atcaaaatgc tggaaactta aactggattt cagggatgtt cgactgatgg tctggaaagg   11160
cgccacagcc tatttccagt tggaagggct gacatggtca gcgctgcccg attatgctag  11220
gttcattcag ctacccaagg atgccgttgt gtacatcgat ccgtgtatag gccggcaac   11280 agccaatcgc aaggttgtgc gaaccacaga ctggcgggcc gacctggcag tgacaccgta  11340
tgattacggt gctcaggtca ttttgacaac agcctggttc gaggaccttg gccgcagtg   11400 gaagattttg gggttgcagc cttttcagacg aacatttggc tttgagaaca ctgaagattg  11460
ggcaattctc gcacgccgta tgaatgacgg caaagattac actgactata attggcattg   11520
tgtacgagaa cgcccacacg caatttacgg gcgcgcccgt gaccatacgt atcattttgc   11580
ccttggcact gaactgcaag tagagctggg cagaccccgg ctgcctcctg agcaagtgcc   11640
gtgaacgcgg agtgatgcaa tgggtttact gtggagtaaa atcagtcagt tgttcgtgga   11700
tgccttcact gagttccttg ttagtgtggt tgacattgtc atctttctcg ccatattgtt   11760
tgggttcact gttgcaggct ggttattggt cttccttctc agagtggttt gctccgcgtt   11820
tctccgttcg cgctctgcca ttcactcttc cgaactatcg aaggtccat gagggcttgc    11880 tacccaactg cagaccggat gtccacaat tcgcagttaa gcaccgttg ggtatacttt     11940 ggcatatgcg agtctcccac ctaattgacg aaatggtctc tcgccgcatt taccggacca  12000
tggaacattc gggtcaagcg gcctggaagc aggttgttag tgaagccact ctcacaaaac  12060
```

```
tgtcaaggct tgacgtagtc actcatttcc aacacctggc cgcagtggag gctgattctt   12120
gccgcttcct tagctcacga ctcgcgatgc tgaaaaacct tgccgttggc aatgtgagcc   12180
tggagtacaa cactactttg gaccgcgttg agctcatctt tcccacacca ggtacgaggc   12240
ccaagttgac cgattttagg caatggctta tcagcgtgca cgcttccatc ttctcctctg   12300
tggcttcgtc tgttaccttg ttcacagtgc tttggcttcg aattccagct ctacgctatg   12360
tttttggttt ccattggccc acggcaacac atcattcgaa ctaactatca attacactat   12420
atgtaagcca tgccctacca gtcaagctgc ccaacaaaga ctcgagcctg ccgtaacgt    12480 gtggtgcaaa atagggcacg acaggtgtga ggaacgtgac catgatgagt tgtcaatgtc   12540
cattccgtcc gggtacgaca acctcaaact tgagggttat tatgcttggc tggcttttttt   12600 gtccttttcc tacgcggccc aattccatcc ggagctgttc ggaataggaa acgtgtcgcg   12660
cgtctttgtg gataagcgac accagttcat ttgcgccgag catgatggac aaaattcaac   12720
catatctgcc agacacaaca tctccgcgtc gtatgcggtg tattaccatc atcaaataga   12780
cgggggcaat tggtttcatt tggaatggct gcgaccattc ttttcctcct ggctggtgct   12840
caacatctca tggtttctga ggcgttcgcc tgcaagccct gcttctcgac gcatctatca   12900
gatattaaga ccaacacgac cgcggctgcc ggtttcatgg tccttcagaa catcaattgt   12960
ttccaatctc acagggcctc aacagcgcaa ggtaccactc ccctcaggag gtcgtcccaa   13020
tgtcgtgaag ccgtcggcat tccccagtac atcacgataa cggctaatgt gaccgatgaa   13080
tcgtatttgt acaacgcgga cttgctgatg cttccgcgt gccttttcta cgcctcggaa    13140
atgagcgaga aaggcttcaa agtcatcttt gggaatattt ctggcgttgt ttccgcttgt   13200
gttaatttca cagattatgt ggcccatgtg acccaacaca ctcagcagca ccatttggta   13260
attgatcaca ttcggttact acacttcttg acaccgtcta cgatgaggtg ggctacaacc   13320
attgcttgtt tgcttgccat tcttttggcg gtatgaaatg ttcttgcaag ttggggcatt   13380
tcttgactcc tcactcttgc ttctggtggc tttttttgct gtgtaccggc ttgtcttggt   13440
cctttgtcga tggcaacgac gacagctcga catcccaata catatataat ttgacgatat   13500
gcgagctgaa tgggaccgaa tggttgtccg gtcattttga ttgggcagtc gaaacctttg   13560
tgctttaccc agttgccact catatcattt cactgggttt tctcacaaca agccatttcc   13620
ttgatgcgct cggtctcggc gctgtgtccg ccacaggatt cattggcgag cggtatgtac   13680
ttagcagcat gtacggcgtt tgcgccttcg cggcgttcgt atgttttgtc atccgtgctg   13740
ctaaaaattg catggcttgc cgctatgccc gcacccggtt taccaacttc atcgtggacg   13800
accggggaag aatccatcga tggaagtctt caatagtggt ggagaaattg gcaaagctg    13860 aagtcggtgg tgaccttgtc aacattaagc atgttgtcct cgaagggggtt aaagctcaac   13920 ctttgacgag gacttcggct gagcaatggg aagcctagac gacttttgca acgatcccac   13980
cgccgcacaa aaactcgtgc tggcctttag catcacatat acacccataa tgatatacgc   14040
ccttaaggtg tcacgcggcc gactcctggg gctgttgcac atcttgatat ttctgaattg   14100
ttcctttact tttgggtaca tgacatatgt gcattttcaa tccaccaacc gtgtcgcatt   14160
cactctgggg gctgtagtcg cccttttgtg gggtgtttac agcctcacag agtcatggaa   14220
gttcatcact tccagatgca gattgtgttg cctaggccgg cgatacattc tggcccctgc   14280
ccatcacgta gaaagtgctg caggcctcca ttcaatccca gcgtctggta accgagcata   14340
cgctgtgaga aagcccggac taacatcagt gaacggcact ctagtacctg gcttcgagg   14400 cctcgtgctg ggcggcaaac gagctgttaa acgaggagtg gttaacctcg tcaagtatgg   14460
```

```
ccggtaagaa ccagagccag aagaaaagaa gaaatgcagc tccgatgggg aaaggccagc      14520
cagtcaatca actgtgccag ttgctgggta caatgataaa gtcccagcgc cagcaatcta      14580
ggggaggaca ggccaaaaag aagaagcctg agaagccaca ttttccccta gctgctgaag      14640
atgacattcg gcaccatctc acccaggccg aacgttccct ctgcttgcaa tcgatccaga      14700
cggctttcaa tcaaggcgca ggaactgcgt cgctttcatc cagcgggaag gtcagtttcc      14760
aggttgagtt catgctgccg gttgctcata cagtgcgcct gattcgcgtg acttctacat      14820
ccgccagtca gggtgcaaat taatttgaca gtcaggtgaa tggccgcgat tgacgtgtgg      14880
cctctaagtc acctattcaa ttagggcgat cacatggggg tcaaacttaa ttaggcagga      14940
accatgtgac cgaaattaaa aaaaaaaaaa aaaaaaaaaa aaaa                       14984

<210> SEQ ID NO 49
<211> LENGTH: 14945
<212> TYPE: DNA
<213> ORGANISM: Porcine reproductive and respiratory syndrome virus

<400> SEQUENCE: 49
atgatgtgta gggtattccc cctacataca cgacactctt agtgtttgtg taccttggag        60
gcgtgggtac agccctgccc cacccttttgg tccctgttct agcccgacag gtacccttct      120
ctctcggggc gagcgcgccg cctgctgctc ccttgcggcg ggaaggacct cccgagtatt       180
tccggagagc acctgcttta cgggatctcc gcccttaaac catgtctggg atgttctccc       240
ggtgcatgtg cacccccggct gcccgggtat tttggaacgc cggccaagtc tattgcacac      300
ggtgtctcag tgcacggtct cttctctctc cagaacttca ggacacggac ctcggtgcag      360
ttggcttgtt tcacaagcct aaagacaagc tccattggaa agttcccatt ggtatccccc      420
aggtggaatg ttctccatct gggtgttgct ggctgtcaac cattttcct ttagcgcgca       480 tgacctccgg caatcacaac ttccttcaac gactcgtgaa ggttgctgat gtattgtacc      540
gtgacggttg cttaaccct agacacctcc gtgaactcca gtttacgag cgtggttgca        600 attggtatcc gattacgggg cctgtgcctg ggatggctgt gtacgcgaac tccatgcacg      660
tgtccgacca accgttccct ggtgccactc atgtgttaac aaattcccct ttgcctcaac      720
gggcttgtcg gcagccgttc tgtccgttcg aagaggccca ttctagcata tacaggtggg      780
aaaaatttgt aattttttatg gattcctcct ccgacggtcg atctcgcatg atgtggactc      840
cggaatccga tgactccacg gctttggaag ttctgccgcc cgagctagaa caccaggtca      900
aggtccttgt tcggagcttt cccgcccatc accttgtcga ccttgccgat gggagctca       960 ctgagtcccc tgataacggt ttttccttca gcacgtcaca tccttgcggc taccttgttc      1020
gggacccggc tgtatccgaa ggcaagtgtt ggctttcctg ctttttgagc cagtcagccg      1080
aagtgctcag tcgcgaggcg catctggcta ccgcctatgg ttaccaaacc aagtggggtg      1140
tgcctggcaa gtacatccag cgcagacttc aagttcacgg tctccgtgct gtggtcgacc      1200
ctgatggtcc cattcacgtt gaagcattgt cttgccccca gtcttggatc aggcacttga      1260
ccctgaatga tgatgtcacc ccgggattcg ttcgcctaat gtctcttcgc attgtgccga      1320
acacagagcc taccacacac cggatctttc gttttggagt gcacaagtgg tatggtgcca      1380
ccggcaaacg ggcccgtggc aagcgtgccg ccaaaagtga gaaagactcg gcttccaccc      1440
tcaaggttgc ccgaccgact tccaccagtg gaatcgtcac ctactcccca cctgcggacg      1500
ggtcttgtgg ttggcatgcc cttgccgcca tactgaaccg gatgattaat aatgacttca      1560
```

```
cgtcccctct gcctcggtac aacaggccgg aggacgattg gcttctgat ggtgaccttg    1620 ctcaggccat tcaatgtttg caactacctg ccgccatagc tcggaaccgc gcctgccta     1680 acgccaaata cctcataaaa ctcaacggag ttcattggga ggtagaggtg aggcctggaa    1740
tggctcctcg ctccctctct cgtgagtgcg ttgttggcgt ctgctctgaa ggctgtgtcg    1800
cgtcgcctta cccggaggac gggttgccta aacgtgcact tgaggccctg gcgtctgctt    1860
atagactgcc ttcagactgt gtttgtgatg gtattattga cttccttgcc aatccacctc    1920
cccaggagtt ctggactctt gacaaaatgt tgacttcccc gtcaccggag cagtccggct    1980
tctctagtct gtataaattg ttgttagaga tcttgccgca gaaatgcgga tccacagaag    2040
gggaattcat ctatactgtt gagaggatgt tgaaggattg tccgagctcc aaacaggcca    2100
tggccctcct tgcaaaaatt aaggtcccat cctcaaaggc cccatccgtg actctgaacg    2160
agtgcttccc cacggatgtt ccagtcaact ctgagttaat atcttgggaa gagcccaaag    2220
accctggcgc tgctgttgtc ctatgtccat cggatgcaaa agaatctaag gaaacagccc    2280
ctgaagaagc tcaagcgaga aaccgtaagg tccttcaccc tgtggtcctt accgaggaac    2340
ttagcgagca acaggtgcag gtggttgagg gtgatcagga tatgccactg gatttgactt    2400
ggccaacctt aaccgctacg gcgacccctg ttagagggcc ggtaccggac aatttgagct    2460
ctggcattgg tgcccagccc gctaccgttc aagaactcat tctggcgagg cctgcacccc    2520
gtcttgttga gcgctgtggc acggagtcga acggcagcag ttcatttctg gatttgcctg    2580
acgtgcagac ctcggaccag cctttagacc tgtccctggc cgcgtggcct gtaagggcta    2640
ccgcgtctga ccccggttgg atccacggta ggcgtgagcc tgtctttgtg aagcctcgag    2700
gtgttttctc tgatggcgag tcggcccttc agttcggaga gctttccgaa gccagttctg    2760
tcgtcgatga ccggacaaaa gaagctccgg tggttgacgc ccccatcgat ttgacaactt    2820
cgaacgagac gctctctggg tctgaccct ttgaattcgc caaattcagg cgcccgcgtt    2880
tctccgcgca agctttaatc gaccgaggtg gtccgcttgc cgatgttcat gcaaagataa    2940
agagtcgggt atatgaacaa tgccttcaag cttgtgaacc tggtagtcgt gcgaccccag    3000
ccaccaagaa gtggctcgac aaaatgtggg acagggtgga catgaaaact tggcgctgca    3060
cctcgcagtt ccaagctggt cacattcttg agtccctcaa attcctccct gacatgattc    3120
aagacacacc gcctcctgtt cccaggaaga accgagctgg tgacagtgcc ggcctgaagc    3180
aactggtggc gcagtgggat aggaaatcga gtgtgacacc cccacaaaa ccggttggac     3240 cggtgcttga ccaggccgtc cctctgccta tggacatcca gcaaggagat gccatctccg    3300
ctgacaagcc accccattcg caaaacccctt ctagtcaagt agatgtgggt ggaggttgga   3360
aaagttttat gctctccggc acccgtttcg cggggtccgt tagtcagcgc cttacgacat    3420 gggttttga ggttctctcc catctcccag cttttatgct cacacttttc tcgccacggg     3480
gctctatggc tccaggtgat tggctgtttg caggtgctgt tctacttgct ctcctgctct    3540
gccgttctta cccaatactc ggatgccttc ccttattggg tgtctttct ggttctgtgc     3600 ggtgtgttcg tttgggtgtt tttggttctt ggatggcttt tgctgtattt ttattctcga    3660
ctccacccga cccagtcggt tcttcttgtg accacgattc gccggagtgt catgctgagc    3720
ttttggctct tgagcagcgc caactttggg aacctgtgcg cagccttgtg tcgggccat     3780 cgggcctctt atgcgtcatt cttggcaagt tactcggtgg gtcacgttgt ctctggtttg    3840
ttctcctacg tatatgcatg ctcgcagatt tggcaatttc tcttatttat gtggtgtccc    3900
aagggcgttg tcacaagtgt tggggaaagt gtataaggac ggctcctgca gaagtggccc    3960
```

```
ttaatgtgtt tccttttcg cgcgccaccc gctcatctct tgtgtccttg tgtgatcggt    4020
tccaagcgcc aaaaggagtt gaccccgtgc acttggcgac aggctggcgc gggtgctggt    4080
gtggtgagag ccctattcat caatcacacc aaaaaccgat agcttatgcc aacttggatg    4140
aaaagaagat atccgcccag acggtgattg ctgtcccgta tgatcctagt caggccatta    4200
aatgcctgaa agttttgcag gcaggagggg ctattgtgga ccagcctacg cccgaggtcg    4260
tccgtgtgtc tgagattccc ttctcggccc cattttttcc gaaggtccca gtcaacccag    4320
actgcagggt tgtggtagat tcggacactt ttgtggctgc ggtccgctgc ggttattcga    4380
cagcacaact ggtccttggt cggggcaact ttgccaagct aaatcagacc ccctcagga    4440 actctgtccc caccaaaaca actggtgggg cctcatacac ccttgccgtg gcccaggtat    4500
ctgtgtggac tcttgttcat ttcatcctcg gcctttggtt aacgtcacct caagtgtgtg    4560
gtcgagggac ctctgacccg tggtgttcga acccttttc gtatcctact tatggccccg    4620
gagttgtgtg ttcctctcga ctctgcgtgt ctgccgacgg agttaccctg ccattgttct    4680
cagccgttgc ccatctttcc ggtagagagg tggggatttt tattttggtg cttgcctcct    4740
tgggcgcttt agcccaccgc ttggctctta aggcagacat gtcaatggtc tttttggcgt    4800
tttgtgctta cgcctggccc atgagctcct ggttaatttg cttctttcct atgctcttga    4860
ggtgggtaac ccttcatcct ctcactatgc tttgggtgca ctcattttg gtgttttgcc    4920 taccagctgc cggcgttctc tcgctgggaa taaccggtct tctttgggca gttggccgtt    4980
tcacccaggt tgccggaatt atcacacctt atgacatcca ccagtatacc tccggaccac    5040
gtggtgcagc tgctgtagca acggctccag aaggtactta catggcggcc gttcggagag    5100
ccgctttgac tggacggact ttgatcttca caccatctgc agtcggatcc cttcttgaag    5160
gtgctttcag aactcaaaag ccctgcctta acaccgtgaa tgtcgtaggc tcttcccttg    5220
gttctggagg agttttcacc attgatggca gaagagtcat cgtcactgcc acccatgtgt    5280
tgaatggtaa cacagccagg gtcactggtg attcctacaa ccgcatgcac acgttcaata    5340
ctaatggtga ttatgcctgg tcccatgctg atgactggca aggcgttgcc cctatggtta    5400
agatcgctaa ggggtatcgc ggtcgtgcct actggcaaac gtcaaccgga gtcgaacctg    5460
gcatcatggg ggaaggattc gccttctgtt tcactaactg tggcgactca gggtcacctg    5520
tcatttcaga agctggtgac cttattggag tccataccgg ttcaaacaaa ctcggttctg    5580
gtcttgtgac aacccctgaa ggggagacct gctccatcaa ggaaactagg ctctctgacc    5640
tttctagaca ttttgcaggt ccaagcgtcc ctcttgggga cattaagttg agcccagcca    5700
tcatccctga tgtgacaact attccgagtg acttggcatc gctccttgct tctgtccccg    5760
tgatggaagg tggcctctca actgtccagc ttttgtgcgt ctttttcctt ctctggcgca    5820
tgatgggcca tgcctggaca cccattgttg ccgtaggctt cttttgctg aatgaaattc    5880 tcccagcagt cttggtccga gctgtgttct cttttgcact ctttgtactt gcatgggca    5940 cccctggtc ggcacaagtg ttgatgatta gactcctcac ggcggctctc aaccgcaaca    6000
ggttgtccct ggcgttctac gcattcgag gtgtcgttgg cctggccaca gaaatcggga    6060
cttttgctgg tggatggcct gaactgtccc aagccctctc gacatactgc ttcctgccca    6120
ggttccttgc tgtgactagt tatgtcccca ccatcatcat cggtgggctc catgccctcg    6180
gcgtaatttt gtggttattc aaataccgat gcctccacaa catgctggtt ggtgatggga    6240
gtttctcaag cgctttcttc ctacggtatt ttgctgaggg taatcttagg aaaggcgtgt    6300
```

```
cgcagtcctg tggcatgaat aacgaatccc tgacagctgc tttggcttgc aagttgtcgc    6360
aagctgacct tgattttttg tccagtttaa cgaacttcaa gtgctttgtg tccgcttcaa    6420
acatgaaaaa tgcagctggc caatacatcg aggcggcgta tgctagagct ctgcgtcagg    6480
agctggcctc cttggttcag gttgacaaga tgaaaggagt attggccaag ctcgaggctt    6540
tcgctgagac ggccactccg tcacttgaca caggggacgt gattgttctg cttgggcaac    6600 accccatgg atccatcctc gacattaatg tgggggtga aggaaaact gtgtctgtgc       6660 aagaaacacg atgcctgggt ggttccaaat tcagtgtctg cactgtcgtg tccaacacgc    6720
ccgtggatac cttgaccggt atcccacttc agacgccaac cccacttttt gaaaatggcc    6780
cgcgccatcg cagcgaggac gacgacctca agttgagag aatgaaaaaa cactgtgtat     6840
ccctcggctt ccacaaaatc aatggtaaag tttactgcaa aatttgggac aagtctaacg    6900
gcgacacctt ttacacggat gattcccgat acactcaaga ccatgctttt caggacaggt    6960
caaccgacta tagagacagg gattatgaag gtgtacagac cgcccccaa cagggattcg     7020 atccaaagtc cgaagcccct gttggcactg ttgtaatcgg tggcattacg tataacaggc    7080
atctggtcaa aggtaaggag gtcctagttc ccaaacctga caactgcctt gaagctgcca    7140
gactgtccct tgagcaagct cttgctggga tgggccaaac ttgtgacctt acagctaccg    7200
aagtggagaa actaaagcgc atcattagtc aactccaagg tctgaccact gaacaggctt    7260
taaactgcta gccgccagcg gcttgacccg ctgtggccgc ggcggcctag ttgtaactga    7320
aacggcggta aaaatcgtaa ataccacag cagaactttc accttaggct ctttagacct     7380
aaaagtcacc tccgaggtgg aggtgaagaa atcaactgag caggggcacg ctgtcgtggc    7440
gaacttatgt tccggtgtcg tcttgatgag gcctcaccca ccgtcccttg ttgacgttct    7500
cctcaaaccc ggacttgaca caacacccgg cattcaacca gggcatgggg ccgggaatat    7560
gggcgtgaac ggttctattt gggattttga aactgcaccc acaaaggtag aactagagtt    7620
gtccaagcaa ataatccaag catgtgaagt caggcgcggg gacgcccta acctccaact     7680 cccctacaag ctttatcctg tcagggggga ccccgagcgg cgtaaaggtc gccttgtcaa    7740
cactaggttt ggagatttac cttacaaaac tccccaagac accaagtccg caattcatgc    7800
ggcttgttgc ctgcatccca atggggtcct cgtgtctgat ggcaaatcca cgctgggtac    7860
cactcttcaa catggtttcg agctttatgt ccccactgta cctttatagtg tcatggaata    7920 ccttgattca cgccctgaca ccccttttat gtgtactaaa catggcactt ccaaggctgc    7980
tgcagaggac ctccaaaaat atgacctatc cactcaaggg tttgtcttgc ctggggtcct    8040
acgcctagtg cgcaggttca tctttagcca tgttggtaag gcgccaccac tgttccttcc    8100
atcaacctac cctgccaaga actccatggc agggtcaat ggccagaggt tcccaacaaa     8160
ggatgtccag agcatacctg aaattgatga atgtgcgcc cgtgccgtca aggaaaattg     8220
gcagactgtg acaccttgca ccctcaaaaa acagtactgt tccaaaccta aaactagaac    8280
catcctaggt accaacaact tcatagcctt ggctcacagg tcagcactca gtggtgtcac    8340
ccaggcgttc atgaagaagg cctggaagtc cccaattgcc ttggggaaaa acaagtttaa    8400
ggaattgcat tgcactgtcg ccggcagatg ccttgaggct gacctggctt cctgcgatcg    8460 cagcacccc gccattgtga ggtggtttgt tgccaacctc tgtatgaac ttgcaggatg      8520 tgaagagtac ttgcctagct acgtgctcaa ctgttgccat gaccttgtgg caacgcagga    8580
tggcgctttc acaaaacgcg gtggcctgtc gtccggggac cccgtcacca gtgtgtccaa    8640
caccgtctac tcactgataa tttacgccca gcacatggtg ctttcggcct tgaagatggg    8700
```

```
tcatgaaatt ggtctcaagt tccttgagga acagctcaaa tttgaggacc ttcttgaaat    8760
ccagcccatg ttagtgtatt ctgatgacct cgtcttgtat gcggaaagac ccactttttcc   8820 caactaccat tggtgggtcg agcatcttga cctgatgttg ggctttaaaa cggacccaaa    8880
gaaaactgtc ataactgata aacccagttt tctcggctgc agaattgaag caggacggca    8940
gttagtcccc aatcgcgacc gtattctggc tgctcttgca tatcatatga aggcgcagaa    9000
cgcctcagag tattatgcgt ccgctgccgc aattctgatg gattcgtgtg cttgcattga    9060
ccatgacccc gagtggtatg aggatcttat ctgcggcatc gcccggtgtg ctcgccagga    9120
cggttaccgt tttccaggcc cggcattttt catgtccatg tgggagaagc tgaaaagtca    9180
taatgaaggg aagaaatgcc gtcactgcgg catctgcgac gccaaagccg actatgcgtc    9240
cgcctgtgga cttgatttgt gtttgttcca ttcacacttt catcaacact gcccagtcac    9300
tctgagctgt ggccaccatg ccggttcaaa ggaatgttcg cagtgtcagt cacctgtcgg    9360
ggctggcaaa tcccccctttg acgctgtgct gaaacaaatc ccgtacaaac ctcctcgtac    9420
cattatcatg aaggtggaca acaaaacaac gacccttgac ccgggaagat atcagtcccg    9480
tcgaggtctt gttgcagtca aaagaggtat tgcaggtaat gaggttgatc tttctgatgg    9540
agactaccaa gtggtgcctc ttttgccgac ttgcaaagac ataaacatgg tgaaggtggc    9600
ttgcaacgta ctactcagca agtttatagt agggccgcca ggttccggaa aaaccacctg    9660
gctactgaac caagtccagg acgatgatgt catttacaca cctactcatc agacaatgtt    9720
tgacatagtc agtgctctta aagtttgcag gtattccatc ccaggagcct caggactccc    9780
ttttccacca cctgccaggt ccgggccgtg ggttaggctc atcgccagcg acatgtccc    9840 tggccgagtg tcatatctcg atgaggcagg atattgcaat catctagaca ttctaaggct    9900
gctttccaaa acacccccttg tgtgtttggg tgaccttcag caacttcacc cggtcggctt    9960
tgattcctat tgttatgtgt tcgatcagat gcctcagaag cagctgacca ccatttatag   10020
atttggccct aacatctgtg cagccatcca gccttgttac agggagaaac ttgaatccaa   10080
ggccaggaac accagagtgg ttttcaccac ccggcctgtg gcctttggtc aggtcctgac   10140
accgtaccac aaagatcgta ccggctctgc aataactata gattcatccc aggggcgac   10200 cttcgacatt gtgacattgc atctaccatc gccaaagtcc ctaaacaaat cccgagcact   10260
tgtagccatc actcgggcaa gacatgggtt gttcatttat gaccctcatg accaactcca   10320
ggagtttttc aacttaaccc ccgagcgcac tgattgtaac cttgcgttca gccgtgggga   10380
tgagctggtt gttttgaatg tggataatgc ggtcacaact gtagcgaagg ccctagagac   10440
aggttcaccc cgatttcgag tatcggaccc gaggtgcaag tctctcttag ccgcttgttc   10500
ggccagtcta gaaggagct gcatgccact accacaagta gcacataacc tggggttttta   10560 cttttccccg gacagcccag cttttgcacc cctgccaaaa gagctggcgc acattggcc   10620 agtggtcacc caccagaata atcgagcgtg gcctgatcga cttgtcgcta gtatgcgccc   10680
aattgatgcc cgctacagca agccaatggt cggtgcaggg tatgtggtcg ggccatccat   10740
ttttcttggc actcctggtg tggtgtcata ctatctcaca ttatacatcg ggggcgagcc   10800
tcaggccctg ccagaaacac tcgtttcaac aggacgtata gccacagatt gtcgggaata   10860
tctcgacgcg gctgaggaag aggcagcgag agaacttccc cacgcattta ttggcgatgt   10920
caaaggcact acgatcgggg ggtgtcacca cattacatcg aaatacctac ctaggtccct   10980
gcctaaagac tctgttgctg tggttggggt gagttcgccc ggtagggctg ctaaagccgt   11040
```

```
gtgcactctc accgatgtgt acctccccga actccgacca tatttgcaac cggagacggc    11100
atcaaaatgc tggaaactta aactggattt cagggatgtt cgactgatgg tctggaaagg    11160
cgccacagcc tatttccagt tggaagggct gacatggtca gcgctgcccg attatgctag    11220
gttcattcag ctacccaagg atgccgttgt gtacatcgat ccgtgtatag ggccggcaac    11280
agccaatcgc aaggttgtgc gaaccacaga ctggcgggcc gacctggcag tgacaccgta    11340
tgattacggt gctcaggtca ttttgacaac agcctggttc gaggaccttg gccgcagtg     11400 gaagattttg gggttgcagc ctttcagacg aacatttggc tttgagaaca ctgaagattg    11460
ggcaattctc gcacgccgta tgaatgacgg caaagattac actgactata attggcattg    11520
tgtacgagaa cgcccacacg caatttacgg gcgcgcccgt gaccatacgt atcattttgc    11580
ccttggcact gaactgcaag tagagctggg cagaccccgg ctgcctcctg agcaagtgcc    11640
gtgaacgcgg agtgatgcaa tgggtttact gtggagtaaa atcagtcagt tgttcgtgga    11700
tgccttcact gagttccttg ttagtgtggt tgacattgtc atctttctcg ccatattgtt    11760
tgggttcact gttgcaggct ggttattggt cttccttctc agagtggttt gctccgcgtt    11820
tctccgttcg cgctctgcca ttcactcttc cgaactatcg aaggtcctat gagggcttgc    11880
tacccaactg cagaccggat gtcccacaat tcgcagttaa gcaccgttg ggtatacttt     11940 ggcatatgcg agtctcccac ctaattgacg aaatggtctc tcgccgcatt taccggacca    12000
tggaacattc gggtcaagcg gcctggaagc aggttgttag tgaagccact ctcacaaaac    12060
tgtcaaggct tgacgtagtc actcatttcc aacacctggc cgcagtggag gctgattctt    12120
gccgcttcct tagctcacga ctcgcgatgc tgaaaaacct tgccgttggc aatgtgagcc    12180
tggagtacaa cactactttg gaccgcgttg agctcatctt tcccacacca ggtacgaggc    12240
ccaagttgac cgatttttagg caatggctta tcagcgtgca cgcttccatc ttctcctctg    12300
tggcttcgtc tgttaccttg ttcacagtgc tttggcttcg aattccagct ctacgctatg    12360
tttttggttt ccattggccc acggcaacac atcattcgaa ctaactatca attacactat    12420
atgtaagcca tgccctacca gtcaagctgc ccaacaaaga ctcgagcctg ccgtaacgt     12480 gtggtgcaaa ataggggcacg acaggtgtga ggaacgtgac catgatgagt tgtcaatgtc    12540
cattccgtcc gggtacgaca acctcaaact tgagggttat tatgcttggc tggcttttt     12600 gtccttttcc tacgcggccc aattccatcc ggagctgttc ggaataggaa acgtgtcgcg    12660
cgtctttgtg gataagcgac accagttcat ttgcgccgag catgatggac aaaattcaac    12720
catatctgcc agacacaaca tctccgcgtc gtatgcggtg tattaccatc atcaaataga    12780 cggggggcaat tggtttcatt tggaatggct gcgaccattc ttttcctcct ggctggtgct    12840
caacatctca tggtttctga ggcgttcgcc tgcaagccct gcttctcgac gcatctatca    12900
gatattaaga ccaacacgac cgcggctgcc ggtttcatgg tccttcagaa catcaattgt    12960
ttccaatctc actcgtccca atgtcgtgaa gccgtcggca ttccccagta catcacgata    13020
acggctaatg tgaccgatga atcgtatttg tacaacgcgg acttgctgat gctttccgcg    13080
tgccttttct acgcctcgga aatgagcgag aaaggcttca agtcatctt tgggaatatt    13140 tctggcgttg tttccgcttg tgttaatttc acagattatg tggcccatgt gacccaacac    13200
actcagcagc accatttggt aattgatcac attcggttac tacacttctt gacaccgtct    13260
acgatgaggt gggctacaac cattgcttgt ttgcttgcca ttcttttggc ggtatgaaat    13320
gttcttgcaa gttggggcat tcttgactc ctcactcttg cttctggtgg cttttttttgc    13380 tgtgtaccgg cttgtcttgg tcctttgtcg atggcaacga cgacagctcg acatcccaat    13440
```

```
acatatataa tttgacgata tgcgagctga atgggaccga atggttgtcc ggtcattttg    13500
attgggcagt cgaaaccttt gtgctttacc cagttgccac tcatatcatt tcactgggtt    13560
ttctcacaac aagccatttc cttgatgcgc tcggtctcgg cgctgtgtcc gccacaggat    13620
tcattggcga gcgtatgta cttagcagca tgtacgcgt ttgcgccttc gcggcgttcg      13680
tatgttttgt catccgtgct gctaaaaatt gcatggcttg ccgctatgcc cgcacccggt    13740
ttaccaactt catcgtggac gaccggggaa gaatccatcg atggaagtct caatagtgg     13800 tggagaaatt gggcaaagct gaagtcggtg gtgaccttgt caacattaag catgttgtcc    13860
tcgaaggggt taaagctcaa cctttgacga ggacttcggc tgagcaatgg gaagcctaga    13920
cgacttttgc aacgatccca ccgccgcaca aaaactcgtg ctggccttta gcatcacata    13980
tacacccata atgatatacg cccttaaggt gtcacgcggc cgactcctgg ggctgttgca    14040
catcttgata tttctgaatt gttcctttac ttttgggtac atgacatatg tgcattttca    14100
atccaccaac cgtgtcgcat tcactctggg gctgtagtc gcccttttgt ggggtgttta     14160
cagcctcaca gagtcatgga agttcatcac ttccagatgc agattgtgtt gcctaggccg    14220
gcgatacatt ctggcccctg cccatcacgt agaaagtgct gcaggcctcc attcaatccc    14280
agcgtctggt aaccgagcat acgctgtgag aaagcccgga ctaacatcag tgaacggcac    14340
tctagtacct gggcttcgga gcctcgtgct gggcggcaaa cgagctgtta acgaggagt     14400 ggttaacctc gtcaagtatg gccggtaaga accagagcca gaagaaaaga agaaatgcag    14460
ctccgatggg gaaaggccag ccagtcaatc aactgtgcca gttgctgggt acaatgataa    14520
agtcccagcg ccagcaatct aggggaggac aggccaaaaa gaagaagcct gagaagccac    14580 atttcccct agctgctgaa gatgacattc ggcaccatct cacccaggcc gaacgttccc     14640
tctgcttgca atcgatccag acggctttca atcaaggcgc aggaactgcg tcgctttcat    14700
ccagcgggaa ggtcagtttc caggttgagt tcatgctgcc ggttgctcat acagtgcgcc    14760
tgattcgcgt gacttctaca tccgccagtc agggtgcaaa ttaatttgac agtcaggtga    14820
atggccgcga ttgacgtgtg gcctctaagt cacctattca attagggcga tcacatgggg    14880
gtcaaactta attaggcagg aaccatgtga ccgaaattaa aaaaaaaaaa aaaaaaaaaa    14940
aaaaa                                                                14945
```

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SEQ ID NO:39 with substitution N->Q at position 9

<400> SEQUENCE: 50

Ser Ser His Leu Gln Leu Ile Tyr Gln Leu Thr Ile Cys Glu Leu Asn
1               5                   10                  15

Gly

<210> SEQ ID NO 51
<211> LENGTH: 11
<212> TYPE: PRT
<213> ORGANISM: Porcine reproductive and respiratory syndrome virus

<400> SEQUENCE: 51

Ser Ser His Leu Gln Leu Ile Tyr Asn Leu Thr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO:51 with substitution N->Q at position
      9

<400> SEQUENCE: 52

Ser Ser His Leu Gln Leu Ile Tyr Gln Leu Thr
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO:51 with Gly-Gly linker

<400> SEQUENCE: 53

Gly Ser Ser His Leu Gln Leu Ile Tyr Asn Leu Thr Gly
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO:52 with Gly-Gly linker

<400> SEQUENCE: 54

Gly Ser Ser His Leu Gln Leu Ile Tyr Gln Leu Thr Gly
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO:53 with N-terminal P

<400> SEQUENCE: 55

Pro Gly Ser Ser His Leu Gln Leu Ile Tyr Asn Leu Thr Gly
1               5                   10

<210> SEQ ID NO 56
<211> LENGTH: 14984
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SEQ ID NO:49 with insert coding for SEQ ID NO:53

<400> SEQUENCE: 56

```
atgatgtgta gggtattccc cctacataca cgacactctt agtgtttgtg taccttggag    60
gcgtgggtac agccctgccc caccctttgg tccctgttct agcccgacag gtaccttct   120
ctctcggggc gagcgcgccg cctgctgctc ccttgcggcg ggaaggacct cccgagtatt   180
tccggagagc acctgcttta cgggatctcc gcccttttaac catgtctggg atgttctccc   240
ggtgcatgtg cacccggct gcccgggtat tttggaacgc cggccaagtc tattgcacac   300
ggtgtctcag tgcacggtct cttctctctc cagaacttca ggacacggac ctcggtgcag   360
ttggcttgtt tcacaagcct aaagacaagc tccattggaa agttcccatt ggtatcccc    420
aggtggaatg ttctccatct gggtgttgct ggctgtcaac catttttcct ttagcgcgca   480
tgacctccgg caatcacaac ttccttcaac gactcgtgaa ggttgctgat gtattgtacc   540
gtgacggttg cttaaccct agacacctcc gtgaactcca agtttacgag cgtggttgca   600
attggtatcc gattacgggg cctgtgcctg ggatggctgt gtacgcgaac tccatgcacg   660
tgtccgacca accgttccct ggtgccactc atgtgttaac aaattcccct ttgcctcaac   720
gggcttgtcg gcagccgttc tgtccgttcg aagaggccca ttctagcata tacaggtggg   780
aaaaatttgt aatttttatg gattcctcct ccgacggtcg atctcgcatg atgtggactc   840
cggaatccga tgactccacg gctttggaag ttctgccgcc cgagctagaa caccaggtca   900
aggtccttgt tcggagcttt cccgcccatc accttgtcga ccttgccgat gggagctca    960
ctgagtcccc tgataacggt ttttccttca gcacgtcaca tccttgcggc taccttgttc  1020
gggacccggc tgtatccgaa ggcaagtgtt ggctttcctg ctttttgagc cagtcagccg  1080
aagtgctcag tcgcgaggcg catctggcta ccgcctatgg ttaccaaacc aagtggggtg  1140
tgcctggcaa gtacatccag cgcagacttc aagttcacgg tctccgtgct gtggtcgacc  1200
ctgatggtcc cattcacgtt gaagcattgt cttgccccca gtcttggatc aggcacttga  1260
ccctgaatga tgatgtcacc ccgggattcg ttcgcctaat gtctcttcgc attgtgccga  1320
acacagagcc taccacacac cggatctttc gttttggagt gcacaagtgg tatggtgccg  1380
ccggcaaacg ggcccgtggc aagcgtgccg ccaaaagtga gaaagactcg gcttccaccc  1440
tcaaggttgc ccgaccgact tccaccagtg gaatcgtcac ctactcccca cctgcggacg  1500
ggtcttgtgg ttggcatgcc cttgccgcca tactgaaccg gatgattaat aatgacttca  1560
cgtcccctct gcctcggtac aacaggccgg aggacgattg gcttctgat ggtgaccttg   1620
ctcaggccat tcaatgtttg caactacctg ccgccatagc tcggaaccgc gcctgcccta  1680
acgccaaata cctcataaaa ctcaacggag ttcattggga ggtagaggtg aggcctggaa  1740
tggctcctcg ctccctctct cgtgagtgcg ttgttggcgt ctgctctgaa ggctgtgtcg  1800
cgtcgcctta cccggaggac gggttgccta acgtgcact gaggccctg gcgtctgctt   1860
atagactgcc ttcagactgt gtttgtgatg gtattattga cttccttgcc aatccacctc  1920
cccaggagtt ctgactctt gacaaaatgt tgacttcccc gtcaccggag cagtccggct   1980
tctctagtct gtataaattg ttgttagaga tcttgccgca gaaatgcgga tccacagaag  2040
gggaattcat ctatactgtt gagaggatgt tgaaggattg tccgagctcc aaacaggcca  2100
tggccctcct tgcaaaaatt aaggtcccat cctcaaaggc cccatccgtg actctgaacg  2160
agtgcttccc cacggatgtt ccagtcaact ctgagttaat atcttgggaa gagcccaaag  2220
accctggcgc tgctgttgtc ctatgtccat cggatgcaaa agaatctaag gaaacagccc  2280
```

| | |
|---|---|
| ctgaagaagc tcaagcgaga aaccgtaagg tccttcaccc tgtggtcctt accgaggaac | 2340 |
| ttagcgagca acaggtgcag gtggttgagg gtgatcagga tatgccactg gatttgactt | 2400 |
| ggccaacctt aaccgctacg gcgacccctg ttagagggcc ggtaccggac aatttgagct | 2460 |
| ctggcattgg tgcccagccc gctaccgttc aagaactcat tctggcgagg cctgcacccc | 2520 |
| gtcttgttga gcgctgtggc acggagtcga acggcagcag ttcatttctg gatttgcctg | 2580 |
| acgtgcagac ctcggaccag cctttagacc tgtccctggc cgcgtggcct gtaagggcta | 2640 |
| ccgcgtctga ccccggttgg atccacggta ggcgtgagcc tgtctttgtg aagcctcgag | 2700 |
| gtgttttctc tgatggcgag tcggcccttc agttcggaga gctttccgaa gccagttctg | 2760 |
| tcgtcgatga ccggacaaaa gaagctccgg tggttgacgc ccccatcgat ttgacaactt | 2820 |
| cgaacgagac gctctctggg tctgacccct tgaattcgc caaattcagg cgcccgcgtt | 2880 |
| tctccgcgca agctttaatc gaccgaggtg gtccgcttgc cgatgttcat gcaaagataa | 2940 |
| agagtcgggt atatgaacaa tgccttcaag cttgtgaacc tggtagtcgt gcgaccccag | 3000 |
| ccaccaagaa gtggctcgac aaaatgtggg acagggtgga catgaaaact tggcgctgca | 3060 |
| cctcgcagtt ccaagctggt cacattcttg agtccctcaa attcctccct gacatgattc | 3120 |
| aagacacacc gcctcctgtt cccaggaaga accgagctgg tgacagtgcc ggcctgaagc | 3180 |
| aactggtggc gcagtgggat aggaaatcga gtgtgacacc ccccacaaaa ccggttggac | 3240 |
| cggtgcttga ccaggccgtc cctctgccta tggacatcca gcaaggagat gccatctccg | 3300 |
| ctgacaagcc accccattcg caaaacccct ctagtcaagt agatgtgggt ggaggttgga | 3360 |
| aaagttttat gctctccggc acccgtttcg cggggtccgt tagtcagcgc cttacgacat | 3420 |
| gggtttttga ggttctctcc catctcccag cttttatgct cacactttc tcgccacggg | 3480 |
| gctctatggc tccaggtgat tggctgtttg caggtgctgt tctacttgct ctcctgctct | 3540 |
| gccgttctta cccaatactc ggatgccttc ccttattggg tgtcttttct ggttctgtgc | 3600 |
| ggtgtgttcg tttgggtgtt tttggttctt ggatggcttt gctgtatttt ttattctcga | 3660 |
| ctccacccga cccagtcggt tcttcttgtg accacgattc gccggagtgt catgctgagc | 3720 |
| ttttggctct tgagcagcgc caactttggg aacctgtgcg cagccttgtg gtcgggccat | 3780 |
| cgggcctctt atgcgtcatt cttggcaagt tactcggtgg gtcacgttgt ctctggtttg | 3840 |
| ttctcctacg tatatgcatg ctcgcagatt tggcaatttc tcttatttat gtggtgtccc | 3900 |
| aagggcgttg tcacaagtgt tggggaaagt gtataaggac ggctcctgca gaagtggccc | 3960 |
| ttaatgtgtt tcctttttcg cgcgccaccc gctcatctct tgtgtccttg tgtgatcggt | 4020 |
| tccaagcgcc aaaaggagtt gaccccgtgc acttggcgac aggctggcgc gggtgctggt | 4080 |
| gtggtgagag ccctattcat caatcacacc aaaaaccgat agcttatgcc aacttggatg | 4140 |
| aaaagaagat atccgcccag acggtgattg ctgtcccgta tgatcctagt caggccatta | 4200 |
| aatgcctgaa agttttgcag gcaggagggg ctattgtgga ccagcctacg cccgaggtcg | 4260 |
| tccgtgtgtc tgagattccc ttctcggccc cattttttcc gaaggtccca gtcaacccag | 4320 |
| actgcagggt tgtggtagat tcggacactt tgtggctgc ggtccgctgc ggttattcga | 4380 |
| cagcacaact ggtccttggt cggggcaact ttgccaagct aaatcagacc ccctcagga | 4440 |
| actctgtccc caccaaaaca actggtgggg cctcatacac ccttgccgtg cccaggtat | 4500 |
| ctgtgtggac tcttgttcat ttcatcctcg gcctttggtt aacgtcacct caagtgtgtg | 4560 |
| gtcgaggac ctctgacccg tggtgttcga acccttttc gtatcctact tatggccccg | 4620 |
| gagttgtgtg ttcctctcga ctctgcgtgt ctgccgacgg agttaccctg ccattgttct | 4680 |

```
cagccgttgc ccatctttcc ggtagagagg tggggatttt tattttggtg cttgcctcct   4740
tgggcgcttt agcccaccgc ttggctctta aggcagacat gtcaatggtc tttttggcgt   4800
tttgtgctta cgcctggccc atgagctcct ggttaatttg cttctttcct atgctcttga   4860
ggtgggtaac ccttcatcct ctcactatgc tttgggtgca ctcattttg gtgttttgcc    4920
taccagctgc cggcgttctc tcgctgggaa taaccggtct tctttgggca gttggccgtt   4980
tcacccaggt tgccggaatt atcacacctt atgacatcca ccagtatacc tccgaccac    5040
gtggtgcagc tgctgtagca acggctccag aaggtactta catggcggcc gttcggagag   5100
ccgctttgac tggacggact ttgatcttca caccatctgc agtcggatcc cttcttgaag   5160
gtgctttcag aactcaaaag ccctgcctta acaccgtgaa tgtcgtaggc tcttcccttg   5220
gttctggaga gttttcacc attgatggca aagagtcat cgtcactgcc acccatgtgt     5280
tgaatggtaa cacagccagg gtcactggtg attcctacaa ccgcatgcac acgttcaata   5340
ctaatggtga ttatgcctgg tcccatgctg atgactggca aggcgttgcc cctatggtta   5400
agatcgctaa ggggtatcgc ggtcgtgcct actggcaaac gtcaaccgga gtcgaacctg   5460
gcatcatggg ggaaggattc gccttctgtt tcactaactg tggcgactca gggtcacctg   5520
tcatttcaga agctggtgac cttattggag tccataccgg ttcaaacaaa ctcggttctg   5580
gtcttgtgac aacccctgaa ggggagacct gctccatcaa ggaaactagg ctctctgacc   5640
tttctagaca ttttgcaggt ccaagcgtcc ctcttgggga cattaagttg agcccagcca   5700
tcatccctga tgtgacaact attccgagtg acttggcatc gctccttgct tctgtccccg   5760
tgatggaagg tggcctctca actgtccagc ttttgtgcgt ctttttcctt ctctggcgca   5820
tgatgggcca tgcctggaca cccattgttg ccgtaggctt ctttttgctg aatgaaattc   5880
tcccagcagt cttggtccga gctgtgttct cttttgcact ctttgtactt gcatgggcca   5940
cccctggtc ggcacaagtg ttgatgatta gactcctcac ggcggctctc aaccgcaaca    6000
ggttgtccct ggcgttctac gcattcggag gtgtcgttgg cctggccaca gaaatcggga   6060
cttttgctgg tggatggcct gaactgtccc aagccctctc gacatactgc ttcctgccca   6120
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgctttcttc ctacggtatt ttgctgaggg taatcttagg aaaggcgtgt   6300
cgcagtcctg tggcatgaat aacgaatccc tgacagctgc tttggcttgc aagttgtcgc   6360
aagctgacct tgattttttg tccagtttaa cgaacttcaa gtgctttgtg tccgcttcaa   6420
acatgaaaaa tgcagctggc aatacatcg aggcggcgta tgctagagct ctgcgtcagg    6480
agctggcctc cttggttcag gttgacaaga tgaaaggagt attggccaag ctcgaggctt   6540
tcgctgagac ggccactccg tcacttgaca caggggacgt gattgttctg cttgggcaac   6600
accccatgg atccatcctc gacattaatg tgggggtga aggaaaact gtgtctgtgc     6660
aagaaacacg atgcctgggt ggttccaaat tcagtgtctg cactgtcgtg tccaacacgc   6720
ccgtggatac cttgaccggt atcccacttc agacgccaac cccactttt gaaaatggcc    6780
cgcgccatcg cagcgaggac gacgacctca agttgagag aatgaaaaaa cactgtgtat    6840
ccctcggctt ccacaaaatc aatggtaaag tttactgcaa aatttgggac aagtctaacg   6900
gcgacacctt ttacacggat gattcccgat acactcaaga ccatgctttt caggacaggt   6960
caaccgacta tagagacagg gattatgaag gtgtacagac cgcccccaa cagggattcg    7020
```

```
atccaaagtc cgaagcccct gttggcactg ttgtaatcgg tggcattacg tataacaggc    7080
atctggtcaa aggtaaggag gtcctagttc ccaaacctga caactgcctt gaagctgcca    7140
gactgtccct tgagcaagct cttgctggga tgggccaaac ttgtgacctt acagctaccg    7200
aagtggagaa actaaagcgc atcattagtc aactccaagg tctgaccact gaacaggctt    7260
taaactgcta gccgccagcg gcttgacccg ctgtggccgc ggcggcctag ttgtaactga    7320
aacggcggta aaaatcgtaa ataccacag cagaactttc accttaggct ctttagacct    7380
aaaagtcacc tccgaggtgg aggtgaagaa atcaactgag caggggcacg ctgtcgtggc    7440
gaacttatgt tccggtgtcg tcttgatgag gcctcaccca ccgtcccttg ttgacgttct    7500
cctcaaaccc ggacttgaca caacacccgg cattcaacca gggcatgggg ccgggaatat    7560
gggcgtgaac ggttctattt ggattttga actgcaccc acaaaggtag aactagagtt    7620
gtccaagcaa ataatccaag catgtgaagt caggcgcggg gacgccccta acctccaact    7680
cccctacaag ctttatcctg tcagggggga ccccgagcgg cgtaaaggtc gccttgtcaa    7740
cactaggttt ggagatttac cttacaaaac tccccaagac accaagtccg caattcatgc    7800
ggcttgttgc ctgcatccca atggggtcct cgtgtctgat ggcaaatcca cgctgggtac    7860
cactcttcaa catggtttcg agctttatgt ccccactgta ccttatagtg tcatggaata    7920
ccttgattca cgccctgaca ccccttttat gtgtactaaa catggcactt ccaaggctgc    7980
tgcagaggac ctccaaaaat atgacctatc cactcaaggg tttgtcttgc ctggggtcct    8040
acgcctagtg cgcaggttca tctttagcca tgttggtaag gcgccaccac tgttccttcc    8100
atcaacctac cctgccaaga actccatggc agggtcaat ggccagaggt tcccaacaaa    8160
ggatgtccag agcataccgt aaattgatga aatgtgcgcc cgtgccgtca aggaaaattg    8220
gcagactgtg acaccttgca ccctcaaaaa acagtactgt tccaaaccta aaactagaac    8280
catcctaggt accaacaact tcatagcctt ggctcacagg tcagcactca gtggtgtcac    8340
ccaggcgttc atgaagaagg cctggaagtc cccaattgcc ttggggaaaa acaagtttaa    8400
ggaattgcat tgcactgtcg ccggcagatg ccttgaggct gacctggctt cctgcgatcg    8460
cagcaccccc gccattgtga ggtggttttgt tgccaacctc ctgtatgaac ttgcaggatg    8520
tgaagagtac ttgcctagct acgtgctcaa ctgttgccat gaccttgtgg caacgcagga    8580
tggcgctttc acaaaacgcg gtggcctgtc gtccggggac cccgtcacca gtgtgtccaa    8640
caccgtctac tcactgataa tttacgccca gcacatggtg ctttcggcct tgaagatggg    8700
tcatgaaatt ggtctcaagt tccttgagga acagctcaaa tttgaggacc ttcttgaaat    8760
ccagcccatg ttagtgtatt ctgatgacct cgtcttgtat gcggaaagac ccacttttcc    8820
caactaccat tggtgggtcg agcatctga cctgatgttg ggcttttaaaa cggacccaaa    8880 gaaaactgtc ataactgata aacccagttt tctcggctgc agaattgaag caggacggca    8940
gttagtcccc aatcgcgacc gtattctggc tgctcttgca tatcatatga aggcgcagaa    9000
cgcctcagag tattatgcgt ccgctgccgc aattctgatg gattcgtgtg cttgcattga    9060
ccatgacccc gagtggtatg aggatcttat ctgcggcatc gcccggtgtg ctcgccagga    9120
cggttaccgt tttccaggcc cggcatttt catgtccatg tgggagaagc tgaaaagtca    9180
taatgaaggg aagaaatgcc gtcactgcgg catctgcgac gccaaagccg actatgcgtc    9240
cgcctgtgga cttgatttgt gtttgttcca ttcacacttt catcaacact gcccagtcac    9300
tctgagctgt ggccaccatg ccggttcaaa ggaatgttcg cagtgtcagt cacctgtcgg    9360
ggctggcaaa tcccccttg acgctgtgct gaaacaaatc ccgtacaaac tcctcgtac    9420
```

-continued

```
cattatcatg aaggtggaca acaaaacaac gaccettgac ccgggaagat atcagtcccg    9480
tcgaggtctt gttgcagtca aaagaggtat tgcaggtaat gaggttgatc tttctgatgg    9540
agactaccaa gtggtgcctc ttttgccgac ttgcaaagac ataaacatgg tgaaggtggc    9600
ttgcaacgta ctactcagca agtttatagt agggccgcca ggttccggaa aaaccacctg    9660
gctactgaac caagtccagg acgatgatgt catttacaca cctactcatc agacaatgtt    9720
tgacatagtc agtgctctta aagtttgcag gtattccatc ccaggagcct caggactccc    9780
ttttccacca cctgccaggt ccgggccgtg ggttaggctc atcgccagcg acatgtccc    9840 tggccgagtg tcatatctcg atgaggcagg atattgcaat catctagaca ttctaaggct    9900
gctttccaaa acaccccttg tgtgtttggg tgaccttcag caacttcacc cggtcggctt    9960
tgattcctat tgttatgtgt tcgatcagat gcctcagaag cagctgacca ccatttatag   10020
atttggccct aacatctgtg cagccatcca gccttgttac agggagaaac ttgaatccaa   10080
ggccaggaac accagagtgg ttttcaccac ccggcctgtg gcctttggtc aggtcctgac   10140
accgtaccac aaagatcgta ccggctctgc ataactata gattcatccc aggggcgac    10200 cttcgacatt gtgacattgc atctaccatc gccaaagtcc ctaaacaaat cccgagcact   10260
tgtagccatc actcgggcaa gacatgggtt gttcatttat gaccctcatg accaactcca   10320 ggagttttc aacttaaccc ccgagcgcac tgattgtaac cttgcgttca gccgtgggga   10380
tgagctggtt gttttgaatg tggataatgc ggtcacaact gtagcgaagg ccctagagac   10440
aggttcaccc cgatttcgag tatcggaccc gaggtgcaag tctctcttag ccgcttgttc   10500
ggccagtcta gaagggagct gcatgccact accacaagta gcacataacc tggggttta    10560 cttttcccg acagcccag cttttgcacc cctgccaaaa gagctggcgc acattggcc     10620 agtggtcacc caccagaata atcgagcgtg gcctgatcga cttgtcgcta gtatgcgccc   10680
aattgatgcc cgctacagca agccaatggt cggtgcaggg tatgtggtcg ggccatccat   10740
ttttcttggc actcctggtg tggtgtcata ctatctcaca ttatacatcg ggggcgagcc   10800
tcaggccctg ccagaaacac tcgttttcaac aggacgtata gccacagatt gtcgggaata   10860
tctcgacgcg gctgaggaag aggcagcgag agaacttccc cacgcattta ttggcgatgt   10920
caaaggcact acgatcgggg ggtgtcacca cattacatcg aaataccac ctaggtccct    10980 gcctaaagac tctgttgctg tggttggggt gagttcgccc ggtagggctg ctaaagccgt   11040
gtgcactctc accgatgtgt acctccccga actccgacca tatttgcaac cggagacggc   11100
atcaaaatgc tggaaactta aactggattt cagggatgtt cgactgatgg tctggaaagg   11160
cgccacagcc tatttccagt tggaagggct gacatggtca gcgctgcccg attatgctag   11220
gttcattcag ctaccaaagg atgccgttgt gtacatcgat ccgtgtatag gccggcaac    11280 agccaatcgc aaggttgtgc gaaccacaga ctggcgggcc gacctggcag tgacaccgta   11340
tgattacggt gctcaggtca ttttgacaac agcctggttc gaggaccttg gccgcagtg    11400 gaagattttg ggggttgcagc ctttcagacg aacatttggc tttgagaaca ctgaagattg   11460
ggcaattctc gcacgccgta tgaatgacgg caaagattac actgactata attggcattg   11520
tgtacgagaa cgcccacacg caatttacgg gcgcgcccgt gaccatacgt atcattttgc   11580
ccttggcact gaactgcaag tagagctggg cagaccccgg ctgcctcctg agcaagtgcc   11640
gtgaacgcgg agtgatgcaa tgggttact gtggagtaaa atcagtcagt tgttcgtgga    11700
tgccttcact gagttccttg ttagtgtggt tgacattgtc atctttctcg ccatattgtt   11760
```

```
tgggttcact gttgcaggct ggttattggt cttccttctc agagtggttt gctccgcgtt    11820
tctccgttcg cgctctgcca ttcactcttc cgaactatcg aaggtcctat gagggcttgc    11880
tacccaactg cagaccggat gtcccacaat tcgcagttaa gcacccgttg ggtatacttt    11940
ggcatatgcg agtctcccac ctaattgacg aaatggtctc tcgccgcatt taccggacca    12000
tggaacattc gggtcaagcg gcctggaagc aggttgttag tgaagccact ctcacaaaac    12060
tgtcaaggct tgacgtagtc actcatttcc aacacctggc cgcagtggag gctgattctt    12120
gccgcttcct tagctcacga ctcgcgatgc tgaaaaacct tgccgttggc aatgtgagcc    12180
tggagtacaa cactactttg gaccgcgttg agctcatctt tcccacacca ggtacgaggc    12240
ccaagttgac cgattttagg caatggctta tcagcgtgca cgcttccatc ttctcctctg    12300
tggcttcgtc tgttaccttg ttcacagtgc tttggcttcg aattccagct ctacgctatg    12360
tttttggttt ccattggccc acggcaacac atcattcgaa ctaactatca attacactat    12420
atgtaagcca tgccctacca gtcaagctgc ccaacaaaga ctcgagcctg gccgtaacgt    12480
gtggtgcaaa atagggcacg acaggtgtga ggaacgtgac catgatgagt tgtcaatgtc    12540
cattccgtcc gggtacgaca acctcaaact tgagggttat tatgcttggc tggcttttttt    12600 gtccttttcc tacgcggccc aattccatcc ggagctgttc ggaataggaa acgtgtcgcg    12660
cgtctttgtg gataagcgac accagttcat ttgcgccgag catgatggac aaaattcaac    12720
catatctgcc agacacaaca tctccgcgtc gtatgcggtg tattaccatc atcaaataga    12780
cgggggcaat tggtttcatt tggaatggct gcgaccattc ttttcctcct ggctggtgct    12840
caacatctca tggtttctga ggcgttcgcc tgcaagccct gcttctcgac gcatctatca    12900
gatattaaga ccaacacgac cgcggctgcc ggtttcatgg tccttcagaa catcaattgt    12960
ttccaatctc acggtagctc ccatttacag ttgatttata acttaacggg ctcatcccaa    13020
tgtcgtgaag ccgtcggcat tccccagtac atcacgataa cggctaatgt gaccgatgaa    13080
tcgtatttgt acaacgcgga cttgctgatg cttttccgcgt gccttttcta cgcctcgaaa    13140
atgagcgaga aaggcttcaa agtcatcttt gggaatattt ctggcgttgt ttccgcttgt    13200
gttaatttca cagattatgt ggcccatgtg acccaacaca ctcagcagca ccatttggta    13260
attgatcaca ttcggttact acacttcttg acaccgtcta cgatgaggtg ggctacaacc    13320
attgcttgtt tgcttgccat tcttttggcg gtatgaaatg ttcttgcaag ttggggcatt    13380
tcttgactcc tcactcttgc ttctggtggc ttttttttgct gtgtaccggc ttgtcttggt    13440
cctttgtcga tggcaacgac gacagctcga catcccaata catatataat ttgacgatat    13500
gcgagctgaa tgggaccgaa tggttgtccg gtcatttga ttgggcagtc gaaacctttg    13560
tgctttaccc agttgccact catatcattt cactgggttt tctcacaaca agccatttcc    13620
ttgatgcgct cggtctcggc gctgtgtccg ccacaggatt cattggcgag cggtatgtac    13680
ttagcagcat gtacgcgtt tgcgccttcg cggcgttcgt atgttttgtc atccgtgctg    13740
ctaaaaattg catggcttgc cgctatgccc gcacccggtt taccaacttc atcgtggacg    13800
accggggaag aatccatcga tggaagtctt caatagtggt ggagaaattg gcaaagctg    13860 aagtcggtgg tgaccttgtc aacattaagc atgttgtcct cgaagggtt aaagctcaac    13920 cttttgacgag gacttcggct gagcaatggg aagcctagac gacttttgca acgatcccac    13980
cgccgcacaa aaactcgtgc tggccttag catcacatat acaccataa tgatatacgc    14040 ccttaaggtg tcacgcggcc gactcctggg gctgttgcac atcttgatat ttctgaattg    14100
ttcctttact tttgggtaca tgacatatgt gcattttcaa tccaccaacc gtgtcgcatt    14160
```

```
cactctgggg gctgtagtcg ccctttgtg gggtgtttac agcctcacag agtcatggaa    14220
gttcatcact tccagatgca gattgtgttg cctaggccgg cgatacattc tggcccctgc    14280
ccatcacgta gaaagtgctg caggcctcca ttcaatccca gcgtctggta accgagcata    14340
cgctgtgaga aagcccggac taacatcagt gaacggcact ctagtacctg ggcttcggag    14400
cctcgtgctg ggcggcaaac gagctgttaa acgaggagtg gttaacctcg tcaagtatgg    14460
ccggtaagaa ccagagccag aagaaaagaa gaaatgcagc tccgatgggg aaaggccagc    14520
cagtcaatca actgtgccag ttgctgggta caatgataaa gtcccagcgc cagcaatcta    14580
ggggaggaca ggccaaaaag aagaagcctg agaagccaca ttttccccta gctgctgaag    14640
atgacattcg gcaccatctc acccaggccg aacgttccct ctgcttgcaa tcgatccaga    14700
cggctttcaa tcaaggcgca ggaactgcgt cgctttcatc cagcgggaag gtcagtttcc    14760
aggttgagtt catgctgccg gttgctcata cagtgcgcct gattcgcgtg acttctacat    14820
ccgccagtca gggtgcaaat taatttgaca gtcaggtgaa tggccgcgat tgacgtgtgg    14880
cctctaagtc acctattcaa ttagggcgat cacatggggg tcaaacttaa ttaggcagga    14940
accatgtgac cgaaattaaa aaaaaaaaaa aaaaaaaaa aaaa                      14984

<210> SEQ ID NO 57
<211> LENGTH: 14984
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SEQ ID NO:49 with insert coding for SEQ ID
      NO:54

<400> SEQUENCE: 57
atgatgtgta gggtattccc cctacataca cgacactctt agtgtttgtg taccttggag       60
gcgtgggtac agccctgccc caccctttgg tccctgttct agcccgacag gtacccttct      120
ctctcggggc gagcgcgccg cctgctgctc ccttgcggcg ggaaggacct cccgagtatt      180
tccggagagc acctgcttta cgggatctcc gcccttaac catgtctggg atgttctccc      240
ggtgcatgtg caccccggct gcccgggtat tttggaacgc cggccaagtc tattgcacac      300
ggtgtctcag tgcacggtct cttctctctc cagaacttca ggacacggac ctcggtgcag      360
ttggcttgtt tcacaagcct aaagacaagc tccattggaa agttcccatt ggtatccccc      420
aggtggaatg ttctccatct gggtgttgct ggctgtcaac catttttcct ttagcgcgca      480
tgacctccgg caatcacaac ttccttcaac gactcgtgaa ggttgctgat gtattgtacc      540
gtgacggttg cttaaccccct agacacctcc gtgaactcca agtttacgag cgtggttgca      600
attggtatcc gattacgggg cctgtgcctg ggatggctgt gtacgcgaac tccatgcacg      660
tgtccgacca accgttccct ggtgccactc atgtgttaac aaattcccct ttgcctcaac      720
gggcttgtcg gcagccgttc tgtccgttcg aagaggccca ttctagcata tacaggtggg      780
aaaaatttgt aattttatg gattcctcct ccgacggtcg atctcgcatg atgtggactc      840
cggaatccga tgactccacg gctttggaag ttctgccgcc cgagctagaa caccaggtca      900
aggtccttgt tcggagcttt cccgcccatc accttgtcga ccttgccgat tgggagctca      960
ctgagtcccc tgataacggt ttttccttca gcacgtcaca tccttgcggc tacccttgttc    1020 gggacccggc tgtatccgaa ggcaagtgtt ggctttcctg ctttttgagc cagtcagccg    1080
```

```
aagtgctcag tcgcgaggcg catctggcta ccgcctatgg ttaccaaacc aagtggggtg    1140
tgcctggcaa gtacatccag cgcagacttc aagttcacgg tctccgtgct gtggtcgacc    1200
ctgatggtcc cattcacgtt gaagcattgt cttgccccca gtcttggatc aggcacttga    1260
ccctgaatga tgatgtcacc ccgggattcg ttcgcctaat gtctcttcgc attgtgccga    1320
acacagagcc taccacacac cggatctttc gttttggagt gcacaagtgg tatggtgccg    1380
ccggcaaacg ggcccgtggc aagcgtgccg ccaaaagtga aaagactcg gcttccaccc     1440 tcaaggttgc ccgaccgact ccaccagtg gaatcgtcac ctactcccca cctgcggacg     1500
ggtcttgtgg ttggcatgcc cttgccgcca tactgaaccg gatgattaat aatgacttca    1560
cgtcccctct gcctcggtac aacaggccgg aggacgattg ggcttctgat ggtgaccttg    1620
ctcaggccat tcaatgtttg caactacctg ccgccatagc tcggaaccgc gcctgccta    1680 acgccaaata cctcataaaa ctcaacggag ttcattggga ggtagaggtg aggcctggaa    1740
tggctcctcg ctccctctct cgtgagtgcg ttgttggcgt ctgctctgaa ggctgtgtcg    1800
cgtcgcctta cccggaggac gggttgccta acgtgcact tgaggccctg gcgtctgctt     1860
atagactgcc ttcagactgt gtttgtgatg gtattattga cttccttgcc aatccacctc    1920
cccaggagtt ctgactctt gacaaaatgt tgacttcccc gtcaccggag cagtccggct     1980
tctctagtct gtataaattg ttgttagaga tcttgccgca gaaatgcgga tccacagaag    2040
gggaattcat ctatactgtt gagaggatgt tgaaggattg tccagctcc aaacaggcca     2100 tggccctcct tgcaaaaatt aaggtcccat cctcaaaggc cccatccgtg actctgaacg    2160
agtgcttccc cacggatgtt ccagtcaact ctgagttaat atcttgggaa gagcccaaag    2220
accctggcgc tgctgttgtc ctatgtccat cggatgcaaa agaatctaag gaaacagccc    2280
ctgaagaagc tcaagcgaga aaccgtaagg tccttcaccc tgtggtcctt accgaggaac    2340
ttagcgagca acaggtgcag gtggttgagg gtgatcagga tatgccactg gatttgactt    2400
ggccaacctt aaccgctacg gcgacccctg ttagagggcc ggtaccggac aatttgagct    2460
ctggcattgg tgcccagccc gctaccgttc aagaactcat tctgcgagg cctgcacccc     2520 gtcttgttga gcgctgtggc acggagtcga acggcagcag ttcatttctg gatttgcctg    2580
acgtgcagac ctcggaccag cctttagacc tgtccctggc cgcgtggcct gtaagggcta    2640
ccgcgtctga ccccggttgg atccacggta ggcgtgagcc tgtctttgtg aagcctcgag    2700
gtgttttctc tgatggcgag tcggcccttc agttcggaga gctttccgaa gccagttctg    2760
tcgtcgatga ccggacaaaa gaagctccgg tggttgacgc ccccatcgat ttgacaactt    2820
cgaacgagac gctctctggg tctgacccct ttgaattcgc caaattcagg cgcccgcgtt    2880
tctccgcgca agctttaatc gaccgaggtg gtccgcttgc cgatgttcat gcaaagataa    2940
agagtcgggt atatgaacaa tgccttcaag cttgtgaacc tggtagtcgt gcgacccag     3000 ccaccaagaa gtggctcgac aaaatgtggg acagggtgga catgaaaact tggcgctgca    3060
cctcgcagtt ccaagctggt cacattcttg agtccctcaa attcctccct gacatgattc    3120
aagacacacc gctcctgtt cccaggaaga accgagctgg tgacagtgcc ggcctgaagc     3180
aactggtggc gcagtgggat aggaaatcga gtgtgacacc cccacaaaaa ccggttggac    3240
cggtgcttga ccaggccgtc cctctgccta tggacatcca gcaaggagat gccatctccg    3300
ctgacaagcc accccattcg caaaaccctt ctagtcaagt agatgtgggt ggaggttgga    3360
aaagttttat gctctccggc acccgttccg cggggtccgt tagtcagcgc cttacgacat    3420 gggttttga ggttctctcc catctcccag cttttatgct cacactttc tcgccacggg      3480
```

```
gctctatggc tccaggtgat tggctgtttg caggtgctgt tctacttgct ctcctgctct   3540
gccgttctta cccaatactc ggatgccttc ccttattggg tgtcttttct ggttctgtgc   3600
ggtgtgttcg tttgggtgtt tttggttctt ggatggcttt tgctgtattt ttattctcga   3660
ctccacccga cccagtcggt tcttcttgtg accacgattc gccggagtgt catgctgagc   3720
ttttggctct tgagcagcgc caactttggg aacctgtgcg cagccttgtg gtcgggccat   3780
cgggcctctt atgcgtcatt cttggcaagt tactcggtgg gtcacgttgt ctctggtttg   3840
ttctcctacg tatatgcatg ctcgcagatt tggcaatttc tcttatttat gtggtgtccc   3900
aagggcgttg tcacaagtgt tggggaaagt gtataaggac ggctcctgca gaagtggccc   3960
ttaatgtgtt tccttttcg cgcgccaccc gctcatctct tgtgtccttg tgtgatcggt   4020
tccaagcgcc aaaaggagtt gaccccgtgc acttggcgac aggctggcgc gggtgctggt   4080
gtggtgagag ccctattcat caatcacacc aaaaaccgat agcttatgcc aacttggatg   4140
aaaagaagat atccgcccag acggtgattg ctgtcccgta tgatcctagt caggccatta   4200
aatgcctgaa agttttgcag gcaggagggg ctattgtgga ccagcctacg cccgaggtcg   4260
tccgtgtgtc tgagattccc ttctcggccc cattttttcc gaaggtccca gtcaacccag   4320
actgcagggt tgtggtagat tcggacactt ttgtggctgc ggtccgctgc ggttattcga   4380
cagcacaact ggtccttggt cggggcaact ttgccaagct aaatcagacc cccctcagga   4440
actctgtccc caccaaaaca actggtgggg cctcatacac ccttgccgtg cccaggtat    4500
ctgtgtggac tcttgttcat ttcatcctcg gcctttggtt aacgtcacct caagtgtgtg   4560
gtcgagggac ctctgacccg tggtgttcga acccttttc gtatcctact tatggccccg   4620
gagttgtgtg ttcctctcga ctctgcgtgt ctgccgacgg agttaccctg ccattgttct   4680
cagccgttgc ccatctttcc ggtagagagg tggggatttt tattttggtg cttgcctcct   4740
tgggcgcttt agcccaccgc ttggctctta aggcagacat gtcaatggtc tttttggcgt   4800
tttgtgctta cgcctggccc atgagctcct ggttaatttg cttctttcct atgctcttga   4860
ggtgggtaac ccttcatcct ctcactatgc tttgggtgca ctcattttg gtgttttgcc    4920
taccagctgc cggcgttctc tcgctgggaa taaccggtct tctttgggca gttggccgtt   4980
tcacccaggt tgccggaatt atcacaccct atgacatcca ccagtatacc tccggaccac   5040
gtggtgcagc tgctgtagca acggctccag aaggtactta catggcggcc gttcggagag   5100
ccgctttgac tggacggact ttgatcttca caccatctgc agtcggatcc cttcttgaag   5160
gtgctttcag aactcaaaag ccctgcctta acaccgtgaa tgtcgtaggc tcttcccttg   5220
gttctggagg agttttcacc attgatggca gaagagtcat cgtcactgcc acccatgtgt   5280
tgaatggtaa cacagccagg gtcactggtg attcctacaa ccgcatgcac acgttcaata   5340
ctaatggtga ttatgcctgg tcccatgctg atgactggca aggcgttgcc cctatggtta   5400
agatcgctaa ggggtatcgc ggtcgtgcct actggcaaac gtcaaccgga gtcgaacctg   5460
gcatcatggg ggaaggattc gccttctgtt tcactaactg tggcgactca gggtcacctg   5520
tcatttcaga agctggtgac cttattggag tccataccgg ttcaaacaaa ctcggttctg   5580
gtcttgtgac aaccctgaa ggggagacct gctccatcaa ggaaactagg ctctctgacc    5640
tttctagaca ttttgcaggt ccaagcgtcc ctcttgggga cattaagttg agcccagcca   5700
tcatccctga tgtgacaact attccgagtg acttggcatc gctccttgct tctgtccccg   5760
tgatggaagg tggcctctca actgtccagc ttttgtgcgt cttttccctt tctgggcgca   5820
```

```
tgatgggcca tgcctggaca cccattgttg ccgtaggctt cttttgctg aatgaaattc   5880
tcccagcagt cttggtccga gctgtgttct cttttgcact ctttgtactt gcatgggcca   5940
cccctggtc ggcacaagtg ttgatgatta gactcctcac ggcggctctc aaccgcaaca    6000
ggttgtccct ggcgttctac gcattcggag gtgtcgttgg cctggccaca gaaatcggga   6060
cttttgctgg tggatggcct gaactgtccc aagccctctc gacatactgc ttcctgccca   6120
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgcttcttc ctacggtatt ttgctgaggg taatcttagg aaaggcgtgt    6300
cgcagtcctg tggcatgaat aacgaatccc tgacagctgc tttggcttgc aagttgtcgc   6360
aagctgacct tgattttttg tccagtttaa cgaacttcaa gtgctttgtg tccgcttcaa   6420
acatgaaaaa tgcagctggc caatacatcg aggcggcgta tgctagagct ctgcgtcagg   6480
agctggcctc cttggttcag gttgacaaga tgaaggagt attggccaag ctcgaggctt    6540
tcgctgagac ggccactccg tcacttgaca caggggacgt gattgttctg cttgggcaac   6600
accccccatgg atccatcctc gacattaatg tggggggtga aggaaaact gtgtctgtgc    6660
aagaaacacg atgcctgggt ggttccaaat tcagtgtctg cactgtcgtg tccaacacgc   6720
ccgtggatac cttgaccggt atcccacttc agacgccaac cccactttt gaaaatggcc     6780
cgcgccatcg cagcgaggac gacgacctca agttgagag aatgaaaaaa cactgtgtat    6840
ccctcggctt ccacaaaatc aatggtaaag tttactgcaa aatttgggac aagtctaacg   6900
gcgacacctt ttacacggat gattcccgat acactcaaga ccatgctttt caggacaggt   6960
caaccgacta tagagacagg gattatgaag gtgtacagac cgccccccaa cagggattcg   7020
atccaaagtc cgaagcccct gttggcactg ttgtaatcgg tggcattacg tataacaggc   7080
atctggtcaa aggtaaggag gtcctagttc ccaaacctga caactgcctt gaagctgcca   7140
gactgtccct tgagcaagct cttgctggga tgggccaaac ttgtgacctt acagctaccg   7200
aagtggagaa actaaagcgc atcattagtc aactccaagg tctgaccact gaacaggctt   7260
taaactgcta gccgccagcg gcttgacccg ctgtggccgc ggcggcctag ttgtaactga   7320
aacggcggta aaaatcgtaa aataccacag cagaactttc accttaggct ctttagacct   7380
aaaagtcacc tccagaggtgg aggtgaagaa atcaactgag caggggcacg ctgtcgtggc   7440
gaacttatgt tccggtgtcg tcttgatgag gcctcaccca ccgtcccttg ttgacgttct   7500
cctcaaaccc ggacttgaca caacacccgg cattcaacca gggcatgggg ccggaatat    7560
gggcgtgaac ggttctattt gggattttga aactgcaccc acaaaggtag aactagagtt   7620
gtccaagcaa ataatccaag catgtgaagt caggcgcggg gacgccccta acctccaact   7680
ccctacaag ctttatcctg tcaggggga ccccgagcgg cgtaaaggtc gccttgtcaa     7740
cactaggttt ggagatttac cttacaaaac tccccaagac accaagtccg caattcatgc   7800
ggcttgttgc ctgcatccca atggggtcct cgtgtctgat ggcaaatcca cgctgggtac   7860
cactcttcaa catggtttcg agctttatgt ccccactgta ccttatagtg tcatggaata   7920
ccttgattca cgccctgaca cccctttat gtgtactaaa catggcactt ccaaggctgc   7980
tgcagaggac ctccaaaaat atgacctatc cactcaaggg tttgtcttgc ctgggtcct    8040
acgcctagtg cgcaggttca tctttagcca tgttggtaag cgccaccac tgttccttcc    8100
atcaacctac cctgccaaga actccatggc aggggtcaat ggcagaggt tcccaacaaa    8160
ggatgtccag agcataccctg aaattgatga aatgtgcgcc cgtgccgtca aggaaaattg   8220
```

```
gcagactgtg acaccttgca ccctcaaaaa acagtactgt tccaaaccta aaactagaac    8280
catcctaggt accaacaact tcatagcctt ggctcacagg tcagcactca gtggtgtcac    8340
ccaggcgttc atgaagaagg cctggaagtc cccaattgcc ttggggaaaa acaagtttaa    8400
ggaattgcat tgcactgtcg ccggcagatg ccttgaggct gacctggctt cctgcgatcg    8460
cagcaccccc gccattgtga ggtggtttgt tgccaacctc ctgtatgaac ttgcaggatg    8520
tgaagagtac ttgcctagct acgtgctcaa ctgttgccat gaccttgtgg caacgcagga    8580
tggcgctttc acaaaacgcg gtggcctgtc gtccggggac cccgtcacca gtgtgtccaa    8640
caccgtctac tcactgataa tttacgccca gcacatggtg ctttcggcct tgaagatggg    8700
tcatgaaatt ggtctcaagt tccttgagga acagctcaaa tttgaggacc ttcttgaaat    8760
ccagcccatg ttagtgtatt ctgatgacct cgtcttgtat gcggaaagac ccacttttcc    8820
caactaccat tggtgggtcg agcatcttga cctgatgttg ggctttaaaa cggacccaaa    8880
gaaaactgtc ataactgata aacccagttt tctcggctgc agaattgaag caggacggca    8940
gttagtcccc aatcgcgacc gtattctggc tgctcttgca tatcatatga aggcgcagaa    9000
cgcctcagag tattatgcgt ccgctgccgc aattctgatg gattcgtgtg cttgcattga    9060
ccatgacccc gagtggtatg aggatcttat ctgcggcatc gcccggtgtg ctcgccagga    9120
cggttaccgt tttccaggcc cggcattttt catgtccatg tgggagaagc tgaaaagtca    9180
taatgaaggg aagaaatgcc gtcactgcgg catctgcgac gccaaagccg actatgcgtc    9240
cgcctgtgga cttgatttgt gtttgttcca ttcacacttt catcaacact gcccagtcac    9300
tctgagctgt ggccaccatg ccggttcaaa ggaatgttcg cagtgtcagt cacctgtcgg    9360
ggctggcaaa tccccccttg acgctgtgct gaaacaaatc ccgtacaaac ctcctcgtac    9420
cattatcatg aaggtggaca caaaacaac gacccttgac ccgggaagat atcagtcccg    9480
tcgaggtctt gttgcagtca aaagaggtat tgcaggtaat gaggttgatc tttctgatgg    9540
agactaccaa gtggtgcctc ttttgccgac ttgcaaagac ataaacatgg tgaaggtggc    9600
ttgcaacgta ctactcagca agtttatagt agggccgcca ggttccggaa aaaccacctg    9660
gctactgaac caagtccagg acgatgatgt catttacaca cctactcatc agacaatgtt    9720
tgacatagtc agtgctctta aagtttgcag gtattccatc ccaggagcct caggactccc    9780 tttttccacca cctgccaggt ccgggccgtg ggttaggctc atcgccagcg acatgtccc    9840 tggccgagtg tcatatctcg atgaggcagg atattgcaat catctagaca ttctaaggct    9900
gctttccaaa acaccccttg tgtgtttggg tgaccttcag caacttcacc cggtcggctt    9960
tgattcctat tgttatgtgt tcgatcagat gcctcagaag cagctgacca ccatttatag   10020
atttggccct aacatctgtg cagccatcca gccttgttac agggagaaac ttgaatccaa   10080
ggccaggaac accagagtgg ttttcaccac ccggcctgtg gcctttggtc aggtcctgac   10140
accgtaccac aaagatcgta ccggctctgc aataactata gattcatccc aggggcgac    10200 cttcgacatt gtgacattgc atctaccatc gccaaagtcc ctaaacaaat cccgagcact   10260
tgtagccatc actcgggcaa gacatgggtt gttcatttat gaccctcatg accaactcca   10320 ggagttttc aacttaaccc ccgagcgcac tgattgtaac cttgcgttca gccgtgggga   10380
tgagctggtt gttttgaatg tggataatgc ggtcacaact gtagcgaagg ccctagagac   10440
aggttcaccc cgatttcgag tatcggaccc gaggtgcaag tctctcttag ccgcttgttc   10500
ggccagtcta gaagggagct gcatgccact accacaagta gcacataacc tggggttta    10560
```

```
cttttccccg acagcccag cttttgcacc cctgccaaaa gagctggcgc cacattggcc    10620
agtggtcacc caccagaata atcgagcgtg gcctgatcga cttgtcgcta gtatgcgccc    10680
aattgatgcc cgctacagca agccaatggt cggtgcaggg tatgtggtcg ggccatccat    10740
ttttcttggc actcctggtg tggtgtcata ctatctcaca ttatacatcg ggggcgagcc    10800
tcaggccctg ccagaaacac tcgtttcaac aggacgtata gccacagatt gtcgggaata    10860
tctcgacgcg gctgaggaag aggcagcgag agaacttccc cacgcattta ttggcgatgt    10920
caaaggcact acgatcgggg ggtgtcacca cattacatcg aaatacctac ctaggtccct    10980
gcctaaagac tctgttgctg tggttggggt gagttcgccc ggtagggctg ctaaagccgt    11040
gtgcactctc accgatgtgt acctccccga actccgacca tatttgcaac cggagacggc    11100
atcaaaatgc tggaaactta aactggattt cagggatgtt cgactgatgg tctggaaagg    11160
cgccacagcc tatttccagt tggaagggct gacatggtca gcgctgcccg attatgctag    11220
gttcattcag ctacccaagg atgccgttgt gtacatcgat ccgtgtatag ggccggcaac    11280
agccaatcgc aaggttgtgc gaaccacaga ctggcgggcc gacctggcag tgacaccgta    11340
tgattacggt gctcaggtca ttttgacaac agcctggttc gaggaccttg gccgcagtg     11400
gaagattttg gggttgcagc cttttcagacg aacatttggc tttgagaaca ctgaagattg    11460
ggcaattctc gcacgccgta tgaatgacgg caaagattac actgactata attggcattg    11520
tgtacgagaa cgcccacacg caatttacgg gcgcgcccgt gaccatacgt atcattttgc    11580
ccttggcact gaactgcaag tagagctggg cagaccccgg ctgcctcctg agcaagtgcc    11640
gtgaacgcgg agtgatgcaa tgggtttact gtggagtaaa atcagtcagt tgttcgtgga    11700
tgccttcact gagttccttg ttagtgtggt tgacattgtc atctttctcg ccatattgtt    11760
tgggttcact gttgcaggct ggttattggt cttccttctc agagtggttt gctccgcgtt    11820
tctccgttcg cgctctgcca ttcactcttc cgaactatcg aaggtcctat gagggcttgc    11880
tacccaactg cagaccggat gtcccacaat tcgcagttaa gcaccgttg ggtatactt      11940
ggcatatgcg agtctcccac ctaattgacg aaatggtctc tcgccgcatt taccggacca    12000
tggaacattc gggtcaagcg gcctggaagc aggttgttag tgaagccact ctcacaaaac    12060
tgtcaaggct tgacgtagtc actcatttcc aacacctggc cgcagtggag gctgattctt    12120
gccgcttcct tagctcacga ctcgcgatgc tgaaaaacct tgccgttggc aatgtgagcc    12180
tggagtacaa cactactttg gaccgcgttg agctcatctt tcccacacca ggtacgaggc    12240
ccaagttgac cgatttttagg caatggctta tcagcgtgca cgcttccatc ttctcctctg    12300
tggcttcgtc tgttaccttg ttcacagtgc tttggcttcg aattccagct ctacgctatg    12360
tttttggttt ccattggccc acggcaacac atcattcgaa ctaactatca attacactat    12420
atgtaagcca tgccctacca gtcaagctgc ccaacaaaga ctcgagcctg gccgtaacgt    12480
gtggtgcaaa ataggggcacg acaggtgtga ggaacgtgac catgatgagt tgtcaatgtc    12540
cattccgtcc gggtacgaca acctcaaact tgagggttat tatgcttggc tggcttttt      12600
gtccttttcc tacgcggccc aattccatcc ggagctgttc ggaataggaa acgtgtcgcg    12660
cgtctttgtg gataagcgac accagttcat ttgcgccgag catgatggac aaaattcaac    12720
catatctgcc agacacaaca tctccgcgtc gtatgcggtg tattaccatc atcaaataga    12780
cgggggcaat ggtttcatt tggaatggct gcgaccattc ttttcctcct ggctggtgct     12840
caacatctca tggtttctga ggcgttcgcc tgcaagccct gcttctcgac gcatctatca    12900
gatattaaga ccaacacgac cgcggctgcc ggtttcatgg tccttcagaa catcaattgt    12960
```

```
ttccaatctc acggtagctc ccatttacag ttgatttatc agttaacggg ctcatcccaa    13020
tgtcgtgaag ccgtcggcat tccccagtac atcacgataa cggctaatgt gaccgatgaa    13080
tcgtatttgt acaacgcgga cttgctgatg ctttccgcgt gccttttcta cgcctcggaa    13140
atgagcgaga aaggcttcaa agtcatcttt gggaatattt ctggcgttgt ttccgcttgt    13200
gttaatttca cagattatgt ggcccatgtg acccaacaca ctcagcagca ccatttggta    13260
attgatcaca ttcggttact acacttcttg acaccgtcta cgatgaggtg ggctacaacc    13320
attgcttgtt tgcttgccat tcttttggcg gtatgaaatg ttcttgcaag ttggggcatt    13380
tcttgactcc tcactcttgc ttctggtggc tttttttgct gtgtaccggc ttgtcttggt    13440
cctttgtcga tggcaacgac gacagctcga catcccaata catatataat ttgacgatat    13500
gcgagctgaa tgggaccgaa tggttgtccg gtcattttga ttgggcagtc gaaacctttg    13560
tgctttaccc agttgccact catatcattt cactgggttt tctcacaaca agccatttcc    13620
ttgatgcgct cggtctcggc gctgtgtccg ccacaggatt cattggcgag cggtatgtac    13680
ttagcagcat gtacggcgtt tgcgccttcg cggcgttcgt atgttttgtc atccgtgctg    13740
ctaaaaattg catggcttgc cgctatgccc gcacccggtt taccaacttc atcgtggacg    13800
accggggaag aatccatcga tggaagtctt caatagtggt ggagaaattg ggcaaagctg    13860
aagtcggtgg tgaccttgtc aacattaagc atgttgtcct cgaaggggtt aaagctcaac    13920
cttttgacgag gacttcggct gagcaatggg aagcctagac gacttttgca acgatcccac    13980
cgccgcacaa aaactcgtgc tggcctttag catcacatat acacccataa tgatatacgc    14040
ccttaaggtg tcacgcggcc gactcctggg gctgttgcac atcttgatat ttctgaattg    14100
ttcctttact tttgggtaca tgacatatgt gcattttcaa tccaccaacc gtgtcgcatt    14160
cactctgggg gctgtagtcg cccttttgtg gggtgtttac agcctcacag agtcatgaa    14220
gttcatcact tccagatgca gattgtgttg cctaggccgg cgatacattc tggcccctgc    14280
ccatcacgta gaaagtgctg caggcctcca ttcaatccca gcgtctggta accgagcata    14340
cgctgtgaga aagcccggac taacatcagt gaacggcact ctagtacctg gcttcggag    14400
cctcgtgctg ggcggcaaac gagctgttaa acgaggagtg gttaacctcg tcaagtatgg    14460
ccggtaagaa ccagagccag aagaaaagaa gaaatgcagc tccgatgggg aaaggccagc    14520
cagtcaatca actgtgccag ttgctgggta caatgataaa gtcccagcgc cagcaatcta    14580
ggggaggaca ggccaaaaag aagaagcctg agaagccaca ttttccccta gctgctgaag    14640
atgacattcg gcaccatctc acccaggccg aacgttccct ctgcttgcaa tcgatccaga    14700
cggctttcaa tcaaggcgca ggaactgcgt cgctttcatc cagcgggaag gtcagttcc    14760
aggttgagtt catgctgccg gttgctcata cagtgcgcct gattcgcgtg acttctacat    14820
ccgccagtca gggtgcaaat taatttgaca gtcaggtgaa tggccgcgat tgacgtgtgg    14880
cctctaagtc accattcaa ttagggcgat cacatgggg tcaaacttaa ttaggcagga    14940
accatgtgac cgaaattaaa aaaaaaaaaa aaaaaaaaaa aaaa                     14984
```

<210> SEQ ID NO 58
<211> LENGTH: 14984
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SEQ ID NO:48 with deletion encoding ORF4 protein with deletion of 14 aa (aa 56-69), wherein insert coding
for SEQ ID NO:55 is included

<400> SEQUENCE: 58

| | | | | |
|---|---|---|---|---|
| atgatgtgta | gggtattccc | cctacataca | cgacactctt | agtgtttgtg | taccttggag | 60 |
| gcgtgggtac | agcccgccc | caccctttgg | tccctgttct | agcccgacag | gtacccttct | 120 |
| ctctcggggc | gagcgcgccg | cctgctgctc | ccttgcggcg | ggaaggacct | cccgagtatt | 180 |
| tccggagagc | acctgcttta | cgggatctcc | gcccttaac | catgtctggg | atgttctccc | 240 |
| ggtgcatgtg | cacccggct | gcccgggtat | tttggaacgc | cggccaagtc | tattgcacac | 300 |
| ggtgtctcag | tgcacggtct | cttctctctc | cagaacttca | ggacacggac | ctcggtgcag | 360 |
| ttggcttgtt | tcacaagcct | aaagacaagc | tccattggaa | agttcccatt | ggtatccccc | 420 |
| aggtggaatg | ttctccatct | gggtgttgct | ggctgtcaac | cattttttcct | ttagcgcgca | 480 |
| tgacctccgg | caatcacaac | ttccttcaac | gactcgtgaa | ggttgctgat | gtattgtacc | 540 |
| gtgacggttg | cttaacccct | agacacctcc | gtgaactcca | agtttacgag | cgtggttgca | 600 |
| attggtatcc | gattacgggg | cctgtgcctg | ggatggctgt | gtacgcgaac | tccatgcacg | 660 |
| tgtccgacca | accgttccct | ggtgccactc | atgtgttaac | aaattcccct | ttgcctcaac | 720 |
| gggcttgtcg | gcagccgttc | tgtccgttcg | aagaggccca | ttctagcata | tacaggtggg | 780 |
| aaaaatttgt | aattttatg | gattcctcct | ccgacggtcg | atctcgcatg | atgtggactc | 840 |
| cggaatccga | tgactccacg | gctttggaag | ttctgccgcc | cgagctagaa | caccaggtca | 900 |
| aggtccttgt | tcggagcttt | cccgcccatc | accttgtcga | ccttgccgat | gggagctca | 960 |
| ctgagtcccc | tgataacggt | ttttccttca | gcacgtcaca | tccttgcggc | taccttgttc | 1020 |
| gggacccggc | tgtatccgaa | ggcaagtgtt | ggctttcctg | cttttttgagc | cagtcagccg | 1080 |
| aagtgctcag | tcgcgaggcg | catctggcta | ccgcctatgg | ttaccaaacc | aagtggggtg | 1140 |
| tgcctggcaa | gtacatccag | cgcagacttc | aagttcacgg | tctccgtgct | gtggtcgacc | 1200 |
| ctgatggtcc | cattcacgtt | gaagcattgt | cttgccccca | gtcttggatc | aggcacttga | 1260 |
| ccctgaatga | tgatgtcacc | ccgggattcg | ttcgcctaat | gtctcttcgc | attgtgccga | 1320 |
| acacagagcc | taccacacac | cggatctttc | gttttggagt | gcacaagtgg | tatggtgccg | 1380 |
| ccggcaaacg | ggcccgtggc | aagcgtgccg | ccaaaagtga | gaaagactcg | gcttccaccc | 1440 |
| tcaaggttgc | ccgaccgact | tccaccagtg | gaatcgtcac | ctactcccca | cctgcggacg | 1500 |
| ggtcttgtgg | ttggcatgcc | cttgccgcca | tactgaaccg | gatgattaat | aatgacttca | 1560 |
| cgtcccctct | gcctcggtac | aacaggccgg | aggacgattg | ggcttctgat | ggtgaccttg | 1620 |
| ctcaggccat | tcaatgtttg | caactacctg | ccgccatagc | tcggaaccgc | gcctgccta | 1680 |
| acgccaaata | cctcataaaa | ctcaacggag | ttcattggga | ggtagaggtg | aggcctggaa | 1740 |
| tggctcctcg | ctccctctct | cgtgagtgcg | ttgttggcgt | ctgctctgaa | ggctgtgtcg | 1800 |
| cgtcgccta | cccggaggac | gggttgccta | acgttgcact | tgaggccctg | gcgtctgctt | 1860 |
| atagactgcc | ttcagactgt | gttttgtgatg | gtattattga | cttccttgcc | aatccacctc | 1920 |
| cccaggagtt | ctggactctt | gacaaaatgt | tgacttcccc | gtcaccggag | cagtccggct | 1980 |
| tctctagtct | gtataaattg | ttgttagaga | tcttgccgca | gaaatgcgga | tccacagaag | 2040 |
| gggaattcat | ctatactgtt | gagaggatgt | tgaaggattg | tccgagctcc | aaacaggcca | 2100 |
| tggcccctcct | tgcaaaaatt | aaggtccat | cctcaaggc | cccatccgtg | actctgaacg | 2160 |
| agtgcttccc | cacggatgtt | ccagtcaact | ctgagttaat | atcttgggaa | gagcccaaag | 2220 |

```
accctggcgc tgctgttgtc ctatgtccat cggatgcaaa agaatctaag gaaacagccc    2280
ctgaagaagc tcaagcgaga aaccgtaagg tccttcaccc tgtggtcctt accgaggaac    2340
ttagcgagca acaggtgcag gtggttgagg gtgatcagga tatgccactg gatttgactt    2400
ggccaacctt aaccgctacg gcgacccctg ttagagggcc ggtaccggac aatttgagct    2460
ctggcattgg tgcccagccc gctaccgttc aagaactcat tctggcgagg cctgcacccc    2520
gtcttgttga gcgctgtggc acggagtcga acggcagcag ttcatttctg gatttgcctg    2580
acgtgcagac ctcggaccag cctttagacc tgtccctggc cgcgtggcct gtaagggcta    2640
ccgcgtctga ccccggttgg atccacggta ggcgtgagcc tgtctttgtg aagcctcgag    2700
gtgttttctc tgatggcgag tcggcccttc agttcggaga gctttccgaa gccagttctg    2760
tcgtcgatga ccggacaaaa gaagctccgg tggttgacgc ccccatcgat ttgacaactt    2820
cgaacgagac gctctctggg tctgacccct ttgaattcgc caaattcagg cgcccgcgtt    2880
tctccgcgca agctttaatc gaccgaggtg gtccgcttgc cgatgttcat gcaaagataa    2940
agagtcgggt atatgaacaa tgccttcaag cttgtgaacc tggtagtcgt gcgacccag    3000 ccaccaagaa gtggctcgac aaaatgtggg acagggtgga catgaaaact tggcgctgca    3060
cctcgcagtt ccaagctggt cacattcttg agtccctcaa attcctccct gacatgattc    3120
aagacacacc gcctcctgtt cccaggaaga accgagctgg tgacagtgcc ggcctgaagc    3180
aactggtggc gcagtgggat aggaaatcga gtgtgacacc ccccacaaaa ccggttggac    3240
cggtgcttga ccaggccgtc cctctgccta tggacatcca gcaaggagat gccatctccg    3300
ctgacaagcc accccattcg caaaacccctt ctagtcaagt agatgtgggt ggaggttgga    3360
aaagttttat gctctccggc acccgtttcg cggggtccgt tagtcagcgc cttacgacat    3420 gggttttga ggttctctcc catctcccag cttttatgct cacactttc tcgccacggg    3480 gctctatggc tccaggtgat tggctgtttg caggtgctgt tctacttgct ctcctgctct    3540
gccgttctta cccaatactc ggatgccttc ccttattggg tgtcttttct ggttctgtgc    3600
ggtgtgttcg tttgggtgtt tttggttctt ggatggcttt tgctgtattt ttattctcga    3660 ctccaccccga cccagtcggt tcttcttgtg accacgattc gccggagtgt catgctgagc    3720
ttttggctct tgagcagcgc caactttggg aacctgtgcg cagccttgtg gtcgggccat    3780
cgggcctctt atgcgtcatt cttggcaagt tactcggtgg gtcacgttgt ctctggtttg    3840
ttctcctacg tatatgcatg ctcgcagatt tggcaatttc tcttatttat gtggtgtccc    3900
aagggcgttg tcacaagtgt tggggaaagt gtataaggac ggctcctgca gaagtggccc    3960
ttaatgtgtt tccttttcg cgcgccaccc gctcatctct tgtgtccttg tgtgatcggt    4020
tccaagcgcc aaaaggagtt gacccgtgc acttggcgac aggctggcgc gggtgctggt    4080
gtggtgagag ccctattcat caatcacacc aaaaaccgat agcttatgcc aacttggatg    4140
aaaagaagat atccgcccag acggtgattg ctgtcccgta tgatcctagt caggccatta    4200
aatgcctgaa agttttgcag gcaggagggg ctattgtgga ccagcctacg cccgaggtcg    4260
tccgtgtgtc tgagattccc ttctcggccc cattttttcc gaaggtccca gtcaacccag    4320
actgcagggt tgtggtagat tcggacactt ttgtggctgc ggtccgctgc ggttattcga    4380
cagcacaact ggtccttggt cggggcaact ttgccaagct aaatcagacc cccctcagga    4440
actctgtccc caccaaaaca actggtgggg cctcatacac ccttgccgtg gcccaggtat    4500
ctgtgtggac tcttgttcat ttcatcctcg gcctttggtt aacgtcacct caagtgtgtg    4560
gtcgagggac ctctgacccg tggtgttcga acccttttc gtatcctact tatggccccg    4620
```

```
gagttgtgtg ttcctctcga ctctgcgtgt ctgccgacgg agttaccctg ccattgttct    4680
cagccgttgc ccatctttcc ggtagagagg tggggatttt tattttggtg cttgcctcct    4740
tgggcgcttt agcccaccgc ttggctctta aggcagacat gtcaatggtc tttttggcgt    4800
tttgtgctta cgcctggccc atgagctcct ggttaatttg cttctttcct atgctcttga    4860
ggtgggtaac ccttcatcct ctcactatgc tttgggtgca ctcattttttg gtgttttgcc    4920 taccagctgc cggcgttctc tcgctgggaa taaccggtct tctttgggca gttggccgtt    4980
tcacccaggt tgccggaatt atcacacctt atgacatcca ccagtatacc tccggaccac    5040
gtggtgcagc tgctgtagca acggctccag aaggtactta catggcggcc gttcggagag    5100
ccgctttgac tggacggact ttgatcttca caccatctgc agtcggatcc cttcttgaag    5160
gtgctttcag aactcaaaag ccctgcctta acaccgtgaa tgtcgtaggc tcttcccttg    5220
gttctggagg agttttcacc attgatggca gaagagtcat cgtcactgcc acccatgtgt    5280
tgaatggtaa cacagccagg gtcactggtg attcctacaa ccgcatgcac acgttcaata    5340
ctaatggtga ttatgcctgg tcccatgctg atgactggca aggcgttgcc cctatggtta    5400
agatcgctaa ggggtatcgc ggtcgtgcct actggcaaac gtcaaccgga gtcgaacctg    5460
gcatcatggg ggaaggattc gccttctgtt tcactaactg tggcgactca gggtcacctg    5520
tcatttcaga agctggtgac cttattggag tccataccgg ttcaaacaaa ctcggttctg    5580
gtcttgtgac aacccctgaa ggggagacct gctccatcaa ggaaactagg ctctctgacc    5640
tttctagaca ttttgcaggt ccaagcgtcc tccttgggga cattaagttg agcccagcca    5700
tcatccctga tgtgacaact attccgagtg acttggcatc gctccttgct tctgtccccg    5760
tgatggaagg tggcctctca actgtccagc ttttttgtgcgt cttttttcctt ctctggcgca    5820 tgatgggcca tgcctggaca cccattgttg ccgtaggctt cttttttgctg aatgaaattc    5880 tcccagcagt cttggtccga gctgtgttct cttttgcact cttttgtactt gcatgggcca    5940 cccctggtc ggcacaagtg ttgatgatta gactcctcac ggcggctctc aaccgcaaca    6000
ggttgtccct ggcgttctac gcattcggag gtgtcgttgg cctggccaca gaaatcggga    6060
cttttgctgg tggatggcct gaactgtccc aagccctctc gacatactgc ttcctgccca    6120
ggttccttgc tgtgactagt tatgtcccca ccatcatcat cggtgggctc catgccctcg    6180
gcgtaatttt gtggttattc aaataccgat gcctccacaa catgctggtt ggtgatggga    6240
gtttctcaag cgcttttctt ctacggtatt ttgctgaggg taatcttagg aaaggcgtgt    6300
cgcagtcctg tggcatgaat aacgaatccc tgacagctgc tttggcttgc aagttgtcgc    6360
aagctgacct tgattttttg tccagtttaa cgaacttcaa gtgctttgtg tccgcttcaa    6420
acatgaaaaa tgcagctggc caatacatcg aggcggcgta tgctagagct ctgcgtcagg    6480
agctggcctc cttggttcag gttgacaaga tgaaaggagt attggccaag ctcgaggctt    6540
tcgctgagac ggccactccg tcacttgaca caggggacgt gattgttctg cttgggcaac    6600 accccccatgg atccatcctc gacattaatg tgggggggtga aggaaaaact gtgtctgtgc    6660
aagaaacacg atgcctgggt ggttccaaat tcagtgtctg cactgtcgtg tccaacacgc    6720
ccgtggatac cttgaccggt atcccacttc agacgccaac cccactttttt gaaaatggcc    6780 cgcgccatcg cagcgaggac gacgacctca agttgagag aatgaaaaaa cactgtgtat    6840
ccctcggctt ccacaaaatc aatggtaaag tttactgcaa aatttgggac aagtctaacg    6900
gcgacacctt ttacacggat gattcccgat acactcaaga ccatgctttt caggacaggt    6960
```

```
caaccgacta tagagacagg gattatgaag gtgtacagac cgcccccaa cagggattcg    7020
atccaaagtc cgaagcccct gttggcactg ttgtaatcgg tggcattacg tataacaggc    7080
atctggtcaa aggtaaggag gtcctagttc ccaaacctga caactgcctt gaagctgcca    7140
gactgtccct tgagcaagct cttgctggga tgggccaaac ttgtgacctt acagctaccg    7200
aagtggagaa actaaagcgc atcattagtc aactccaagg tctgaccact gaacaggctt    7260
taaactgcta gccgccagcg gcttgacccg ctgtggccgc ggcggcctag ttgtaactga    7320
aacggcggta aaaatcgtaa aataccacag cagaactttc accttaggct ctttagacct    7380
aaaagtcacc tccgaggtgg aggtgaagaa atcaactgag caggggcacg ctgtcgtggc    7440
gaacttatgt tccggtgtcg tcttgatgag gcctcaccca ccgtcccttg ttgacgttct    7500
cctcaaaccc ggacttgaca caacacccgg cattcaacca gggcatgggg ccggaatat    7560
gggcgtgaac ggttctattt gggattttga aactgcaccc acaaaggtag aactagagtt    7620
gtccaagcaa ataatccaag catgtgaagt caggcgcggg gacgccccta acctccaact    7680
cccctacaag ctttatcctg tcagggggga ccccgagcgg cgtaaaggtc gccttgtcaa    7740
cactaggttt ggagatttac cttacaaaac tccccaagac accaagtccg caattcatgc    7800
ggcttgttgc ctgcatccca atgggtcct cgtgtctgat ggcaaatcca cgctgggtac    7860
cactcttcaa catggtttcg agctttatgt ccccactgta ccttatagtg tcatggaata    7920
ccttgattca cgccctgaca ccccttttat gtgtactaaa catggcactt ccaaggctgc    7980
tgcagaggac ctccaaaaat atgacctatc cactcaaggg tttgtcttgc ctggggtcct    8040
acgcctagtg cgcaggttca tctttagcca tgttggtaag cgccaccac tgttccttcc    8100
atcaacctac cctgccaaga actccatggc aggggtcaat ggccagaggt tcccaacaaa    8160
ggatgtccag agcatacctg aaattgatga aatgtgcgcc cgtgccgtca aggaaaattg    8220
gcagactgtg acaccttgca ccctcaaaaa acagtactgt tccaaaccta aaactagaac    8280
catcctaggt accaacaact tcatagcctt ggctcacagg tcagcactca gtggtgtcac    8340
ccaggcgttc atgaagaagg cctggaagtc cccaattgcc ttggggaaaa acaagtttaa    8400
ggaattgcat tgcactgtcg ccggcagatg ccttgaggct gacctggctt cctgcgatcg    8460
cagcaccccc gccattgtga ggtggtttgt tgccaacctc ctgtatgaac ttgcaggatg    8520
tgaagagtac ttgcctagct acgtgctcaa ctgttgccat gaccttgtgg caacgcagga    8580
tggcgctttc acaaaacgcg gtggcctgtc gtccggggac cccgtcacca gtgtgtccaa    8640
caccgtctac tcactgataa tttacgccca gcacatggtg ctttcggcct tgaagatggg    8700
tcatgaaatt ggtctcaagt tccttgagga acagctcaaa tttgaggacc ttcttgaaat    8760
ccagccatg ttagtgtatt ctgatgacct cgtcttgtat gcggaaagac ccactttcc    8820
caactaccat tggtgggtcg agcatcttga cctgatgttg ggctttaaaa cggacccaaa    8880
gaaaactgtc ataactgata aacccagttt tctcggctgc agaattgaag caggacggca    8940
gttagtcccc aatcgcgacc gtattctggc tgctcttgca tatcatatga aggcgcagaa    9000
cgcctcagag tattatgcgt ccgctgccgc aattctgatg gattcgtgtg cttgcattga    9060
ccatgacccc gagtggtatg aggatctat ctgcggcatc gcccgtgtg ctcgccagga    9120
cggttaccgt tttccaggcc cggcattttt catgtccatg tgggagaagc tgaaaagtca    9180
taatgaaggg aagaaatgcc gtcactgcgg catctgcgac gccaaagccg actatgcgtc    9240
cgcctgtgga cttgatttgt gtttgttcca ttcacacttt catcaacact gcccagtcac    9300
tctgagctgt ggccaccatg ccggttcaaa ggaatgttcg cagtgtcagt cacctgtcgg    9360
```

```
ggctggcaaa tccccccttg acgctgtgct gaaacaaatc ccgtacaaac ctcctcgtac   9420
cattatcatg aaggtggaca acaaaacaac gacccttgac ccgggaagat atcagtcccg   9480
tcgaggtctt gttgcagtca aaagaggtat tgcaggtaat gaggttgatc tttctgatgg   9540
agactaccaa gtggtgcctc ttttgccgac ttgcaaagac ataaacatgg tgaaggtggc   9600
ttgcaacgta ctactcagca agtttatagt agggccgcca ggttccggaa aaaccacctg   9660
gctactgaac caagtccagg acgatgatgt catttacaca cctactcatc agacaatgtt   9720
tgacatagtc agtgctctta aagtttgcag gtattccatc ccaggagcct caggactccc   9780
ttttccacca cctgccaggt ccgggccgtg ggttaggctc atcgccagcg acatgtccc    9840 tggccgagtg tcatatctcg atgaggcagg atattgcaat catctagaca ttctaaggct   9900
gctttccaaa acaccccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc aggggcgac   10200 cttcgacatt gtgacattgc atctaccatc gccaaagtcc ctaaacaaat cccgagcact  10260
tgtagccatc actcgggcaa gacatgggtt gttcatttat gaccctcatg accaactcca  10320 ggagttttc aacttaaccc cgagcgcac tgattgtaac cttgcgttca gccgtgggga   10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta aagggagct gcatgccact accacaagta gcacataacc tgggttttta  10560
cttttccccg acagcccag cttttgcacc cctgccaaaa gagctggcgc acattggcc    10620 agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg ggggcgagcc  10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaatacctac ctaggtcc     10980 gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt ggaagggct gacatggtca cgcgctgccg attatgctag   11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg gccgcagtg    11400 gaagattttg gggttgcagc ctttcagacg aacatttggc tttgagaaca ctgaagattg  11460
ggcaattctc gcacgccgta tgaatgacgg caaagattac actgactata attggcattg  11520
tgtacgagaa cgcccacacg caatttacgg gcgcgcccgt gaccatacgt atcattttgc  11580
ccttggcact gaactgcaag tagagctggg cagacccgg ctgcctcctg agcaagtgcc    11640
gtgaacgcgg agtgatgcaa tgggtttact gtggagtaaa atcagtcagt tgttcgtgga  11700
```

```
tgccttcact gagttccttg ttagtgtggt tgacattgtc atctttctcg ccatattgtt    11760
tgggttcact gttgcaggct ggttattggt cttccttctc agagtggttt gctccgcgtt    11820
tctccgttcg cgctctgcca ttcactcttc cgaactatcg aaggtcctat gagggcttgc    11880
tacccaactg cagaccggat gtcccacaat tcgcagttaa gcacccgttg ggtatacttt    11940
ggcatatgcg agtctcccac ctaattgacg aaatggtctc tcgccgcatt taccggacca    12000
tggaacattc gggtcaagcg gcctggaagc aggttgttag tgaagccact ctcacaaaac    12060
tgtcaaggct tgacgtagtc actcatttcc aacacctggc cgcagtggag gctgattctt    12120
gccgcttcct tagctcacga ctcgcgatgc tgaaaaacct tgccgttggc aatgtgagcc    12180
tggagtacaa cactactttg gaccgcgttg agctcatctt tcccacacca ggtacgaggc    12240
ccaagttgac cgattttagg caatggctta tcagcgtgca cgcttccatc ttctcctctg    12300
tggcttcgtc tgttaccttg ttcacagtgc tttggcttcg aattccagct ctacgctatg    12360
tttttggttt ccattggccc acggcaacac atcattcgaa ctaactatca attacactat    12420
atgtaagcca tgccctacca gtcaagctgc ccaacaaaga ctcgagcctg gccgtaacgt    12480
gtggtgcaaa atagggcacg acaggtgtga ggaacgtgac catgatgagt tgtcaatgtc    12540
cattccgtcc gggtacgaca acctcaaact tgagggttat tatgcttggc tggcttttttt   12600 gtccttttcc tacgcggccc aattccatcc ggagctgttc ggaataggaa acgtgtcgcg    12660
cgtctttgtg gataagcgac accagttcat ttgcgccgag catgatggac aaaattcaac    12720
catatctgcc agacacaaca tctccgcgtc gtatgcggtg tattaccatc atcaaataga    12780
cgggggcaat tggtttcatt tggaatggct gcgaccattc ttttcctcct ggctggtgct    12840
caacatctca tggttctga ggcgttcgcc tgcaagccct gcttctcgac gcatctatca    12900
gatattaaga ccaacacgac cgcggctgcc ggtttcatgg tccttcagaa catcaattgt    12960
ttccaatctc ccggtagctc ccatttacag ttgatttata acttaacggg ctcatcccaa    13020
tgtcgtgaag ccgtcggcat tccccagtac atcacgataa cggctaatgt gaccgatgaa    13080
tcgtatttgt acaacgcgga cttgctgatg ctttccgcgt gccttttcta cgcctcggaa    13140
atgagcgaga aaggcttcaa agtcatcttt gggaatattt ctggcgttgt ttccgcttgt    13200
gttaatttca cagattatgt ggcccatgtg acccaacaca ctcagcagca ccatttggta    13260
attgatcaca ttcggttact acacttcttg acaccgtcta cgatgaggtg ggctacaacc    13320
attgcttgtt tgcttgccat tcttttggcg gtatgaaatg ttcttgcaag ttggggcatt    13380
tcttgactcc tcactcttgc ttctggtggc tttttttgct gtgtaccggc ttgtcttggt    13440
cctttgtcga tggcaacgac gacagctcga catcccaata catatataat ttgacgatat    13500
gcgagctgaa tgggaccgaa tggttgtccg gtcattttga ttgggcagtc gaaacctttg    13560
tgctttaccc agttgccact catatcattt cactggtttt tctcacaaca agccatttcc    13620
ttgatgcgct cggtctcggc gctgtgtccg ccacaggatt cattggcgag cggtatgtac    13680
ttagcagcat gtacggcgtt tgcgccttcg cggcgttcgt atgttttgtc atccgtgctg    13740
ctaaaaattg catggcttgc cgctatgccc gcacccggtt taccaacttc atcgtggacg    13800
accggggaag aatccatcga tggaagtctt caatagtggt ggagaaattg gcaaagctg     13860 aagtcggtgg tgaccttgtc aacattaagc atgttgtcct cgaagggggtt aaagctcaac    13920 ctttgacgag gacttcggct gagcaatggg aagcctagac gacttttgca acgatcccac    13980
cgccgcacaa aaactcgtgc tggccttttag catcacatat acacccataa tgatatacgc    14040
ccttaaggtg tcacgcggcc gactcctggg gctgttgcac atcttgatat ttctgaattg    14100
```

```
ttcctttact tttgggtaca tgacatatgt gcattttcaa tccaccaacc gtgtcgcatt    14160
cactctgggg gctgtagtcg cccttttgtg gggtgtttac agcctcacag agtcatggaa    14220
gttcatcact tccagatgca gattgtgttg cctaggccgg cgatacattc tggcccctgc    14280
ccatcacgta gaaagtgctg caggcctcca ttcaatccca gcgtctggta accgagcata    14340
cgctgtgaga aagcccggac taacatcagt gaacggcact ctagtacctg gcttcggag     14400 cctcgtgctg gcggcaaac gagctgttaa acgaggagtg gttaacctcg tcaagtatgg     14460
ccggtaagaa ccagagccag aagaaaagaa gaaatgcagc tccgatgggg aaaggccagc    14520
cagtcaatca actgtgccag ttgctgggta caatgataaa gtcccagcgc cagcaatcta    14580
ggggaggaca ggccaaaaag aagaagcctg agaagccaca ttttcccta gctgctgaag     14640 atgacattcg gcaccatctc acccaggccg aacgttccct ctgcttgcaa tcgatccaga    14700
cggctttcaa tcaaggcgca ggaactgcgt cgctttcatc cagcgggaag gtcagtttcc    14760
aggttgagtt catgctgccg gttgctcata cagtgcgcct gattcgcgtg acttctacat    14820
ccgccagtca gggtgcaaat taatttgaca gtcaggtgaa tggccgcgat tgacgtgtgg    14880
cctctaagtc acctattcaa ttagggcgat cacatggggg tcaaacttaa ttaggcagga    14940
accatgtgac cgaaattaaa aaaaaaaaaa aaaaaaaaa aaaa                     14984
```

```
<210> SEQ ID NO 59
<211> LENGTH: 6
<212> TYPE: PRT
<213> ORGANISM: Porcine reproductive and respiratory syndrome virus

<400> SEQUENCE: 59

Trp Tyr Gly Ala Gly Arg
1               5

<210> SEQ ID NO 60
<211> LENGTH: 6
<212> TYPE: PRT
<213> ORGANISM: Porcine reproductive and respiratory syndrome virus

<400> SEQUENCE: 60

Trp Tyr Gly Ala Ala Gly
1               5

<210> SEQ ID NO 61
<211> LENGTH: 9
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 61

Glu Cys Ala Met Ala Xaa Val Tyr Asp
1               5

<210> SEQ ID NO 62
<211> LENGTH: 9
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 62
```

```
Glu Glu Ala His Ser Xaa Val Tyr Arg
1               5

<210> SEQ ID NO 63
<211> LENGTH: 4
<212> TYPE: PRT
<213> ORGANISM: Porcine reproductive and respiratory syndrome virus

<400> SEQUENCE: 63

Ala Leu Glu Val
1

<210> SEQ ID NO 64
<211> LENGTH: 6
<212> TYPE: PRT
<213> ORGANISM: Porcine reproductive and respiratory syndrome virus

<400> SEQUENCE: 64

Ser Asp Gly Arg Ser Arg
1               5

<210> SEQ ID NO 65
<211> LENGTH: 64
<212> TYPE: PRT
<213> ORGANISM: Porcine reproductive and respiratory syndrome virus

<400> SEQUENCE: 65

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 66
<211> LENGTH: 64
<212> TYPE: PRT
<213> ORGANISM: Porcine reproductive and respiratory syndrome virus

<400> SEQUENCE: 66

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 67
<211> LENGTH: 64
<212> TYPE: PRT
<213> ORGANISM: Porcine reproductive and respiratory syndrome virus

<400> SEQUENCE: 67

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30
```

```
Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 68
<211> LENGTH: 64
<212> TYPE: PRT
<213> ORGANISM: Porcine reproductive and respiratory syndrome virus

<400> SEQUENCE: 68

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 69
<211> LENGTH: 64
<212> TYPE: PRT
<213> ORGANISM: Porcine reproductive and respiratory syndrome virus

<400> SEQUENCE: 69

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 70
<211> LENGTH: 64
<212> TYPE: PRT
<213> ORGANISM: Porcine reproductive and respiratory syndrome virus

<400> SEQUENCE: 70

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60

<210> SEQ ID NO 71
<211> LENGTH: 64
<212> TYPE: PRT
<213> ORGANISM: Porcine reproductive and respiratory syndrome virus

<400> SEQUENCE: 71

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
```

20                  25                  30

Pro Val Pro Lys Glu Leu Lys Leu Val Ala Asn Arg Leu His Thr Ser
            35                  40                  45

Phe Pro Pro His His Val Val Asp Met Ser Arg Phe Thr Phe Met Thr
        50                  55                  60

<210> SEQ ID NO 72
<211> LENGTH: 64
<212> TYPE: PRT
<213> ORGANISM: Porcine reproductive and respiratory syndrome virus

<400> SEQUENCE: 72

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
            35                  40                  45

Phe Pro Pro His His Val Val Asp Met Ser Glu Phe Thr Phe Met Thr
        50                  55                  60

<210> SEQ ID NO 73
<211> LENGTH: 64
<212> TYPE: PRT
<213> ORGANISM: Porcine reproductive and respiratory syndrome virus

<400> SEQUENCE: 73

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
            35                  40                  45

Phe Pro Pro His His Val Val Asp Met Ser Glu Phe Thr Phe Met Thr
        50                  55                  60

<210> SEQ ID NO 74
<211> LENGTH: 64
<212> TYPE: PRT
<213> ORGANISM: Porcine reproductive and respiratory syndrome virus

<400> SEQUENCE: 74

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
            35                  40                  45

Phe Pro Pro His His Val Val Asp Met Ser Lys Phe Thr Phe Met Thr
        50                  55                  60

<210> SEQ ID NO 75
<211> LENGTH: 64
<212> TYPE: PRT
<213> ORGANISM: Porcine reproductive and respiratory syndrome virus

<400> SEQUENCE: 75

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
            35                  40                  45

Phe Pro Pro His His Val Val Asp Met Ser Lys Phe Thr Phe Met Thr
    50                  55                  60

<210> SEQ ID NO 76
<211> LENGTH: 64
<212> TYPE: PRT
<213> ORGANISM: Porcine reproductive and respiratory syndrome virus

<400> SEQUENCE: 76

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
            35                  40                  45

Phe Pro Pro His His Val Val Asp Met Ser Lys Phe Thr Phe Ile Thr
    50                  55                  60

<210> SEQ ID NO 77
<211> LENGTH: 68
<212> TYPE: PRT
<213> ORGANISM: Porcine reproductive and respiratory syndrome virus

<400> SEQUENCE: 77

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
            35                  40                  45

Leu Ile Arg Ser Phe Pro Ala His His Pro Val Asp Leu Ala Asp Trp
    50                  55                  60

Glu Leu Thr Glu
65

<210> SEQ ID NO 78
<211> LENGTH: 68
<212> TYPE: PRT
<213> ORGANISM: Porcine reproductive and respiratory syndrome virus

<400> SEQUENCE: 78

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
            35                  40                  45

Leu Ile Arg Ser Phe Pro Ala His His Pro Val Asp Leu Ala Asp Trp
    50                  55                  60

Glu Leu Thr Glu
65

<210> SEQ ID NO 79
<211> LENGTH: 68
<212> TYPE: PRT

```
<213> ORGANISM: Porcine reproductive and respiratory syndrome virus

<400> SEQUENCE: 79

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65

<210> SEQ ID NO 80
<211> LENGTH: 68
<212> TYPE: PRT
<213> ORGANISM: Porcine reproductive and respiratory syndrome virus

<400> SEQUENCE: 80

Ser Ser Val Tyr Arg Trp Lys Lys Phe Val Val Phe Thr Asp Ser Ser
1               5                   10                  15

Pro Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65

<210> SEQ ID NO 81
<211> LENGTH: 68
<212> TYPE: PRT
<213> ORGANISM: Porcine reproductive and respiratory syndrome virus

<400> SEQUENCE: 81

Ser Ser Val Tyr Arg Trp Lys Lys Phe Val Val Phe Thr Asp Ser Ser
1               5                   10                  15

Pro Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65

<210> SEQ ID NO 82
<211> LENGTH: 68
<212> TYPE: PRT
<213> ORGANISM: Porcine reproductive and respiratory syndrome virus

<400> SEQUENCE: 82

Ser Ser Val Tyr Arg Trp Lys Arg Phe Val Val Phe Thr Asp Ser Ser
1               5                   10                  15

Pro Asn Gly Arg Ser Arg Met Met Trp Thr Pro Glu Ser Asp Asp Ser
            20                  25                  30
```

```
Ala Ala Leu Glu Val Leu Pro Pro Glu Leu Glu Arg Gln Val Glu Ile
            35                  40                  45

Leu Ile Arg Ser Phe Pro Ala His His Pro Val Asn Leu Ala Asp Trp
 50                  55                  60

Glu Leu Thr Glu
 65

<210> SEQ ID NO 83
<211> LENGTH: 68
<212> TYPE: PRT
<213> ORGANISM: Porcine reproductive and respiratory syndrome virus

<400> SEQUENCE: 83

Ser Ser Val Tyr Arg Trp Lys Arg Phe Val Val Phe Thr Asp Ser Ser
 1               5                  10                  15

Pro Asn Gly Arg Ser Arg Met Met Trp Thr Pro Glu Ser Asp Asp Ser
                20                  25                  30

Ala Ala Leu Glu Val Leu Pro Pro Glu Leu Glu Arg Gln Val Glu Ile
            35                  40                  45

Leu Ile Arg Ser Phe Pro Ala His His Pro Val Asn Leu Ala Asp Trp
 50                  55                  60

Glu Leu Thr Glu
 65

<210> SEQ ID NO 84
<211> LENGTH: 68
<212> TYPE: PRT
<213> ORGANISM: Porcine reproductive and respiratory syndrome virus

<400> SEQUENCE: 84

Ser Ser Val Tyr Arg Trp Lys Arg Phe Val Val Phe Thr Asp Ser Ser
 1               5                  10                  15

Pro Asn Gly Arg Ser Arg Met Met Trp Thr Pro Glu Ser Asp Asp Ser
                20                  25                  30

Ala Ala Leu Glu Val Leu Pro Pro Glu Leu Glu Arg Gln Val Glu Ile
            35                  40                  45

Leu Ile Arg Ser Phe Pro Ala His His Pro Val Asn Leu Ala Asp Trp
 50                  55                  60

Glu Leu Thr Glu
 65

<210> SEQ ID NO 85
<211> LENGTH: 68
<212> TYPE: PRT
<213> ORGANISM: Porcine reproductive and respiratory syndrome virus

<400> SEQUENCE: 85

Ser Asp Val Tyr Arg Trp Lys Lys Phe Val Ile Phe Thr Asp Ser Ser
 1               5                  10                  15

Pro Asn Gly Arg Phe Arg Met Met Trp Thr Pro Glu Ser Asp Asp Ser
                20                  25                  30

Ala Ala Leu Glu Val Leu Pro Pro Glu Leu Glu Arg Gln Val Glu Ile
            35                  40                  45

Leu Thr Arg Ser Phe Pro Ala His His Pro Ile Asn Leu Ala Asp Trp
 50                  55                  60

Glu Leu Thr Glu
 65
```

```
<210> SEQ ID NO 86
<211> LENGTH: 68
<212> TYPE: PRT
<213> ORGANISM: Porcine reproductive and respiratory syndrome virus

<400> SEQUENCE: 86

Ser Asp Val Tyr Arg Trp Lys Lys Phe Val Ile Phe Thr Asp Ser Ser
1               5                   10                  15

Pro Asn Gly Arg Phe Arg Met Met Trp Thr Pro Glu Ser Asp Asp Ser
                20                  25                  30

Ala Ala Leu Glu Val Leu Pro Pro Glu Leu Glu Arg Gln Val Glu Ile
            35                  40                  45

Leu Thr Arg Ser Phe Pro Ala His His Pro Ile Asn Leu Ala Asp Trp
        50                  55                  60

Glu Leu Thr Glu
65

<210> SEQ ID NO 87
<211> LENGTH: 68
<212> TYPE: PRT
<213> ORGANISM: Porcine reproductive and respiratory syndrome virus

<400> SEQUENCE: 87

Ser Ser Val Tyr Arg Trp Lys Lys Phe Val Val Phe Thr Asp Ser Ser
1               5                   10                  15

Pro Asn Gly Arg Pro Arg Met Met Trp Thr Pro Glu Ser Asp Asp Ser
                20                  25                  30

Ala Asp Leu Glu Ala Leu Pro Pro Glu Leu Glu Arg Gln Val Glu Ile
            35                  40                  45

Leu Ile Arg Ser Phe Pro Ala His His Pro Val Ser Leu Ala Asp Trp
        50                  55                  60

Glu Leu Ala Glu
65

<210> SEQ ID NO 88
<211> LENGTH: 68
<212> TYPE: PRT
<213> ORGANISM: Porcine reproductive and respiratory syndrome virus

<400> SEQUENCE: 88

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
                20                  25                  30

Thr Ala Leu Glu Val Leu Pro Pro Glu Leu Glu His Gln Val Lys Val
            35                  40                  45

Leu Val Arg Ser Phe Pro Ala His His Leu Val Asp Leu Ala Asp Trp
        50                  55                  60

Glu Leu Thr Glu
65

<210> SEQ ID NO 89
<211> LENGTH: 65
<212> TYPE: PRT
<213> ORGANISM: Porcine reproductive and respiratory syndrome virus

<400> SEQUENCE: 89

Ser Ser Ile Tyr Arg Trp Glu Lys Phe Val Ile Phe Met Asp Ser Ser
1               5                   10                  15
```

```
Ser Asp Gly Arg Ser Arg Met Met Trp Thr Pro Glu Ser Asp Ser
            20                  25                  30

Thr Leu Pro Pro Glu Leu Glu His Gln Val Lys Val Leu Val Arg Ser
            35                  40                  45

Phe Pro Ala His His Leu Val Asp Leu Ala Asp Trp Glu Leu Thr Glu
    50                  55                  60

Ser
65

<210> SEQ ID NO 90
<211> LENGTH: 67
<212> TYPE: PRT
<213> ORGANISM: Porcine reproductive and respiratory syndrome virus

<400> SEQUENCE: 90

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Leu Pro Pro Glu Leu Glu His Gln Val Lys Val Leu Val
            35                  40                  45

Arg Ser Phe Pro Ala His His Leu Val Asp Leu Ala Asp Trp Glu Leu
    50                  55                  60

Thr Glu Ser
65

<210> SEQ ID NO 91
<211> LENGTH: 65
<212> TYPE: PRT
<213> ORGANISM: Porcine reproductive and respiratory syndrome virus

<400> SEQUENCE: 91

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Pro Pro Glu Leu Glu His Gln Val Lys Val Leu Val Arg Ser
            35                  40                  45

Phe Pro Ala His His Leu Val Asp Leu Ala Asp Trp Glu Leu Thr Glu
    50                  55                  60

Ser
65

<210> SEQ ID NO 92
<211> LENGTH: 67
<212> TYPE: PRT
<213> ORGANISM: Porcine reproductive and respiratory syndrome virus

<400> SEQUENCE: 92

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Val Leu Pro Pro Glu Leu Glu His Gln Val Lys Val Leu Val
            35                  40                  45

Arg Ser Phe Pro Ala His His Leu Val Asp Leu Ala Asp Trp Glu Leu
    50                  55                  60

Thr Glu Ser
```

<210> SEQ ID NO 93
<211> LENGTH: 67
<212> TYPE: PRT
<213> ORGANISM: Porcine reproductive and respiratory syndrome virus

<400> SEQUENCE: 93

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Ser Thr Ala
            20                  25                  30

Leu Glu Val Leu Pro Pro Glu Leu Glu His Gln Val Lys Val Leu Val
        35                  40                  45

Arg Ser Phe Pro Ala His His Leu Val Asp Leu Ala Asp Trp Glu Leu
    50                  55                  60

Thr Glu Ser
65

<210> SEQ ID NO 94
<211> LENGTH: 65
<212> TYPE: PRT
<213> ORGANISM: Porcine reproductive and respiratory syndrome virus

<400> SEQUENCE: 94

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Thr Ala Leu Glu
            20                  25                  30

Val Leu Pro Pro Glu Leu Glu His Gln Val Lys Val Leu Val Arg Ser
        35                  40                  45

Phe Pro Ala His His Leu Val Asp Leu Ala Asp Trp Glu Leu Thr Glu
    50                  55                  60

Ser
65

<210> SEQ ID NO 95
<211> LENGTH: 67
<212> TYPE: PRT
<213> ORGANISM: Porcine reproductive and respiratory syndrome virus

<400> SEQUENCE: 95

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Glu Val Leu Pro Pro Glu Leu Glu His Gln Val Lys Val
        35                  40                  45

Leu Val Arg Ser Phe Pro Ala Leu Val Asp Leu Ala Asp Trp Glu Leu
    50                  55                  60

Thr Glu Ser
65

<210> SEQ ID NO 96
<211> LENGTH: 65
<212> TYPE: PRT
<213> ORGANISM: Porcine reproductive and respiratory syndrome virus

<400> SEQUENCE: 96

```
Ser Ser Ile Tyr Arg Trp Glu Lys Phe Val Ile Phe Met Asp Ser Ser
1               5                   10                  15

Ser Asp Met Met Trp Thr Pro Glu Ser Asp Ser Thr Ala Leu Glu
            20                  25                  30

Val Leu Pro Pro Glu Leu Glu His Gln Val Lys Val Leu Val Arg Ser
            35                  40                  45

Phe Pro Ala His His Leu Val Asp Leu Ala Asp Trp Glu Leu Thr Glu
        50                  55                  60

Ser
65

<210> SEQ ID NO 97
<211> LENGTH: 66
<212> TYPE: PRT
<213> ORGANISM: Porcine reproductive and respiratory syndrome virus

<400> SEQUENCE: 97

Ser Ser Ile Tyr Arg Trp Glu Lys Phe Val Ile Phe Met Asp Ser Ser
1               5                   10                  15

Ser Asp Gly Met Met Trp Thr Pro Glu Ser Asp Ser Thr Ala Leu
            20                  25                  30

Glu Val Leu Pro Pro Glu Leu Glu His Gln Val Lys Val Leu Val Arg
            35                  40                  45

Ser Phe Pro Ala His His Leu Val Asp Leu Ala Asp Trp Glu Leu Thr
        50                  55                  60

Glu Ser
65

<210> SEQ ID NO 98
<211> LENGTH: 63
<212> TYPE: PRT
<213> ORGANISM: Porcine reproductive and respiratory syndrome virus

<400> SEQUENCE: 98

Ser Ser Ile Tyr Arg Trp Glu Lys Phe Val Ile Phe Met Asp Ser Ser
1               5                   10                  15

Met Met Trp Thr Pro Glu Ser Asp Asp Ser Thr Ala Leu Glu Val Leu
            20                  25                  30

Pro Pro Glu Leu Glu His Gln Val Lys Val Leu Val Arg Ser Phe Pro
            35                  40                  45

Ala His His Leu Val Asp Leu Ala Asp Trp Glu Leu Thr Glu Ser
        50                  55                  60

<210> SEQ ID NO 99
<211> LENGTH: 69
<212> TYPE: PRT
<213> ORGANISM: Porcine reproductive and respiratory syndrome virus

<400> SEQUENCE: 99

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Glu Val Leu Pro Pro Glu Leu Glu His Gln Val Lys Val
            35                  40                  45

Leu Val Arg Ser Phe Pro Ala His His Leu Val Asp Leu Ala Asp Trp
        50                  55                  60

Glu Leu Thr Glu Ser
```

PRRS VIRUS VARIANT, EUROPEAN PRRS VIRUS CDNA CLONE, AND USES THEREOF

SEQUENCE LISTING

This application contains a sequence listing in accordance with 37 C.F.R. 1.821-1.825. The Sequence Listing which has been submitted electronically in ASCII format was created on Jan. 31, 2018, is named 01-2959-US-1-AMND-SEQ.txt and is 225,201 bytes in size. The sequence listing accompanying this application is hereby incorporated by reference in its entirety.

BACKGROUND OF THE INVENTION

Technical Field

The present invention belongs to the field of animal health.

In a first consideration, the invention relates to a new PRRS virus variant. The invention also relates to the use of such PRRS virus to study Porcine Reproductive and Respiratory Syndrome (PRRS), a viral disease affecting swine, and in the development of vaccines, therapeutics and diagnostics for the prophylaxis, treatment and diagnosis of PRRS.

In a second consideration, the invention relates to a nucleic acid sequence which comprises the genome of an infectious genotype I (EU) PRRS virus clone. The invention also relates to the use of the nucleic acid sequence of the infectious genotype I PRRS virus clone to produce attenuated live viruses useful for preventing or treating Porcine Reproductive and Respiratory Syndrome (PRRS) in swine and in the development of vaccines, therapeutics and diagnostics for the prophylaxis, treatment and diagnosis of PRRS.

Combining said both considerations, furthermore novel PRRS viruses with improved properties are provided under a third consideration of the invention.

BACKGROUND INFORMATION

Porcine reproductive and respiratory syndrome virus (PRRSV) is a member of the virus family Arteriviridae and belongs, together with the Coronaviridae, to the virus order Nidovirales. PRRSV is an enveloped virus with a single-stranded, positive-sense RNA genome of about 15 kilobases comprising nine open reading frames (ORFs), namely ORF1a, ORF1ab, ORF2a, ORF 2ab, and ORFs 3 through ORF7. ORFs 1a and 1ab encode large polyproteins that are processed into the viral nonstructural proteins (nsp) by auto- and transcleavages of viral proteases nsp1, nsp2, and nsp4 (Snijder and Meulenberg, 1998). ORF4 encodes a minor glycoprotein (GP4) which is, next to a major glycoprotein (GP5) and two other minor glycoproteins (GP2a and GP3), found in the viral envelope, wherein all of said glycoproteins are important for infectious virus production.

PRRSV is considered one of the economically most important infectious agents in pigs causing late-term reproductive failure in sows and respiratory disease in growing pigs. Often, PRRSV infection is complicated by secondary bacterial infections being attributed to the immunosuppressive nature of the virus. Also, PRRSV viremia lasts for weeks, and virus then still can be detected in lymphoid organs for several months, demonstrating difficulties or failure of the host's immune response to clear the virus (Allende et al., 2000).

There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus.

However, in a first consideration, as PRRS virus strains have a high biological diversity and evolve rapidly on individual farms (Badaoui et al. *BMC Veterinary Research* 2013, 9:58), new PRRSV isolates are needed for a better understanding of PRRS, for reproducing said disease in its different forms, for comparative tests, and as platform for the development of new vaccines, medications and diagnostics for the prophylaxis, treatment and diagnosis of PRRS.

In a second consideration, a growing number of infectious cDNA clones of the PRRS virus are becoming available to the scientific community, most of which are based on the US type of the virus. For the EU type, however, only few clones are available. Thus, there is a strong need for new infectious cDNA clones of European (genotype I) PRRS virus, for a better understanding of PRRS, for comparative tests, as platform for the development of new vaccines, medications and diagnostics for the prophylaxis, treatment and diagnosis of PRRS, wherein the use of the cDNA clone results in a high yield of virus production. Thus, for experimental convenience in the PRRS vaccine research an infectious cDNA clone would be needed enabling the production of genotype I PRRS virus in high amounts.

DESCRIPTION OF THE INVENTION

The solution to the above technical problems is achieved by the description and the embodiments characterized in the claims.

Thus, the invention in its different aspects and embodiments is implemented according to the claims.

1. First Consideration of the Present Invention

According to a first consideration, which is detailed in this section, the invention is based on the isolation of a new PRRS virus which is surprisingly capable to induce severe clinical signs in boars. Closer analyses of this PRRS virus variant revealed a significant deletion within the ORF4 gene of said virus.

In one aspect, the invention thus relates to a Porcine Reproductive and Respiratory Syndrome (PRRS) virus, wherein said virus is selected from the group consisting of the following (a), (b), (c), (d), (e), and (f):

(a) a PRRS virus comprising an ORF4 protein which comprises an amino acid sequence selected from the group consisting of SEQ ID NOs: 1-12;

(b) a PRRS virus, preferably a genotype I PRRS virus, comprising an ORF4 protein having a deletion of 9, 10, 11 or more amino acid residues in the region located between the first two predicted N-terminal β-sheets, as compared to the ORF4 protein of a wild type genotype I PRRS virus;

(c) a genotype II PRRS virus, comprising an ORF4 protein having a deletion of 5, 6, 7 or more amino acid residues in the region between the first two predicted N-terminal β-sheets, as compared to a wild type genotype II PRRS virus;

(d) a PRRS virus, preferably a genotype I PRRS virus, comprising an ORF4 protein having a deletion of 9, 10, 11 or more amino acid residues between amino acid positions 50 to 71, wherein the numbering of the amino acid positions refers to the amino acid sequence of ORF4 protein of the Lelystad virus;

(e) a genotype II PRRS virus, comprising an ORF4 protein having a deletion of 5, 6, 7 or more amino acid residues between amino acid positions 50 to 67, wherein the numbering of the amino acid positions refers to the amino acid sequence of ORF4 protein of the PRRS virus VR2332;

(f) a combination of any of (a), (b), (c), (d), and (e);

and, in a further aspect, the invention relates, respectively, to a Porcine Reproductive and Respiratory Syndrome (PRRS) virus selected from the group consisting of the following A), B), C), D), E), and F):

A) a PRRS virus whose genome comprises a nucleic acid molecule which encodes an ORF4 protein comprising an amino acid sequence selected from the group consisting of SEQ ID NO: 1-12;

B) a PRRS virus, preferably a genotype I PRRS virus, whose genome comprises a nucleic acid molecule which encodes an ORF4 protein having a deletion of 9, 10, 11 or more amino acid residues in the region located between the first two predicted N-terminal β-sheets, as compared to the ORF4 protein of a wild type genotype I PRRS virus;

C) a genotype II PRRS virus whose genome comprises a nucleic acid molecule which encodes an ORF4 protein having a deletion of 5, 6, 7 or more amino acid residues in the region between the first two predicted N-terminal β-sheets, as compared to a wild type genotype II PRRS virus;

D) a PRRS virus, preferably a genotype I PRRS virus, whose genome comprises a nucleic acid molecule which encodes an ORF4 protein having a deletion of 9, 10, 11 or more amino acid residues between amino acid positions 50 to 71, wherein the numbering of the amino acid positions refers to the amino acid sequence of ORF4 protein of the Lelystad virus;

E) a genotype II PRRS virus whose genome comprises a nucleic acid molecule which encodes an ORF4 protein having a deletion of 5, 6, 7 or more amino acid residues between amino acid positions 50 to 67, wherein the numbering of the amino acid positions refers to the amino acid sequence of ORF4 protein of the PRRS virus VR2332;

F) a combination of any of A), B), C), D), and E).

Preferably, said PRRS virus, which is also termed "PRRS virus of the present invention" hereinafter, is an isolated PRRS virus.

Within the context of the invention, it is in particular understood that the phrase "amino acid residues in the region" is equivalent to the phrase "amino acid residues located in the region" and, respectively, it is particularly understood that the term "amino acid residues between amino acid positions" is interchangeable with the term "amino acid residues located in the region between amino acid positions".

It is further understood that the terms "genotype I" and "genotype II" are equivalent to the terms "genotype 1" and "genotype 2" or to the terms "type 1" and "type 2", as frequently used in the literature in the context of PRRSV.

According to the first aspect ((a)), the PRRS virus of the present invention is thus a PRRS virus comprising an ORF4 protein which comprises an amino acid sequence selected from the group consisting of SEQ ID NOs: 1-12, wherein said ORF4 protein preferably comprises an amino acid sequence selected from the group consisting of SEQ ID NO: 13-24, and wherein said ORF4 protein in an exemplary non-limiting embodiment comprises the amino acid sequence of SEQ ID NO: 31.

Respectively, according to the first aspect ((A)), the PRRS virus of the present invention is a PRRS virus whose genome comprises a nucleic acid molecule which encodes an ORF4 protein comprising an amino acid sequence selected from the group consisting of SEQ ID NOs: 1-12, wherein said ORF4 protein preferably comprises an amino acid sequence selected from the group consisting of SEQ ID NO: 13-24, and wherein said ORF4 protein in an exemplary non-limiting embodiment comprises the amino acid sequence of SEQ ID NO: 31.

According to the second aspect ((b)), the PRRS virus of the present invention is a PRRS virus, in particular a genotype I PRRS virus, comprising an ORF4 protein having a deletion of 9, 10, 11 or more amino acid residues in the region between the first two predicted N-terminal β-sheets, as compared to the ORF4 protein of a wild type genotype I PRRS virus, wherein said first two predicted N-terminal β-sheets are preferably the two amino acid sequences set forth in SEQ ID NO:25 and SEQ ID NO:26, or are preferably the two amino acid sequences set forth in SEQ ID NO:29 and SEQ ID NO:30, and wherein in an exemplary non-limiting embodiment said ORF4 protein comprises the amino acid sequence of SEQ ID NO:32.

Respectively, according to the second aspect ((B)), the PRRS virus of the present invention is a PRRS virus, in particular a genotype I PRRS virus, whose genome comprises a nucleic acid molecule which encodes an ORF4 protein having a deletion of 9, 10, 11 or more amino acid residues in the region between the first two predicted N-terminal β-sheets, as compared to the ORF4 protein of a wild type genotype I PRRS virus, wherein said first two predicted N-terminal β-sheets are preferably the two amino acid sequences set forth in SEQ ID NO:25 and SEQ ID NO:26, or are preferably the two amino acid sequences set forth in SEQ ID NO:29 and SEQ ID NO:30, and wherein in an exemplary non-limiting embodiment said ORF4 protein comprises the amino acid sequence of SEQ ID NO:32.

As described herein, for purposes of comparison, the wild type genotype I PRRS virus is preferably the prototype genotype I Lelystad virus. The genome of the Lelystad virus is encoded by the nucleic acid sequence of SEQ ID NO:41.

According to the third aspect ((c)), the PRRS virus of the present invention is a genotype II PRRS virus, comprising an ORF4 protein having a deletion of 5, 6, 7 or more amino acid residues in the region between the first two predicted N-terminal β-sheets, as compared to a wild type genotype II PRRS virus, wherein the first two predicted N-terminal β-sheets are preferably the two amino acid sequences set forth in SEQ ID NO: 27 and SEQ ID NO: 28, and wherein said ORF4 protein in an exemplary non-limiting example comprises the amino acid sequence of SEQ ID NO:33.

Respectively, according to the third aspect ((C)), the PRRS virus of the present invention is a genotype II PRRS virus whose genome comprises a nucleic acid molecule which encodes an ORF4 protein having a deletion of 5, 6, 7 or more amino acid residues in the region between the first two predicted N-terminal β-sheets, as compared to a wild type genotype II PRRS virus, wherein the first two predicted N-terminal β-sheets are preferably the two amino acid sequences set forth in SEQ ID NO: 27 and SEQ ID NO: 28, and wherein said ORF4 protein in an exemplary non-limiting example comprises the amino acid sequence of SEQ ID NO:33.

As mentioned herein, for purposes of comparison, the wild type genotype II PRRS virus is preferably the prototype genotype II virus VR2332. The genome of the virus VR2332 is encoded by the nucleic acid sequence of SEQ ID NO:42.

In the context of the invention, a deletion of amino acid residues is preferably a deletion of consecutive amino acid residues. Thus, for example, a deletion of 9, 10, 11 or more amino acid residues, as described herein, is preferably a deletion of 9, 10, 11 or more consecutive amino acid residues and, respectively, a deletion of 5, 6, 7 or more amino acid residues, as described herein, is preferably a deletion of 5, 6, 7 or more consecutive amino acid residues.

According to the fourth aspect ((d)), the PRRS virus of the present invention is a PRRS virus, preferably a genotype I PRRS virus, comprising an ORF4 protein having a deletion of 9, 10, 11 or more amino acid residues, or preferably a deletion of 11, 12, 13, 14, 15, 16, or 17 amino acid residues, between amino acid positions 50 to 71, wherein the numbering of the amino acid positions refers to the amino acid sequence of ORF4 protein of the Lelystad virus, and wherein in a non-limiting exemplary embodiment an ORF4 protein having a deletion of 11 amino acid residues between amino acid positions 50 to 71 is an ORF4 protein which comprises the amino acid sequence of SEQ ID NO:34.

Respectively, according to the fourth aspect ((D)), the PRRS virus of the present invention is a PRRS virus, preferably a genotype I PRRS virus, whose genome comprises a nucleic acid molecule which encodes an ORF4 protein having a deletion of 9, 10, 11 or more amino acid residues, or preferably a deletion of 11, 12, 13, 14, 15, 16, or 17 amino acid residues, between amino acid positions 50 to 71, wherein the numbering of the amino acid positions refers to the amino acid sequence of ORF4 protein of the Lelystad virus, and wherein in a non-limiting exemplary embodiment an ORF4 protein having a deletion of 11 amino acid residues between amino acid positions 50 to 71 is an ORF4 protein which comprises the amino acid sequence of SEQ ID NO:34.

As described herein, the numbering of amino acid positions relating to the Lelystad virus refers to the amino acid sequence of full length ORF4 protein of the Lelystad virus. Hence, the numbering of the amino positions as mentioned in this context is with reference to the ORF4 protein of the Lelystad protein having 183 amino acid residues, including a methionine residue at the (N-terminal) amino acid position 1.

Thus, the phrase "wherein the numbering of the amino acid positions refers to the amino acid sequence of ORF4 protein of the Lelystad virus", as used in the context of the present invention, relates to the sequence of ORF4 protein as set forth in SEQ ID NO:43.

According to the fifth aspect ((e)), the PRRS virus of the present invention is a genotype II PRRS virus, comprising an ORF4 protein having a deletion of 5, 6, 7 or more amino acid residues, or preferably a deletion of 8, 9, 10, 11 or more amino acid residues, between amino acid positions 50 to 67, wherein the numbering of the amino acid positions refers to the amino acid sequence of ORF4 protein of the PRRS virus VR2332, and wherein in a non-limiting exemplary embodiment an ORF4 protein having a deletion of 7 amino acid residues between amino acid positions 50 to 67 is an ORF4 protein which comprises the amino acid sequence of SEQ ID NO:35.

Respectively, according to the fifth aspect ((E)), the PRRS virus of the present invention is a genotype II PRRS virus whose genome comprises a nucleic acid molecule which encodes an ORF4 protein having a deletion of 5, 6, 7 or more amino acid residues, or preferably a deletion of 8, 9, 10, 11 or more amino acid residues, between amino acid positions 50 to 67, wherein the numbering of the amino acid positions refers to the amino acid sequence of ORF4 protein of the PRRS virus VR2332, and wherein in a non-limiting exemplary embodiment an ORF4 protein having a deletion of 7 amino acid residues between amino acid positions 50 to 67 is an ORF4 protein which comprises the amino acid sequence of SEQ ID NO:35.

As described herein, the numbering of amino acid positions relating to the PRRS virus VR2332 refers to the amino acid sequence of full length ORF4 protein of the PRRS virus VR2332. Hence, the numbering of the amino positions as mentioned in this context is with reference to the ORF4 protein of the VR2332 virus having 178 amino acid residues, including a methionine residue at the (N-terminal) amino acid position 1.

Thus, the phrase "wherein the numbering of the amino acid positions refers to the amino acid sequence of ORF4 protein of the PRRS virus VR2332 having 178 amino acid residues, as used in the context of the present invention, relates to the sequence of ORF4 protein as set forth in SEQ ID NO:44.

According to the sixth aspect ((f)), the PRRS virus of the present invention is a combination of any of the aspects (a), (b), (c), (d), and (e), as described herein, preferably a combination of any of the aspects (a), (b), and (d) or a combination of any of the aspects (a), (c), and (e). Within this context it is in particular understood that the phrase "combination of any of (a), (b), (c), (d), and (e)" and "combination of any of the aspects (a), (b), (c), (d), and (e)", respectively, means a PRRS virus having a combination of the features of any PRRS viruses of (a), (b), (c), (d), and (e), as described herein, wherein a combination of the features of any of the PRRS viruses of the aspects (a), (b) and/or (c) or a combination of the features of any of the PRRS viruses of the aspects (a), (c), and (e) is in particular preferred.

Respectively, according to the sixth aspect ((F)), the PRRS virus of the present invention is a combination of any of the aspects (A), (B), (C), (D), and (E), as described herein, preferably a combination of any of the aspects (A), (B), and (D) or a combination of any of the aspects (A), (C), and (E). Within this context it is in particular understood that the phrase "combination of any of (A), (B), (C), (D), and (E)" and "combination of any of the aspects (A), (B), (C), (D), and (E)", respectively, means a PRRS virus having a combination of the features of any PRRS viruses of (A), (B), (C), (D), and (E), as described herein, wherein a combination of the features of any of the PRRS viruses of the aspects (A), (B) and/or (D) or a combination of the features of any of the PRRS viruses of the aspects (A), (C), and (E) is in particular preferred.

The PRRS virus of the present invention preferably comprises
    an ORF4 protein which comprises or consists of an amino acid sequence having a least 84.5% preferably at least 90%, more preferably at least 95%, still more preferably at least 97%, and in particular preferably at least 99% sequence identity with the amino acid sequence of SEQ ID NO:36, or
    an ORF4 protein which comprises or consists of an amino acid sequence encoded by a nucleic acid sequence having a least 83.5% preferably at least 90%, more preferably at least 95%, still more preferably at least 97%, and in particular preferably at least 99% sequence identity with the nucleic acid sequence of SEQ ID NO:37, wherein said PRRS virus is preferably a genotype I PRRS virus, and wherein said PRRS virus is in particular a genotype I PRRS virus.

As used herein, it is in particular understood that the term "sequence identity with the amino acid sequence of SEQ ID NO: 36" is equivalent to the term "sequence identity with the amino acid sequence of SEQ ID NO: 36 over the length of SEQ ID NO: 36" or to the term "sequence identity with the amino acid sequence of SEQ ID NO: 36 over the whole length of SEQ ID NO: 36", respectively.

Further, as used herein, it is particularly understood that the term "sequence identity with the nucleic acid sequence of SEQ ID NO: 37" is equivalent to the term "sequence identity with the nucleic acid sequence of SEQ ID NO: 37 over the length of SEQ ID NO: 37" or to the term "sequence identity with the nucleic acid sequence of SEQ ID NO: 37 over the whole length of SEQ ID NO: 37", respectively.

Sequence identity in the context of the first consideration of the invention is understood as being based on progressive alignment (Feng, D. F. and Doolittle, R. F. (1987). *Progressive sequence alignment as a prerequisite to correct phylogenetic trees*. J. Mol. Evol., 25(4):351-360, herein incorporated by reference). This method is based on combining sequences into alignments, which can in turn be combined with other sequences or alignments to form larger alignments. The procedure is repeated until all the input sequences have been joined in a single multiple alignment. For purposes of the present invention, percent sequence identity is determined with the software CLC MAIN WORKBENCH 4.1.1 (CLC BIO).

In one exemplary and non-limiting embodiment the PRRS virus of the present invention is a genotype I PRRS whose genome comprises an RNA molecule encoded by a nucleic acid molecule having at least 84.5%, preferably at least 90%, more preferably at least 95%, still more preferably at least 97%, and in particular preferably at least 99% sequence identity with the nucleic acid sequence of SEQ ID NO: 38.

As used herein, it is in particular understood that the term "sequence identity with the nucleic acid sequence of SEQ ID NO: 38" is equivalent to the term "sequence identity with the nucleic acid sequence of SEQ ID NO: 38 over the length of SEQ ID NO: 38" or to the term "sequence identity with the nucleic acid sequence of SEQ ID NO: 38 over the whole length of SEQ ID NO: 38", respectively.

According to another preferred aspect, the PRRS virus of the present invention is able to induce reproductive symptoms in pregnant sows and/or respiratory symptoms in piglets.

According to further preferred aspect, the PRRS virus of the present invention is able to induce respiratory symptoms in boars.

Thus, the PRRS virus of the present invention is preferably an infectious PRRS virus.

The term "infectious PRRS virus" according to the invention is particularly understood as a PRRS virus which infects swine, causing the associated disease, Porcine reproductive and respiratory syndrome (PRRS).

Said infection of swine by the PRRS virus of the present invention in particular includes attachment of the virus to a host cell, entry of the virus into the cell, disassembly of the virion, replication and transcription of the viral genome, expression of viral proteins and assembly and release of new infectious viral particles.

In another aspect, the invention further relates to a PRRS virus, preferably the PRRS virus of the present invention, genetically modified to contain therein exogenous RNA, wherein the exogenous RNA is inserted into the ORF4 gene of said virus, and wherein the exogenous RNA is preferably inserted a) into the region of the ORF4 gene of said virus encoding the amino acid sequence selected from the group consisting of SEQ ID NOs: 1-12 or 13-24;

b) into the region of the ORF4 gene of said virus encoding the region located between the first two predicted N-terminal β-sheets, as compared to the ORF4 protein of a wild type genotype I PRRS virus;

c) into the region of the ORF4 gene of said virus encoding the region located between the first two predicted N-terminal β-sheets, as compared to the ORF4 protein of a wild type genotype II PRRS virus;

d) into the region of the ORF4 gene of said virus encoding the region located between amino acid positions 50 to 71, wherein the numbering of the amino acid positions refers to the amino acid sequence of ORF4 protein of the Lelystad virus; or e) into the region of the ORF4 gene of said virus encoding the region located between amino acid positions 50 to 67, wherein the numbering of the amino acid positions refers to the amino acid sequence of ORF4 protein of the PRRS virus VR2332.

As used herein, the term "exogenous RNA" or "exogenous nucleic acid sequence" in particular refers to a nucleic acid sequence that was introduced into the genome of a PRRS virus from an external source, such as from a recombinant sequence. Examples of such external source comprise PRRSV derived sequences as well as non PRRSV derived sequences. More particular, the introduction of the exogenous nucleic acid sequence results in a genome or a gene, respectively, having a non-naturally occuring portion. As used herein, the term "exogenous RNA" thus in particular refers to a nucleotide sequence, which is not naturally found in the PRRS virus genome. Such non-naturally occuring portion or not naturally found sequence, respectively, can also be the result of the insertion of one naturally occuring nucleotide sequence into another naturally occuring nucleotide sequence.

The exogenous RNA, as described herein, in particular encodes an expression product selected from the group consisting of an epitope of interest, a biological response modulator, a growth factor, a recognition sequence, and a fusion protein, and wherein said epitope of interest is preferably an epitope of interest from an antigen or a veterinary pathogen or toxin.

In one preferred embodiment, said epitope of interest is a peptide encoded by the ORF5 gene of PRRS virus, wherein said peptide encoded by the ORF5 gene of PRRS virus in particular comprises or consists of at least 4 consecutive amino acid residues of the sequence set forth in SEQ ID NO: 39 or, more particular, said peptide encoded by the ORF5 gene of PRRS virus comprises or consists of the amino acid sequence of SEQ ID NO:39.

In another preferred embodiment, said epitope of interest is the ectodomain of the ORF4 protein (GP4) of a different PRRS virus strain, wherein said ectodomain of GP4 of a different PRRS virus strain in particular comprises or consists of at least 4 consecutive amino acid residues of the sequence set forth in SEQ ID NO:40 or, more particular, said ectodomain of GP4 of a different PRRS virus strain comprises or consists of the amino acid sequence of SEQ ID NO:40.

The invention further provides the PRRS virus genetically modified to contain therein exogenous RNA, as described herein, for use as a medicament.

The present invention also provides the PRRS virus described herein for use as a challenge virus, in particular if said PRRS virus inherently induces a vaccinating effect when administered to an animal.

The present invention additionally provides the use of the PRRS virus of the present invention as a challenge virus, in particular if said PRRS virus does not induce a vaccinating effect when administered to an animal.

The term "animal", as mentioned herein, is in particular directed to swine, more particular to a pig, preferably a domestic pig.

Preferably, the PRRS virus is to be administered, or is administered, respectively, via the intranasal, intramuscular, oral, or intrauterine route to an animal.

Also, the present invention provides the use of the PRRS virus described herein as a detection marker, preferably for the differentiation between infected and vaccinated animals (DIVA).

According to a further aspect, the invention also relates to a DNA molecule which encodes the PRRS virus described herein, wherein said DNA molecule is preferably an isolated DNA molecule and/or wherein said DNA molecule preferably comprises a nucleic acid molecule having at least 84.5%, preferably at least 90%, more preferably at least 95%, still more preferably at least 97%, and in particular preferably at least 99% sequence identity with the nucleic acid sequence of SEQ ID NO: 38.

The present invention further provides a DNA construct comprising the DNA molecule described herein, wherein said DNA construct is in particular a DNA vector such as a plasmid. DNA vectors or plasmids into which the DNA molecule of the present invention can be inserted will be recognized by those of ordinary skill in the art. The DNA construct, as described herein, is preferably an isolated DNA construct. As used herein, the term "comprising the DNA molecule" is in particular understood to be equivalent to the term "comprising the sequence of the DNA molecule".

Further, the present invention provides a RNA transcript of the DNA construct described herein, wherein said RNA transcript is preferably an isolated RNA transcript.

The present invention also provides a cell transfected with the DNA construct described herein, wherein said cell is preferably an isolated cell.

Further, the present invention provides a cell transfected with the RNA transcript mentioned herein, wherein said cell is preferably an isolated cell.

The term "cells" or "cell", as mentioned herein, is preferably directed to mammalian cells, in particular porcine or simian cells, such as MA-104 cells or MARC-145 cells or Vero cells, more preferably it is understood that the term "cells" or "cell" is directed to the host cells of PRRS virus, namely to porcine macrophages. Hence, a cell, as mentioned herein, is preferably selected from the group consisting of porcine cell, simian cell, MA-104 cell, MARC-145 cell, Vero cell and porcine macrophage.

In a further aspect, the invention provides a method for producing the PRRS virus described herein, wherein the method comprises the step of transfecting a cell with the DNA construct described herein and optionally harvesting the virus from the cell and/or the medium.

In another aspect, the invention provides a method for producing the PRRS virus described herein, wherein the method comprises the step of transfecting a host cell with the RNA transcript described herein and optionally harvesting the virus from the cell and/or the medium.

Production of the nucleic acid/DNA molecules described herein, is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

2. Second Consideration of the Present Invention

According to a second consideration, which is detailed in this section, the invention provides, in one aspect, a nucleic acid molecule which encodes a genotype I PRRS virus and which is capable of producing live virus when transfected into cells, wherein said molecule comprises a first nucleic acid sequence having at least 95% sequence identity with the nucleic acid sequence of SEQ ID NO:45, a second nucleic acid sequence flanking the 5' end of the first nucleic acid sequence and having at least 95% sequence identity with the nucleic acid sequence of SEQ ID NO:46, a third nucleic acid sequence flanking the 3' end of the first nucleic acid sequence and having at least 95% sequence identity with the nucleic acid sequence of SEQ ID NO:47, and a polyadenine nucleotide sequence flanking the 3' end of the third nucleic acid sequence.

Preferably, said first nucleic acid sequence has at least 96%, preferably at least 97%, more preferably at least 98%, still more preferably at least 99%, and in particular preferably 100% sequence identity with the nucleic acid sequence of SEQ ID NO:45; and/or said second nucleic acid sequence having at least 96%, preferably at least 97%, more preferably at least 98%, still more preferably at least 99%, and in particular preferably 100% sequence identity with the nucleic acid sequence of SEQ ID NO:46; and/or said third nucleic acid sequence having at least 96%, preferably at least 97%, more preferably at least 98%, still more preferably at least 99%, and in particular preferably 100% sequence identity with the nucleic acid sequence of SEQ ID NO:47; and/or said polyadenine nucleotide sequence is composed of n adenine nucleotides, wherein n is any integer between 1 and 51, and wherein n is preferably 12, 13 or 14.

The nucleic acid molecule of the present invention is preferably a DNA molecule. Preferably, said nucleic acid molecule is an isolated nucleic acid molecule.

Within the context of the present invention it is in particular understood that the term "polyadenine nucleotide sequence" is equivalent to the term "polyadenylic acid sequence" or "poly (A) tail", respectively. The term "adenine nucleotide(s)", as described herein, is in particular understood to be equivalent to the term "deoxyadenylate(s)".

The phrase "nucleotide sequence flanking the 5' end of" as described herein is in particular equivalent to the phrase "nucleotide sequence covalently linked with the 5' end of" or, respectively, with the phrase "nucleotide sequence, wherein the 3' terminal nucleotide thereof is covalently linked with the 5' terminal nucleotide of", and wherein it is particularly understood that said two terminal nucleotides are linked covalently between the phosphate group attached to the 5' carbon of the pentose and the 3' carbon atom of the adjacent pentose.

The phrase "nucleotide sequence flanking the 3' end of" as described herein is in particular equivalent to the phrase "nucleotide sequence covalently linked with the 3' end of" or, respectively, to the phrase "nucleotide sequence, wherein the 5' terminal nucleotide thereof is covalently linked with the 3' terminal nucleotide of", and wherein it is particularly understood that said two terminal nucleotides are linked covalently between the 3' carbon atom of the pentose and the phosphate group attached to the 5' carbon of the adjacent pentose.

It is further particularly understood that the phrase "having 100% sequence identity with the nucleic acid sequence of", as used herein, is equivalent to the phrase "being identical to the the nucleic acid sequence of" or "consisting of the nucleic acid sequence of", respectively.

In a particular preferred aspect, the nucleic acid molecule of the present invention comprises a nucleic acid sequence having at least 99% sequence identity with the nucleic acid sequence of SEQ ID NO:48, or wherein said nucleic acid molecule comprises or consists of a RNA copy of a nucleic acid sequence having at least 99% sequence identity with the nucleic acid sequence of SEQ ID NO:48.

The term "cells" or "cell", as mentioned herein, is preferably directed to mammalian cells, in particular porcine or simian cells, such as MA-104 cells or MARC-145 cells or Vero cells, more preferably it is understood that the term "cells" or "cell" is directed to the host cells of PRRS virus, namely to porcine macrophages. Hence, a cell, as mentioned herein, is preferably selected from the group consisting of porcine cell, simian cell, MA-104 cell, MARC-145 cell, Vero cell and porcine macrophage.

The term "live virus" according to the invention is particularly understood as a PRRS virus having the ability of infecting an appropriate subject (as opposed to an inactivated (killed) virus) and/or whose infectivity is similar or identical to a native virus. In particular, a live virus can infect its native host cells.

Said infection of host cells by the PRRS virus produced by the nucleic acid molecule of the present invention in particular includes attachment of the virus to a host cell, entry of the virus into the cell, disassembly of the virion, replication and transcription of the viral genome, expression of viral proteins and assembly and release of new infectious viral particles. Said infection of host cells by the PRRS virus produced by the nucleic acid molecule of the present invention further preferably includes the transcription of the cDNA sequence, in particular in BHK cells, to yield a functional RNA molecule, transfection of cultured cells, preferably porcine cell, simian cell, MA-104 cell, MARC-145 cell, Vero cell and porcine macrophage, with said RNA molecule, generation of live virions by viral replication in said cultured cells, isolation of such virions and infection of host cells.

In particular, the nucleic acid molecule of the present invention preferably encodes an attenuated genotype I PRRS virus or, respectively, the nucleic acid molecule of the present invention is capable of producing live attenuated virus when transfected into cells.

More particular the nucleic acid molecule of the present invention encodes a genotype I PRRS virus which is not able to induce a severe Porcine Reproductive and Respiratory Syndrome (PRRS) in swine or, respectively, the nucleic acid molecule of the present invention is capable of producing live virus when transfected into cells, wherein said live virus is not able to induce a severe, wild-type virus-like Porcine Reproductive and Respiratory Syndrome (PRRS) in swine as caused by virulent field PRRS viruses.

In one particular embodiment, the nucleic acid molecule of the present invention encodes a genotype I PRRS virus which is able to reach titers of at least $5\times10^5$ to $1\times10^6$ tissue culture infectious dose 50 ($TCID_{50}$) per milliliter (ml) within 24 hours post infection of MA104 cells, wherein said MA104 cells are preferably infected with said virus at an MOI (multiplicity of infection) of 0.001 to 0.1.

Particularly, the nucleic acid molecule of the present invention encodes a genotype I PRRS virus which is able to reach titers of $5\times10^6$ to $1\times10^7$ or more tissue culture infectious dose 50 ($TCID_{50}$) per milliliter (ml) within 48 hours post infection of MA104 cells, wherein said MA104 cells are preferably infected with said virus at an MOI (multiplicity of infection) of 0.001 to 0.1.

Thus, the nucleic acid molecule of the present invention preferably encodes a genotype I PRRS virus which is able to
reach titers of at least $5\times10^5$ to $1\times10^6$ tissue culture infectious dose 50 ($TCID_{50}$) per milliliter (ml) within 24 hours and/or
reach titers of at least $5\times10^6$ to $1\times10^7$ tissue culture infectious dose 50 ($TCID_{50}$) per milliliter (ml) within 48 hours post infection of MA104 cells
at an MOI (multiplicity of infection) of 0.001 to 0.1,
in particular at an MOI of 0.001 or 0.01 or 0.1.

In the context of the PRRS virus as described herein, it is understood that the term "genotype I" is equivalent to the terms "genotype 1" or "type 1" or "European (EU)" as frequently used in the literature in the context of PRRSV.

In another preferred embodiment, the nucleic acid molecule of the present invention comprises a nucleic acid sequence having at least 99.1% or 99.2%, preferably at least 99.3% or 99.4%, more preferably at least 99.5% or 99.6%, still more preferably at least 99.8% or 99.9%, and in particular preferably at least 99.95% sequence identity with the nucleic acid sequence set forth in SEQ ID NO:48.

Sequence identity in the context of the second consideration of the invention is understood as being based on pairwise determined similarity between nucleotide sequences. The determination of percent identity between two sequences is preferably accomplished using a mathematical algorithm, in particular the well-known Smith-Waterman algorithm (Smith and Waterman, M. S. (1981) J Mol Biol, 147(1):195-197). For purposes of the present invention, percent sequence identity of a nucleotide sequence is determined using the Smith-Waterman homology search algorithm using a gap open penalty of 25 and a gap extension penalty of 5. The Smith-Waterman homology search algorithm is taught in Smith and Waterman (1981) Adv. Appl. Math 2:482-489, herein incorporated by reference. Such a determination of sequence identity can be performed using, for example, the DeCypher Hardware Accelerator from TimeLogic Version G, or the sequence identity is determined with the software CLC MAIN WORKBENCH 4.1.1 (CLC BIO).

As used herein, it is in particular understood that the term "having at least X % sequence identity with the nucleic acid sequence of SEQ ID NO:Y" (or, alternatively, the term "having at least X % sequence identity with the nucleic acid sequence set forth in SEQ ID NO:Y") is equivalent to the term "having at least X % sequence identity with the nucleic acid sequence of SEQ ID NO:Y over the length of SEQ ID NO:Y" or to the term "having at least X % sequence identity with the nucleic acid sequence of SEQ ID NO:Y over the whole length of SEQ ID NO:Y", respectively. In this context, "X" is any number from 95 to 100, in particular any integer selected from 95 to 99, such that "X % sequence identity" represents any of the percent sequence identities mentioned herein. Respectively, "Y" in this context is any integer selected from 1 to 6, such that "SEQ ID NO:Y" represents any of the SEQ ID NOs mentioned herein.

In a particular preferred embodiment, the nucleic acid molecule of the present invention comprises the nucleic acid sequence of SEQ ID NO:48.

In another preferred embodiment, the nucleic acid molecule of the present invention encodes a genotype I PRRS virus which is not able to induce Porcine Reproductive and Respiratory Syndrome (PRRS) in swine or, respectively, the nucleic acid molecule of the present invention is capable of producing live virus when transfected into cells, wherein said infectious virus is not able to induce Porcine Reproductive and Respiratory Syndrome (PRRS) in swine.

As used herein, the term "is not able to induce Porcine Reproductive and Respiratory Syndrome (PRRS)" in particular refers to a reduction of the clinical signs of PRRS or of signs associated with PRRSV infection, respectively, such as lung lesions in piglets, reproductive failure in pregnant sows, and/or prolonged PRRSV viremia, when compared to a wild-type PRRS virus. In one aspect, the genotype I PRRS virus which is not able to induce PRRS in swine is thus a virus showing one or more reduced clinical signs when administered to swine, in comparison with a wild type PRRS virus administered to swine. The term "wild type PRRS virus", as mentioned herein, in particular relates to a wild type genotype I PRRS virus.

The present invention further provides a DNA construct comprising the nucleic acid molecule according to the invention, wherein said DNA construct is in particular a DNA vector such as a plasmid. DNA vectors or plasmids into which the nucleotide molecule of the present invention can be inserted will be recognized by those of ordinary skill in the art. The DNA construct, as described herein, is preferably an isolated DNA construct. As used herein, the term "comprising the nucleic acid molecule" or "comprising a DNA molecule", respectively, is in particular understood to be equivalent to the term "comprising the sequence of the nucleic acid molecule" or "comprising the sequence of a DNA molecule", respectively.

Further, the present invention provides a RNA transcript of the DNA construct described herein, wherein said RNA transcript is preferably an isolated RNA transcript.

The present invention also provides a cell transfected with the DNA construct described herein, wherein said cell is preferably an isolated cell.

Thus, the present invention also provides genotype I PRRS virus produced by the aforementioned cell, wherein said genotype I PRRS virus is preferably an isolated genotype I PRRS virus.

Further, the present invention provides a cell transfected with the RNA transcript mentioned herein, wherein said cell is preferably an isolated cell.

Hence, the present invention also provides genotype I PRRS virus produced by the aforementioned cell, wherein said genotype I PRRS virus is preferably an isolated genotype I PRRS virus.

The present invention further provides a genotype I PRRS virus whose genome comprises the nucleic acid molecule of the present invention or whose genome comprises an RNA molecule encoded by a nucleic acid molecule of the present invention, wherein said genotype I PRRS virus is preferably an isolated genotype I PRRS virus.

In another aspect, the present invention provides a method for producing a genotype I PRRS virus, said method comprising transfecting a cell with the DNA construct described herein.

Moreover, the present invention provides a method for producing a genotype I PRRS virus, said method comprising transfecting a cell with the RNA transcript mentioned herein.

In yet another aspect, the present invention provides a composition, said composition comprising the nucleic acid molecule according to the invention suspended in a suitable amount of a pharmaceutically acceptable diluent or excipient.

Production of the nucleic acid molecules described herein is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

In still another aspect, the invention further relates to the use of the nucleic acid molecule according to the invention or of the DNA construct described herein for producing an attenuated genotype I PRRS virus, wherein one or more mutations are introduced into the nucleic acid molecule or into the DNA construct.

The invention also provides a method of producing an attenuated genotype I PRRS virus comprising the step of introducing one or more mutations into the nucleic acid molecule according to the invention or into the DNA construct described herein.

Preferably, the one or more mutations described herein are introduced into the first nucleic acid sequence having at least 95% sequence identity with the nucleic acid sequence of SEQ ID NO:45.

The term "attenuated PRRS virus", as described herein, is in particular directed to a PRRS virus which is attenuated in vitro and/or in vivo, more particular in susceptible cell lines and/or the host.

The term "host", as used herein, is in particular directed to animals infectable with PRRS virus, in particular swine, more particular pigs, such as domestic pigs.

As mentioned herein, "attenuated" particularly relates to a reduced virulence of a pathogen, in particular of a wild type PRRS virus, wherein "virulence" is understood to be the degree of pathogenicity, and wherein "pathogenicity" is directed to the ability of the pathogen to induce clinical signs in the host or the offspring of the host, such as reproductive failure.

The term "wild type PRRS virus" or "wild type PRRSV", respectively, as used herein, is in particular directed to an infectious pathogenic PRRS virus, which is particularly capable of causing PRRS in swine. In one particular preferred embodiment, the term "wild type PRRS virus" is directed to a PRRS virus whose genome comprises a RNA sequence or consists of a RNA polynucleotide, wherein said RNA sequence or RNA polynucleotide is a RNA copy of SEQ ID NO:41 (corresponding to Lelystad virus complete genome).

Preferably, the one or more mutations, as described herein, comprise or consist of one or more point mutations and/or one or more genomic deletions and/or one or more insertions.

Also, the invention provides an attenuated genotype I PRRS virus whose genome comprises an RNA molecule encoded by a nucleic acid molecule according to the invention but wherein said first nucleic acid sequence having at least 95% sequence identity with the nucleic acid sequence of SEQ ID NO:45 contains one or more mutations that attenuate the encoded PRRS virus and/or that disable the encoded PRRS virus to suppress the interferon type I production and secretion by a cell infected by said virus, and wherein said attenuated genotype I PRRS virus is preferably an isolated attenuated genotype I PRRS virus.

The invention further provides the use of the attenuated genotype I PRRS virus described herein for the preparation of a medicament, in particular of a vaccine or vaccine composition, for preventing an animal from clinical signs of a PRRSV infection, such as by reducing the clinical signs of a PRRSV infection, e.g. reducing the duration of PRRSV viremia.

The term "preventing" or "reducing", respectively, as used herein, means, but is not limited to, a process which includes the administration of a PRRSV antigen, namely of the attenuated genotype I PRRS virus described herein, to an animal, wherein said PRRSV antigen, when administered to said animal elicits or is able to elicit an immune response in said animal against PRRSV. Altogether, such treatment results in reduction of the clinical signs of PRRS or of signs associated with PRRSV infection, respectively. More specifically, the term "preventing, as used herein, means generally a process of prophylaxis in which an animal is exposed to the immunogenic composition of the present invention prior to the induction or onset of the disease process (PRRS).

Herein, "reducing the clinical signs of a PRRSV infection" means, but is not limited to, reducing the number of infected subjects in a group, reducing or eliminating the number of subjects exhibiting clinical signs of infection, or reducing the severity of any clinical signs that are present in the subjects, in comparison to wild type PRRS virus infection. For example, it should refer to any reduction of pathogen load, pathogen shedding, reduction in pathogen transmission, or reduction of any clinical sign typical of PRRSV infection, in particular of reproductive failure and/or induction of lung lesions. Preferably these clinical signs are reduced in subjects receiving the attenuated genotype I PRRS virus of the present invention by at least 10% in comparison to subjects not receiving the composition and may become infected. More preferably, clinical signs are reduced in subjects receiving the composition of the present invention by at least 20%, preferably by at least 30%, more preferably by at least 40%, even more preferably by at least 50%, even more preferably by at least 60%, even more preferably by at least 70%, even more preferably by at least 80%, even more preferably by at least 90%, and most preferably by 100%.

The term "subject", as mentioned herein, in particular relates to an animal.

The term "animal", as mentioned herein, is in particular directed to swine, more particular to a pig, preferably a domestic pig.

The term "reducing the duration of PRRSV viremia" means, but is not limited to, the reduction of the duration of PRRS virus entering the bloodstream of an animal by at least one day in comparison to subjects not receiving the composition and become infected by a wild type PRRSV.

The term "viremia" refers to the presence of PRRSV in the blood of infected animals as reflected by e.g. the detection of PRRSV RNA copies in blood serum.

Also, the invention relates to a vaccine composition comprising the attenuated genotype I PRRS virus described herein suspended in a suitable amount of a pharmaceutically acceptable diluent or excipient.

The one or more pharmaceutically acceptable carriers or excipients, as mentioned herein, are preferably selected from the group consisting of solvents, dispersion media, adjuvants, stabilizing agents, diluents, preservatives, antibacterial and antifungal agents, isotonic agents, and adsorption delaying agents.

In a preferred aspect, the immunogenic composition of the invention comprises an amount of $10^1$ to $10^7$ viral particles of the attenuated genotype I PRRS virus described herein per dose, preferably $10^3$ to $10^6$ particles per dose, more preferably $10^4$ to $10^6$ particles per dose.

In another preferred aspect, the immunogenic composition of the invention comprises an amount of the PRRS virus according to the invention which is equivalent to a virus titer of at least about $10^3$ $TCID_{50}$/mL per dose, preferably between $10^3$ to $10^5$ $TCID_{50}$/mL per dose As used herein, the term "vaccine composition" in particular refers to a composition that will elicit a protective immune response in an animal that has been exposed to the composition. An immune response may include induction of antibodies and/or induction of a T-cell response.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion.

Thus, an "immune response" in particular means but is not limited to the development in a subset of a cellular and/or antibody-mediated immune response to the composition or vaccine of interest.

Further, the invention relates to the vaccine composition of the invention for use in a method for preventing an animal from clinical signs of a PRRSV infection, such as by reducing the clinical signs of a PRRSV infection, e.g. reducing the duration of PRRSV viremia.

Moreover, the invention provides a method for preventing an animal from clinical signs of a PRRSV infection, such as by reducing the clinical signs of a PRRSV infection, e.g. reducing the duration of PRRSV viremia, wherein said method comprises the step of administering the vaccine of the invention to an animal in need thereof.

Embodiments According to the Second Consideration of the Present Invention

The following clauses are also described herein:
1. A nucleic acid molecule which encodes a genotype I PRRS virus and which is capable of producing live virus when transfected into cells, wherein said molecule comprises
a first nucleic acid sequence having at least 95% sequence identity with the nucleic acid sequence of SEQ ID NO:45, a second nucleic acid sequence flanking the 5' end of the first nucleic acid sequence and having at least 95% sequence identity with the nucleic acid sequence of SEQ ID NO:46, a third nucleic acid sequence flanking the 3' end of the first nucleic acid sequence and having at least 95% sequence identity with the nucleic acid sequence of SEQ ID NO:47, and a polyadenine nucleotide sequence flanking the 3' end of the third nucleic acid sequence.

2. The nucleic acid molecule of clause 1, wherein said first nucleic acid sequence having at least 96%, preferably at least 97%, more preferably at least 98%, still more preferably at least 99%, and in particular preferably 100% sequence identity with the nucleic acid sequence of SEQ ID NO:45; and/or said second nucleic acid sequence having at least 96%, preferably at least 97%, more preferably at least 98%, still more preferably at least 99%, and in particular preferably 100% sequence identity with the nucleic acid sequence of SEQ ID NO:46; and/or said third nucleic acid sequence having at least 96%, preferably at least 97%, more preferably at least 98%, still more preferably at least 99%, and in particular preferably 100% sequence identity with the nucleic acid sequence of SEQ ID NO:47; and/or said polyadenine nucleotide sequence is composed of n adenine nucleotides, wherein n is any integer between 1 and 51, and wherein n is preferably 12, 13 or 14.

3. The nucleic acid molecule of clause 1 or 2, wherein said virus is attenuated and/or wherein said virus is able to induce a protective immune response against respiratory and/or reproductive signs of disease after infection with Porcine Reproductive and Respiratory Syndrome (PRRS) virus in swine.

4. The nucleic acid molecule of any one of clauses 1 to 3, wherein said virus is able to reach titers of at least $5 \times 10^5$ to $1 \times 10^6$ tissue culture infectious dose 50 ($TCID_{50}$) per milliliter (ml) within 24 hours post infection of MA104 cells, preferably at an MOI (multiplicity of infection) of 0.001 to 0.1.

5. The nucleic acid molecule of any one of clauses 1 to 4, wherein said virus is able to reach titers of at least $5 \times 10^6$ to $1 \times 10^7$ tissue culture infectious dose 50 ($TCID_{50}$) per milliliter (ml) within 48 hours post infection of MA104 cells, preferably at an MOI (multiplicity of infection) of 0.001 to 0.1.

6. The nucleic acid molecule of any one of clauses 1 to 5, wherein said molecule comprises a nucleic acid sequence having at least 91% or 92%, preferably at least 93% or 94%, more preferably at least 95% or 96%, still more preferably at least 98% or 99%, and in particular preferably at least 99% sequence identity with the nucleic acid sequence of SEQ ID NO:48.

7. The nucleic acid molecule of any one of clauses 1 to 6, wherein said molecule comprises a nucleic acid sequence having at least 99.1% or 99.2%, preferably at least 99.3% or 99.4%, more preferably at least 99.5% or 99.6%, still more preferably at least 99.8% or 99.9%, and in particular preferably at least 99.95% sequence identity with the nucleic acid sequence of SEQ ID NO:48.

8. The nucleic acid molecule of any one of clauses 1 to 7, wherein said molecule comprises the nucleic acid sequence of SEQ ID NO:48.

9. The nucleic acid molecule of any one of clauses 1 to 8, wherein said virus is not able to induce a severe, Porcine Reproductive and Respiratory Syndrome (PRRS) in swine as caused by virulent field PRRS viruses.

10. The nucleic acid molecule of any one of clauses 1 to 9, wherein said molecule is a DNA molecule.

11. A DNA construct comprising a DNA molecule according to clause 10.

12. An RNA transcript of the DNA construct of clause 11.

13. A cell transfected with the DNA construct of clause 11.

14. A cell transfected with the RNA transcript of clause 12.

15. A genotype I PRRS virus produced by the cell of clause 13.

16. A genotype I PRRS virus produced by the cell of clause 14.

17. A genotype I PRRS virus whose genome comprises a nucleic acid molecule according to any one of clauses 1 to 9 or whose genome comprises an RNA molecule encoded by a nucleic acid molecule according to any one of clauses 1 to 10.

18. A method for producing a genotype I PRRS virus comprising transfecting a cell with the DNA construct of clause 11.

19. A method for producing a genotype I PRRS virus comprising transfecting a host cell with the RNA transcript of clause 12.

20. A composition comprising a nucleic acid molecule of any one of clauses 1 to 10 suspended in a suitable amount of a pharmaceutically acceptable diluent or excipient.

21. Use of the nucleic acid molecule of any one of clauses 1 to 10 or of the DNA construct of clause 11 for producing an attenuated genotype I PRRS virus, wherein one or more mutations are introduced into the nucleic acid molecule or into the DNA construct.

22. Method of producing an attenuated genotype I PRRS virus comprising the step of introducing one or more mutations into the nucleic acid molecule of any one of clauses 1 to 10 or into the DNA construct of clause 11.

23. An attenuated genotype I PRRS virus whose genome comprises an RNA molecule encoded by a nucleic acid molecule according to any one of clauses 1 to 10 but wherein said first nucleic acid sequence having at least 95% sequence identity with the nucleic acid sequence of SEQ ID NO:45 contains one or more mutations that disable the encoded PRRS virus to suppress the interferon type I production and secretion by a cell infected by said virus.

24. Use of the attenuated genotype I PRRS virus of any one of clauses 21 to 23 for the preparation of a medicament for preventing an animal from clinical signs of a PRRSV infection.

25. A vaccine composition comprising the attenuated genotype I PRRS virus of any one of clauses 21 to 23 suspended in a suitable amount of a pharmaceutically acceptable diluent or excipient.

26. The vaccine composition of clause 25 for use in a method for preventing an animal from clinical signs of a PRRSV infection.

27. Method for preventing an animal from clinical signs of a PRRSV infection comprising the step of administering the vaccine composition of clause 26 to an animal in need thereof.

3. Third Consideration of the Present Invention

According to a third consideration, which is detailed in this section, the invention is based on the finding that the first consideration of the present invention can be combined with the second consideration of the present invention. Thus, the third consideration of the present invention relates to a combination of (1) the aspects and embodiments of the first consideration of the present invention and (2) the aspects and embodiments of the second consideration of the present invention. Hence, it is understood that all possible features and definitions, in particular the features and definitions relating to a genotype I PRRS virus, of the first consideration of the present invention can be arbitrarily combined with all features and definitions of the second consideration of the present invention.

In one aspect, the nucleic acid molecule according to the second consideration of the present invention thus encodes the Porcine Reproductive and Respiratory Syndrome (PRRS) virus according to the first consideration of the present invention, as recited.

In another aspect, respectively, the Porcine Reproductive and Respiratory Syndrome (PRRS) virus according to the first consideration of the present invention is thus encoded by the nucleic acid molecule according to the second consideration of the present invention, as recited.

Hence, the combination of all possible aspects of the first consideration of the present invention with all possible aspects of the second consideration of the present invention is in particular also reflected by said claims and the claims depending thereon.

The invention is directed, furthermore, to a genotype I PRRS virus, in particular the aforementioned PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of SEQ ID NO:48, but wherein said nucleic acid sequence contains a mutation resulting in the production of said virus comprising an ORF4 protein having a deletion of 9, 10, 11 or more amino acid residues between amino acid positions 50 to 71, wherein the numbering of the amino acid positions refers to the amino acid sequence of ORF4 protein of the Lelystad virus.

The invention also concerns a genotype I PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of the nucleic acid sequence of SEQ ID NO:48, but wherein said nucleic acid sequence contains a mutation resulting in the production of said virus comprising an ORF4 protein having a deletion of 11, 12, 13, 14, 15, 16, or 17 amino acid residues between amino acid positions 50 to 71, wherein the numbering of the amino acid positions refers to the amino acid sequence of ORF4 protein of the Lelystad virus.

The invention moreover contemplates a genotype I PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of SEQ ID NO:48, but wherein said nucleic acid sequence contains a mutation resulting in the production of said virus comprising an ORF4 protein having a deletion of 13 amino acid residues between amino acid positions 56 to 70 or between amino acid positions 57 to 69, wherein the numbering of the amino acid positions refers to the amino acid sequence of ORF4 protein of the Lelystad virus.

The mutation, as referred to herein, is preferably a deletion.

Peferably, the PRRS virus of the invention is genetically modified to contain therein exogenous RNA, wherein the exogenous RNA is inserted into the orf4 gene of said virus, and wherein the exogenous RNA is in particular inserted into the region of the orf4 gene of said virus encoding the region located between amino acid positions 50 to 71, wherein the numbering of the amino acid positions refers to the amino acid sequence of ORF4 protein of the Lelystad virus.

In another preferred aspect, the exogenous RNA is inserted into the orf4 gene of the virus and replaces the nucleotide sequence encoding the amino acid residues deleted within the context of the invention.

According to a further preferred aspect, the exogenous RNA encodes an expression product selected from the group consisting of an epitope of interest, a biological response modulator, a growth factor, a recognition sequence, a fusion protein, wherein the epitope of interest is preferably an epitope of interest from an antigen or a veterinary pathogen or toxin.

In particular, the epitope of interest is a peptide encoded by the orf5 gene of PRRS virus or is an amino acid sequence encoded by the orf5 gene of PRRS virus, wherein said peptide or amino acid sequence encoded by the orf5 gene of PRRS virus preferably comprises or consists of the amino acid sequence of SEQ ID NO:39 or SEQ ID NO:50 or preferably comprises or consists of at least 4 consecutive amino acid residues of the sequence set forth in SEQ ID NO: 39 or SEQ ID NO:50, or preferably comprises or consists of the amino acid sequence of SEQ ID NO:51 or SEQ ID NO:52.

According to a another preferred aspect, the exogenous RNA encodes an amino acid sequence selected from the group consisting of SEQ ID NOs: 53-55.

In a particular preferred aspect, the invention provides, as a non limiting example, a genotype I PRRS virus, whose genome is encoded by a nucleic acid molecule comprising a nucleic acid sequence selected from the group consisting of any one of SEQ ID NOs:56-59.

The PRRS virus, as mentioned to herein, is preferably an isolated virus and/or a non-naturally occurring virus.

The invention is directed, furthermore, to a genotype I PRRS virus, wherein said virus comprises an ORF4 protein having a proline residue at amino acid position 56 and/or having a glutamine residue at amino acid position 66, wherein the numbering of the amino acid positions refers to the amino acid sequence of ORF4 protein of the Lelystad virus, and wherein the amino acid sequence of ORF4 protein of the Lelystad virus is the sequence set forth in SEQ ID NO:43.

The invention also concerns a genotype I PRRS virus, whose genome comprises a nucleic acid molecule which encodes an ORF4 protein having a proline residue at amino acid position 56 and/or having a glutamine residue at amino acid position 66, wherein the numbering of the amino acid positions refers to the amino acid sequence of ORF4 protein of the Lelystad virus, and wherein the genome of said virus is preferably is encoded by a nucleic acid molecule, wherein said molecule comprises a nucleic acid sequence having at least 91% or 92%, preferably at least 93% or 94%, more preferably at least 95% or 96%, still more preferably at least 98% or 99%, and in particular preferably at least 99% sequence identity with the nucleic acid sequence of the nucleic acid sequence of SEQ ID NO:45 or SEQ ID NO:48.

Such a genotype I PRRS virus, whose genome comprises a nucleic acid molecule which encodes an ORF4 protein having a proline residue at amino acid position 56, is in an exemplary non-limiting aspect a PRRS virus, whose genome is encoded by a nucleic acid molecule comprising the nucleic acid sequence SEQ ID NO:58.

In another exemplary non-limiting aspect, such a genotype I PRRS virus, whose genome comprises a nucleic acid molecule which encodes an ORF4 protein having a glutamine residue at amino acid position 66, is a PRRS virus, whose genome is encoded by a nucleic acid molecule comprising the nucleic acid sequence SEQ ID NO:57.

The PRRS virus of the invention is preferably for use as a medicament or for use in the prophylaxis or treatment of Porcine Reproductive and Respiratory Syndrome, in particular in swine, and wherein optionally said virus is to be administered, or is administered, respectively, via the intranasal, intramuscular, oral, or intrauterine route to an animal, in particular to a pig.

A medicament as referred to throughout this disclosure is preferably a vaccine.

According to another aspect, the PRRS virus of the invention is preferably used as a detection marker, preferably for the differentiation between infected and vaccinated animals (DIVA).

In still a further aspect, the invention relates to a DNA molecule which encodes the PRRS virus of the invention, and wherein said DNA molecule preferably comprises a nucleic acid molecule having a sequence selected from the group consisting of SEQ ID NOs:56-58.

In yet a further aspect, the invention relates to a preferably isolated DNA construct comprising said DNA molecule and to a preferably isolated RNA transcript thereof.

According to still another aspect the invention also relates to a preferably isolated cell transfected with said DNA construct or said RNA transcript.

The invention furthermore relates to a method for producing the PRRS virus of the invention, wherein said method comprises the step of transfecting a cell with said DNA construct or comprises the step of transfecting a host cell with said RNA transcript.

In conclusion, the knowledge of having the possibility to insert a deletion to the extent according to the present invention into the sequence coding for the ectodomain of GP4 of a PRRS virus, such as a genotype I PRRSV, now provides a number of beneficial uses:

The virus based on this knowledge can be used as a challenge isolate for parenteral, oral, intranasal, intrauterine infection and for infection by means of sperm in PRRSV positive and PRRSV naive and/or PRRSV sensitive species.

The invention provides deletion markers for serological differentiation or for sequence differentiation (DIVA concept), of each conceivable PRRSV strain, to PRRSV strains of the genotype II, regardless of whether deletions are already present at the respective site or not.

Further, deletion markers are provided for serological differentiation also in connection or in combination with other epitopes. For example, PRRS viruses without deletion could be distinguished serologically from PRRS viruses with a complete or partial deletion of these epitopes (e.g. Lelystad GP4 aa60-aa70: AAQEKISFGKS as included in SEQ ID NO:43) by using antibodies directed against this epitope. For instance, two PRRS viruses having a deletion in this region/domain could be differentiated from each other in conjunction with other epitopes.

The invention further provides an insertion region/domain for the introduction of foreign RNA instead of the viral RNA at the position, where the deletion according to the invention is located (ectodomain of GP4).

The insertion can be done for various purposes and for every conceivable PRRSV strain, also for PRRSV strains of the genotype II which already have a small deletion in this region.

The insertion of the foreign sequence can take place e.g. in the PRRSV genotype I strain BI EU described herein and replace the sequence coding for the ectodomain of GP4 of said strain with the amino acid (aa) sequence aa54-aa70 (QSHRASTAQGTTPLRRS (SEQ ID NO:40)) or with shortened or mutagenized derivatives thereof.

Moreover, for the improvement of the immune response it is also possible to insert one or more sequential T-oder B-cell epitopes a) from other gene/genomic regions of PRRSV, e.g. from (i) the region coding for the glycoprotein 5 (aa) of the PRRSV genotype I strain BI EU described herein, e.g. sequences coding for the amino acids (aa) aa36-aa52 (SSHLQLIYNLTICELNG (SEQ ID NO:39)) or for shortened or for mutagenized derivatives thereof, also with suitable linker(s), for instance with the aa motif GSS; accordingly also from other PRRSV isolates, e.g. from the PRRSV genotype I protype isolate Lelystad or, accordingly, from other genotypes of PRRSV, such as e.g. from the PRRSV genotype II prototype isolate VR2332;

b) from other pathogens, e.g. from another swine pathogen, for establishing an or enhancing the immune response against said pathogen(s);

c) from non-PRRSV-specific T-oder B-cell epitopes as a genetic or serological positive marker, also in combination with a);

d) from immuno-enhancers different from a), e.g. cytokines, as for instance interleukins, also in combination with b).

For the improvement of the immune response it is also possible to insert one or more sequential T-oder B-cell epitopes for the reduction of the pathogenicity of the virus.

EXAMPLES

Example 1 a) Isolation of PRRSV

PRRSV was isolated from blood samples (bS-720789) previously tested positive in a PRRSV EU-type detection PCR. Isolation of virus was performed on MA104 cells. After propagation of the isolated EU-type PRRSV on MA104 cells, a virus stock for full genome sequencing was prepared by ultracentrifugation on a sucrose cushion, followed by RNase and DNase treatment. Finally, viral RNA was extracted from the virus stock and submitted for full genome sequencing (Roche 454 platform). The genome sequence obtained (14 854 nucleotides) was compared to the EU-type reference genome sequence of strain Lelystad, revealing a deletion of 33 nucleotides in ORF4.

b) Infection

Infection of boars with the virus of a) produces severe clinical signs of PRRS.

Example 2 a) Generation and Characterization of a Novel EU Type PRRSV Infectious cDNA Clone This example describes the generation and characterization of a novel EU type PRRSV infectious cDNA clone which is designated "BI EU" in the following. BI EU is based on but not identical to an attenuated EU type PRRSV strain and is 89% identical on nucleotide level to the EU prototype strain Lelystad virus or 87% identical to the PRRSV cDNA insert of the EU type PRRSV infectious cDNA clone LoN94-13 (WO 2013017568 A1) respectively. The cDNA sequence of BI EU is provided in SEQ ID NO:48.

Live virus was recovered from cDNA clone BI EU after transfecting synthetic capped transcripts into BHK21 cells and subsequent transfer of cell culture supernatant from transfected cells onto PRRSV-susceptible MA104 cells. A strong cytopathic effect (CPE) was detectable within 3 to 4 days post transfer of cell culture supernatant from transfected BHK21 cells to MA104 cells (FIG. 1A). After staining the cells with the PRRSV capsid protein-specific monoclonal antibody SDOW17 (Rural Technologies), a strong signal was detectable in the CPE positive MA104 cells (FIG. 1B) but not in cells which received supernatants of mock transfected BHK21 cells (not shown).

Figure 2:
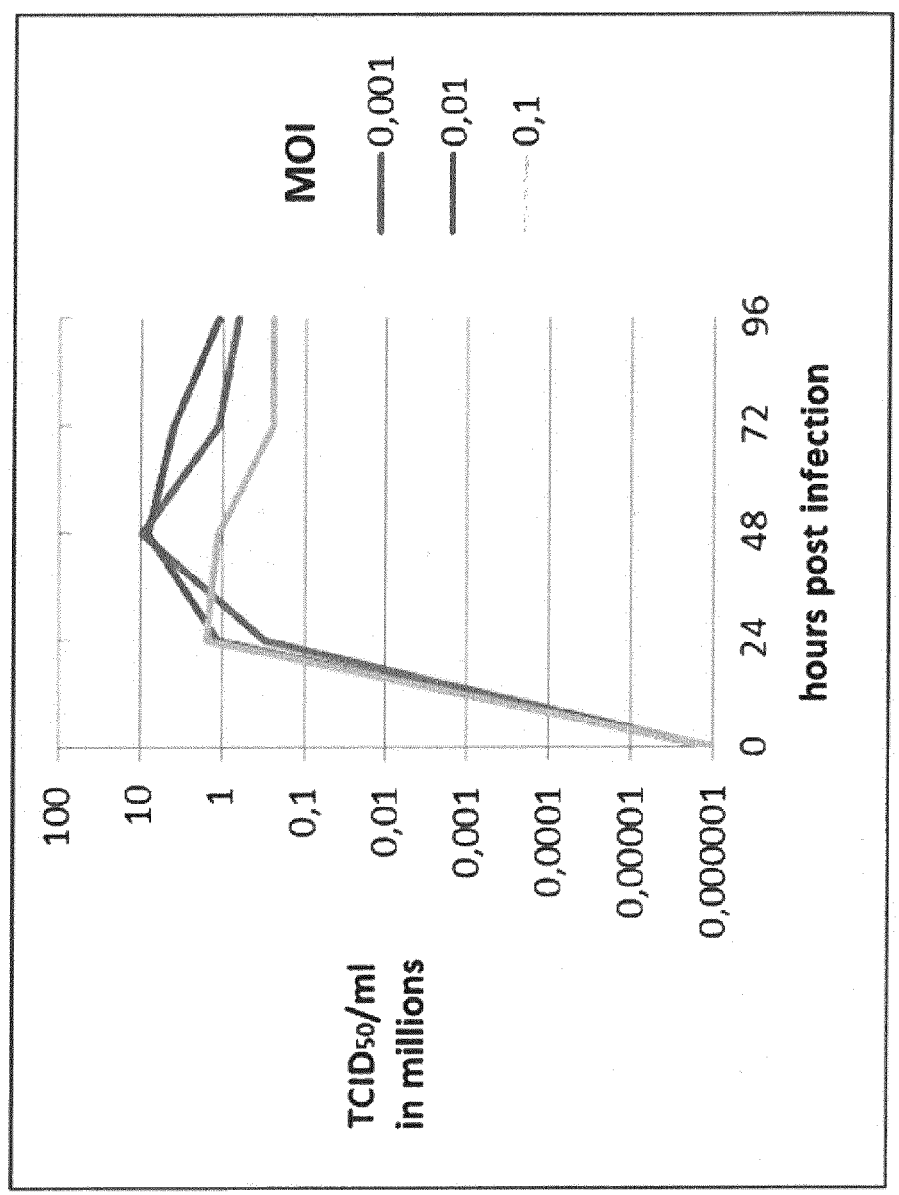

To test growth of the BI EU cDNA clone-derived virus, MA104 cells were infected with the recovered virus using a multiplicity of infection (M01) of 0.001, 0.01 or 0.1, respectively. Supernatants of infected cells were collected at 0, 24, 48, 72 and 96 hours post infection and virus titers were determined by serial virus dilutions on 96-well plates containing MA104 cells. The resulting growth curve for virus recovered from BI EU is shown in FIG. 2.

Independent of the MOI used for infection of MA104 cells, the virus BI EU reached titers of $5 \times 10^5$ to $1 \times 10^6$ tissue culture infectious dose 50 ($TCID_{50}$) per milliliter (ml) within 24 hours post infection. Titers peaked around 48 hours post infection with $1 \times 10^6$ to $1 \times 10^7$ $TCID_{50}$/ml, demonstrating highly efficient replication of the BI EU virus on MA104 cells.

This finding allows to use BI EU as a platform for PRRSV vaccine research, e.g., as one of many applications, to investigate the PRRSV interplay with host immune responses to viral infection.

b) Use of the Novel EU Type PRRSV Infectious cDNA Clone in PRRS Vaccine Research The specific immune response to PRRSV infection is characterized by delayed induction of neutralizing antibodies (Lopez and Osorio, 2004) and short cell-mediated immune response (Xiao et al., 2004). It is commonly accepted that these effects can in part be attributed, along with presentation of decoy epitopes (Ostrowski et al., 2002; Ansari et al., 2006) and glycan shielding of viral envelope proteins (Ansari et al., 2006), to the viral inhibition of the host's innate immune system. It has been demonstrated that PRRSV infection does not or only weakly or delayedly induce production of type I interferon (IFN), (interferon-α and interferon-β; (Miller et al., 2004)) or type II IFN, (interferon-γ; (Meier et al., 2003)) in susceptible cell lines (swine pumonary alveolar macrophages, monkey kidney cells MARC-145) and/or pigs (Buddaert et al., 1998).

IFNs play an important role in establishing an effective adaptive immune response against viral infections, and many viruses therefore have developed strategies to counteract onset of the host's innate immune system (Haller and Weber, 2009). In the interest to identify the anticipated PRRSV IFN antagonist(s), extensive screening analyses based on cell lines stably expressing genes of interest or on cells transfected with protein-expressing plasmids have identified several PRRSV nonstructural proteins (nsps) including nsp1 (see below), nsp2 (Beura et al., 2010; Li et al., 2010), nsp4 (Beura et al., 2010), and nsp11 (Beura et al., 2010; Shi et al., 2011a) to be involved in blocking the induction of type I IFN.

nsp1 is located at the N-terminus of the PRRSV ORF1a-derived polyprotein 1a and is processed into two multifunctional subunits, nsp1α and nsp1β, each of which contains a papain-like cystein protease (PCP) domain essential for self-release from the viral polyprotein (den Boon et al., 1995; Chen et al., 2010). nsp1α contains an N-terminal zinc-finger domain and the PCPα protease domain, while nsp1β contains PCPβ. For both nsp1 subunits, nsp1α and nsp1β, the tree-dimensional crystal structure has been resolved (Sun et al., 2009; Xue et al., 2010).

According to these analyses, nsp1β consists of an N-terminal domain (NTD), a linker domain (LKD), the PCP domain (PCP beta), and a C-terminal extension (CTE); (Xue et al., 2010). C-terminal, nsp1β-mediated cleavage of nsp1 from nsp2 occurs at site WYG/AGR (SEQ ID NO: 59) for PRRSV US strains (Kroese et al., 2008) or is predicted at site WYG/AAG (SEQ ID NO: 60) for PRRSV EU strains (Chen et al., 2010), while nsp1α/nsp1β cleavage occurs at site ECAM/AxVYD (SEQ ID NO: 61) for PRRSV US strains or is predicted at site EEAH/SxVYR (SEQ ID NO: 62) for PRRSV EU strains (Chen et al., 2010).

Several studies demonstrated to the mechanistic detail that PRRSV nsp1 and/or its autocleavage-derived subunits nsp1α and/or nsp1β inhibit type I IFN production by interfering with IFN transcription (Song et al., 2010; Kim et al., 2010; Chen et al., 2010; Beura et al., 2010). In addition, it has been demonstrated that nsp1β interferes with the cellular response to interferon (interferon signaling); (Chen et al., 2010). Moreover, it was demonstrated that PRRSV infection inhibits IFN-α and/or IFN-β production in PRRSV infected cells in vitro (Kim et al., 2010; Beura et al., 2010), the subcellular localization of nsp1 (subunits) was determined (Song et al., 2010; Chen et al., 2010), and mechanistic aspects of type I IFN inhibition that were obtained by others from single protein expression experiments were confirmed in cells infected with PRRSV (Shi et al., 2010). Finally, a nsp1 mutagenesis study based on nsp1 protein expression investigated effects on viral IFN inhibition (Shi et al., 2011b).

Previously viable PRRSV (EU) strains have been generated (as described in WO 2013017570 A1) that contained mutations (deletions) in the nsp1β gene that induced type I IFN (IFN-β) production in susceptible cells (MARC145) and that are sensitive to type I IFN (IFN-β).

Figure 3:
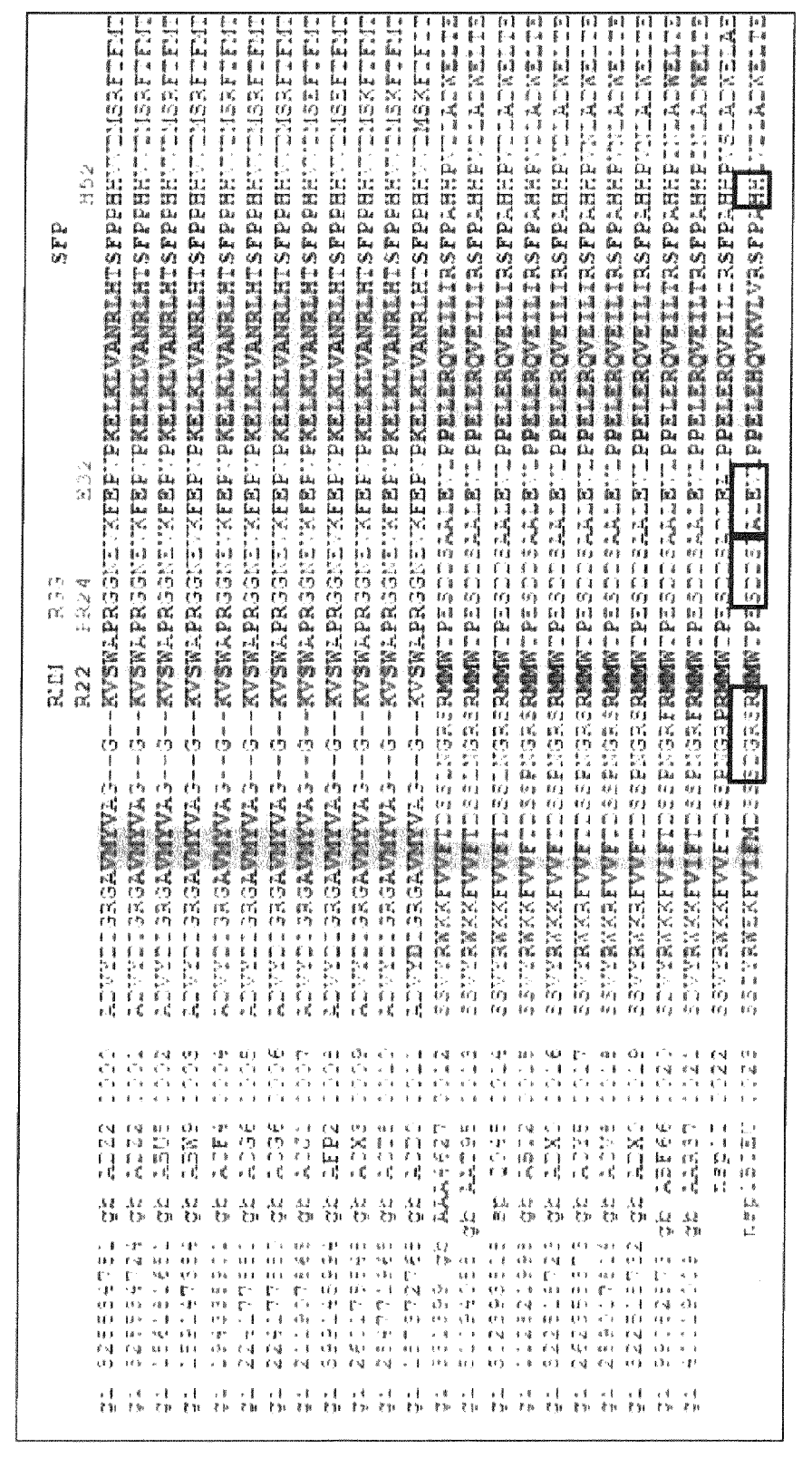

To test whether such and also different IFN inducing virus mutants could get generated based on the novel infectious clone BI EU, a set of viruses harboring deletions in the nsp1β gene was designed. More precisely, these deletions were located in the N-terminal domain (NTD) of nsp1β which has been shown to be required for homodimerization of the protein (Xue et al., 2010). FIG. 3 shows an nsp1β aminoacid sequence alignment of several US and EU type PRRSV strains. Indicated are aminoacids predicted to form strands (blue) or alpha helices (red) formation.

Ten nsp1β deletion mutants were generated on the basis of the infectious cDNA clone BI EU. Deletions included aminoacids that were predictedly not involved in beta strand or alpha helix formation and that were (partially) conserved within all EU type PRRSV strains analyzed in the alignment (framed in red in FIG. 3).

The deletions introduced in the nsp1β gene are visualized in the aminoacid sequence alignment shown in FIG. 4. The BI EU-nsp1β deletion mutants are designated BI EU-nsp1β-delALEV, (SEQ ID NO: 89), BI EU-nsp1β-delEV, (SEQ ID NO: 90), BI EU-nsp1β-delLEVL, (SEQ ID NO: 91), BI EU-nsp1β-delLE, (SEQ ID NO: 92), BI EU-nsp1β-delDD, (SEQ ID NO: 93), BI EU-nsp1β-delSDDS, (SEQ ID NO: 94), BI EU-nsp1β-delHH, (SEQ ID NO: 95), BI EU-nsp1β-delGRSR, (SEQ ID NO: 96), BI EU-nsp1β-delRSR (SEQ ID NO: 97), and BI EU-nsp1β-delSDGRSR (SEQ ID NO: 98), respectively.

Figure 5:
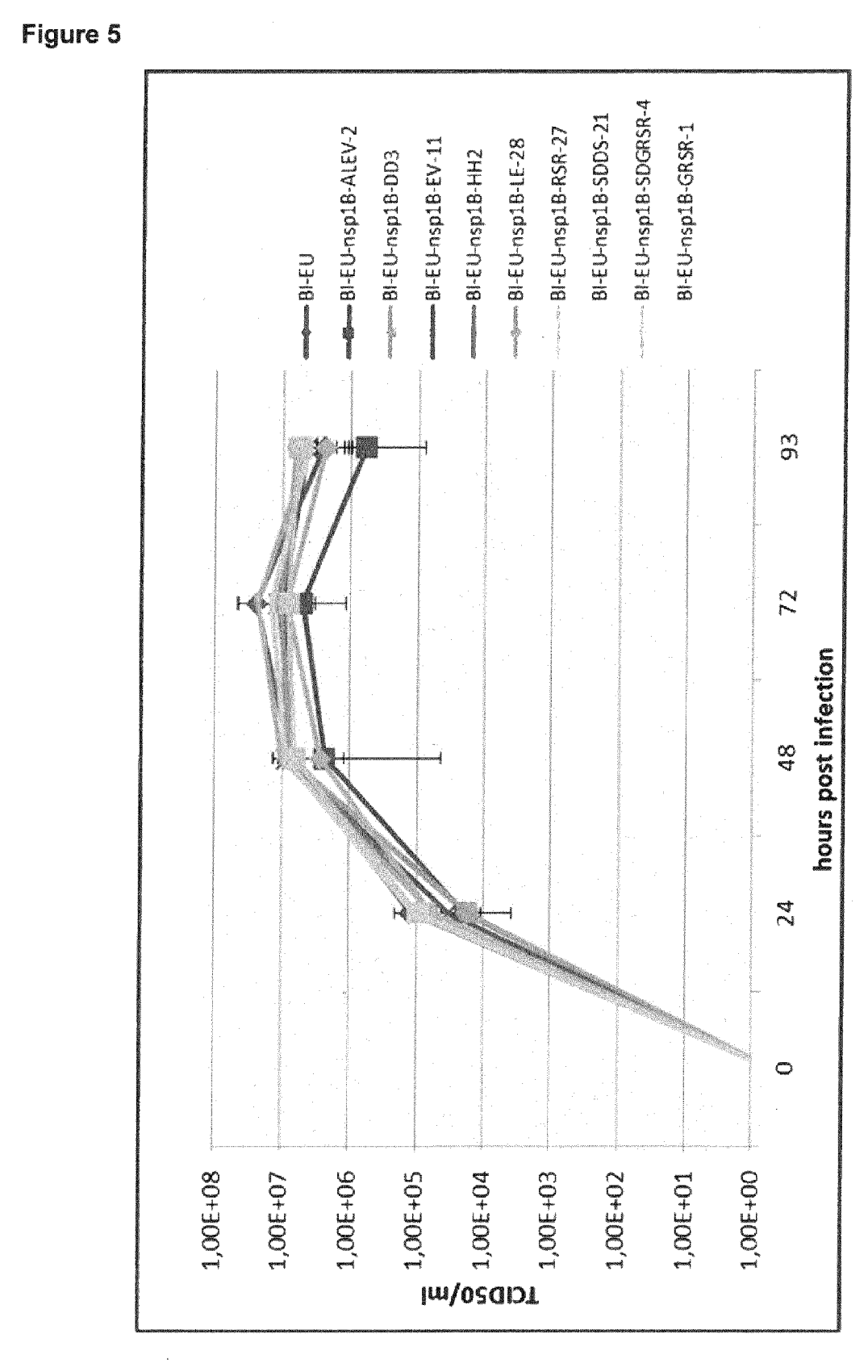

To test viability of the nsp1β deletion mutants, synthetic transcripts of BI EU cDNAs harbouring the respective deletion were transfected into BHK21 cells. After transfer of cell culture supernatant from transfected cells onto PRRSV-susceptible MA104 cells, cytopathic effects (CPE) and nucleocapsid-specific immunofluorescence staining indicating PRRSV mutant viability were detectable for nine of the ten nsp1β deletion mutants generated (not shown). These findings demonstrated that, with the exception of BI EU-nsp1β-delLEVL (SEQ ID NO: 91), all nsp1β deletion mutants were viable. To further analyze whether the nsp1β-deletion mutants could be grown to high titers on IFN-competent MA104 cells, growth curves were performed essentially as described above for the BI EU virus. Briefly, MA104 cells were infected with one of the nine nsp1β deletion mutants or the virus BI EU as control. Cell culture supernatants were harvested at 0, 24, 48, 72 and 93 hours post infection and titrated on MA104 cells on 96-well plates. Viral titers were calculated based on CPE-positive wells. FIG. 5 shows the result of two independent experiments and demonstrates that BI EU-nsp1β deletion mutants can be grown on MA104 cells as efficiently as the parent BI EU virus. Peak titers of $5 \times 10^6$ to $1 \times 10^7$ $TCID_{50}$/ml were observed at 48 hours post infection.

It was next analyzed whether the deletions introduced into the nsp1β gene would indeed abolish the IFN antagonistic activity of the nsp1β protein. Therefore IFN-β levels in 100 μl samples collected at 0, 24, 48, 72 and 93 hours post infection throughout the growth curve experiment described above were measured using a commercial ELISA specific for human IFN-β (Invitrogen). According to the manufacturer, this ELISA can also be applied for the detection of non-human primate IFN-β and worked well for samples from MA104 cells which are epithelial Green Monkey kidney cells (see FIG. 6). For quantification of the obtained results, a calibration curve was included using a positive control of the ELISA manufacturer.

Figure 6:
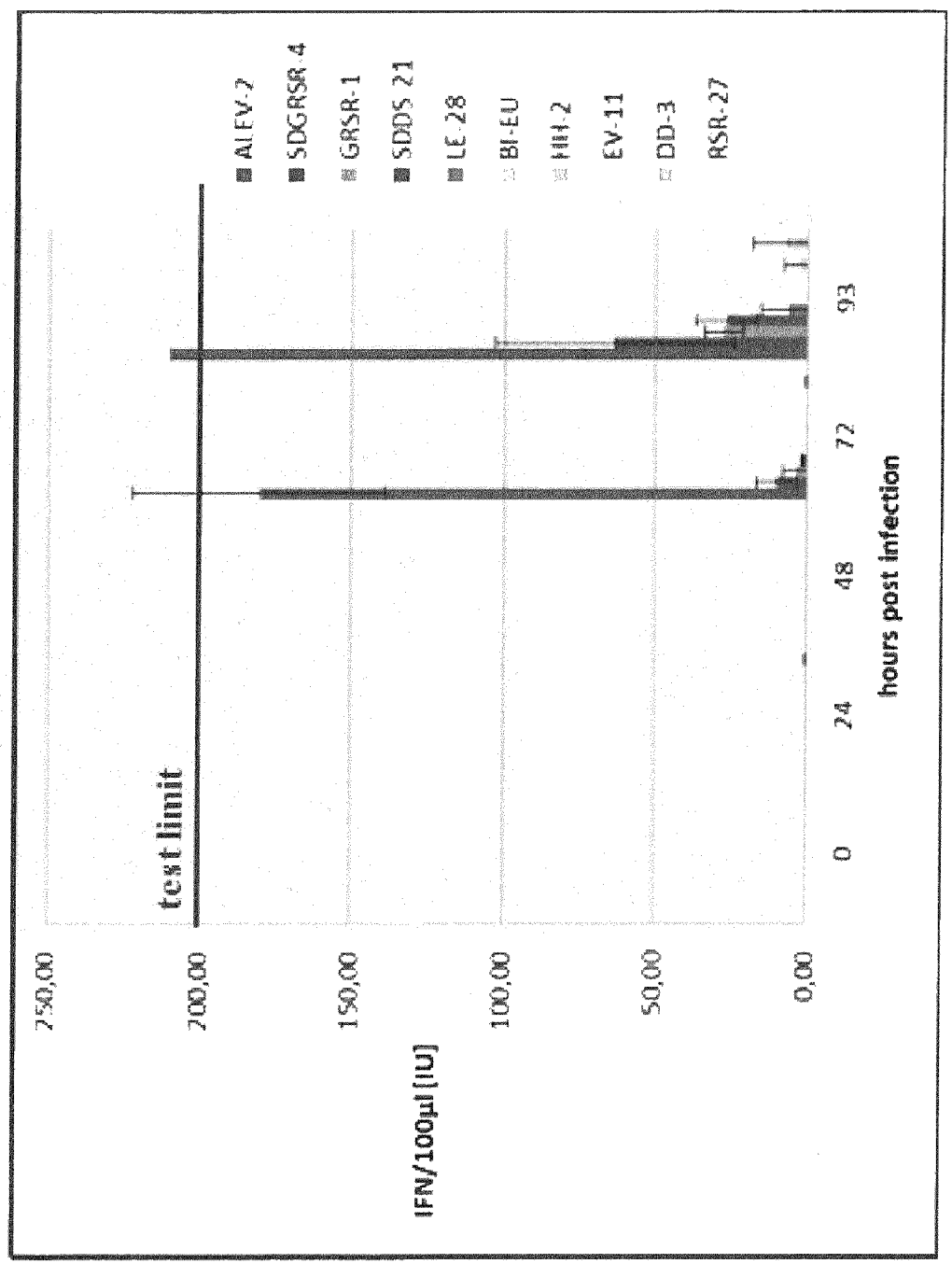

IFN-β levels measured in the supernatants of MA104 cells infected with one of the nine viable nsp1β deletion mutants or with the parent BI EU virus and obtained from two independent experiments are shown in FIG. 6.

As expected, parental BI EU efficiently blocked the secretion of IFN-β throughout the course of infection which is attributed to functional viral IFN antagonist(s). No or only little amounts of IFN-β were detectable in the cell culture supernatant at 0, 24 and 48 hours post infection with the various BI EU-nsp1β deletion mutants. At later timepoints however, some mutants were unable to inhibit the expression of IFN-β in infected MA104 cells, indicating a defect in the nsp1β IFN antagonistic activity. Interestingly, this defect varied significantly between the nine BI EU-nsp1β deletion mutants analyzed. While most of the mutants induced IFN-β levels below 50 international units (IU) per 100 μl cell culture supernatant, the mutant BI EU-nsp1β-delALEV (SEQ ID NO: 89), was completely unable to antagonize the expression of IFN-β in infected MA104 cells. The amounts of IFN-β measured at 72 and 93 hours post infection even exceeded the limit of the ELISA test which is set at ~200 IU per 100 μl. This result clearly demonstrated that the IFN antagonistic activity of the nsp1β protein can be abolished by deleting the aminoacids $A_{30}LE\ V_{33}$ (SEQ ID NO: 63), in the BI EU infectious cDNA clone.

Taken together, a novel EU type PRRSV infectious cDNA clone was generated that can be efficiently grown to titers of $1 \times 10^7$ $TCID_{50}$/ml in Green Monkey kidney MA104 cells. Based on this clone, nine viable BI EU-nsp1β mutants were generated which harboured deletions in the NTD of nsp1β which has been shown to be required for homodimerization of the protein (Xue et al., 2010). These mutants could all be grown to high titers on MA104 cells. Mutants BI EU-nsp1β-delALEV, (SEQ ID NO: 89), BI EU-nsp1β-delEV, (SEQ ID NO: 90), BI EU-nsp1βdelLE (SEQ ID NO: 92), BI EU-nsp1β-delSDDS, (SEQ ID NO: 94), BI EU-nsp1β-delGRSR, (SEQ ID NO: 96), BI EU-nsp1β-delRSR (SEQ ID NO: 97), and BI EU-nsp1β-delSDGRSR (SEQ ID NO: 98), all induced the secretion of IFN-β at late timepoints of infection which is in strict contrast to the parent BI EU virus. Out of these seven mutants, the four mutants BI EU-nsp1β-delALEV, (SEQ ID NO: 89), BI EU-nsp1β-delEV, (SEQ ID NO: 90), BI EU-nsp1β-delLE, (SEQ ID NO: 92), and BI EU-nsp1β-delSDDS (SEQ ID NO: 94), represent a new class of mutants that has not previously been described in WO 2013017570 A1. In particular, infection with the mutant BI EU-nsp1β-delALEV (SEQ ID NO: 89), induced extremely high amounts of IFN-β in MA104 cells which leads to the conclusion that this virus is severely impaired in blocking the induction of IFN type I.

This finding has strong implications for PRRSV vaccine development since it can be assumed that the immune response of the natural host against PRRSV can be significantly enhanced by introducing deletions, e.g. by deleting aminoacids $A_{30}LEV_{33}$ (SEQ ID NO: 63), in the nsp1β protein of genotype I PRRSV strains.

The nsp1β deletion mutants described therein, either alone or in combination with other attenuating mutations, represent promising candidates for life attenuated PRRSV vaccines.

Example 3 a) Introducing a Deletion within the ORF4 Protein of the EU Type PRRSV Infectious cDNA Clone BI EU It was tested whether a deletion, as described according to the first consideration of the present invention, could be introduced into the ORF4 gene of any PRRS virus strain without negatively affecting viral replication. Therefore, a deletion was introduced into the genomic region coding for the ectodomain of the ORF4 protein between amino acid positions 50 to 71 of the EU type PRRSV infectious cDNA clone BI EU (comprising the sequence of SEQ ID NO:48). The deletion within the ORF4 protein of BI EU included amino acids 57-69 (as encoded by SEQ ID NO:49).

To test viability of the ORF4 deletion mutant, a synthetic transcript of BI EU cDNA harboring the deletion was transfected into BHK21 cells. After transfer of cell culture supernatants from transfected cells onto PRRSV-susceptible MA104 cells, a cytopathic effect (CPE) was detectable within 3 to 4 days post transfer of cell culture supernatants from transfected BHK21 cells to MA104 cells. After staining the cells with the PRRSV capsid protein-specific monoclonal antibody SDOW17 (Rural Technologies), a strong signal was detectable in the CPE positive MA104 cells but not in cells which received supernatants of mock transfected BHK21 cells (not shown). These findings demonstrated that the BI EU-ORF4 deletion mutant was viable. The recovered mutant virus is designated as BI EU-GP5-36-46-ctr (compare example b) in the following.

Figures 7, 8:
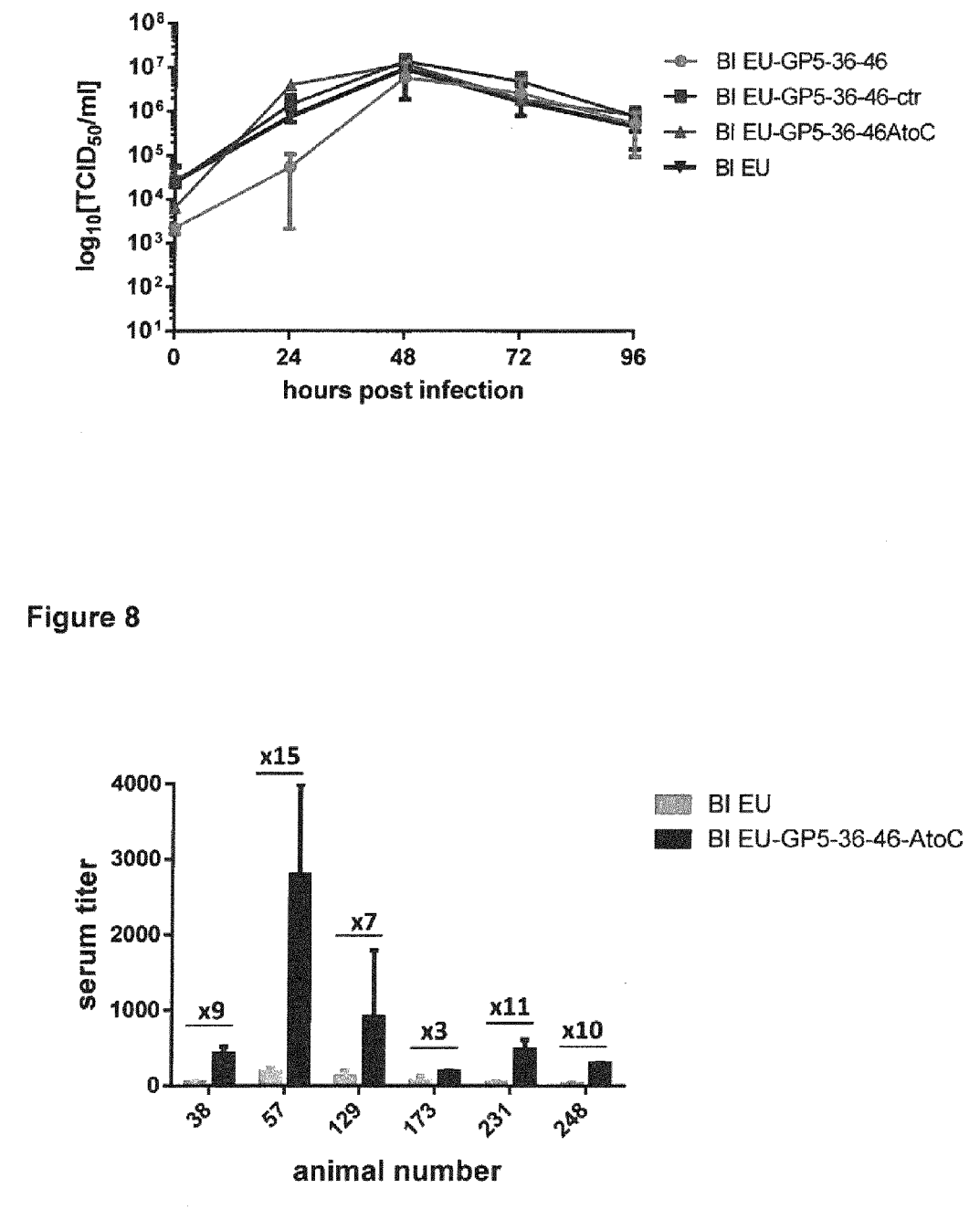

To further analyze whether BI EU-GP5-36-46-ctr could be grown to high titers on MA104 cells, growth kinetics were performed. Therefore, MA104 cells were infected with the recovered virus and with the parental BI EU virus as control using a multiplicity of infection (MOI) of 0.01. Supernatants of infected cells were collected at 0, 24, 48, 72 and 96 hours post infection and virus titers were determined by serial virus dilutions on 96-well plates containing MA104 cells. FIG. 7 shows the result of three independent experiments and demonstrates that BI EU-GP5-36-46-ctr can be grown on MA104 cells as efficiently as the parental BI EU virus. Peak titers of ~1×10$^7$ TCID$_{50}$/ml were observed for both viruses at 48 hours post infection.

Taken together, deletion of amino acids 57-69 within the ORF4 protein does not negatively influence growth of BI EU, indicating that sequence variations within this region are well tolerated by PRRSV in vitro. Concluding from these results, the region located between amino acid positions 50 to 71 of the BI EU ORF4 protein might also be used as insertion site for exogenous sequences.

b) Use of the ORF4 protein deletion site for inserting exogenous RNA: Insertion of the PRRSV ORF5 protein neutralizing epitope sequence into the ORF4 gene of the infectious cDNA clone BI EU This example describes the insertion of an exogenous RNA into the region located between amino acid positions 50 to 71 of the BI EU ORF4 protein. The exogenous RNA in this example codes for the neutralizing epitope located within the ORF5 protein of PRRS virus (Ostrowski, M. et al.) and consists of amino acids 1-11 of SEQ ID NO:39. This sequence (SEQ ID NO:51) was chosen to be inserted into the ectodomain of the ORF4 protein in order to increase accessibility of the ORF5 neutralizing epitope in a potential vaccine candidate allowing improved immune responses in vaccinated animals.

For generating the recombinant virus, the exogenous sequence was introduced into the ORF4 deletion site described in example a) and replaced amino acids 57-69 of the BI EU ORF4 protein by amino acids 1-11 of SEQ ID NO: 39 (representing amino acids 36-46 within the ORF5 protein of type 2 PRRSV strains) flanked by a G-G linker. The insertion resulted in a final sequence of Gly$_{57}$-Ser-Ser-His-Leu-Gln-Leu-Ile-Tyr-Asn-Leu-Thr-Gly$_{69}$ (SEQ ID NO:53) within the ORF4 protein of BI EU. The recombinant virus harboring the insertion is designated as BI EU-GP5-36-46 (comprising the sequence of SEQ ID NO:56) in the following.

In order to test whether BI EU-GP5-36-46 could be recovered, a synthetic transcript of BI EU cDNA harboring the mutation was transfected into BHK21 cells. The recombinant virus could be rescued by the same method as described above. A cytopathic effect (CPE) was observable within 3 to 4 days post transfer of cell culture supernatants from transfected BHK21 cells to PRRSV susceptible MA104 cells. Furthermore, PRRSV capsid protein-specific staining was detectable in CPE positive MA104 cells but not in cells which received supernatants of mock transfected BHK21 cells (not shown).

Growth kinetics were performed in order to test whether the recombinant virus could be grown to high titers. Therefore, MA104 cells were infected with BI EU-GP5-36-46 and with the parental BI EU virus as control using a MOI of 0.01. Supernatants of infected cells were collected at 0, 24, 48, 72 and 96 hours post infection and virus titers were determined by serial virus dilutions on 96-well plates containing MA104 cells. The result of three independent experiments is depicted in FIG. 7. At 48 hours post infection the virus mutant BI EU-GP5-36-46 reached the same peak titer of ~1×10$^7$ TCID$_{50}$/ml as the parental BI EU virus showing that the inserted sequence within the ORF4 protein does not negatively influence high titer virus growth.

Further experiments on MA104 cells revealed that the exogenous RNA sequence was stably maintained over multiple passages. Sequence analyses demonstrated stability of the insert over all passages analyzed. Interestingly a single nucleotide mutation of adenine to thymine, resulting in an amino acid exchange of His to Pro at position 56, upstream of the insertion site was detectable after passage 1 in independent experiments. Therefore, this additional mutation was inserted into BI EU-GP5-36-46 by reverse genetics. For generating this recombinant virus, an exogenous sequence was introduced into the ORF4 deletion site described in example a) and replaced amino acids 56-69 of the BI EU ORF4 protein by amino acids 1-11 of SEQ ID NO: 39 (representing amino acids 36-46 within the ORF5 protein of type 2 PRRSV strains) N-terminally flanked by the amino acid sequence PG and C-terminally flanked by a G-linker. The insertion resulted in a final sequence of Pro$_{56}$-Gly-Ser-Ser-His-Leu-Gln-Leu-Ile-Tyr-Asn-Leu-Thr-Gly$_{69}$(SEQ ID NO:55) within the ORF4 protein of BI EU. The resulting recombinant virus is designated as BI EU-GP5-36-46-AtoC (comprising the sequence of SEQ ID NO:58) in the following. Growth kinetics depicted in FIG. 7 demonstrated that BI EU-GP5-36-46-AtoC could be grown to similar titers as BI EU-GP5-36-46 and BI EU wild type, respectively.

To test whether the ORF5-derived sequences in the ectodomain-encoding region of ORF4 in BI EU-GP5-36-46-AtoC would render the mutant virus more sensitive to serum neutralization, serum neutralization tests (SNTs) were performed. It was postulated that increased accessibility of the inserted ORF5-derived neutralizing epitope located in the ORF4 protein ectodomain would result in enhanced sensitivity of the recombinant virus to the action of neutralizing antibodies as compared to the parental virus BI EU.

For the SNTs sera taken from six sows at 48 days post vaccination with BI EU wild type virus were serially diluted and mixed either with BI EU-GP5-36-46-AtoC or with wild type BI EU.

After incubation for one hour at 37° C. and 5% CO$_2$, MA104 cells were added to the samples. Serum titers were determined four days later based on CPE induced by non-neutralized virus. Sera taken from the same animals previous to vaccination served as negative controls (not shown). Mean values and standard deviations of two independent experiments are depicted in FIG. 8.

It could be demonstrated that BI EU-GP5-36-46-AtoC was consistently more sensitive to in vitro neutralization when compared to BI EU wild type virus despite variations that were observable between the six animals analyzed. Serum titers measured for BI EU-GP5-36-46-AtoC were 3 to 15 fold higher than the titers determined for the parental virus BI EU (FIG. 8). Data obtained from a different experiment further suggested that serum titers for BI EU-GP5-36-46-AtoC might be even more increasable by mutating the N-glycosylation site (amino acid $N_9$ of SEQ ID NO: 39) present in the ORF5-derived sequence from $Asn_9$ to $Gln_9$ (SEQ ID NO: 50 and 52) as N-glycosylation naturally shields the ORF5 neutralizing epitope ((Ansari et al., 2006) and data not shown),In summary, the findings depicted in FIG. 8 strongly indicated that the ORF5-derived neutralizing epitope inserted into the ORF4 protein ectodomain is highly accessible in the recombinant virus BI EU-GP5-36-46-AtoC making the latter a promising vaccine candidate. The demonstrated higher sensitivity to sera containing PRRSV-specific neutralizing antibodies should allow faster clearance and increased safety of the vaccine virus.

Also, it can be expected that PRRSV-specific neutralizing antibodies will be induced to higher levels and at earlier time points in piglets or sows that were vaccinated with BI EU-GP5-36-46-AtoC when compared to animals that were vaccinated with the parental virus BI EU. Early induction of neutralizing antibodies after vaccination should result in faster clearance and therefore less shedding of the vaccine virus (increased safety) and in a more efficient immune response after natural infection with PRRSV (increased efficacy).

The recombinant virus BI EU-GP5-36-46-AtoC therefore represents a promising candidate for a life attenuated PRRSV vaccine with improved safety and efficacy.

LIST OF FIGURES

FIG. 1: A. Infectious virus recovered from the BI EU cDNA clone induced a strong CPE on MA104 cells as shown by bright field microscopy. B. PRRSV capsid protein-specific immunofluorescence (IF) staining of BI EU-infected MA104 cells.

FIG. 2: Growth of virus recovered from the infectious cDNA clone BI EU on MA104 cells.

FIG. 3: nsp1β terminal domain (NTD) amino acid sequence alignment of several US (type II, top) and EU (type I, bottom) PRRSV strains. The NTD aminoacid sequence of BI EU is given at the very bottom. Amino acids R22, PR24, E32, SFP and H52 are indicated above the alignment and have been shown to be crucial for nsp1β homodimerization (Xue et al., 2010). Target regions for nsp1β mutagenesis are framed in red. The SDGRSR motif (SEQ ID NO: 64), corresponds to the region described in WO 2013017570 A1 using PRRSV EU cDNA clone LoN94-13. FIG. 3 discloses SEQ ID NOS 65-88, respectively, in order of appearance.

FIG. 4: Amino acid sequence alignment of BI EU-nsp1β deletion mutants. FIG. 4 discloses SEQ ID NOS 89-99, respectively, in order of appearance.

FIG. 5: Growth of BI EU-nsp1β deletion mutants on IFN-competent MA104 cells. FIG. 5 references SED ID NOS 99, 89, 93, 90, 95, 92, 97, 94, 98, and 96 respectively in order of appearance.

FIG. 6: IFN-β levels measured at different timepoints in the cell culture supernatant of MA104 cells infected with the BI EU-nsp1β deletion mutants or with parent BI EU virus. FIG. 6 references SEQ ID NOS 89, 98, 96, 94, 92, 99, 95, 90, 93, and 97 respectively in order of appearance.

FIG. 7: Growth kinetics of recombinant BI EU viruses harboring deletions or insertions within the ORF4 protein.

FIG. 8: Serum neutralization tests for the recombinant virus BI EU-GP5-36-46-AtoC and the parental virus BI EU.

IN THE SEQUENCE LISTING

SEQ ID NOs:1-24 correspond to sequences of the ectodomain of PRRSV ORF4 protein with a deletion;

SEQ ID NO:25 and SEQ ID NO:26 correspond to sequences of the first two predicted N-terminal β-sheets of PRRSV (genotype I) ORF4 protein;

SEQ ID NO:27 and SEQ ID NO:28 correspond to sequences of the first two predicted N-terminal β-sheets of PRRSV (genotype II) ORF4 protein;

SEQ ID NO:29 and SEQ ID NO:30 correspond to sequences of the first two predicted N-terminal β-sheets of PRRSV (genotype I) ORF4 protein;

SEQ ID NO:31 and SEQ ID NO:32 correspond to sequences of the first two predicted N-terminal β-sheets of PRRSV (genotype II) ORF4 protein;

SEQ ID NO:32 corresponds to a (partial) sequence of a PRRSV (genotype I) ORF4 protein having a deletion of 11 amino acid residues in the region between the first two predicted N-terminal β-sheets;

SEQ ID NO:33 corresponds to a (partial) sequence of a PRRSV (genotype II) ORF4 protein having a deletion of 7 amino acid residues in the region between the first two predicted N-terminal β-sheets;

SEQ ID NO:34 corresponds to the sequence of the ectodomain of a PRRSV (genotype I) ORF4 protein having a deletion of 11 amino acid residues;

SEQ ID NO:35 corresponds to the sequence of the ectodomain of a PRRSV (genotype II) ORF4 protein having a deletion of 7 amino acid residues;

SEQ ID NO:36 corresponds to the sequence of a PRRSV (genotype I) ORF4 protein having a deletion of 11 amino acid residues (and including the sequence of SEQ ID NO:34, respectively);

SEQ ID NO:37 corresponds to a nucleotide sequence encoding the sequence of SEQ ID NO:36;

SEQ ID NO:38 corresponds to a nucleotide sequence encoding a genotype I PRRSV whose genome comprises a nucleic acid molecule which codes for the sequence of SEQ ID NO:36;

SEQ ID NO:39 corresponds to the sequence of a peptide encoded by the ORF5 gene of PRRS virus;

SEQ ID NO:40 corresponds to the sequence of a peptide encoded by the ORF5 gene of PRRS virus;

SEQ ID NO:41 corresponds to Lelystad virus complete genome;

SEQ ID NO:42 corresponds to VR2332 virus complete genome;

SEQ ID NO:43 corresponds to the sequence of ORF4 protein of the Lelystad virus;

SEQ ID NO:44 corresponds to the sequence of ORF4 protein of the VR2332 virus;

SEQ ID NO:45 corresponds to a first nucleic acid sequence as described herein;

SEQ ID NO:46 corresponds to a second nucleic acid sequence as described herein, which flanks the 5' end of the first nucleic acid sequence;

SEQ ID NO:47 corresponds to a third nucleic acid sequence as described herein, which flanks the 3' end of the first nucleic acid sequence;

SEQ ID NO:48 corresponds to BI EU complete viral cDNA insert;

SEQ ID NO:49 corresponds to the sequence of SEQ ID NO:48 with a deletion, thereby encoding an ORF4 protein having a deletion of 13aa (aa 57-69);

SEQ ID NO:50 corresponds to the sequence of SEQ ID NO:39 with the substitution N→Q at position 9;

SEQ ID NO:51 corresponds to the sequence of aa 1-11 of SEQ ID NO:39;

SEQ ID NO:52 corresponds to the sequence of SEQ ID NO:51 with the substitution N→Q at position 9;

SEQ ID NO:53 corresponds to the sequence of SEQ ID NO:51 with a Gly-Gly linker;

SEQ ID NO:54 corresponds to the sequence of SEQ ID NO:52 with a Gly-Gly linker;

SEQ ID NO:55 corresponds to the sequence of SEQ ID NO:53 with an N-terminal proline residue;

SEQ ID NO:56 corresponds to the sequence of SEQ ID NO:49 with an insert, thereby encoding the sequence of SEQ ID NO:53;

SEQ ID NO:57 corresponds to the sequence of SEQ ID NO:49 with an insert, thereby encoding the sequence of SEQ ID NO:54;

SEQ ID NO:58 corresponds to the sequence of SEQ ID NO:48 with a deletion, thereby encoding an ORF4 protein having a deletion of 14aa (aa 56-69), wherein an insert coding for the sequence of SEQ ID NO: 55 is included.

Reference List

Allende, R., Laegreid, W. W., Kutish, G. F., Galeota, J. A., Wills, R. W., Osorio, F. A., 2000. Porcine reproductive and respiratory syndrome virus: description of persistence in individual pigs upon experimental infection. J. Virol. 74, 10834-10837.

Ansari, I. H., Kwon, B., Osorio, F. A., Pattnaik, A. K., 2006. Influence of N-linked glycosylation of porcine reproductive and respiratory syndrome virus GP5 on virus infectivity, antigenicity, and ability to induce neutralizing antibodies. J. Virol. 80, 3994-4004.

Beura, L. K., Sarkar, S. N., Kwon, B., Subramaniam, S., Jones, C., Pattnaik, A. K., Osorio, F. A., 2010. Porcine reproductive and respiratory syndrome virus nonstructural protein 1beta modulates host innate immune response by antagonizing IRF3 activation. J. Virol. 84, 1574-1584.

Buddaert, W., Van, R. K., Pensaert, M., 1998. In vivo and in vitro interferon (IFN) studies with the porcine reproductive and respiratory syndrome virus (PRRSV). Adv. Exp. Med. Biol. 440, 461-467.

Chen, Z., Lawson, S., Sun, Z., Zhou, X., Guan, X., Christopher-Hennings, J., Nelson, E. A., Fang, Y., 2010. Identification of two auto-cleavage products of nonstructural protein 1 (nsp1) in porcine reproductive and respiratory syndrome virus infected cells: nsp1 function as interferon antagonist. Virology 398, 87-97.

den Boon, J. A., Faaberg, K. S., Meulenberg, J. J., Wassenaar, A. L., Plagemann, P. G., Gorbalenya, A. E., Snijder, E. J., 1995. Processing and evolution of the N-terminal region of the arterivirus replicase ORF1a protein: identification of two papainlike cysteine proteases. J. Virol. 69, 4500-4505.

Haller, O., Weber, F., 2009. The interferon response circuit in antiviral host defense. Verh. K. Acad. Geneeskd. Belg. 71, 73-86.

Kim, O., Sun, Y., Lai, F. W., Song, C., Yoo, D., 2010. Modulation of type I interferon induction by porcine reproductive and respiratory syndrome virus and degradation of CREB-binding protein by non-structural protein 1 in MARC-145 and HeLa cells. Virology 402, 315-326.

Kroese, M. V., Zevenhoven-Dobbe, J. C., Bos-de Ruijter, J. N., Peeters, B. P., Meulenberg, J. J., Cornelissen, L. A., Snijder, E. J., 2008. The nsp1 alpha and nsp1 papain-like autoproteinases are essential for porcine reproductive and respiratory syndrome virus RNA synthesis. J. Gen. Virol. 89, 494-499.

Li, H., Zheng, Z., Zhou, P., Zhang, B., Shi, Z., Hu, Q., Wang, H., 2010. The cysteine protease domain of porcine reproductive and respiratory syndrome virus non-structural protein 2 antagonizes interferon regulatory factor 3 activation. J. Gen. Virol. 91, 2947-2958.

Lopez, O. J., Osorio, F. A., 2004. Role of neutralizing antibodies in PRRSV protective immunity. Vet. Immunol. Immunopathol. 102, 155-163.

Meier, W. A., Galeota, J., Osorio, F. A., Husmann, R. J., Schnitzlein, W. M., Zuckermann, F. A., 2003. Gradual development of the interferon-gamma response of swine to porcine reproductive and respiratory syndrome virus infection or vaccination. Virology 309, 18-31.

Miller, L. C., Laegreid, W. W., Bono, J. L., Chitko-McKown, C. G., Fox, J. M., 2004. Interferon type I response in porcine reproductive and respiratory syndrome virus-infected MARC-145 cells. Arch. Virol. 149, 2453-2463.

Ostrowski, M., Galeota, J. A., Jar, A. M., Platt, K. B., Osorio, F. A., Lopez, O. J., 2002. Identification of neutralizing and nonneutralizing epitopes in the porcine reproductive and respiratory syndrome virus GP5 ectodomain. J. Virol. 76, 4241-4250.

Shi, X., Wang, L., Li, X., Zhang, G., Guo, J., Zhao, D., Chai, S., Deng, R., 2011a. Endoribonuclease activities of porcine reproductive and respiratory syndrome virus nsp11 was essential for nsp11 to inhibit IFN-beta induction. Mol. Immunol. 48, 1568-1572.

Shi, X., Wang, L., Zhi, Y., Xing, G., Zhao, D., Deng, R., Zhang, G., 2010. Porcine reproductive and respiratory syndrome virus (PRRSV) could be sensed by professional beta interferon-producing system and had mechanisms to inhibit this action in MARC-145 cells. Virus Res. 153, 151-156.

Shi, X., Zhang, G., Wang, L., Li, X., Zhi, Y., Wang, F., Fan, J., Deng, R., 2011b. The Nonstructural Protein 1 Papain-Like Cysteine Protease Was Necessary for Porcine Reproductive and Respiratory Syndrome Virus Nonstructural Protein 1 to Inhibit Interferon-beta Induction. DNA Cell Biol. 30, 355-362.

Snijder, E. J., Meulenberg, J. J., 1998. The molecular biology of arteriviruses. J. Gen. Virol. 79 (Pt 5), 961-979.

Song, C., Krell, P., Yoo, D., 2010. Nonstructural protein 1alpha subunit-based inhibition of NF-kappaB activation and suppression of interferon-beta production by porcine reproductive and respiratory syndrome virus. Virology 407, 268-280.

Sun, Y., Xue, F., Guo, Y., Ma, M., Hao, N., Zhang, X. C., Lou, Z., Li, X., Rao, Z., 2009. Crystal structure of porcine reproductive and respiratory syndrome virus leader protease Nsp1alpha. J. Virol. 83, 10931-10940.

Xiao, Z., Batista, L., Dee, S., Halbur, P., Murtaugh, M. P., 2004. The level of virus-specific T-cell and macrophage recruitment in porcine reproductive and respiratory syndrome virus infection in pigs is independent of virus load. J. Virol. 78, 5923-5933.

Xue, F., Sun, Y., Yan, L., Zhao, C., Chen, J., Bartlam, M., Li, X., Lou, Z., Rao, Z., 2010. The crystal structure of porcine reproductive and respiratory syndrome virus nonstructural protein Nsp1beta reveals a novel metal-dependent
nuclease. J. Virol. 84, 6461-6471.

The invention claimed is:

1. A DNA molecule which encodes a genotype I PRRS virus and which is capable of producing live virus when transfected into cells, wherein said molecule comprises a nucleic acid sequence having at least 99.1% sequence identity with the nucleic acid sequence of SEQ ID NO:48, wherein maximally 0.8% of the differences in sequence identity are located within the first 110 nucleotides of the 5' end of SEQ ID NO:48 and within the the last 97 nucleotides of the 3' end of SEQ ID NO:48 and wherein maximally 0.1% of the differences in sequence identity are located in the remaining nucleotides of SEQ ID NO:48.

2. The DNA molecule of claim 1, wherein said virus is attenuated and/or wherein said virus is able to induce a protective immune response against respiratory and/or reproductive signs of disease after infection with Porcine Reproductive and Respiratory Syndrome (PRRS) virus in swine; and/or wherein said virus is able to reach titers of at least $5 \times 10^5$ to $1 \times 10^6$ tissue culture infectious dose 50 ($TCID_{50}$) per milliliter (ml) within 24 hours post infection of MA104 cells, preferably at an MOI (multiplicity of infection) of 0.001 to 0.1, and/or wherein said virus is able to reach titers of at least $5 \times 10^6$ to $1 \times 10^7$ tissue culture infectious dose 50 ($TCID_{50}$) per milliliter (ml) within 48 hours post infection of MA104 cells, at an MOI (multiplicity of infection) of 0.001 to 0.1.

3. An RNA transcript of the DNA construct of claim 1.

4. A cell transfected with the DNA construct of claim 1 or with the RNA transcript of claim 3.

5. A genotype I PRRS virus produced by the cell of claim 4.

6. A genotype I PRRS virus whose genome comprises a nucleic acid molecule according to claim 1.

7. A method for producing a genotype I PRRS virus comprising transfecting a cell with the DNA construct of claim 1.

8. A composition comprising a nucleic acid molecule of claim 1 suspended in a suitable amount of a pharmaceutically acceptable diluent or excipient.

9. A method of prophylaxis or treatment of Porcine Reproductive and Respiratory Syndrome comprising administering the virus according to claim 5 to an animal.

10. A kit comprising the PRRS virus or a fragment thereof according to claim 5 as a detection marker for the differentiation between infected and vaccinated animals (DIVA).

11. A nucleic acid molecule of claim 1, wherein said nucleic acid sequence of SEQ ID NO: 48 comprises an nsp2 region from 1380 to 3808 and an ORF4 region encoding GP4 from 12805 to 13356.

* * * * *